(12) United States Patent
Ting et al.

(10) Patent No.: US 8,716,312 B2
(45) Date of Patent: May 6, 2014

(54) INHIBITORS OF DIACYLGLYCEROL ACYLTRANSFERASE

(75) Inventors: Pauline C. Ting, New Providence, NJ (US); Robert Aslanian, Rockaway, NJ (US); Mary Ann Caplen, Sayreville, NJ (US); Jianhua Cao, Edison, NJ (US); Tin-Yau Chan, Edison, NJ (US); David Kim, North Bergen, NJ (US); Hyunjin Kim, Livingston, NJ (US); Jae-Hun Kim, Scotch Plains, NJ (US); Rongze Kuang, Green Brook, NJ (US); Joe F. Lee, Brooklyn, NY (US); John Schwerdt, Lake Hiawatha, NJ (US); Heping Wu, Edison, NJ (US); Nicolas Zorn, Short Hills, NJ (US)

(73) Assignee: Merck Sharp & Dohme Corporation, Rahway, NJ (US)

( * ) Notice: Subject to any disclaimer, the term of this patent is extended or adjusted under 35 U.S.C. 154(b) by 211 days.

(21) Appl. No.: 13/129,843

(22) PCT Filed: Nov. 17, 2009

(86) PCT No.: PCT/US2009/064738
§ 371 (c)(1),
(2), (4) Date: May 18, 2011

(87) PCT Pub. No.: WO2010/059602
PCT Pub. Date: May 27, 2010

(65) Prior Publication Data
US 2011/0224137 A1    Sep. 15, 2011

Related U.S. Application Data

(60) Provisional application No. 61/115,987, filed on Nov. 19, 2008, provisional application No. 61/116,000, filed on Nov. 19, 2008.

(51) Int. Cl.
*A61P 3/00* (2006.01)
*A61P 9/00* (2006.01)
*A61K 31/445* (2006.01)
*C07D 413/12* (2006.01)
*C07D 413/14* (2006.01)
*C07D 417/12* (2006.01)
*C07D 417/14* (2006.01)

(52) U.S. Cl.
USPC ........ 514/316; 514/218; 514/250; 514/253.1; 514/307; 514/318; 540/492; 540/575; 544/350; 544/364; 546/144; 546/187; 546/194; 546/203

(58) Field of Classification Search
USPC .......................... 514/316; 540/187; 546/187
See application file for complete search history.

(56) References Cited

U.S. PATENT DOCUMENTS

| 2009/0076275 A1 | 3/2009 | Bolin et al. |
| 2009/0093497 A1 | 4/2009 | Bolin et al. |
| 2009/0105273 A1 | 4/2009 | Bolin et al. |

FOREIGN PATENT DOCUMENTS

| CA | 2 649 043 A1 | 11/2007 |
| WO | 98/57937 A2 | 12/1998 |
| WO | 98/57937 A3 | 12/1998 |
| WO | 2005/013907 A2 | 2/2005 |
| WO | 2005/013907 A3 | 2/2005 |
| WO | 2005/044250 A1 | 5/2005 |
| WO | 2007/060140 A2 | 5/2007 |
| WO | 2007/060140 A3 | 5/2007 |
| WO | 2008/011130 A2 | 1/2008 |
| WO | 2008/011130 A3 | 1/2008 |
| WO | 2008/141976 A1 | 11/2008 |

*Primary Examiner* — Brenda Coleman
(74) *Attorney, Agent, or Firm* — Kenrick L. Vidale; Janet E. Fair; Anna L. Cocuzzo

(57) ABSTRACT

The present invention relates to novel heterocyclic compounds as diacylglycerol acyltransferase ("DGAT") inhibitors, pharmaceutical compositions comprising the heterocyclic compounds and the use of the compounds for treating or preventing a cardiovascular disease, a metabolic disorder, obesity or an obesity-related disorder, diabetes, dyslipidemia, a diabetic complication, impaired glucose tolerance or impaired fasting glucose. An illustrative compound of the invention is shown below:

(I)

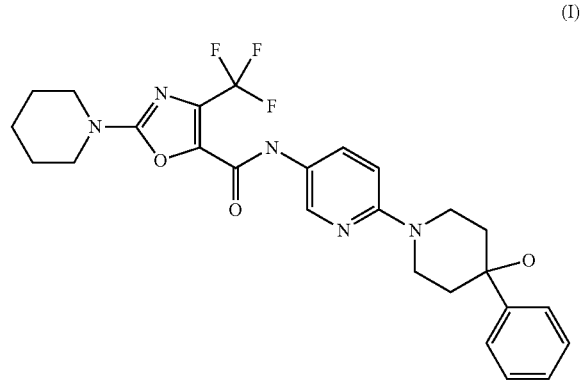

6 Claims, No Drawings

INHIBITORS OF DIACYLGLYCEROL ACYLTRANSFERASE

CROSS-REFERENCE TO RELATED APPLICATIONS

This application is a U.S. National Phase application under 35 U.S.C. §371 of PCT Application No. PCT/US2009/064738, filed Nov. 17, 2009, which published as WO 2010/059602 A1 on May 27, 2011, and claims priority under 35 U.S.C. §365(b) from U.S. provisional application Ser. Nos. 61/115,987, filed Nov. 19, 2008 and 61/116,000, filed Nov. 19, 2008.

FIELD OF THE INVENTION

The present invention relates to certain heterocyclic compounds useful as diacylglycerol acyltransferase ("DGAT") inhibitors, especially diacylglycerol acyltransferase 1 ("DGAT1") inhibitors, pharmaceutical compositions containing the compounds, and methods of treatment using the compounds and compositions to treat or prevent various diseases including cardiovascular disease, dyslipidemia, obesity and diabetes (e.g., Type 2 diabetes).

BACKGROUND OF THE INVENTION

There is a need for additional ways of treating diseases associated with metabolic syndrome such as, for example, dyslipidemia, cardiovascular disease, obesity and diabetes (e.g., Type 2 diabetes).

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets—Immune, Endocrine & Metabolic Disorders (2003) 3, pp. 263-270).

Diacylglycerol O-acyltransferase, also known as diglyceride acyltransferase or DGAT, is a key enzyme in triglyceride synthesis. DGAT catalyzes the final and rate-limiting step in the triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, pp. 395-400).

Two forms of DGAT have been cloned and are designated DGAT1 and DGAT2 [see Cases et al, Proceedings of the National Academy of Science, USA (1998) 95, pp. 13018-13023, Lardizabal et al, Journal of Biological Chemistry (2001) 276, pp. 38862-38869 and Cases et al, Journal of Biological Chemistry (2001) 276, pp. 38870-38876]. Although both enzymes utilize the same substrates, there is no homology between DGAT1 and DGAT2. Both enzymes are widely expressed however some differences do exist in the relative abundance of expression in various tissues.

Disorders or imbalances in triglyceride metabolism, both absorption as well as de novo synthesis, have been implicated in the pathogenesis of a variety of disease risks. These include obesity, insulin resistance syndrome, Type II diabetes, dyslipidemia, metabolic syndrome (syndrome X) and coronary heart disease [see Kahn, Nature Genetics (2000) 25, pp. 6-7, Yanovski and Yanovski, New England Journal of Medicine (2002) 346, pp. 591-602, Lewis et al, Endocrine Reviews (2002) 23, pp. 201, Brazil, Nature Reviews Drug Discovery (2002) 1, pp. 408, Malloy and Kane, Advances in Internal Medicine (2001) 47, pp. 111, Subauste and Burant, Current Drug Targets—Immune, Endocrine & Metabolic Disorders (2003) 3, pp. 263-270 and Yu and Ginsberg, Annals of Medicine (2004) 36, pp. 252-261]. Compounds that can decrease the synthesis of triglycerides from diacylglycerol by inhibiting or lowering the activity of the DGAT enzyme would be of value as therapeutic agents for the treatment of diseases associated with abnormal metabolism of triglycerides.

Known inhibitors of DGAT include: dibenzoxazepinones (see Ramharack et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, pp. 683-687 and Casaschi et al, Journal of Nutrition (2004) 134, pp. 1340-1346), substituted benzyl-phosphonates (see Kurogi et al, Journal of Medicinal Chemistry (1996) 39, pp. 1433-1437, Goto et al, Chemistry and Pharmaceutical Bulletin (1996) 44, pp. 547-551, Ikeda et al, Thirteenth International Symposium on Atherosclerosis (2003), abstract 2P-0401, and Miyata et al, JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), and substituted sulfonamides (see Budd Haeberlein and Buckett, WO20050442500).

Also known to be inhibitors of DGAT are: 2-bromo-palmitic acid (see Colman et al, Biochimica et Biophysica Acta (1992) pp. 1125, 203-9), 2-bromo-octanoic acid (see Mayorek and Bar-Tana, Journal of Biological Chemistry (1985) 260, pp. 6528-6532), roselipins (see Noriko et al, (Journal of Antibiotics (1999) 52, pp. 815-826), amidepsin (see Tomoda et al, Journal of Antibiotics (1995) 48, pp. 42-7), isochromophilone, prenylflavonoids (see Chung et al, Planta Medica (2004) 70, v58-260), polyacetylenes (see Lee et al, Planta Medica (2004) 70, pp. 97-200), cochlioquinones (see Lee et al, Journal of Antibiotics (2003) 56, pp. 967-969), tanshinones (see Ko et al, Archives of Pharmaceutical Research (2002) 25, pp. 446-448), gemfibrozil (see Zhu et al, Atherosclerosis (2002) 164, pp. 221-228), and substituted quinolones (see Ko et al, Planta Medica (2002) 68, pp. 1131-1133). Also known to be modulators of DGAT activity are antisense oligonucleotides (see Monia and Graham, US20040185559).

Particular mention is made to PCT publication WO 2007/060140 (published May 31, 2007; applicant: F. Hoffmann-La Roche AG). Claim 1 therein discloses compounds of the formula:

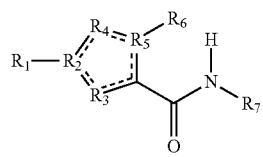

wherein $R_1$, $R_2$, $R_3$, $R_4$, $R_5$, $R_6$ and $R_7$ are described. Additional publications include WO 2008/141976 (published May 13, 2008); US 2009/0093497 (published May 1, 2009) and US 2009/0105273 (published May 1, 2009).

A need exists in the art, however, for additional DGAT inhibitors that have efficacy for the treatment of metabolic disorders such as, for example, obesity, Type II diabetes mellitus and metabolic syndrome.

SUMMARY OF THE INVENTION

In an embodiment, this invention discloses a compound, or pharmaceutically acceptable salts, solvates, ester or prodrugs of said compound, or pharmaceutically acceptable salts, solvates or esters of said prodrug, the compound being represented by the general formula I:

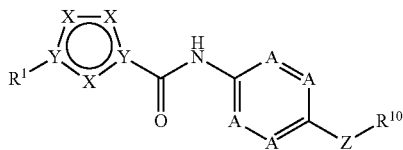

wherein:
each A is independently selected from $C(R^3)$ and N;
or alternately the moiety:

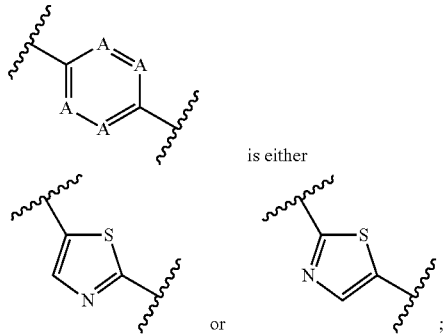

X is independently selected from $C(R^3)$, $N, N(R^4)$, O and S, provided that no more than one X is S or O, and at least one X or one Y is N, O, or S;
Y is independently selected from C and N;
Z is independently a bond, O or $NR^4$;
$R^1$ is selected from heterocycloalkyl containing 1-4 heteroatoms which can be the same or different and is selected from the group consisting of O, S and N, wherein said heterocycloalkyl is unsubstituted or optionally independently substituted with one or more moieties which are the same or different, each substituent being independently selected from the group consisting of alkyl, alkoxy, alkoxyalkyl, haloalkoxy, alkenyl, alkynyl, cycloalkyl, cycloalkylalkyl, cycloalkenyl, cycloalkenylalkyl, aryl, arylalkyl, heteroaryl, heteroarylalkyl, halo, —CN, —$OR^c$, =O, —$C(O)R^c$, —$C(O)OR^c$, —$C(O)N(R^c)(R^d)$, —$SF_5$, —$OSF_5$, —$Si(R^c)_3$, —$SR^c$, —$S(O)N(R^c)(R^d)$, —$CH(R^c)(R^d)$, —$S(O)_2N(R^c)(R^d)$, —$C(=NOR^c)R^d$, —$P(O)(OR^c)(OR^d)$, —$N(R^c)(R^d)$, -alkyl-$N(R^c)(R^d)$, —$N(R^c)C(O)R^d$, —$CH_2$—$N(R^c)C(O)R^d$, —$CH_2$—$N(R^c)C(O)N(R^d)(R^b)$, —$CH_2$—$R^c$; —$CH_2N(R^c)(R^d)$, —$N(R^c)S(O)R^d$, —$N(R^c)S(O)_2R^d$, —$CH_2$—$N(R^c)S(O)_2R^d$, —$N(R^c)S(O)_2N(R^d)(R^b)$, —$N(R^c)S(O)N(R^d)(R^b)$, —$N(R^c)C(O)N(R^d)(R^b)$, —$CH_2$—$N(R^c)C(O)N(R^d)(R^b)$, —$N(R^c)C(O)OR^d$, —$CH_2$—$N(R^c)C(O)OR^d$, —$S(O)R^c$, =$NOR^c$, —$N_3$, —$NO_2$ and —$S(O)_2R^c$, wherein each $R^b$, $R^c$ and $R^d$ is independently selected;
or alternatively, said heterocycloalkyl can be fused with aryl, wherein said aryl can be unsubstituted or optionally independently substituted with one or more moieties which are the same or different, each substituent being selected from the group consisting of alkyl, alkoxy, alkoxyalkyl, haloalkoxy, alkenyl, alkynyl, cycloalkyl, cycloalkylalkyl, cycloalkenyl, cycloalkenylalkyl, aryl, arylalkyl, heteroaryl, heteroarylalkyl, halo, —CN, —$OR^c$, —$C(O)R^c$, —$C(O)OR^c$, —$C(O)N(R^c)(R^d)$, —$SF_5$, —$OSF_5$, —$Si(R^c)_3$, —$SR^c$, —$S(O)N(R^c)(R^d)$, —$CH(R^c)(R^d)$, —$S(O)_2N(R^c)(R^d)$, —$C(=NOR^c)R^d$, —$P(O)(OR^c)(OR^d)$, —$N(R^c)(R^d)$, -alkyl-$N(R^c)(R^d)$, —$N(R^c)C(O)R^d$, —$CH_2$—$N(R^c)C(O)R^d$, —$CH_2$—$N(R^c)C(O)N(R^d)(R^b)$, —$CH_2$—$R^c$; —$CH_2N(R^c)(R^d)$, —$N(R^c)S(O)R^d$, —$N(R^c)S(O)_2R^d$, —$CH_2$—$N(R^c)S(O)_2R^d$, —$N(R^c)S(O)_2N(R^d)(R^b)$, —$N(R^c)S(O)N(R^d)(R^b)$, —$N(R^c)C(O)N(R^d)(R^b)$, —$CH_2$—$N(R^c)C(O)N(R^d)(R^b)$, —$N(R^c)C(O)OR^d$, —$CH_2$—$N(R^c)C(O)OR^d$, —$S(O)R^c$, —$N_3$, —$NO_2$ and —$S(O)_2R^c$, wherein each $R^b$, $R^c$ and $R^d$ is independently selected;
or alternatively, said heterocycloalkyl can be fused with aryl, wherein each of said heterocycloalkyl and aryl can be unsubstituted or optionally independently substituted with one or more moieties which are the same or different, each substituent being independently selected from the group consisting of alkyl, alkoxy, alkoxyalkyl, haloalkoxy, alkenyl, alkynyl, cycloalkyl, cycloalkylalkyl, cycloalkenyl, cycloalkenylalkyl, aryl, arylalkyl, heteroaryl, heteroarylalkyl, halo, —CN, —$OR^c$, =O, —$C(O)R^c$, —$C(O)OR^c$, —$C(O)N(R^c)(R^d)$, —$SF_5$, —$OSF_5$, —$Si(R^c)_3$, —$SR^c$, $S(O)N(R^c)(R^d)$, —$CH(R^c)(R^d)$, —$S(O)_2N(R^c)(R^d)$, —$C(=NOR^c)R^d$, $P(O)(OR^c)(OR^d)$, —$N(R^c)(R^d)$, -alkyl-$N(R^c)(R^d)$, —$N(R^c)C(O)R^d$, —$CH_2$—$N(R^c)C(O)R^d$, —$CH_2$—$N(R^c)C(O)N(R^d)(R^b)$, —$CH_2$—$R^c$; —$CH_2N(R^c)(R^d)$, —$N(R^c)S(O)R^d$, —$N(R^c)S(O)_2R^d$, —$CH_2$—$N(R^c)S(O)_2R^d$, —$N(R^c)S(O)_2N(R^d)(R^b)$, —$N(R^c)S(O)N(R^d)(R^b)$, —$N(R^c)C(O)N(R^d)(R^b)$, —$CH_2$—$N(R^c)C(O)N(R^d)(R^b)$, —$N(R^b)C(O)OR^d$, —$CH_2$—$N(R^c)C(O)OR^d$, —$S(O)R^c$, =$NOR^c$, —$N_3$, —$NO_2$ and —$S(O)_2R^c$, wherein each $R^b$, $R^c$ and $R^d$ is independently selected;
$R^3$ is selected from the group of H, lower alkyl, hydroxy, halo, O-alkyl, O-haloalkyl, O-cycloalkyl, S-alkyl, S-haloalkyl, CN, $CF_3$, —$SF_5$, —$OSF_5$, —$Si(R^c)_3$, —$SR^c$, cycloalkyl, heterocyclyl, haloalkyl, aryl, heteroaryl, N-alkyl, N-haloalkyl, $NH_2$, and N-cycloalkyl;
$R^4$ is selected from the group of H, lower alkyl, cycloalkyl, heterocyclyl, haloalkyl, aryl, and heteroaryl;
$R^5$ is selected from the group of lower alkyl, cycloalkyl, heterocyclyl, haloalkyl, aryl, and heteroaryl; and
$R^{10}$ is either (i) a 4-8 membered heterocyclyl ring having from 1 to 3 ring N atoms, or (ii) a bicyclic heterocyclyl ring having from 1 to 3 ring N atoms, or (iii) an aryl group, or (iv) a heteroaryl group,
wherein said aryl or heteroaryl group for $R^{10}$ is unsubstituted or optionally independently substituted with one or more G moieties wherein said G moieties can be the same or different, each G moiety being independently selected from the group shown below,
and further wherein said heterocyclyl ring for $R^{10}$ is unsubstituted or optionally substituted, off of either (i) a ring N atom or (ii) a ring carbon atom on said heterocyclyl ring, with one or more G moieties wherein said G moieties can be the same or different, each G moiety being independently selected from the group consisting of:
(a) ∿∿∿-$(CHR^{20})_n$—C(O)—$NR^aR^b$, with the proviso that $R^{10}$ is not a 5- or 6-membered heterocyclyl ring when $R^{20}$ is hydrogen and $R^{10}$ can be a 5- or 6-membered heterocyclyl ring when G is present as an oxo group;
(b) ∿∿∿-$(CHR^{20})_n$—C(O)—O—$R^5$, with the proviso that $R^{10}$ is not a 5- or 6-membered heterocyclyl ring when $R^{20}$ is hydrogen;

(c) ~~~-(CHR$^{20}$)$_n$—C(O)—OH, with the proviso that R$^{10}$ is not a 5- or 6-membered heterocyclyl ring when R$^{20}$ is hydrogen;
(d) ~~~-(CHR$^{20}$)$_n$—C(O)—R$^a$;
(e) ~~~-(CHR$^{20}$)$_n$—S(O$_2$)—R$^a$;
(f) ~~~-(CHR$^{20}$)$_n$—S(O$_2$)—(CH$_2$)$_n$—R$^a$;
(g) ~~~-(CHR$^{20}$)$_n$—S(O$_2$)—NR$^a$R$^b$;
(h) ~~~-(CHR$^{20}$)$_n$—R$^a$;
(i) ~~~-(CHR$^{20}$)$_n$—O—R$^a$;
(j) ~~~-NH—C(O)—O—R$^a$ off of only C and not off of N;
(k) ~~~-NH—C(O)—R$^a$ off of only C and not off of N;
(l) ~~~-NH—C(O)—NR$^a$R$^b$ off of only C and not off of N;
(m) ~~~-(CHR$^{20}$)$_n$—C(O)—NH—NH—C(O)—R$^a$;
(n) ~~~-O—P(O)—(R$^a$)$_2$ off of only C and not off of N;
(o) ~~~-O—CH(R$^a$)$_2$ off of only C and not off of N;
(p) an oxo group off of only C and not off of N;
(q) ~~~-C(O)—(CHR$^{20}$)$_n$—C(O)—O—R$^a$;
(r) ~~~-C(O)—(CHR$^{20}$)$_n$—R$^a$;
(s) a spirocyclyl group;
(t) ~~~-C(O)-(cycloalkyl)--C(O)—N(R$^b$)—R$^a$, with the proviso that R$^{10}$ is not a 5- or 6-membered heterocyclyl ring;
(u) ~~~-C(O)-(cycloalkyl)--C(O)—OR$^5$, with the proviso that R$^{10}$ is not a 5- or 6-membered heterocyclyl ring;
(v) ~~~-C(O)-(cycloalkyl)-C(O)OH, with the proviso that R$^{10}$ is not a 5- or 6-membered heterocyclyl ring;
(w) ~~~-C(O)-(cycloalkyl)-C(O)OH bioisostere, with the proviso that R$^{10}$ is not a 5- or 6-membered heterocyclyl ring;
(x) ~~~-C(O)-(aryl)-C(O)OH; and
(y) ~~~-C(O)-(heteroaryl)-C(O)OH, wherein R$^a$ is selected from the group consisting of hydrogen, hydroxy, CN, halo, alkyl, alkenyl, alkynyl, aryl, (aryl)alkyl-, heteroaryl, (heteroaryl)alkyl-, heterocyclyl, (heterocyclyl)alkyl-, cycloalkyl, (cycloalkyl)alkyl-, spirocyclyl or a bicyclic heterocyclyl, wherein each of said alkyl, alkenyl, alkynyl, aryl, heteroaryl, heterocyclyl and cycloalkyl is unsubstituted or optionally independently substituted with one or more moieties which are the same or different, each moiety being selected independently from the group consisting of O-haloalkyl, S-haloalkyl, CN, NO$_2$, CF$_3$, cycloalkyl, heterocyclyl, haloalkyl, aryl, heteroaryl, N-alkyl, N-haloalkyl, and N-cycloalkyl; alkyl, alkenyl, alkynyl, cycloalkylalkyl, cycloalkenyl, heterocyclylalkyl, aryl, arylalkyl, heteroaryl, heteroarylalkyl, halo, —OR$^c$, —C(O)R$^c$, —C(O)OR$^c$, —C(O)N(R$^c$)(R$^d$), —SF$_5$, —OSF$_5$, —Si(R$^c$)$_3$, —SR$^c$, —S(O)N(R$^c$)(R$^d$), —CH(R$^c$)(R$^d$), —S(O)$_2$N(R$^c$)(R$^d$), —C(=NOR$^c$)R$^d$, —P(O)(OR$^c$)(OR$^d$), —N(R$^c$)(R$^d$), -alkyl-N(R$^c$)(R$^d$), —N(R$^c$)C(O)R$^d$, —CH$_2$—N(R$^c$)C(O)R$^d$, —CH$_2$—N(R$^c$)C(O)N(R$^d$)(R$^b$), —CH$_2$—R$^c$; —CH$_2$N(R$^c$)(R$^d$), —N(R$^c$)S(O)R$^d$, —N(R$^c$)S(O)$_2$R$^d$, —CH$_2$—N(R$^c$)S(O)$_2$R$^d$, —N(R$^c$)S(O)$_2$N(R$^d$)(R$^b$), —N(R$^c$)S(O)N(R$^d$)(R$^b$), —N(R$^c$)C(O)N(R$^d$)(R$^b$), —CH$_2$—N(R$^c$)C(O)N(R$^d$)(R$^b$), —N(R$^c$)C(O)OR$^d$, —CH$_2$—N(R$^c$)C(O)OR$^d$, —S(O)R$^c$, =NOR$^c$, —N$_3$, and —S(O)$_2$R$^c$;

wherein each R$^b$, R$^c$ and R$^d$ is independently selected;
R$^b$ is H, lower alkyl, cycloalkyl, aryl, heteroaryl or heterocycloalkyl;
R$^c$ is H, lower alkyl, cycloalkyl, aryl, heteroaryl or heterocycloalkyl;
R$^d$ is H, lower alkyl, cycloalkyl, aryl, heteroaryl or heterocycloalkyl;

wherein each of said alkyl, cycloalkyl, aryl, heteroaryl or heterocycloalkyl in R$^b$, R$^c$, and R$^d$ can be unsubstituted or optionally independently substituted with 1-2 substituents independently selected from halo, OH, NH$_2$, CF$_3$, CN, Oalkyl, NHalkyl, N(alkyl)$_2$ and Si(alkyl)$_3$;

R$^{20}$ is H, —OH, halo, or —CF$_3$;

and m is 1-3, n is 0-3.

The term "spirocyclyl" refers to a cyclic group substituted off the same carbon atom. Some non-limiting examples would be:

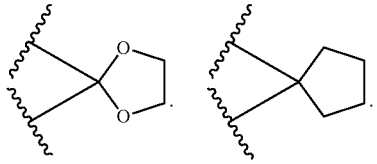 [SMILES: *C1(*)OCCO1 ; *C1(*)CCCC1]

The term "oxo" refers to the moiety =C(O) substituted off the same carbon atom.

The term "bicyclic heterocyclyl" refers to bicyclic compounds containing heteroatom as part of the ring atoms. A non-limiting example would be:

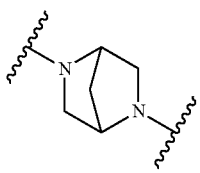 [SMILES: *N1CC2CC1CN2*]

with no limitation as to the position of the heteroatom. The term "bicyclic heterocyclyl" also includes moieties where a heterocyclyl ring has an aryl or heteroaryl or heterocyclyl ring fused to itself. Some non-limiting examples would be:

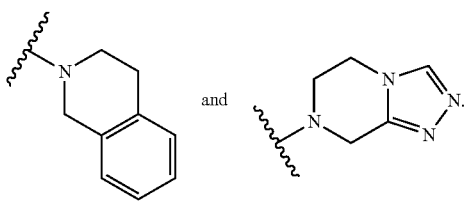 [SMILES: *N1CCc2ccccc2C1 ; *N1CCn2cnnc2C1]

The term "COOH bioisostere" is as defined in *The Practice of Medicinal Chemistry*, C. G. Wermuth Ed.; Academic Press: New York, 1996, p. 203. Non-limiting examples of COOH bioisosteres include —SO$_3$H, —S(O)$_2$NHR$^7$, —S(O)$_2$NHC(O)R$^7$, —CH$_2$S(O)$_2$R$^7$, —C(O)NHS(O)$_2$R$^7$, —C(O)NHOH, —C(O)NHCN, —CH(CF$_3$)OH, —C(CF$_3$)$_2$OH, —P(O)(OH)$_2$ and the groups listed below:

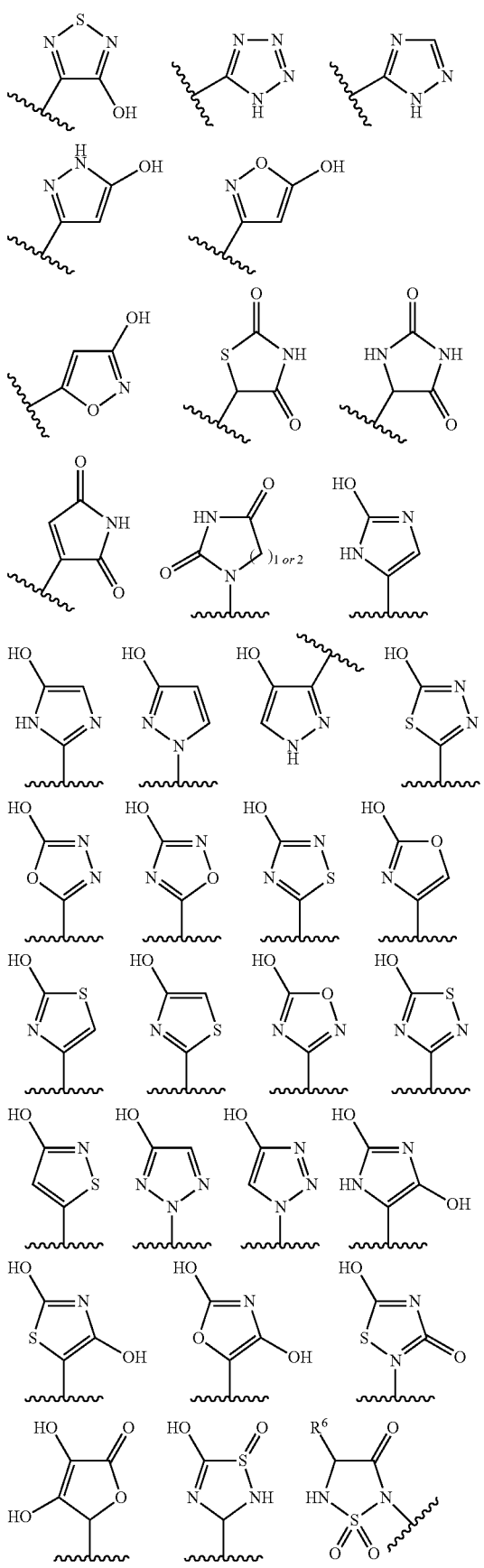

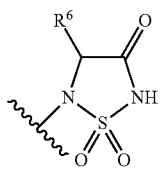

where $R^7$ is selected from alkyl, aryl or heteroaryl. Furthermore, any COOH substituent can optionally be replaced by COOH bioisostere.

When a disubstituted moiety is shown with ~~~ on both sides, the attachment points are from left to right when looking at the parent formula, e.g. Formula I. Thus, for example, if the moiety:

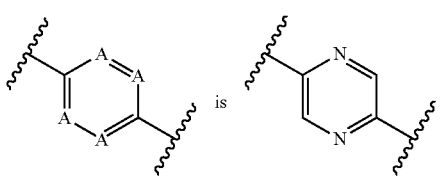

in Formula I,
it means that the pyrazine ring is attached to NH on the left hand side and $R^{10}$ on the right hand side in Formula I.

In another aspect, this invention provides compositions comprising at least one compound of Formula I.

In another aspect, this invention provides pharmaceutical compositions comprising at least one compound of Formula I and at least one pharmaceutically acceptable carrier.

In another aspect, this invention provides a method of treating diabetes in a patient in need of such treatment using therapeutically effective amounts of at least one compound of Formula I, or of a composition comprising at least one compound of Formula I.

In another aspect, this invention provides a method of treating diabetes in a patient in need of such treatment, e.g., Type 2 diabetes, using therapeutically effective amounts of at least one compound of Formula I, or of a composition comprising at least one compound of Formula I.

In another aspect, this invention provides a method of treating metabolic syndrome in a patient in need of such treatment, using therapeutically effective amounts of at least one compound of Formula I, or of a composition comprising at least one compound of Formula I.

In another aspect, this invention provides a method of inhibiting DGAT using therapeutically effective amounts of at least one compound of Formula I, or of a composition comprising at least one compound of Formula I.

In another aspect, this invention provides a method of inhibiting DGAT1 using therapeutically effective amounts of at least one compound of Formula I, or of a composition comprising at least one compound of Formula I.

DESCRIPTION OF THE INVENTION

In an embodiment, the present invention discloses compounds of Formula I, or pharmaceutically acceptable salts, solvates, esters or prodrugs thereof.

The following embodiments (stated as "another embodiment") are independent of each other; different such embodiments can be independently selected and combined in various combinations. Such combinations should be considered as part of the invention.

In another embodiment, A is C(R³).
In another embodiment, A is N.
In another embodiment, one A is N and the other A moieties are C(R³).
In another embodiment, one A is C(R³) and the other A moieties are N.
In another embodiment, two A moieties are N and the other two A moieties are C(R³).
In another embodiment, X is C(R³).
In another embodiment, X is N.
In another embodiment, X is N(R⁴).
In another embodiment, X is O.
In another embodiment, X is S.
In another embodiment, at least one X is O.
In another embodiment, at least one Y is N.
In another embodiment, one X is O and one other X is N.
In another embodiment, one X is O, one X is N and the other X is C(R³).
In another embodiment, Y is C.
In another embodiment, Y is N.
In another embodiment, R¹ is heterocyclyl.
In another embodiment, R¹ is unsubstituted heterocyclyl.
In another embodiment, R¹ is 4-8 membered heterocyclyl, containing 1-3 heteroatoms which can be the same or different and is independently selected from the group consisting of N, O and S, wherein said heterocyclyl can be unsubstituted or optionally substituted, and/or fused as defined earlier.
In another embodiment, R¹ is 3-7 membered heterocyclyl, containing 1-3 heteroatoms which can be the same or different and is independently selected from the group consisting of N, O and S, wherein said heterocyclyl can be unsubstituted or optionally substituted, and/or fused as defined earlier.
In another embodiment, R¹ is pyrrolidinyl, wherein said heterocyclyl can be unsubstituted or optionally substituted, and/or fused as defined earlier.
In another embodiment, R¹ is piperidinyl, wherein said heterocyclyl can be unsubstituted or optionally substituted, and/or fused as defined earlier.
In another embodiment, R¹ is piperazinyl, wherein said heterocyclyl can be unsubstituted or optionally substituted, and/or fused as defined earlier.
In another embodiment, R¹ is morpholinyl, wherein said heterocyclyl can be unsubstituted or optionally substituted, and/or fused as defined earlier.
In another embodiment, R¹ is thiamorpholinyl, wherein said heterocyclyl can be unsubstituted or optionally substituted, and/or fused as defined earlier.
In another embodiment, R¹ is azetidinyl, wherein said heterocyclyl can be unsubstituted or optionally substituted, and/or fused as defined earlier.
In another embodiment, R¹ is azepinyl, wherein said heterocyclyl can be unsubstituted or optionally substituted, and/or fused as defined earlier.
In another embodiment, R¹ is oxazepinyl, wherein said heterocyclyl can be unsubstituted or optionally substituted, and/or fused as defined earlier.
In another embodiment, R¹ is the moiety:

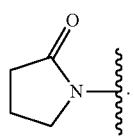

In another embodiment, R¹ is 4-8 membered heterocyclyl, containing 1-3 heteroatoms which can be the same or different and is independently selected from the group consisting of N, O and S, wherein said heterocyclyl can be unsubstituted or optionally substituted as defined earlier, and is fused with an aryl wherein said aryl can be unsubstituted or optionally substituted as defined earlier.
In another embodiment, R¹ is 4-8 membered heterocyclyl, containing 1-3 heteroatoms which can be the same or different and is independently selected from the group consisting of N, O and S, wherein said heterocyclyl can be unsubstituted or optionally substituted as defined earlier, and is fused with a phenyl wherein said phenyl can be unsubstituted or optionally substituted as defined earlier.
In another embodiment, R¹ is pyrrolidinyl, wherein said pyrrolidinyl can be unsubstituted or optionally substituted as defined earlier, and is fused with a phenyl wherein said phenyl can be unsubstituted or optionally substituted as defined earlier.
In another embodiment, R¹ is piperidinyl, wherein said piperidnyl can be unsubstituted or optionally substituted as defined earlier, and is fused with a phenyl wherein said phenyl can be unsubstituted or optionally substituted as defined earlier.
In another embodiment, R¹ is piperazinyl, wherein said piperazinyl can be unsubstituted or optionally substituted as defined earlier, and is fused with a phenyl wherein said phenyl can be unsubstituted or optionally substituted as defined earlier.
In another embodiment, R¹ is morpholinyl, wherein said morpholinyl can be unsubstituted or optionally substituted as defined earlier, and is fused with a phenyl wherein said phenyl can be unsubstituted or optionally substituted as defined earlier.
In another embodiment, R¹ is 4-8 membered heterocyclyl, containing 1-3 heteroatoms which can be the same or different and is independently selected from the group consisting of N, O and S, wherein said heterocyclyl is substituted with an aryl wherein said aryl can be unsubstituted or optionally substituted as defined earlier.
In another embodiment, R¹ is 4-8 membered heterocyclyl, containing 1-3 heteroatoms which can be the same or different and is independently selected from the group consisting of N, O and S, wherein said heterocyclyl is substituted with a phenyl wherein said phenyl can be unsubstituted or optionally substituted as defined earlier.
In another embodiment, R¹ is pyrrolidinyl, wherein said pyrroldinyl is substituted with a phenyl wherein said phenyl can be unsubstituted or optionally substituted as defined earlier.
In another embodiment, R¹ is piperidinyl, wherein said pyrroldinyl is substituted with a phenyl wherein said phenyl can be unsubstituted or optionally substituted as defined earlier.
In another embodiment, R¹ is piperazinyl, wherein said pyrroldinyl is substituted with a phenyl wherein said phenyl can be unsubstituted or optionally substituted as defined earlier.
In another embodiment, R¹ is morpholinyl, wherein said pyrroldinyl is substituted with a phenyl wherein said phenyl can be unsubstituted or optionally substituted as defined earlier.
In another embodiment, R³ is H.
In another embodiment, R³ is lower alkyl.
In another embodiment, R³ is hydroxyl.
In another embodiment, R³ is —O-alkyl.
In another embodiment, R³ is —CN.

In another embodiment, $R^3$ is —$CF_3$.
In another embodiment, $R^3$ is —O— haloalkyl.
In another embodiment, $R^3$ is —$OSF_5$.
In another embodiment, $R^3$ is —$SF_5$.
In another embodiment, $R^4$ is H.
In another embodiment, $R^4$ is lower alkyl.
In another embodiment, $R^{10}$ is a 4-8-membered heterocyclyl ring having from 1 to 3 ring N atoms, wherein said heterocyclyl ring is substituted off of a ring N atom.
In another embodiment, $R^{10}$ is a 4-8-membered heterocyclyl ring having from 1 to 3 ring N atoms, wherein said heterocyclyl ring is substituted off of a ring carbon atom.
In another embodiment, $R^{10}$ is a bicyclic heterocyclyl ring having from 1 to 3 ring N atoms, wherein said bicyclic heterocyclyl ring is substituted off of a ring N atom.
In another embodiment, $R^{10}$ is a bicyclic heterocyclyl ring having from 1 to 3 ring N atoms, wherein said bicyclic heterocyclyl ring is substituted off of a ring carbon atom.
In another embodiment, $R^{10}$ is a 4-8-membered heterocyclyl ring having from 1 to 3 ring N atoms, wherein said heterocyclyl ring is substituted with G, wherein G is as previously described.
In another embodiment, $R^{10}$ is the moiety:

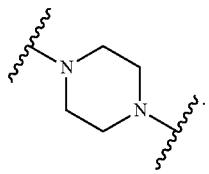 [SMILES: *N1CCN(*)CC1]

In another embodiment, $R^{10}$ is the moiety:

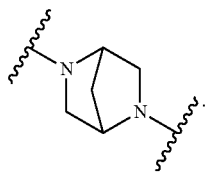 [SMILES: *N1CC2CC1CN2*]

In another embodiment, $R^{10}$ is the moiety:

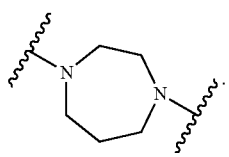 [SMILES: *N1CCCN(*)CC1]

In another embodiment, $R^{10}$ is the moiety:

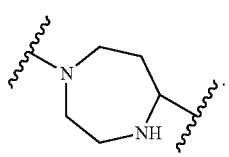 [SMILES: *C1CCN(*)CCN1]

In another embodiment, $R^{10}$ is a piperidinyl ring, wherein said piperidinyl ring is substituted with G, wherein G is as previously described.

In another embodiment, $R^{10}$ is a piperazinyl ring, wherein said piperazinyl ring is with G, wherein G is as previously described.
In another embodiment, $R^{10}$ is a diazepinyl ring, wherein said diazepinyl ring is substituted with G, wherein G is as previously described.
In another embodiment, $R^{10}$ is a diazepinyl ring, wherein said diazepinyl ring is substituted with two G moieties, wherein G is as previously described.
In another embodiment, G is ⌇-$(CHO_2)_n$—C(O)—O—$R^a$.
In another embodiment, G is ⌇-$(CH_2)_n$—C(O)—$R^a$.
In another embodiment, G is ⌇-$(CH_2)_n$—$S(O_2)$—$R^a$.
In another embodiment, G is ⌇-$(CH_2)_n$—$S(O_2)$—$(CH_2)_n$—$R^a$.
In another embodiment, G is ⌇-$(CH_2)_n$—$S(O_2)$—$NR^aR^b$.
In another embodiment, G is ⌇-$(CH_2)_n$—$R^a$.
In another embodiment, G is ⌇-$(CH_2)_n$—O—$R^a$.
In another embodiment, G is ⌇-NH—C(O)—O—$R^a$.
In another embodiment, G is ⌇-NH—C(O)—$R^a$.
In another embodiment, G is ⌇-$(CH_2)_n$—C(O)—$NR^aR^b$.
In another embodiment, G is ⌇-$(CH_2)_n$—C(O)—NH—NH—C(O)—$R^a$.
In another embodiment, G is ⌇-O—P(O)—$(R^a)_2$.
In another embodiment, G is ⌇-O—$CH(R^a)_2$.
In another embodiment, G is an oxo group.
In another embodiment, G is ⌇-$(CHOH)_m$—$R^a$.
In another embodiment, G is a spirocyclyl group.
In another embodiment, G is the moiety:

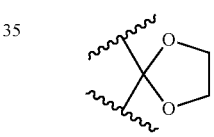

coming off of a carbon atom of $R^{10}$.
In another embodiment, $R^a$ is unsubstituted alkyl.
In another embodiment, $R^a$ is alkyl substituted as previously described under formula I.
In another embodiment, $R^a$ is unsubstituted aryl.
In another embodiment, $R^a$ is aryl substituted as previously described under formula I.
In another embodiment, $R^a$ is unsubstituted heteroaryl.
In another embodiment, $R^a$ is heteroaryl substituted as previously described under formula I.
In another embodiment, $R^a$ is unsubstituted cycloalkyl.
In another embodiment, $R^a$ is cycloalkyl substituted as previously described under formula I.
In another embodiment, $R^a$ is unsubstituted heterocyclyl.
In another embodiment, $R^a$ is heterocyclyl substituted as previously described under formula I.
In another embodiment, $R^a$ is hydroxy.
In another embodiment, $R^a$ is cyano.
In another embodiment, $R^a$ is halo.
In another embodiment, $R^a$ is alkeny.
In another embodiment, $R^a$ is alkynyl.
In another embodiment, $R^a$ is alkoxyalkyl.
In another embodiment, $R^a$ is aralkyl.
In another embodiment, $R^a$ is haloalkyl.
In another embodiment, $R^a$ is $CF_3$.
In another embodiment, $R^a$ is phenyl substituted with one or more halo groups.

In another embodiment, $R^a$ is heteroaryl.
In another embodiment, $R^a$ is pyridyl.
In another embodiment, $R^a$ is oxazolyl.
In another embodiment, $R^a$ is oxadiazolyl.
In another embodiment, the moiety:

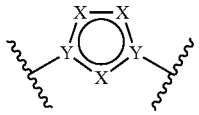

is
selected from the group consisting of the following moieties:

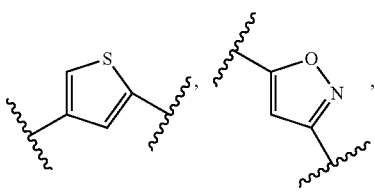

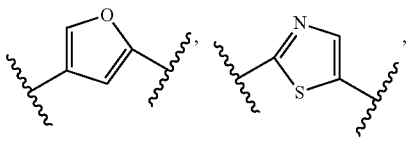

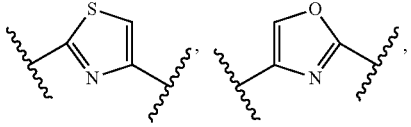

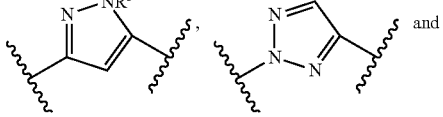

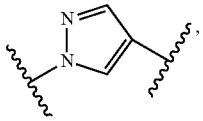

as well as their possible positional isomers, these moieties being unsubstituted or optionally substituted with $R^3$.

In another embodiment, in Formula I, the moiety:

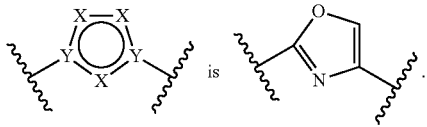

In another embodiment, in Formula I, the moiety:

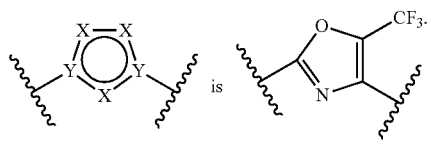

In another embodiment, in Formula I, the moiety:

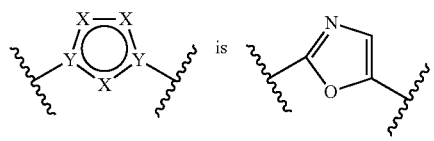

In another embodiment, in Formula I, the moiety:

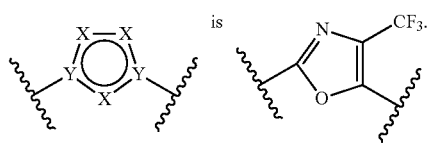

In another embodiment, in Formula I, the moiety:

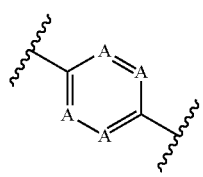

is
selected from the group consisting of the following moieties:

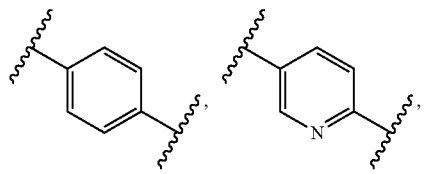

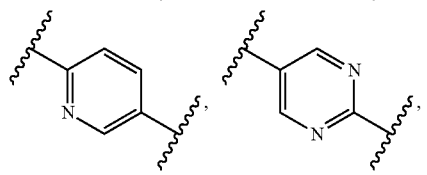

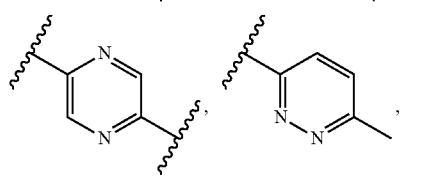

-continued

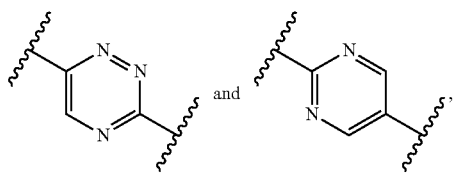

as well as any of their positional isomers.

In another embodiment, in Formula I, the moiety:

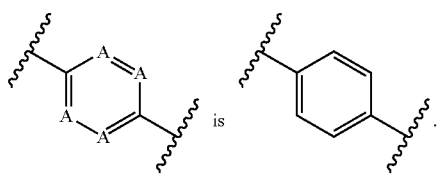

In another embodiment, in Formula I, the moiety:

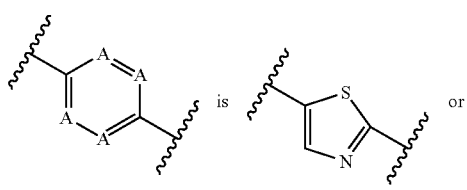 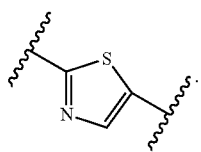

In another embodiment, in Formula I, the moiety:

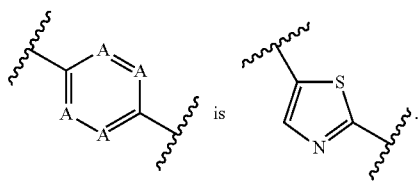

In another embodiment, in Formula I, the moiety:

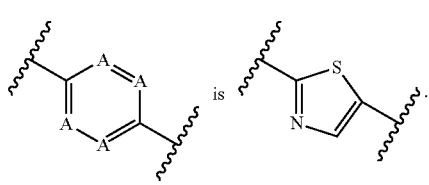

In another embodiment, in Formula I, the moiety:

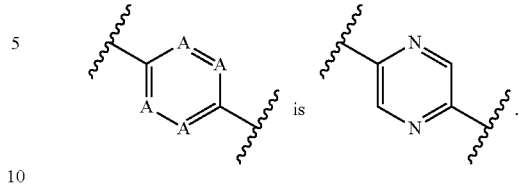

In another embodiment, in Formula I, the moiety:

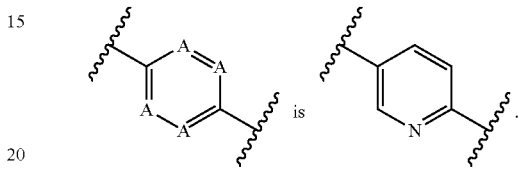

In another embodiment, in Formula I, the moiety:

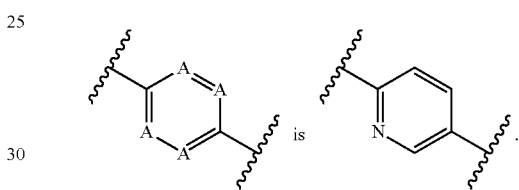

In another embodiment, in Formula I, the moiety:

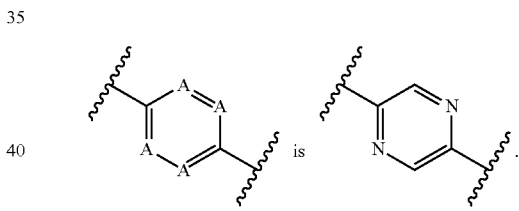

In another embodment, Z is O.
In another embodiment, Z is $NR^4$.
In another embodiment, p is 0.
In another embodiment, p is 1.
In another embodiment of Formula I, wherein X, Y, $R^1$, A, $R^{10}$, $R^a$ and the other moieties are independently selected, one X is N, a second X is C, and the third X is O, both Y are C, one A is N and the other A moieties are C, $R^1$ is unsubstituted heterocyclyl, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A moieties are C, $R^1$ is heterocyclyl substituted as described earlier, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted pyrrolidinyl, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is pyrrolidinyl substituted as described previously under Formula I, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted piperidinyl, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is piperidinyl substituted as described previously under Formula I, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted piperazinyl, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is piperazinyl substituted as described previously under Formula I, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted moepholinyl, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is morpholinyl substituted as described previously under Formula I, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted pyrrolidinyl, $R^{10}$ is piperazinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is pyrrolidinyl as described earlier, $R^{10}$ is piperazinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted piperidinyl, $R^{10}$ is piperazinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is piperidinyl substituted as described earlier, $R^{10}$ is piperidinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted piperazinyl, $R^{10}$ is piperazinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is piperazinyl as described earlier, $R^{10}$ is piperazinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is unsubstituted morpholinyl, $R^{10}$ is piperazinyl ring and $R^a$ is as previously described.

In another embodiment of Formula I, wherein X, Y, $R^1$, A, $R^{10}$, $R^a$ and the other moieties are independently selected, one X is N, a second X is C, and the third X is O, both Y are C, one A is N and the other A's are C, $R^1$ is morpholinyl as described earlier, $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

one A is N and the other A's are C, $R^1$ is heterocyclyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

one A is N and the other A's are C, $R^1$ is heterocyclyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

one A is N and the other A's are C, $R^1$ is heterocyclyl (unsubstituted, substituted and/or fused as described earlier), $R^{10}$ is piperidinyl ring and $R^a$ is as previously described.

In another embodiment of Formula I, wherein X, Y, R¹, A, R¹⁰, Rᵃ and the other moieties are independently selected, the moiety:

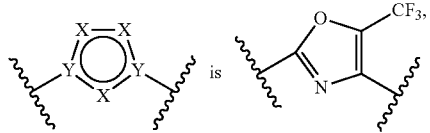

one A is N and the other A's are C, R¹ is R¹ is heterocyclyl (unsubstituted, substituted and/or fused as described earlier), R¹⁰ is piperidinyl ring and Rᵃ is as previously described.

In another embodiment of Formula I, wherein X, Y, R¹, A, R¹⁰, Rᵃ and the other moieties are independently selected, the moiety:

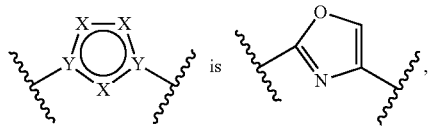

one A is N and the other A's are C, R¹ is pyrrolidinyl (unsubstituted, substituted and/or fused as described earlier), R¹⁰ is piperazinyl ring and Rᵃ is as previously described.

In another embodiment of Formula I, wherein X, Y, R¹, A, R¹⁰, Rᵃ and the other moieties are independently selected, the moiety:

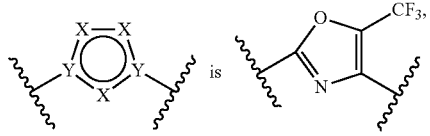

one A is N and the other A's are C, R¹ is piperidinyl (unsubstituted, substituted and/or fused as described earlier), R¹⁰ is piperazinyl ring and Rᵃ is as previously described.

In another embodiment of Formula I, wherein X, Y, R¹, A, R¹⁰, Rᵃ and the other moieties are independently selected, the moiety:

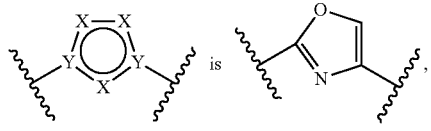

the moiety:

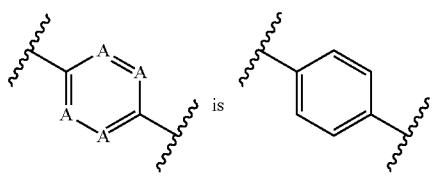

R¹ is piperazinyl (unsubstituted, substituted and/or fused as described earlier), R¹⁰ is piperazinyl ring and Rᵃ is as previously described.

In another embodiment of Formula I, wherein X, Y, R¹, A, R¹⁰, Rᵃ and the other moieties are independently selected, the moiety:

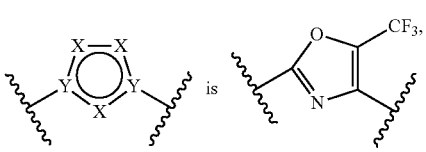

the moiety:

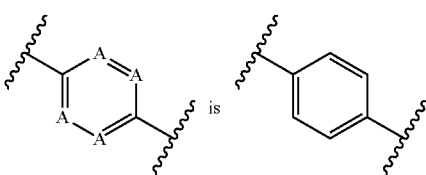

R¹ is morpholinyl (unsubstituted, substituted and/or fused as described earlier), R¹⁰ is piperazinyl ring and Rᵃ is as previously described.

In another embodiment of Formula I, wherein X, Y, R¹, A, R¹⁰, Rᵃ and the other moieties are independently selected, the moiety:

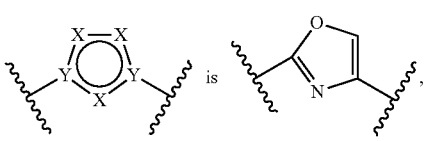

the moiety:

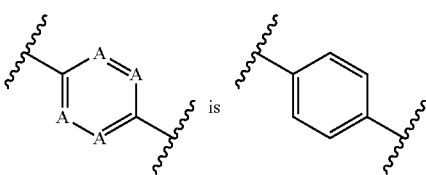

R¹ is pyrrolidinyl (unsubstituted, substituted and/or fused as described earlier), R¹⁰ is piperidinyl ring and Rᵃ is as previously described.

In another embodiment of Formula I, wherein X, Y, R¹, A, R¹⁰, Rᵃ and the other moieties are independently selected, the moiety:

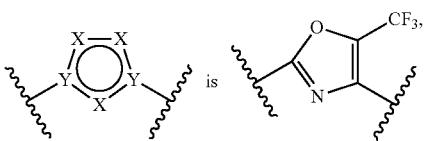

the moiety:

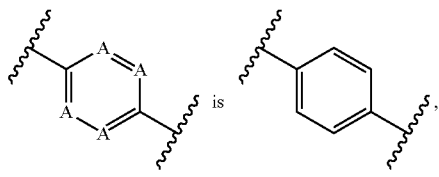

$R^1$ is piperidnyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

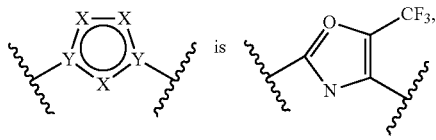

the moiety:

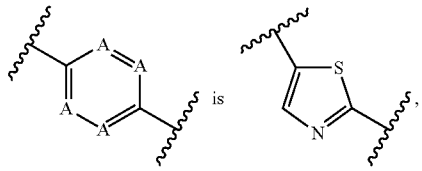

$R^1$ is piperazinyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

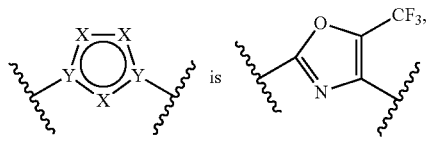

the moiety:

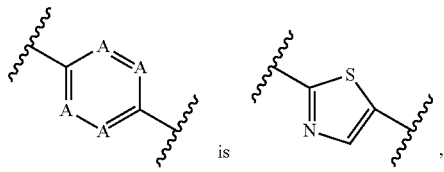

$R^1$ is morpholinyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

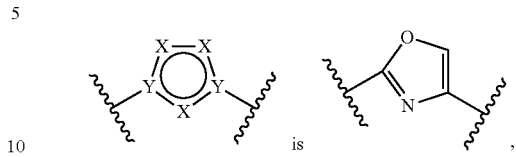

one A is N and the other A's are C, $R^1$ is pyrrolidinyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

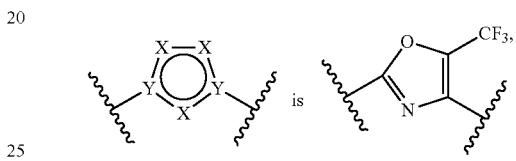

one A is N and the other A's are C, $R^1$ is piperidinyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

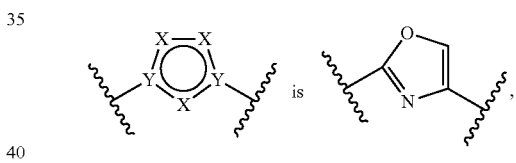

the moiety:

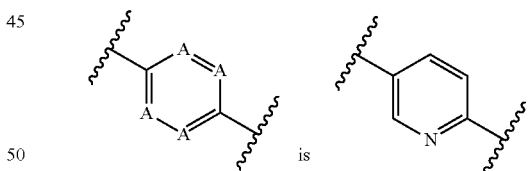

$R^1$ is piperazinyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

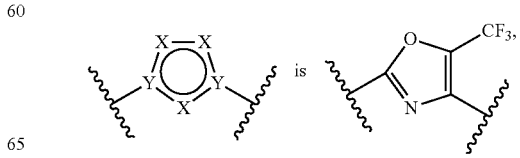

the moiety:

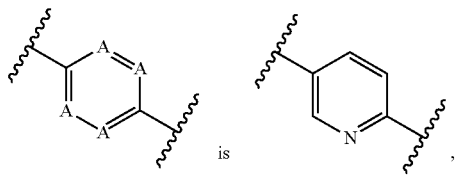

is $R^1$ is morpholinyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

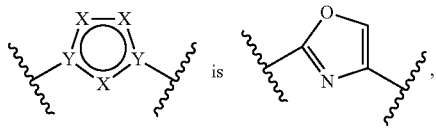

is the moiety:

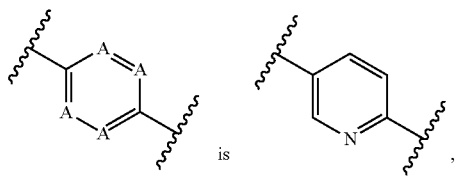

is $R^1$ is pyrrolidinyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

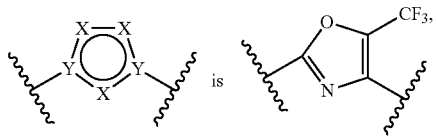

is the moiety:

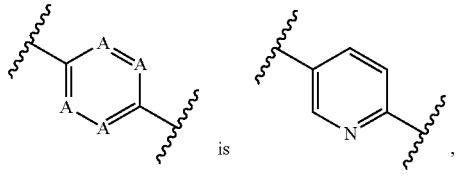

is $R^1$ is piperidnyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

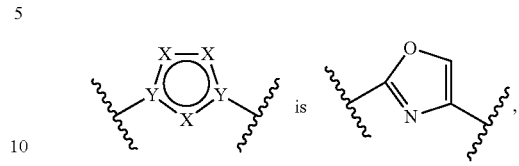

is the moiety:

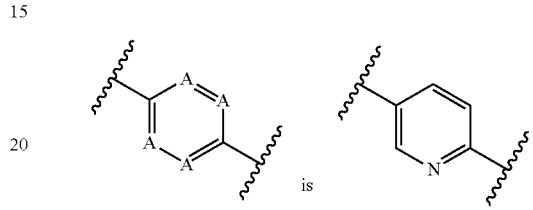

is $R^1$ is piperazinyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

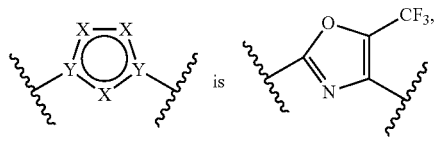

is the moiety:

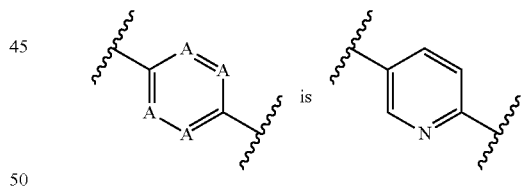

is $R^1$ is morpholinyl (unsubstituted, substituted and/or fused as described earlier), $R^{10}$ is piperidinyl ring and $R^a$ is as previously described.

In another embodiment of Formula I, wherein X, Y, $R^1$, A, $R^{10}$, $R^a$ and the other moieties are independently selected, the moiety:

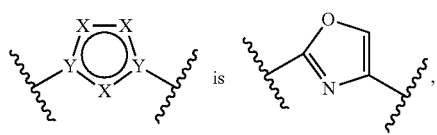

is the moiety:

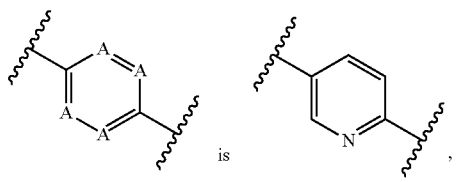

is $R^1$ is pyrrolidinyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

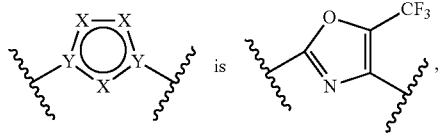

is the moiety:

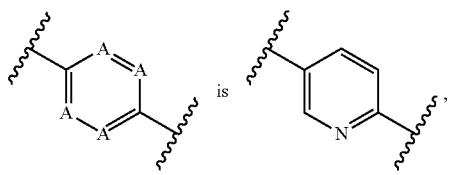

$R^1$ is piperidinyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

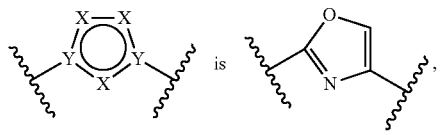

is the moiety:

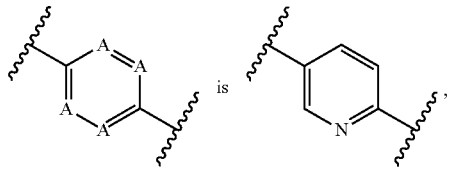

$R^1$ is piperazinyl (unsubstituted, substituted and/or fused as described earlier), $R^{10}$ is piperidinyl ring with —C(O)—O—$R^a$, and $R^a$ is as previously described.

In another embodiment of Formula I, wherein X, Y, $R^1$, A, $R^{10}$, $R^a$ and the other moieties are independently selected, the moiety:

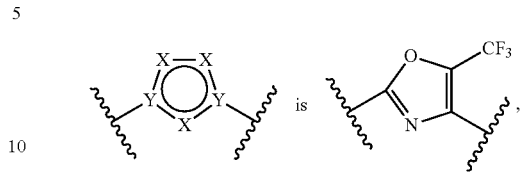

is the moiety:

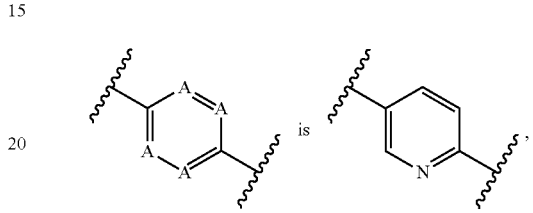

$R^1$ is morpholinyl (unsubstituted, substituted and/or fused as described earlier), $R^{10}$ is piperidinyl ring with —C(O)—O—$R^a$, and $R^a$ is as previously described.

In another embodiment of Formula I, wherein X, Y, $R^1$, A, $R^{10}$, $R^a$ and the other moieties are independently selected, the moiety:

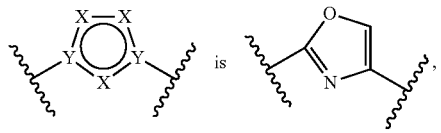

is the moiety:

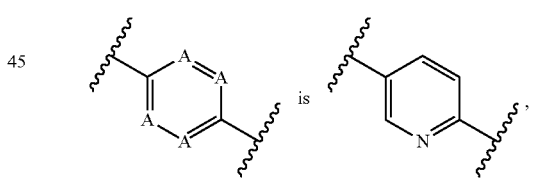

is $R^1$ is pyrrolidinyl (unsubstituted, substituted and/or fused as described earlier), $R^{10}$ is piperazinyl ring with —C(O)—O—$R^a$, and $R^a$ is as previously described.

In another embodiment of Formula I, wherein X, Y, $R^1$, A, $R^{10}$, $R^a$ and the other moieties are independently selected, the moiety:

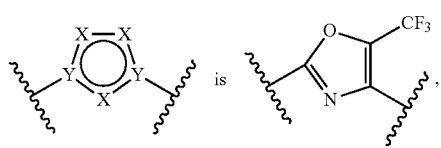

is the moiety:

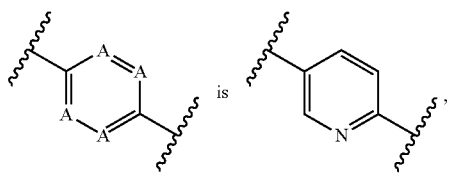 is $R^1$ is piperidinyl (unsubstituted, substituted and/or fused as described earlier), $R^{10}$ is piperazinyl ring with —C(O)—O—$R^a$, and $R^a$ is as previously described.

In another embodiment of Formula I, wherein X, Y, $R^1$, A, $R^{10}$, $R^a$ and the other moieties are independently selected, the moiety:

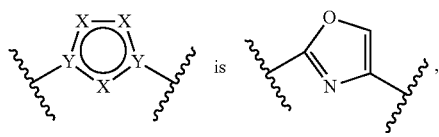 is the moiety:

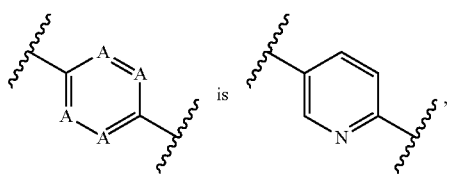 is $R^1$ is piperazinyl (unsubstituted, substituted and/or fused as described earlier), $R^{10}$ is piperidinyl ring with —C(O)—O—$R^a$, and $R^a$ is as previously described.

In another embodiment of Formula I, wherein X, Y, $R^1$, A, $R^{10}$, $R^a$ and the other moieties are independently selected, the moiety:

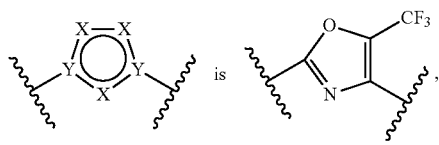 is the moiety:

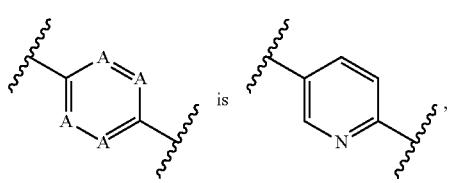 is $R^1$ is morpholinyl (unsubstituted, substituted and/or fused as described earlier), $R^{10}$ is piperidinyl ring with —C(O)—O—$R^a$, and $R^a$ is as previously described.

In another embodiment of Formula I, wherein X, Y, $R^1$, A, $R^{10}$, $R^a$ and the other moieties are independently selected, the moiety:

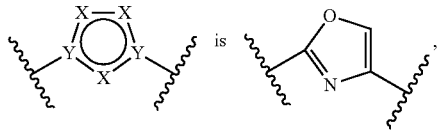 is the moiety:

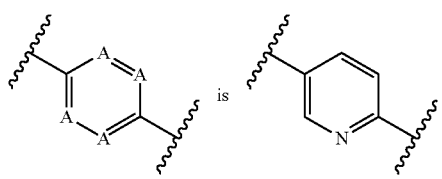 is $R^1$ is azetidinyl (unsubstituted, substituted and/or fused as described earlier), $R^{10}$ is piperazinyl ring with —C(O)—O—$R^a$, and $R^a$ is as previously described.

In another embodiment of Formula I, wherein X, Y, $R^1$, A, $R^{10}$, $R^a$ and the other moieties are independently selected, the moiety:

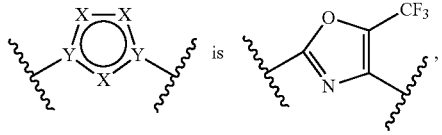 is the moiety:

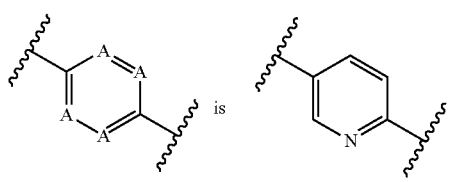 is $R^1$ is thiamorpholinyl (unsubstituted, substituted and/or fused as described earlier), $R^{10}$ is piperazinyl with —C(O)—O—$R^a$, and $R^a$ is as previously described.

In another embodiment of Formula I, wherein X, Y, $R^1$, A, $R^{10}$, $R^a$ and the other moieties are independently selected, the moiety:

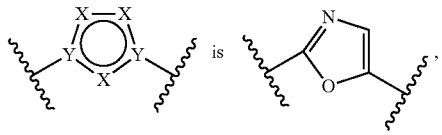 is one A is N and the other A's are C, $R^1$ is azepanyl (unsubstituted, substituted and/or fused as described earlier), $R^{10}$ is piperazinyl ring and $R^a$ is as previously described.

In another embodiment of Formula I, wherein X, Y, $R^1$, A, $R^{10}$, $R^a$ and the other moieties are independently selected, the moiety:

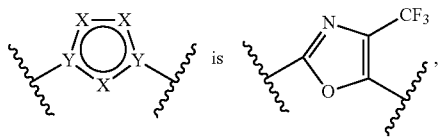

one A is N and the other A's are C, R¹ is oxazepanyl (unsubstituted, substituted and/or fused as described earlier), R¹⁰ is piperazinyl ring and Rᵃ is as previously described.

In another embodiment of Formula I, wherein X, Y, R¹, A, R¹⁰, Rᵃ and the other moieties are independently selected, one X is N, a second X is C, and the third X is O, both Y are C, one A is N and the other A moieties are C, R¹ is pyrrolidinyl (unsubstituted, substituted and/or fused as described earlier), R¹⁰ is piperidinyl ring and Rᵃ is as previously described.

In another embodiment of Formula I, wherein X, Y, R¹, A, R¹⁰, Rᵃ and the other moieties are independently selected, one X is N, a second X is C(R³), and the third X is O, both Y are C, one A is N and the other A's are C, R¹ is piperidinyl (unsubstituted, substituted and/or fused as described earlier), R³ is alkyl, R¹⁰ is piperidinyl ring and Rᵃ is as previously described.

In another embodiment of Formula I, wherein X, Y, R¹, A, R¹⁰, Rᵃ and the other moieties are independently selected, one X is N, a second X is C, and the third X is O, both Y are C, one A is N and the other A's are C, R¹ is piperazinyl (unsubstituted, substituted and/or fused as described earlier), R¹⁰ is piperidinyl ring and Rᵃ is as previously described.

In another embodiment of Formula I, wherein X, Y, R¹, A, R¹⁰, Rᵃ and the other moieties are independently selected, one X is N, a second X is C(R³), and the third X is O, both Y are C, one A is N and the other A's are C, R¹ is morpholinyl (unsubstituted, substituted and/or fused as described earlier), R³ is alkyl, R¹⁰ is piperidinyl ring and Rᵃ is as previously described.

In another embodiment of Formula I, wherein X, Y, R¹, A, R¹⁰, Rᵃ and the other moieties are independently selected, one X is N, a second X is C, and the third X is O, both Y are C, one A is N and the other A's are C, R¹ is thiamorpholinyl (unsubstituted, substituted and/or fused as described earlier), R¹⁰ is piperazinyl ring and Rᵃ is as previously described.

In another embodiment of Formula I, wherein X, Y, R¹, A, R¹⁰, Rᵃ and the other moieties are independently selected, one X is N, a second X is C(R³), and the third X is O, both Y are C, one A is N and the other A's are C, R¹ is azetidinyl (unsubstituted, substituted and/or fused as described earlier), R³ is alkyl, R¹⁰ is piperazinyl ring and Rᵃ is as previously described.

In another embodiment of Formula I, wherein X, Y, R¹, A, R¹⁰, Rᵃ and the other moieties are independently selected, one X is N, a second X is C, and the third X is O, both Y are C, one A is N and the other A's are C, R¹ is azepanyl (unsubstituted, substituted and/or fused as described earlier), R¹⁰ is piperazinyl ring and Rᵃ is as previously described.

In another embodiment of Formula I, wherein X, Y, R¹, A, R¹⁰, Rᵃ and the other moieties are independently selected, one X is N, a second X is C(R³), and the third X is O, both Y are C, one A is N and the other A's are C, R¹ is oxazepanyl (unsubstituted, substituted and/or fused as described earlier), R³ is alkyl, R¹⁰ is piperazinyl ring and Rᵃ is as previously described.

Non-limiting examples of the compounds of Formula I are shown below:

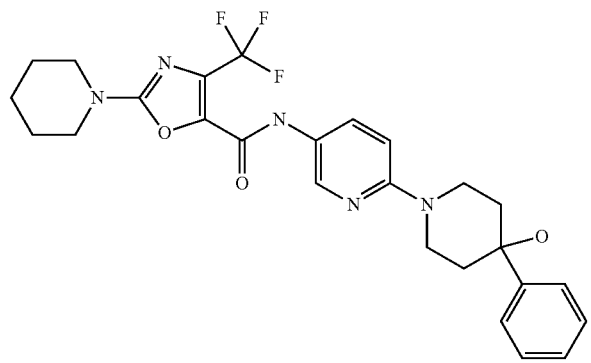

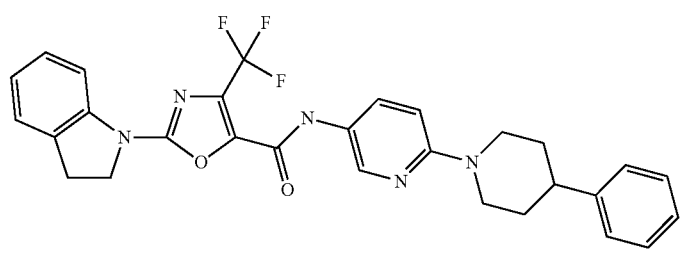

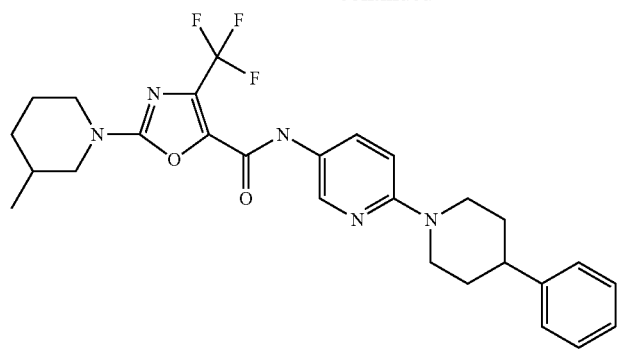
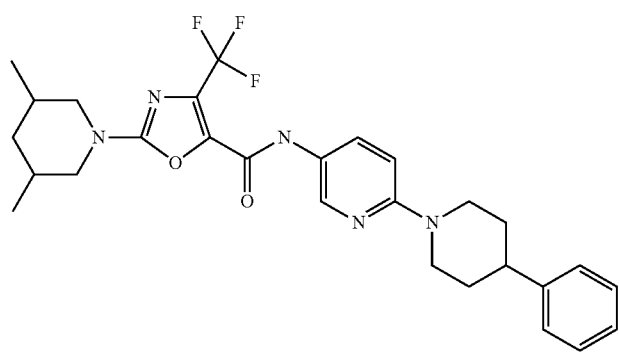
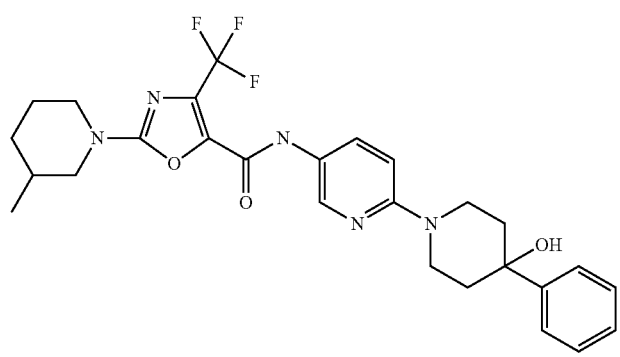
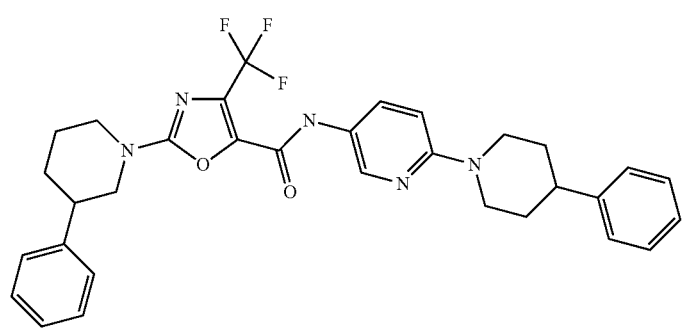
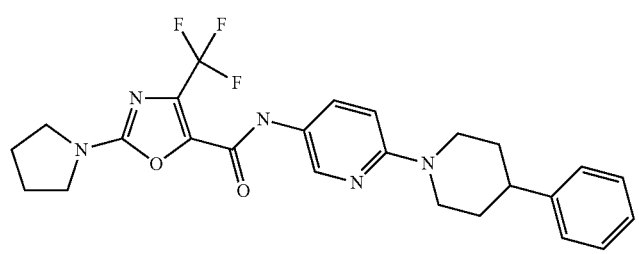

-continued
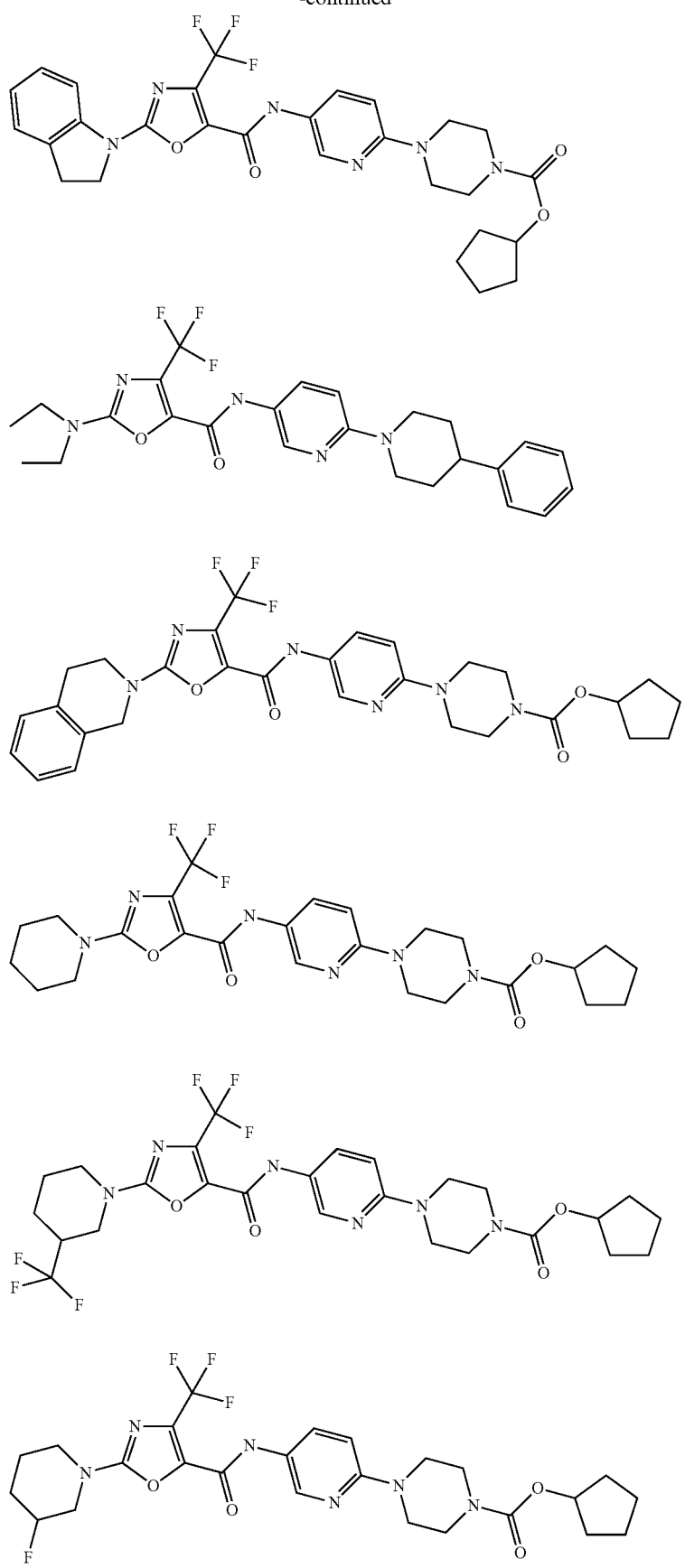

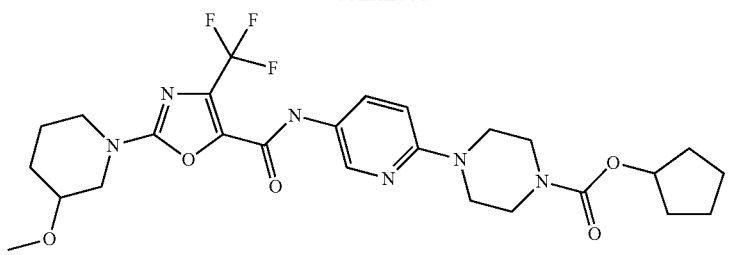
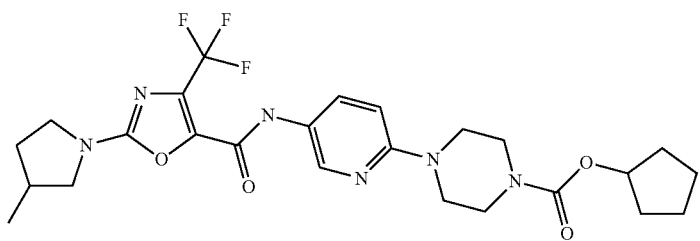
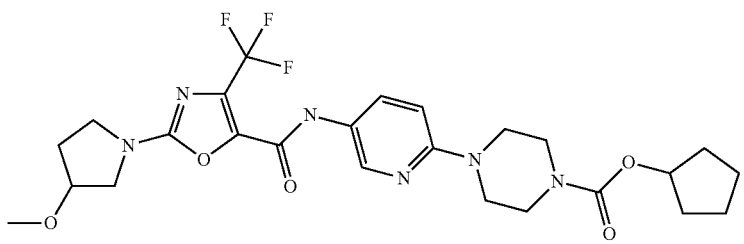
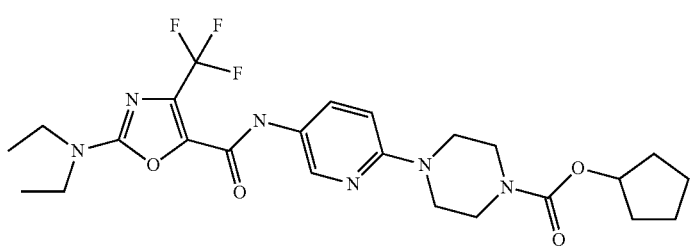
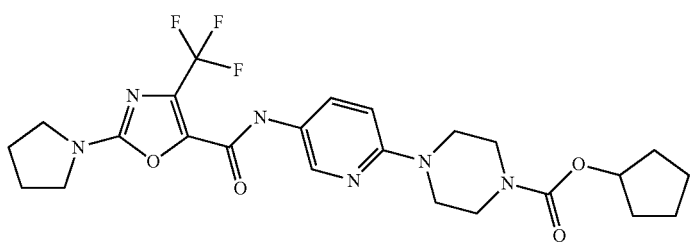
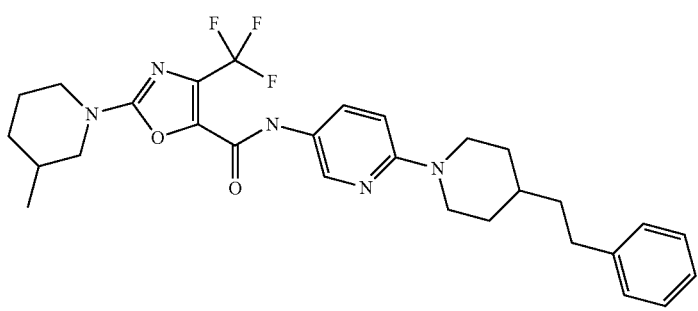

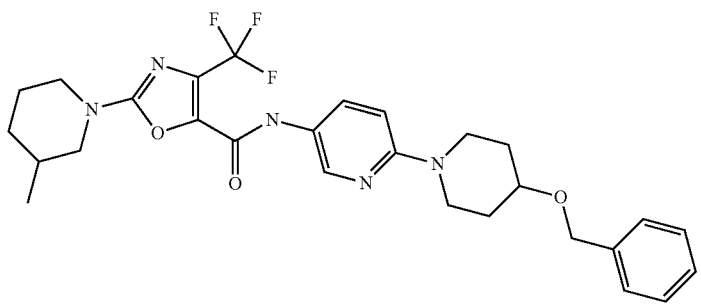
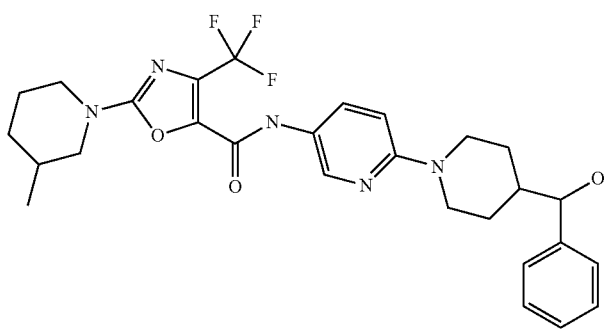
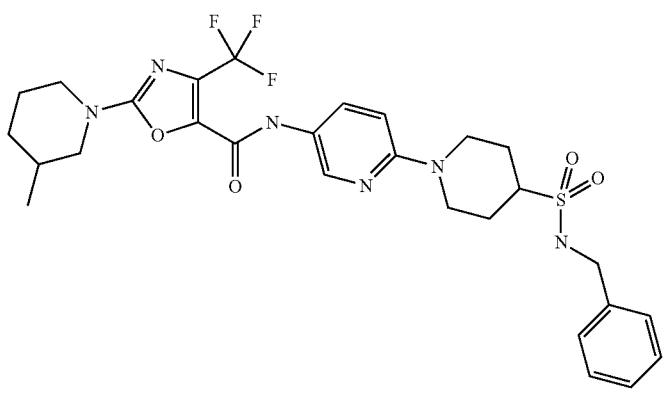
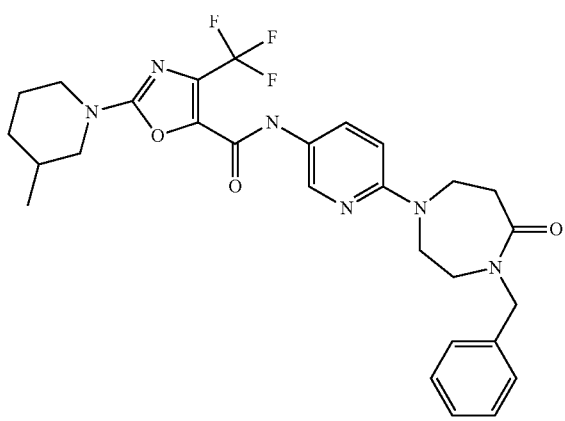

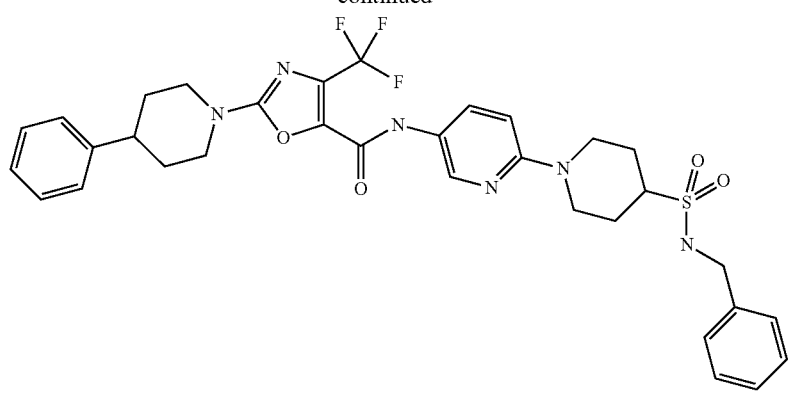
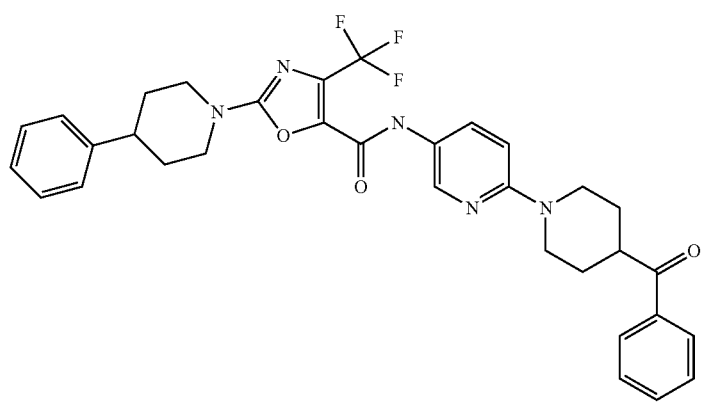
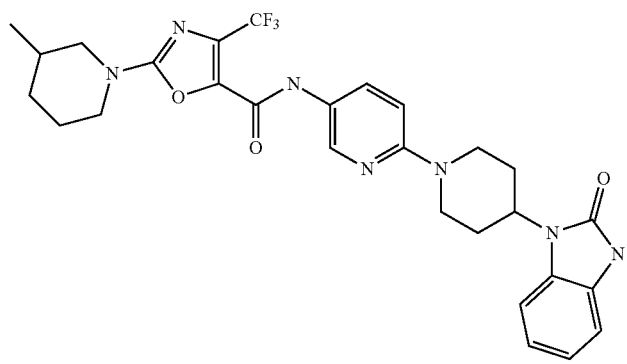
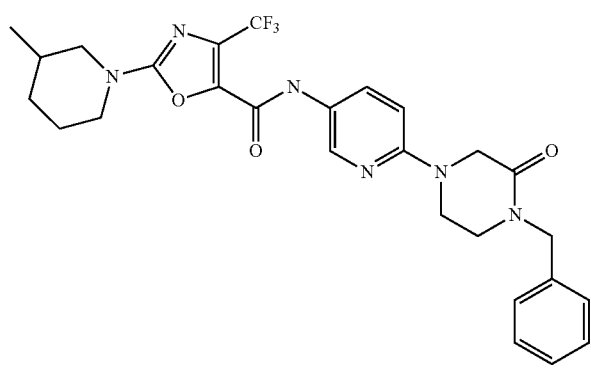

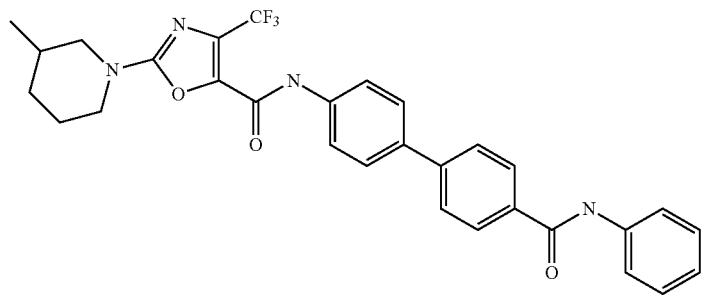
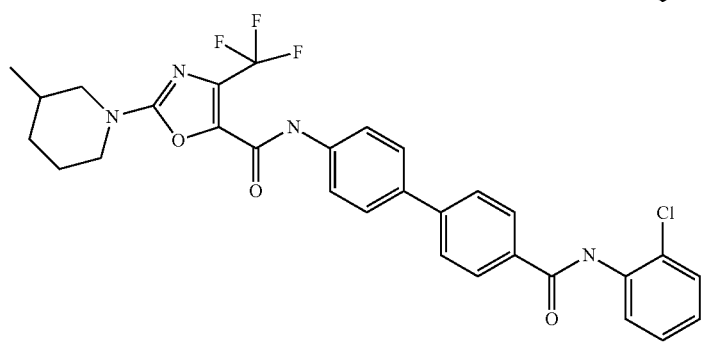
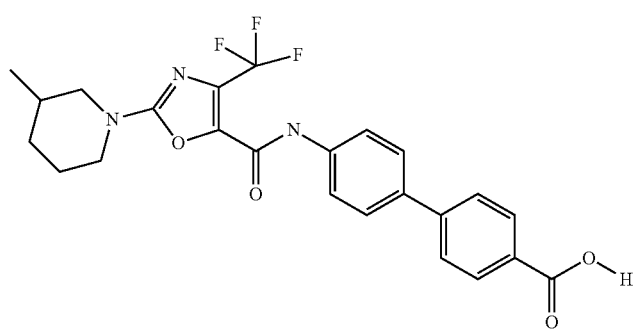
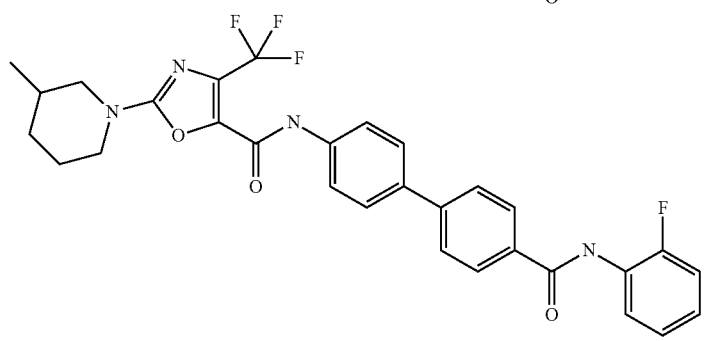
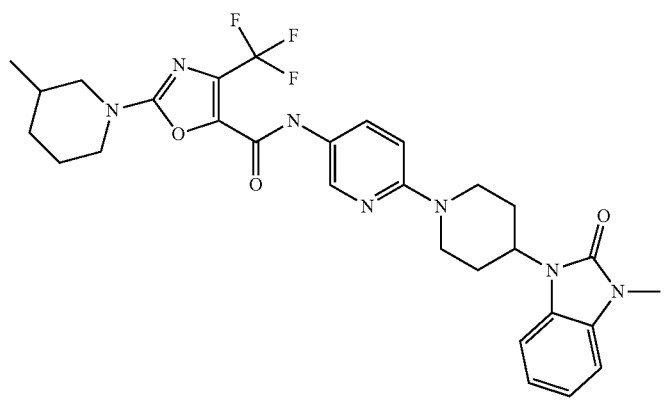

-continued
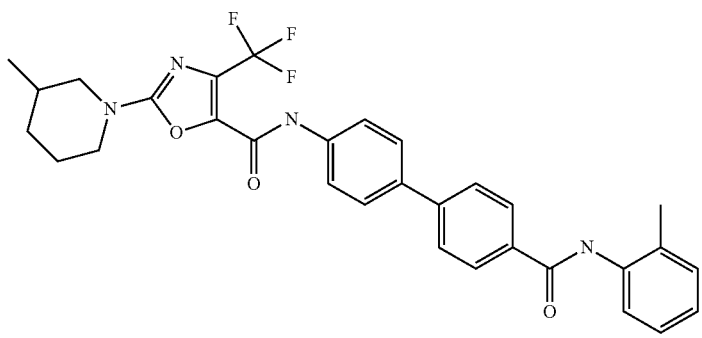
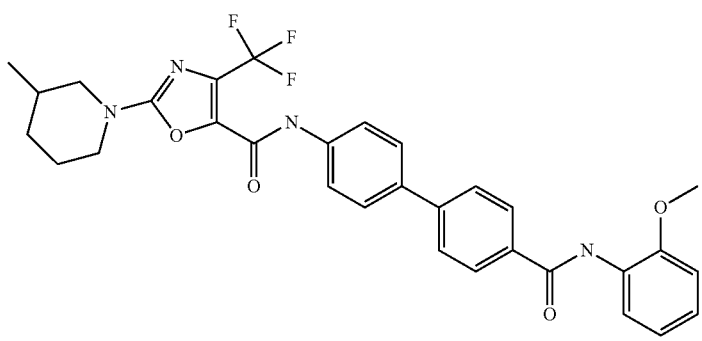
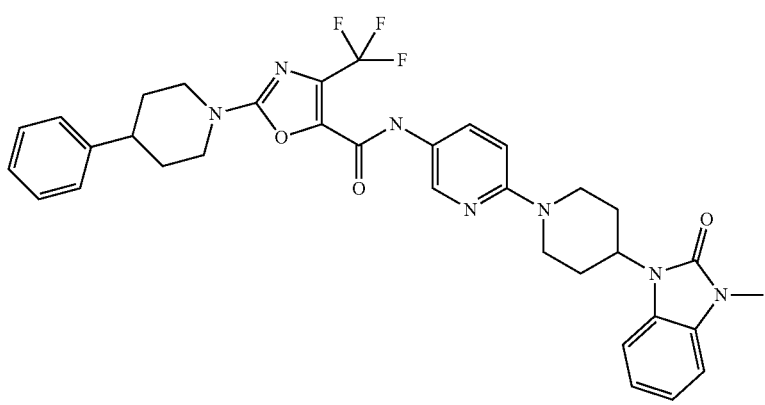
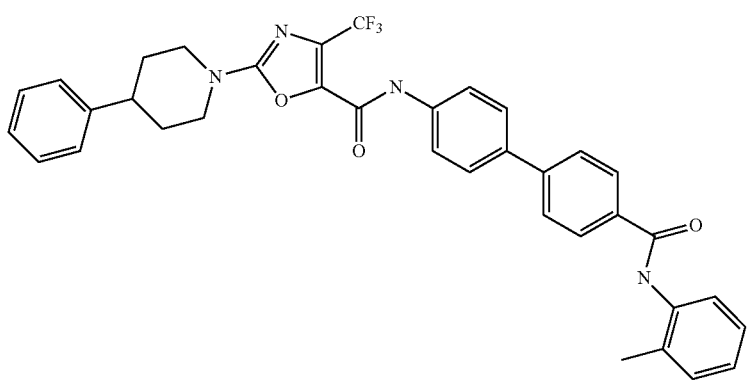

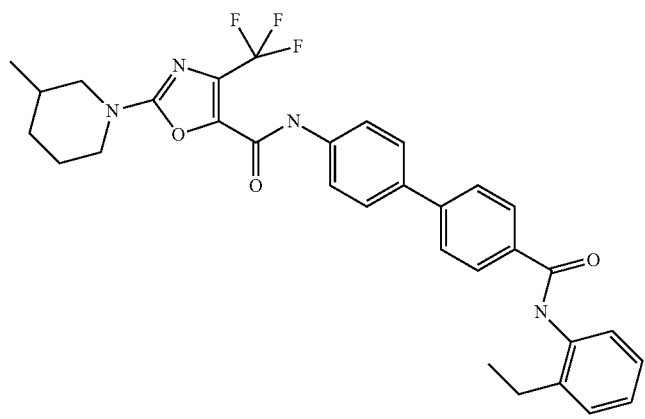
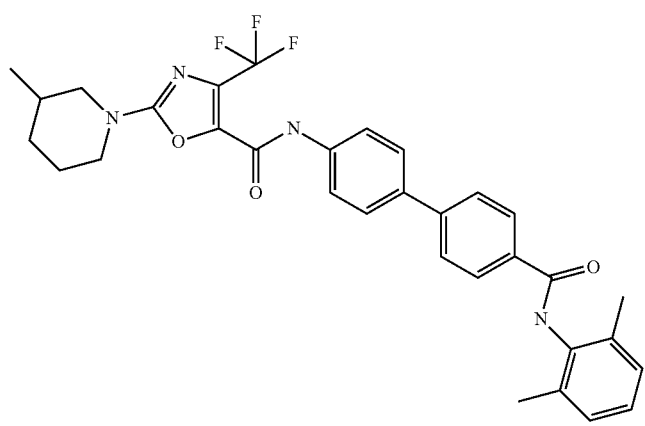
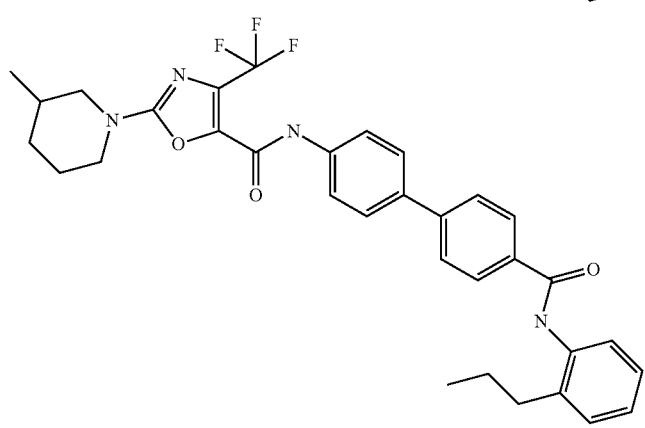
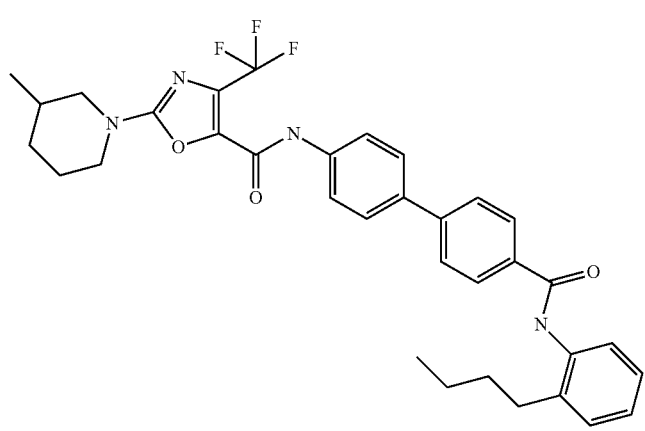

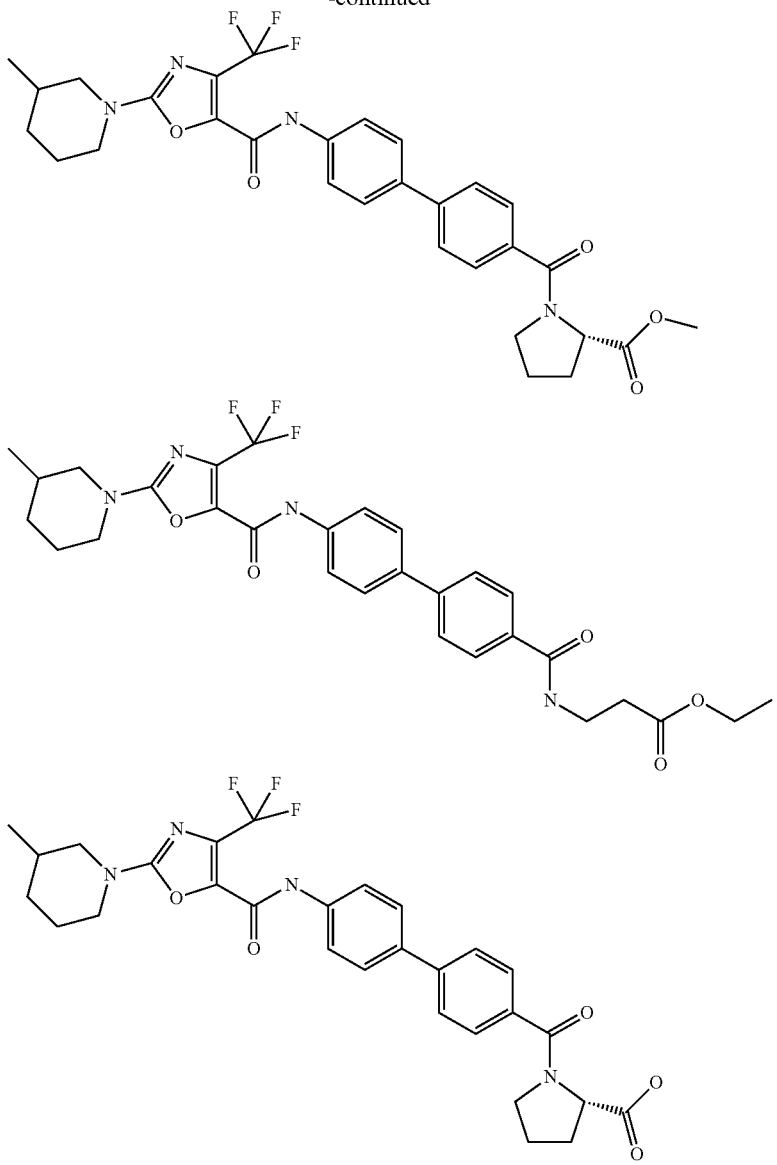

Several of the above-noted compounds exhibited $IC_{50}$ values less than 500 nM in the assay described on page 193. Many compounds exhibited IC50 values less than 100 nM.

As used above, and throughout this disclosure, the following terms, unless otherwise indicated, shall be understood to have the following meanings:

"Patient" includes both humans and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. Lower alkyl means a group having about 1 to about 6 carbon atoms in the chain which may be straight or branched. Alkyl may be unsubstituted or optionally substituted by one or more substituents which may be the same or different, each substituent being independently selected from the group consisting of halo, alkyl, aryl, cycloalkyl, cyano, pyridine, alkoxy, alkylthio, amino, oxime (e.g., =N—OH), —NH (alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. Lower alkenyl means about 2 to about 6 carbon atoms in the chain which may be straight or branched. Alkenyl may be unsubstituted or optionally substituted by one or more substituents which may be the same or different, each substituent being independently selected from the group consisting of halo, alkyl. aryl, cycloalkyl, cyano, alkoxy and —S(alkyl).

Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. Lower alkynyl means about 2 to about 6 carbon atoms in the chain which may be straight or branched. Non-limiting examples of suitable alkynyl groups include ethynyl, propynyl, 2-butynyl and 3-methylbutynyl. Alkynyl may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridine (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), oxime (e.g., =N—OH), $Y_1Y_2N$—, $Y_1Y_2$N-alkyl-, $Y_1Y_2$NC(O)—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —$C(CH_3)_2$— and the like which form moieties such as, for example:

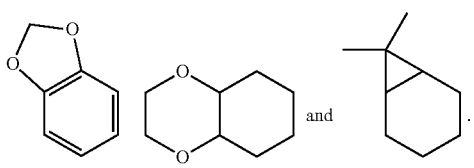

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic (e.g. bicyclic) ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein.

The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, diazepinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

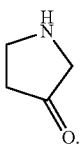

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

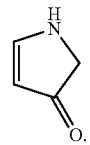

"Heterocyclenylalkyl" means a heterocyclenyl moiety as defined above linked via an alkyl moiety (defined above) to a parent core.

It should be noted that in heteroatom containing ring systems of this invention, there are no hydroxyl groups on carbon atoms adjacent to a N, O or S, as well as there are no N or S groups on carbon adjacent to another heteroatom. Thus, for example, in the ring:

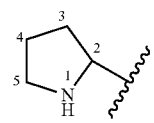

there is no —OH attached directly to carbons marked 2 and 5.

It should also be noted that tautomeric forms such as, for example, the moieties:

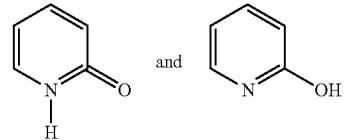

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl-" means an alkyl-O-alkyl-group in which the alkyl group is as previously described. Non-limiting examples of suitable alkoxyalkyl groups include methoxymethyl, ethoxymethyl, n-propoxyethyl, isopropoxyethyl and n-butoxymethyl. The bond to the parent moiety is through the alkyl-.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxyalkyl-" means an aryl-O-alkyl-group in which the aryl and aryl groups are as previously described. Non-limiting examples of suitable aryloxyalkyl groups include phenoxymethyl and naphthoxyethyl. The bond to the parent moiety is through the alkyl.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Alkylthioalkyl-" means an alkyl-S-alkyl-group in which the alkyl group is as previously described. Non-limiting examples of suitable alkylthioalkyl groups include methylthioethyl and ethylthiomethyl. The bond to the parent moiety is through the alkyl.

"Arylthio" means an aryl-S— group in which the aryl group is as previously described. Non-limiting examples of suitable arylthio groups include phenylthio and naphthylthio. The bond to the parent moiety is through the sulfur.

"Arylthioalkyl-" means an aryl-S-alkyl-group in which the aryl group is as previously described. Non-limiting examples of suitable arylthioalkyl groups include phenylthioethyl and phenylthiomethyl. The bond to the parent moiety is through the alkyl.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The present invention further includes the inventive compounds in their isolated form(s).

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of Formula I contains an alcohol functional group, a prodrug can be formed by the replacement of the hydrogen atom of the alcohol group with a group such as, for example, $(C_1-C_6)$alkanoyloxymethyl, 1-(($C_1-C_6)$alkanoyloxy)ethyl, 1-methyl-1-(($C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, (2004) 93(3), pp. 601-611 describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, (2004) an, article 12; and A. L. Bingham et al, *Chem. Commun.*, (2001) pp. 603-604. A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective" or "therapeutically effective" is used herein, unless otherwise indicated, to describe an amount of a compound or composition which, in context, is used to produce or effect an intended result or therapeutic effect as understood in the common knowledge of those skilled in the art.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt (s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) pp. 1-19; P. Gould, *International J. of Pharmaceutics* (1986) (2001) 33 pp. 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.)

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention have pharmacological properties. The compounds of Formula I are inhibitors of DGAT, particularly DGAT1, and can be useful for the therapeutic and/or prophylactic treatment of diseases that are modulated by DGAT, particularly by DGAT1, such as, for example, metabolic syndrome, diabetes (e.g., Type 2 diabetes mellitus), obesity and the like.

The invention also includes methods of treating diseases that are modulated by DGAT, particularly by DGAT1.

The invention also includes methods of treating metabolic syndrome, diabetes (e.g., Type 2 diabetes mellitus), and obesity in a patient by administering at least one compound of Formula I to said patient.

Diabetes refers to a disease process derived from multiple causative factors and is characterized by elevated levels of plasma glucose, or hyperglycemia in the fasting state or after administration of glucose during an oral glucose tolerance test. Persistent or uncontrolled hyperglycemia is associated with increased and premature morbidity and mortality. Abnormal glucose homeostasis is associated with alterations of the lipid, lipoprotein and apolipoprotein metabolism and other metabolic and hemodynamic disease. As such, the diabetic patient is at especially increased risk of macrovascular and microvascular complications, including coronary heart disease, stroke, peripheral vascular disease, hypertension, nephropathy, neuropathy, and retinopathy. Accordingly, therapeutic control of glucose homeostasis, lipid metabolism and hypertension are critically important in the clinical management and treatment of diabetes mellitus.

There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissue (muscle, liver and adipose tissue), and the plasma insulin levels, while elevated, are insufficient to overcome the pronounced insulin resistance.

Insulin resistance is not associated with a diminished number of insulin receptors but rather to a post-insulin receptor binding defect that is not well understood. This resistance to insulin responsiveness results in insufficient insulin activation of glucose uptake, oxidation and storage in muscle, and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic [beta]-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a class of agents that can increase insulin sensitivity and bring about some degree of correction of hyperglycemia. However, the biguanides can induce lactic acidosis and nausea/diarrhea.

The glitazones (i.e. 5-benzylthiazolidine-2,4-diones) are a separate class of compounds with potential for the treatment of Type 2 diabetes. These agents increase insulin sensitivity in muscle, liver and adipose tissue in several animal models of Type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones). Serious side effects (e.g. liver toxicity) have been noted in some patients treated with glitazone drugs, such as troglitazone.

Additional methods of treating the disease are currently under investigation. New biochemical approaches include treatment with alpha-glucosidase inhibitors (e.g. acarbose) and protein tyrosine phosphatase-1B (PTP-1B) inhibitors.

Compounds that are inhibitors of the dipeptidyl peptidase-IV (DPP-IV) enzyme are also under investigation as drugs that may be useful in the treatment of diabetes, and particularly Type 2 diabetes.

The invention includes compositions, e.g., pharmaceutical compositions, comprising at least one compound of Formula I. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Other carriers include Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, or gamma-cyclodextrin or analogs thereof. Examples of pharmaceutically acceptable carriers and methods of manufacture for various compositions may be found in A. Gennaro (ed.), *Remington's Pharmaceutical Sciences,* 18$^{th}$ Edition, (1990), Mack Publishing Co., Easton, Pa.

The therapeutic agents of the present invention are preferably formulated in pharmaceutical compositions and then, in accordance with the methods of the invention, administered to a subject, such as a human subject, in a variety of forms adapted to the chosen route of administration. For example, the therapeutic agents may be formulated for intravenous administration. The formulations may, however, include those suitable for oral, rectal, vaginal, topical, nasal, ophthalmic, or other parenteral administration (including subcutaneous, intramuscular, intrathecal, intraperitoneal and intratumoral, in addition to intravenous) administration.

Formulations suitable for parenteral administration conveniently include a sterile aqueous preparation of the active agent, or dispersions of sterile powders of the active agent, which are preferably isotonic with the blood of the recipient. Parenteral administration of the therapeutic agents (e.g., through an I.V. drip) is an additional form of administration. Isotonic agents that can be included in the liquid preparation include sugars, buffers, and sodium chloride. Solutions of the active agents can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization.

Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the first and/or second therapeutic agents, or as a solution or suspension in an aqueous liquor or non-aqueous liquid such as a syrup, an elixir, an emulsion, or a draught. Such compositions and preparations may contain at least about 0.1 wt-% of the active agent. The amounts of the therapeutic agents should be such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preferably the compound is administered orally, intraperitoneally, or intravenously or intrathecally or some suitable combination(s) thereof.

Methods of administering small molecule therapeutic agents are well-known in the art.

The therapeutic agents described in the present disclosure can be administered to a subject alone or together (coadministered, optionally but not necessarily, in a single formulation) with other active agents as described herein, and are preferably administered with a pharmaceutically acceptable buffer.

The therapeutic agents can be combined with a variety of physiological acceptable carriers, additives for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the therapeutic agent (i.e., the active agent) into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering the therapeutic agents to a subject in an amount effective to produce the desired effect. The therapeutic agents can be administered as a single dose or in multiple doses. Useful dosages of the active agents can be determined by comparing their in vitro activity and the in vivo activity in animal models.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt, solvate, ester or prodrug of said compound and a pharmaceutically acceptable carrier, vehicle or diluent.

Another aspect of the invention includes pharmaceutical compositions comprising at least one compound of Formula I and at least one other therapeutic agent in combination. Non-limiting examples of such combination agents are described below. The agents in the combination can be administered together as a joint administration (e.g., joint single pill), separately, one after the other in any order and the like as is well known in the art.

In the combination therapies of the present invention, an effective amount can refer to each individual agent or to the combination as a whole, wherein the amounts of all agents administered are together effective, but wherein the component agent of the combination may not be present individually in an effective amount.

Combination Therapy

Accordingly, in one embodiment, the present invention provides methods for treating a Condition in a patient, the method comprising administering to the patient one or more Compounds of Formula I, or a pharmaceutically acceptable salt or solvate thereof and at least one additional therapeutic agent that is not a Compound of Formula I, wherein the amounts administered are together effective to treat or prevent a Condition.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Compounds of Formula (I) is administered during a time when the additional therapeutic agent(s) exert their prophylactic or therapeutic effect, or vice versa.

In another embodiment, the one or more Compounds of Formula (I) and the additional therapeutic agent(s) are administered in doses commonly employed when such agents are used as monotherapy for treating a Condition.

In one embodiment, the one or more Compounds of Formula (I) and the additional therapeutic agent(s) are administered in doses lower than the doses commonly employed when such agents are used as monotherapy for treating a Condition.

In still another embodiment, the one or more Compounds of Formula (I) and the additional therapeutic agent(s) act synergistically and are administered in doses lower than the doses commonly employed when such agents are used as monotherapy for treating a Condition.

In one embodiment, the one or more Compounds of Formula (I) and the additional therapeutic agent(s) are present in the same composition. In one embodiment, this composition is suitable for oral administration. In another embodiment, this composition is suitable for intravenous administration.

The one or more Compounds of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Compounds of Formula (I) and the additional therapeutic agent(s) may inhibit the resistance of a Condition to these agents.

In one embodiment, when the patient is treated for diabetes, a diabetic complication, impaired glucose tolerance or impaired fasting glucose, the other therapeutic is an antidiabetic agent which is not a Compound of Formula (I).

In another embodiment, the other therapeutic agent is an agent useful for reducing any potential side effect of a Compound of Formula (I). Such potential side effects include, but are not limited to, nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

Examples of antidiabetic agents useful in the present methods for treating diabetes or a diabetic complication include a sulfonylurea; an insulin sensitizer (such as a PPAR agonist, a DPP-IV inhibitor, a PTP-1B inhibitor and a glucokinase activator); a glucosidase inhibitor; an insulin secretagogue; a hepatic glucose output lowering agent; an anti-obesity agent; a meglitinide; an agent that slows or blocks the breakdown of starches and sugars in vivo; an histamine $H_3$ receptor antagonist; a sodium glucose uptake transporter 2 (SGLT-2) inhibitor; a peptide that increases insulin production; and insulin or any insulin-containing composition.

In one embodiment, the antidiabetic agent is an insulin sensitizer or a sulfonylurea.

Non-limiting examples of sulfonylureas include glipizide, tolbutamide, glyburide, glimepiride, chlorpropamide, acetohexamide, gliamilide, gliclazide, glibenclamide and tolazamide.

Non-limiting examples of insulin sensitizers include PPAR activators, such as rosiglitazone, pioglitazone and englitazone; biguanidines such as metformin and phenformin; DPP-IV inhibitors; PTP-1B inhibitors; and α-glucokinase activators, such as miglitol, acarbose, and voglibose. Non-limiting examples of DPP-IV inhibitors useful in the present methods include sitagliptin (Januvia™, Merck), saxagliptin, denagliptin, vildagliptin (Galvus™, Novartis), alogliptin, alogliptin benzoate, ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer), RO-0730699 (Roche) or a combination of sitagliptin/metformin HCl (Janumet™, Merck).

Non-limiting examples of SGLT-2 inhibitors useful in the present methods include dapagliflozin and sergliflozin, AVE2268 (Sanofi-Aventis) and T-1095 (Tanabe Seiyaku).

Non-limiting examples of hepatic glucose output lowering agents include Glucophage and Glucophage XR.

Non-limiting examples of histamine $H_3$ receptor antagonist agents include the following compound:

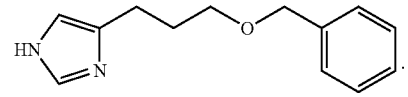

Non-limiting examples of insulin secretagogues include sulfonylurea and non-sulfonylurea drugs such as GLP-1, a GLP-1 mimetic, exendin, GIP, secretin, glipizide, chlorpropamide, nateglinide, meglitinide, glibenclamide, repaglinide and glimepiride.

Non-limiting examples of GLP-1 mimetics useful in the present methods include Byetta-Exenatide, Liraglutide, CJC-1131 (ConjuChem, Exenatide-LAR (Amylin), BIM-51077 (Ipsen/LaRoche), ZP-10 (Zealand Pharmaceuticals), and compounds disclosed in International Publication No. WO 00/07617.

The term "insulin" as used herein, includes all pyridinones of insulin, including long acting and short acting forms of insulin.

Non-limiting examples of orally administrable insulin and insulin containing compositions include AL-401 from Autoimmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In one embodiment, the antidiabetic agent is an anti-obesity agent. Non-limiting examples of anti-obesity agents useful in the present methods for treating diabetes include a 5-HT2C agonist, such as lorcaserin; a neuropeptide Y antagonist; an MCR4 agonist; an MCH receptor antagonist; a protein hormone, such as leptin or adiponectin; an AMP kinase activator; and a lipase inhibitor, such as orlistat. Appetite suppressants are not considered to be within the scope of the anti-obesity agents useful in the present methods.

Non-limiting examples of meglitinides useful in the present methods for treating diabetes include repaglinide and nateglinide.

Non-limiting examples of insulin sensitizing agents include biguanides, such as metformin, metformin hydrochloride (such as GLUCOPHAGE® from Bristol-Myers Squibb), metformin hydrochloride with glyburide (such as GLUCOVANCE™ from Bristol-Myers Squibb) and buformin; glitazones; and thiazolidinediones, such as rosiglitazone, rosiglitazone maleate (AVANDIAT™ from GlaxoSmithKline), pioglitazone, pioglitazone hydrochloride (ACTOST™, from Takeda) ciglitazone and MCC-555 (Mitsubishi Chemical Co.)

In one embodiment, the insulin sensitizer is a thiazolidinedione.

In another embodiment, the insulin sensitizer is a biguanide.

In another embodiment, the insulin sensitizer is a DPP-IV inhibitor.

In a further embodiment, the antidiabetic agent is a SGLT-2 inhibitor.

Non-limiting examples of antidiabetic agents that slow or block the breakdown of starches and sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of orally administrable insulin and insulin containing compositions include AL-401 from Autoimmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Compound(s) of Formula (I) and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Compounds of Formula (I) and the additional therapeutic agent(s) can, when administered as combination therapy, range from about 0.1 to about 2000 mg per day, although variations will necessarily occur depending on the target of the therapy, the patient and the route of administration. In one embodiment, the dosage is from about 0.2 to about 1000 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

General Methods

The general methods described in this paragraph were used unless stated otherwise in the examples below. All solvents and reagents were used as received. Proton NMR spectra were obtained using a Varian XL-400 (400 MHz) or a Bruker (500 MHz) instrument and were reported as parts per million (ppm) downfield from $Me_4Si$. LCMS analysis was performed using a PE SCIEX API-150EX, single quadrupole mass spectrometer equipped with a Phenomenex column: Gemini C-18, 50×4.6 mm, 5 micron; mobile phase A: 0.05% trifluoroacetic acid in water, B: 0.05% trifluoroacetic acid in $CH_3CN$; gradient: 90% A and 10% B to 5% A and 95% B in 5 minutes. Flash column chromatography was performed using Teledyne Isco RediSep Normal Phase Columns. Preparative TLC was performed using Analtech Silica gel GF plates.

Intermediate A-4

2-(1-piperidinyl)-4-trifluoromethyloxazole-5-carboxylic acid (A-4)

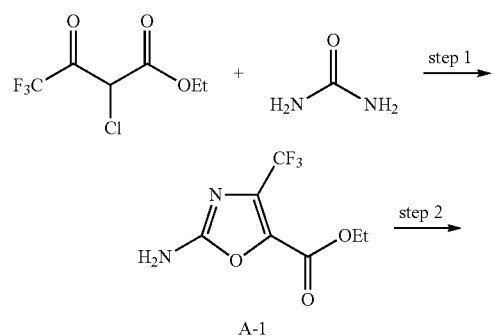

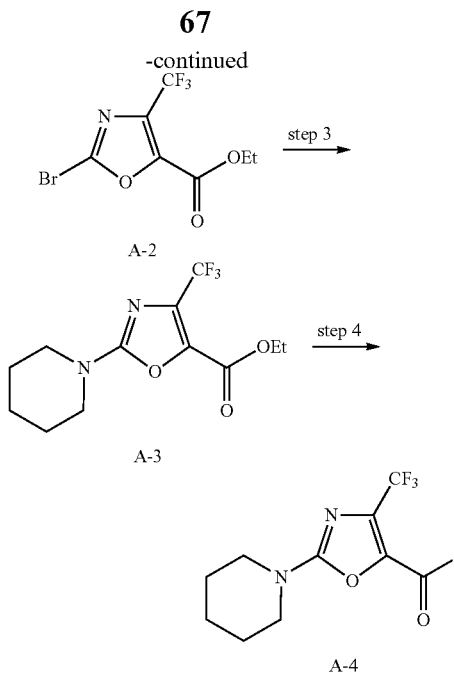

Step 1: ethyl 1-amino-4-trifluoromethyloxazole-5-carboxylate (A-1)

To a suspension of urea (13.5 g) in DMF (50 mL) was added ethyl 4,4,4-trifluoro-2-chloroacetoacetate (10 mL) and the resulting reaction mixture was heated at 120° C. for 3 days. Then, the reaction mixture was cooled to RT and diluted with $H_2O$ (100 mL). Then, the reaction mixture was stirred at 0° C. for 1 h. The resulting precipitate was filtered, washed with $H_2O$ and dried in vacuo to yield ethyl 2-amino-4-trifluoromethyloxazole-5-carboxylate (A-1) as a white powder (9.8 g, 74% yield). LCMS (ESI) calcd for $[M+1]^+$ 225.1. found 225.1.

Step 2: ethyl 2-bromo-4-trifluoromethyloxazole-5-carboxylate (A-2)

To a suspension of ethyl 2-amino-4-trifluoromethyloxazole-5-carboxylate (A-1) (9.8 g) in acetonitrile (100 mL) at 0° C. was first added copper (II) bromide (11.8 g) then tert-butylnitrite (13.8 mL) slowly. The reaction mixture was warmed slowly from 0° C. to RT under a nitrogen atmosphere. After 4 h of stirring at RT, the reaction mixture was concentrated. The residue was suspended in EtOAc (200 mL), washed with 1 N HCl (3×100 mL), brine (1×100 mL), dried over $Na_2SO_4$, filtered, and concentrated. The crude product was purified by flash column chromatography on silica gel (eluant: EtOAc and hexanes) to yield ethyl 2-bromo-4-trifluoromethyloxazole-5-carboxylate (A-2) as a colorless liquid (9.18 g, 73% yield). LCMS (ESI) calcd for $[M+1]^+$ 288.0. found 288.2.

Step 3: ethyl 2-(1-piperidinyl)-4-trifluoromethyloxazole-5-carboxylate (A-3)

To a solution of ethyl 2-bromo-4-trifluoromethyloxazole-5-carboxylate (A-2) (0.85 mL) in α,α,α-trifluorotoluene (10 mL) at RT was added piperidine (1.1 mL). The reaction mixture was heated at 120° C. for 20 min by microwave then cooled to RT and diluted with EtOAc (100 mL). The organic solution was washed with $H_2O$ (2×100 mL), saturated $NH_4Cl$ (1×100 mL), brine (1×100 mL), dried over $Na_2SO_4$, filtered, and concentrated to give ethyl 2-(1-piperidinyl)-4-trifluoromethyloxazole-5-carboxylate (A-3) as a yellow solid (1.28 g, 88% yield). LCMS (ESI) calcd for $[M+1]^+$ 293.1. found 293.2.

Step 4: 2-(1-piperidinyl)-4-trifluoromethyloxazole-5-carboxylic acid (A-4)

To a solution of ethyl 2-(1-piperidinyl)-4-trifluoromethyloxazole-5-carboxylate (A-3) (1.28 g) in THF (20 mL) at RT was added 1 N NaOH (20 mL). The reaction mixture was stirred at RT for 3 h then diluted with $H_2O$ (100 mL) and 1 N NaOH (10 mL). The aqueous solution was washed with $Et_2O$ (2×100 mL) and then acidified to pH=1 by addition of 1 N HCl, and extracted with EtOAc (3×50 mL). The combined organic extract was dried over $Na_2SO_4$, filtered, and concentrated to yield 2-(1-piperidinyl)-4-trifluoromethyloxazole-5-carboxylic acid (A-4) as a white solid (1.16 g, 100% yield). LCMS (ESI) calcd for $[M+1]^+$ 265.1. found 265.1.

Intermediate A-5

2-(pyrrolidin-1-yl)-4-trifluoromethyloxazole-5-carboxylic acid (A-5)

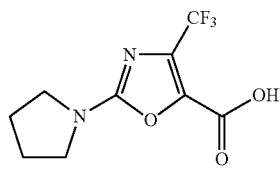

Intermediate A-5 was prepared by the general procedure for intermediate A-4, by using A-2 and pyrrolidine as starting materials. LCMS (ESI) calcd for $[M+1]^+$ 251.1. found 251.1.

Intermediate A-6

2-(4,4-difluoropiperidin-1-yl)-4-trifluoromethyloxazole-5-carboxylic acid (A-6)

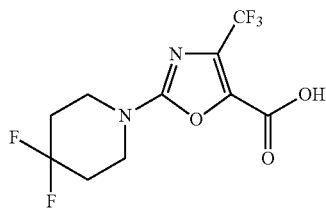

Intermediate A-6 was prepared by the general procedure for intermediate A-4, by using A-2 and 4,4-difluoropiperidine as starting materials. LCMS (ESI) calcd for [M+1]$^+$ 301.1. found 301.2.

Intermediate A-7

2-(2-methylpiperidin-1-yl)-4-trifluoromethyloxazole-5-carboxylic acid (A-7)

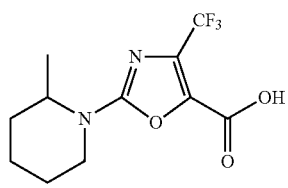

A-7

Intermediate A-7 was prepared by the general procedure for intermediate A-4, by using A-2 and 2-methylpiperidine as starting materials. LCMS (ESI) calcd for [M+1]$^+$ 279.1. found 279.2.

Intermediate A-8

2-morpholino-4-(trifluoromethyl)oxazole-5-carboxylic acid (A-8)

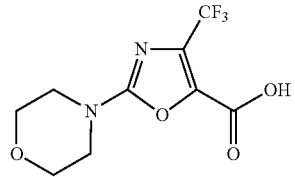

A-8

Intermediate A-8 was prepared by the general procedure for intermediate A-4, by using A-2 and morpholine as starting materials. LCMS (ESI) calcd for [M+1]$^+$ 267.1. found 267.1.

Intermediate A-9

2-(azetidin-1-yl)-4-(trifluoromethyl)oxazole-5-carboxylic acid (A-9)

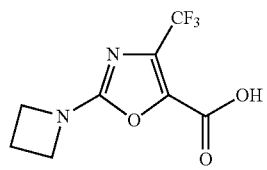

A-9

Intermediate A-9 was prepared by the general procedure for intermediate A-4, by using A-2 and azetidine as starting materials. LCMS (ESI) calcd for [M+1]$^+$ 237.1. found 237.1.

Intermediate A-10

2-(3-methylpiperidin-1-yl)-4-trifluoromethyloxazole-5-carboxylic acid (A-10)

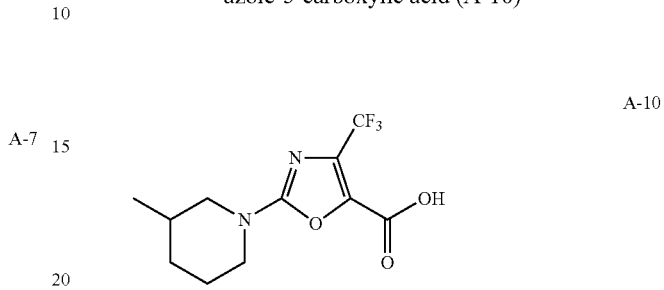

A-10

Intermediate A-10 was prepared by the general procedure for intermediate A-4, by using A-2 and 3-methylpiperidine as starting materials. LCMS (ESI) calcd for [M+1]$^+$ 279.1. found 279.2.

Intermediate A-11

2-(2-methylpiperidin-1-yl)-4-trifluoromethyloxazole-5-carboxylic acid (A-11)

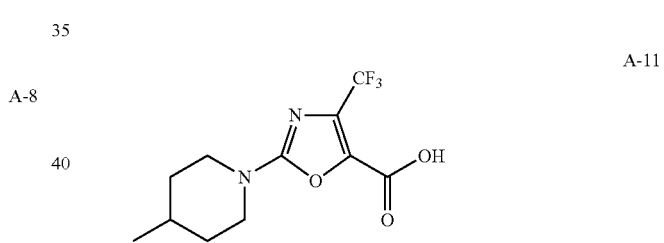

A-11

Intermediate A-11 was prepared by the general procedure for intermediate A-4, by using A-2 and 4-methylpiperidine as starting materials. LCMS (ESI) calcd for [M+1]$^+$ 279.1. found 279.2.

Intermediate A-12

2-(4-(tert-butoxycarbonyl)piperazin-1-yl)-4-(trifluoromethyl)oxazole-5-carboxylic acid (A-12)

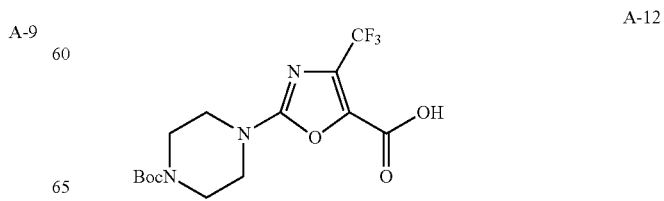

A-12

Intermediate A-12 was prepared by the general procedure for intermediate A-4, by using A-2 and 1-Boc-piperazine as starting materials. LCMS (ESI) calcd for [M+1]⁺ 366.1. found 366.2.

Intermediate A-13

2-(4-hydroxy-4-phenylpiperidin-1-yl)-4-(trifluoromethyl)oxazole-5-carboxylic acid (A-13)

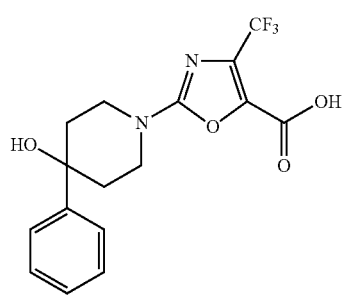

Intermediate A-13 was prepared by the general procedure for intermediate A-4, by using A-2 and 4-hydroxy-4-phenylpiperidine as starting materials. LCMS (ESI) calcd for [M+1]⁺ 357.1. found 357.2.

Intermediate A-14

2-(azepan-1-yl)-4-(trifluoromethyl)oxazole-5-carboxylic acid (A-14)

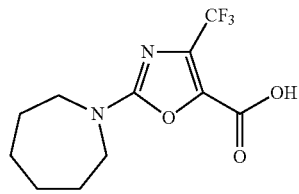

Intermediate A-14 was prepared by the general procedure for intermediate A-4, by using A-2 and hexamethyleneimine as starting materials. LCMS (ESI) calcd for [M+1]⁺ 279.1. found 279.2.

Intermediate A-15

2-(1,4-oxazepan-4-yl)-4-(trifluoromethyl)oxazole-5-carboxylic acid (A-15)

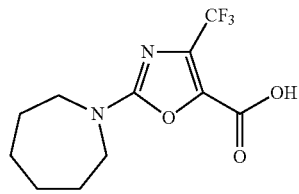

Intermediate A-15 was prepared by the general procedure for intermediate A-4, by using A-2 and homomorpholine hydrochloride as starting materials. LCMS (ESI) calcd for [M+1]⁺ 281.1. found 281.2.

Intermediate A-16

2-(diethylamino)-4-trifluoromethyloxazole-5-carboxylic acid (A-16)

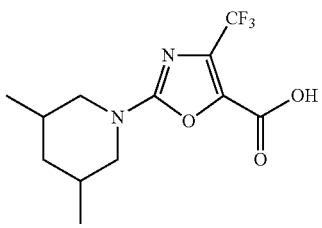

Intermediate A-16 was prepared by the general procedure for intermediate A-4, by using A-2 and N,N-diethylamine as starting materials. MS (M+1): 253.

Intermediate A-17

2-(3,5-dimethylpiperidin-1-yl)-4-trifluoromethyloxazole-5-carboxylic acid (A-17)

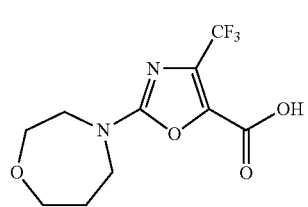

Intermediate A-17 was prepared by the general procedure for intermediate A-4, by using A-2 and 3,5-dimethylpiperidine as starting materials. MS (M+1): 293.

Intermediate A-18

2-(3,3-dimethylpiperidin-1-yl)-4-trifluoromethyloxazole-5-carboxylic acid (A-18)

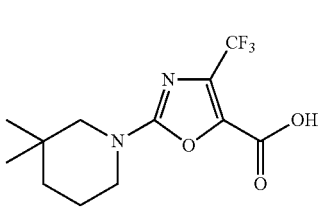

Intermediate A-18 was prepared by the general procedure for intermediate A-4, by using A-2 and 3,3-dimethylpiperidine as starting materials. MS (M+1): 293.

Intermediate A-19

2-(3,4-dihydroquinolin-1(2H)-yl)-4-trifluoromethyloxazole-5-carboxylic acid (A-19)

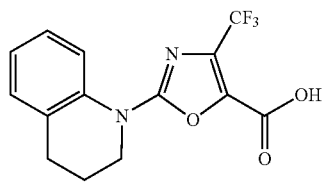

Intermediate A-19 was prepared by the general procedure for intermediate A-4, by using A-2 and 1,2,3,4-tetrahydroquinoline as starting materials. MS (M+1): 313.

Intermediate A-20

2-(indolin-1-yl)-4-trifluoromethyloxazole-5-carboxylic acid (A-20)

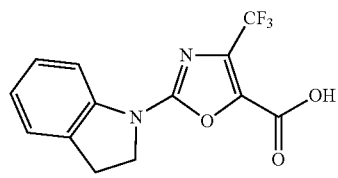

Intermediate A-20 was prepared by the general procedure for intermediate A-4, by using A-2 and indoline as starting materials. MS (M+1): 299.

Intermediate A-21

2-(3,4-dihydroisoquinolin-2(1H)-yl)-4-trifluoromethyloxazole-5-carboxylic acid (A-21)

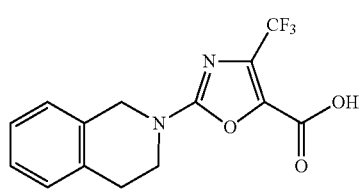

Intermediate A-21 was prepared by the general procedure for intermediate A-4, by using A-2 and 1,2,3,4-tetrahydroisoquinoline as starting materials. MS (M+1): 313.

Intermediate A-22

2-(4-phenylpiperidin-1-yl)-4-trifluoromethyloxazole-5-carboxylic acid (A-22)

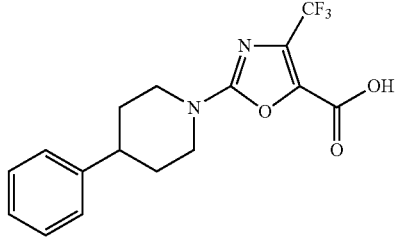

Intermediate A-22 was prepared by the general procedure for intermediate A-4, by using A-2 and 4-phenylpiperidine as starting materials. MS (M+1): 341.

Intermediate A-23

2-(3-phenylpiperidin-1-yl)-4-trifluoromethyloxazole-5-carboxylic acid (A-23)

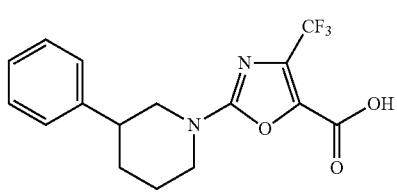

Intermediate A-23 was prepared by the general procedure for intermediate A-4, by using A-2 and 3-phenylpiperidine as starting materials. MS (M+1): 341.

Intermediate A-24

2-(3-(trifluoromethyl)piperidin-1-yl)-4-trifluoromethyloxazole-5-carboxylic acid (A-24)

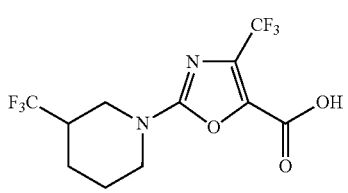

Intermediate A-24 was prepared by the general procedure for intermediate A-4, by using A-2 and 3-(trifluoromethyl)piperidine as starting materials. MS (M+1): 333.

Intermediate A-25

2-(3-fluoropiperidin-1-yl)-4-trifluoromethyloxazole-5-carboxylic acid (A-25)

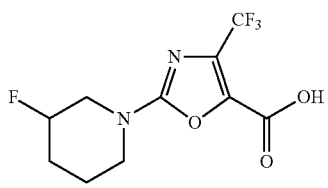

A-25

Intermediate A-25 was prepared by the general procedure for intermediate A-4, by using A-2 and 3-fluoropiperidine hydrochloride as starting materials with N,N-diisopropylethylamine. MS (M+1): 283.

Intermediate A-26

2-(3-hydroxypiperidin-1-yl)-4-trifluoromethyloxazole-5-carboxylic acid (A-26)

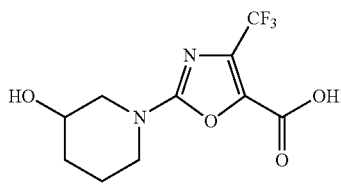

A-26

Intermediate A-26 was prepared by the general procedure for intermediate A-4, by using A-2 and 3-hydroxypiperidine as starting materials. MS (M+1): 281.

Intermediate A-27

2-(3-methoxypiperidin-1-yl)-4-trifluoromethyloxazole-5-carboxylic acid (A-27)

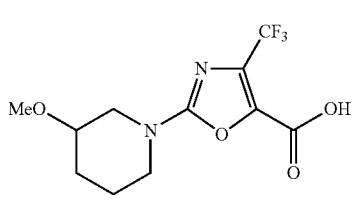

A-27

Intermediate A-27 was prepared by the general procedure for intermediate A-4, by using A-2 and 3-methoxypiperidine as starting materials. MS (M+1): 295.

Intermediate A-28

2-(3-methylpyrrolidin-1-yl)-4-trifluoromethyloxazole-5-carboxylic acid (A-28)

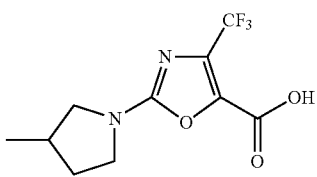

A-28

Intermediate A-28 was prepared by the general procedure for intermediate A-4, by using A-2 and 3-methylpyrrolidine hydrochloride as starting materials with N,N-diisopropylethylamine. MS (M+1): 265.

Intermediate A-29

2-(3-methoxypyrrolidin-1-yl)-4-trifluoromethyloxazole-5-carboxylic acid (A-29)

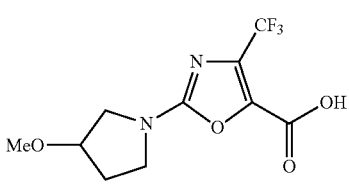

A-29

Intermediate A-29 was prepared by the general procedure for intermediate A-4, by using A-2 and 3-methoxypyrrolidine hydrochloride as starting materials with N,N-diisopropylethylamine. MS (M+1): 281.

Intermediate A-31

2-(2-oxopyrrolidin-1-yl)-4-(trifluoromethyl)oxazole-5-carboxylic acid (A-31)

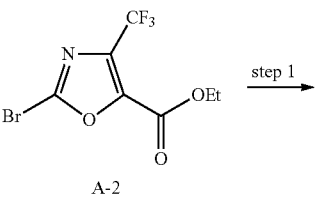

step 1 →

-continued

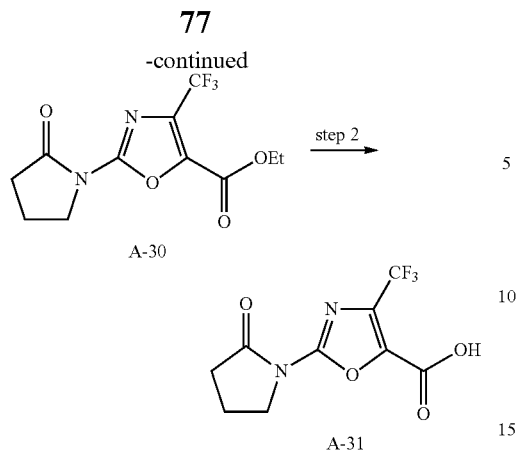

A-30

A-31

Step 1: ethyl 2-(2-oxopyrrolidin-1-yl)-4-(trifluoromethyl)oxazole-5-carboxylate (A-30)

NaH (0.060 mg, 1.5 mmol) (60%) was added to a solution of 2-oxopyrrolidine (0.13 g, 1.5 mmol) in DMF (5.0 mL) at −78° C. followed by stirring for 15 mins at −78° C. Then ethyl 2-bromo-4-trifluoromethyloxazole-5-carboxylate A-2 (0.29 g, 1.0 mmol) was added. The reaction mixture was stirred for 3 h while the temperature was slowly warmed to RT. The reaction mixture was purified by chromatography on a Prep Gilson HPLC to yield ethyl 2-(2-oxopyrrolidin-1-yl)-4-(trifluoromethyl)oxazole-5-carboxylate (A-30) as a white solid (0.15 g, 34% yield). $^1$H NMR (500 MHz, CDCl$_3$) δ 4.44 (m, 2H), 4.09 (t, 2H, J=7.0 Hz), 2.69 (t, 2H, J=8.2 Hz), 2.28 (m, 2H), 2.42 (t, 3H, J=7.3 Hz).

Step 2: 2-(2-oxopyrrolidin-1-yl)-4-(trifluoromethyl)oxazole-5-carboxylic acid (A-31)

LiOH.H$_2$O (0.096 g, 2.28 mmol) was added to a solution of ethyl 2-(2-oxopyrrolidin-1-yl)-4-(trifluoromethyl)oxazole-5-carboxylate (A-30) (0.140 g, 0.48 mmol) in THF/CH$_3$OH/H$_2$O (2/2/0.5 mL) at RT followed by stirring overnight. The reaction mixture was diluted with EtOAc/H$_2$O (25/25 mL) and neutralized with 2.5 mL of 1 M HCl. The organic phase was separated, dried over MgSO$_4$, filtered, and concentrated. The residue was dried in vacuo to yield 2-(2-oxopyrrolidin-1-yl)-4-(trifluoromethyl)oxazole-5-carboxylic acid (A-31) as a white solid (0.120 g, 95% yield). $^1$H NMR (500 MHz, CD$_3$OD) δ 5.18 (br s, 1H), 3.41 (t, 2H, J=6.8 Hz), 2.42 (t, 2H, J=7.2 Hz), 1.93 (m, 2H).

Intermediate A-33

2-(1-piperidinyl)-4-trifluoromethylthiazole-5-carboxylic acid (A-33)

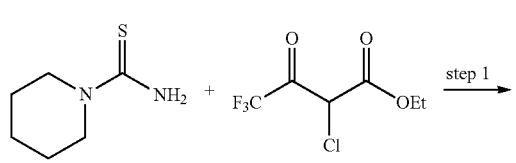

-continued

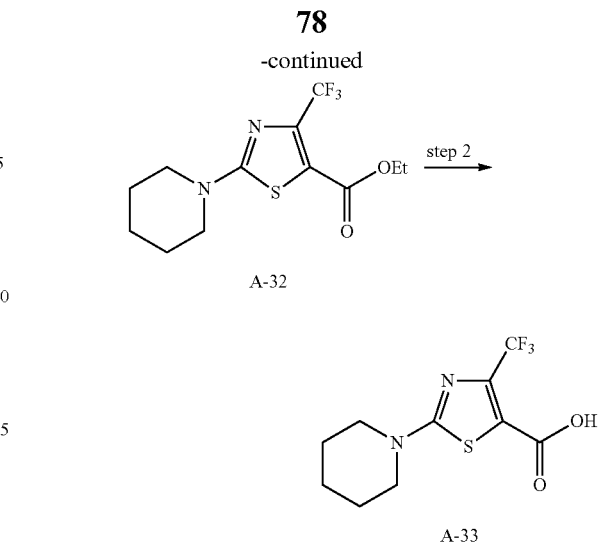

A-32

A-33

Step 1: ethyl 2-amino-4-trifluoromethylthiazole-5-carboxylate (A-32)

To a suspension of thiourea (3.3 g, 22.88 mmol) in EtOH (200 mL) was added ethyl 4,4,4-trifluoro-2-chloroacetoacetate (5 g, 22.88 mmol), and the resulting reaction mixture was heated at 80° C. for 24 h. Then, the reaction mixture was cooled to RT and concentrated in vacuo. The product was purified by column chromatography to give ethyl 2-amino-4-trifluoromethylthiazole-5-carboxylate (A-32) as a colorless oil (5.98 g, 85% yield). $^1$H NMR (500 MHz, CDCl$_3$) δ 4.32 (q, 2H, J=7.0 Hz), 3.56 (m, 4H), 1.70 (m, 6H), 1.36 (t, 3H, J=7.0 Hz); LCMS (ESI) [M+1]$^+$ 309.3.

Step 2: 2-(1-piperidinyl)-4-trifluoromethylthiazole-5-carboxylic acid (A-33)

Compound A-33 was prepared by the general procedure for step 2 of intermediate A-31 using compound A-32 as starting material. $^1$H NMR (500 MHz, CDCl$_3$) δ 3.56 (m, 4H), 1.73 (m, 6H); LCMS (ESI) [M+1]$^+$ 281.2.

Intermediate A-34

2-(cyclohexyl(methyl)amino)-4-trifluoromethyloxazole-5-carboxylic acid (A-34)

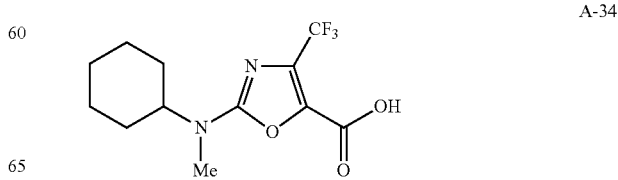

A-34

Intermediate A-34 was prepared by the general procedure for intermediate A-4, by using A-2 and N-methylcyclohexylamine as starting materials. MS (M+1): 293.

Intermediate A-35

2-(cyclopentyl(methyl)amino)-4-trifluoromethyloxazole-5-carboxylic acid (A-35)

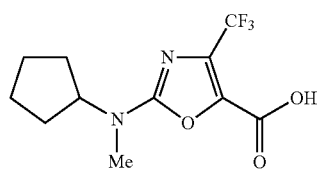

A-35

Intermediate A-35 was prepared by the general procedure for intermediate A-4, by using A-2 and N-methylcyclopentylamine as starting materials. MS (M+1): 279.

Intermediate A-37

2-(cyclohexylthio)-4-trifluoromethyloxazole-5-carboxylic acid (A-37)

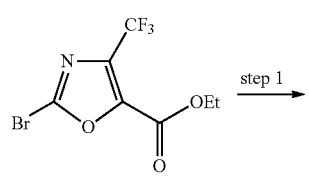

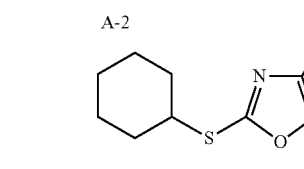

Step 1: ethyl 2-(cyclohexylthio)-4-trifluoromethyloxazole-5-carboxylate (A-36)

To compound A-2 (300 mg, 1.04 mmol) in dry THF (8 mL) was added cyclohexanethiol (242 mg, 2.08 mmol, 0.26 mL) and potassium carbonate (288 mg, 2.08 mmol). The resulting reaction mixture was heated at 80° C. for 5 h then cooled to RT and concentrated. Water (15 mL) was added, and the aqueous solution was extracted with CH₂Cl₂. The combined organic extract was dried (MgSO₄), filtered, and concentrated to give the product ethyl 2-(cyclohexylthio)-4-trifluoromethyloxazole-5-carboxylate (A-36) as a yellow oil (336 mg, 100% yield). MS (M+1): 324.

Step 2: 2-(cyclohexylthio)-4-trifluoromethyloxazole-5-carboxylic acid (A-37)

To compound A-36 (336 mg, 1.04 mmol) in THF (6 mL) and water (2 mL) was added lithium hydroxide (175 mg, 4.16 mmol). The resulting reaction mixture was stirred at RT for 20 h then concentrated. 1 N aqueous HCl (15 mL) was added, and the aqueous solution was extracted with CH₂Cl₂. The combined organic extract was dried (MgSO₄), filtered, and concentrated to give the product 2-(cyclohexylthio)-4-trifluoromethyloxazole-5-carboxylic acid (A-37) as a yellow oil (307 mg, 100% yield). MS (M+1): 296.

Intermediate A-40

1-(5-(2-bromo-4-(trifluoromethyl)oxazole-5-carboxamido)pyridin-2-yl)-4-phenylpiperidine (A-40)

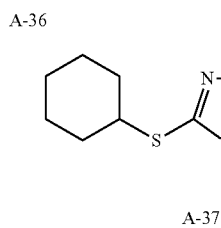

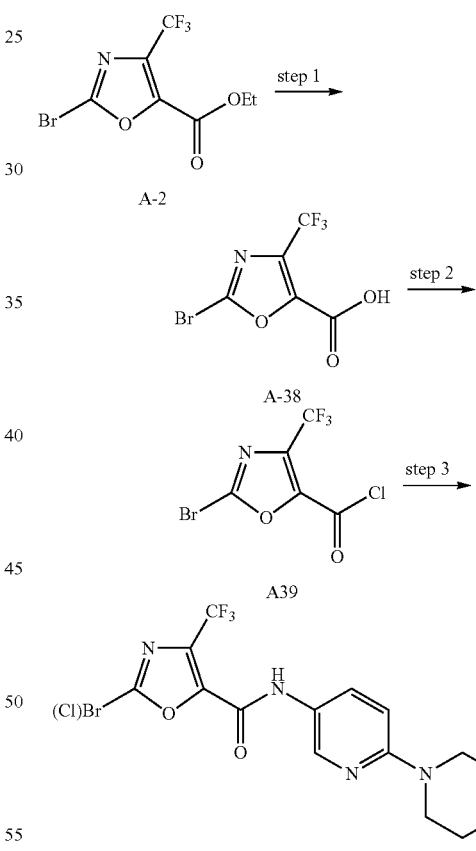

A-40

Step 1:
2-bromo-4-trifluoromethyloxazole-5-carboxylic acid (A-38)

LiOH.H₂O (0.64 g, 15.25 mmol) was added to a solution of ethyl 2-bromo-4-trifluoromethyloxazole-5-carboxylate (A-2) (3.50 g, 12.2 mmol) in THF/H$_2$O (20/5 mL) at 0° C. followed by stirring for 3 h at 0° C. The reaction mixture was diluted with EtOAc/H$_2$O (25/25 mL) and neutralized with 1 M HCl (16 mL) at 0° C. The organic phase was separated, dried over MgSO$_4$, filtered, and concentrated. The product was dried in vacuo to yield 2-bromo-4-trifluoromethyloxazole-5-carboxylic acid (A-38) as a white solid (2.80 g, 88% yield).

Step 2: 2-bromo-4-trifluoromethyloxazole-5-carbonyl chloride (A-39)

To a solution of 2-bromo-4-trifluoromethyloxazole-5-carboxylic acid (A-38) (1.30 g, 5.0 mmol) in CH$_2$Cl$_2$ (25 mL) was added oxalyl chloride (8.5 mL, 10.0 mmol) and DMF (0.019 mL), respectively, at RT under a nitrogen atmosphere. The reaction was stirred for 6 h at RT. The solvent was concentrated, and the residue was dried in vacuo to yield 2-bromo-4-trifluoromethyloxazole-5-carbonyl chloride (A-39) as yellow oil (1.30 g, 96% yield).

Step 3: 1-(5-(2-bromo-4-(trifluoromethyl)oxazole-5-carboxamido)pyridin-2-yl)-4-phenylpiperidine (A-40)

A solution of 2-bromo-4-trifluoromethyloxazole-5-carbonyl chloride (A-39) (0.34 g, 1.2 mmol) and 1-(5-aminopyridin-2-yl)-4-phenylpiperidine (B-6) (0.25 g, 1.0 mmol) in CH$_2$Cl$_2$ (10 mL) was cooled to −78° C. then triethyl amine (0.16 mL, 1.2 mmol) was added. The reaction mixture was stirred for 2 h while the temperature was warmed slowly up to 0° C. The solvent was concentrated, and the residue was purified by chromatography on a silica-gel column (eluant: 0-50% EtOAc/hexane gradient) to yield 1-(5-(2-bromo-4-(trifluoromethyl)oxazole-5-carboxamido)pyridin-2-yl)-4-phenylpiperidine (A-40) (0.19 g, 35% yield) as a yellow solid. Note: the product A-40 contains compound with the bromine atom exchanged for a chlorine atom. $^1$H NMR (500 MHz, CDCl$_3$) δ 9.58 (br s, 1H), 8.59 (br s, 1H), 8.34 (dd, 1H, J=9.5, 1.8 Hz), 7.35 (m, 2H), 7.30-7.22 (m, 3H), 6.89 (d, 1H, J=9.4 Hz), 4.42 (d, 2H, J=13.3 Hz), 3.17 (t, 2H, J=12.7 Hz), 2.85 (m, 1H), 2.05 (m, 2H), 1.84 (m, 2H); LCMS (ESI) calcd for [M+1]$^+$ for chloride 451.1. found 451.4.

Intermediate A-41 cyclopentyl 4-(5-(2-bromo-4-(trifluoromethyl)oxazole-5-carboxamido)pyridin-2-yl)piperazine-1-carboxylate (A-41)

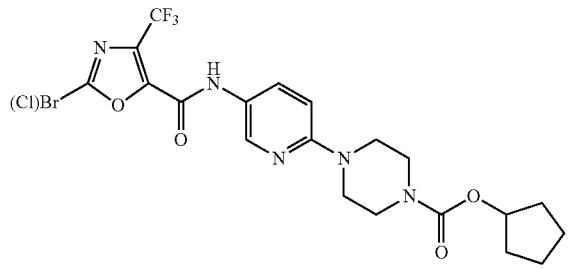

Intermediate A-41 was prepared by the general procedure for intermediate A-40, by using compound A-39 and cyclopentyl 4-(5-aminopyridin-2-yl)piperazine-1-carboxylate (B-10) as starting materials. LCMS (ESI) calcd for [M+1]$^+$ for bromide (chloride) 533.1 (488.1). found 533.9 (488.0).

Intermediate B-2

1-(5-aminopyridin-2-yl)-4-hydroxy-4-phenylpiperidine (B-2)

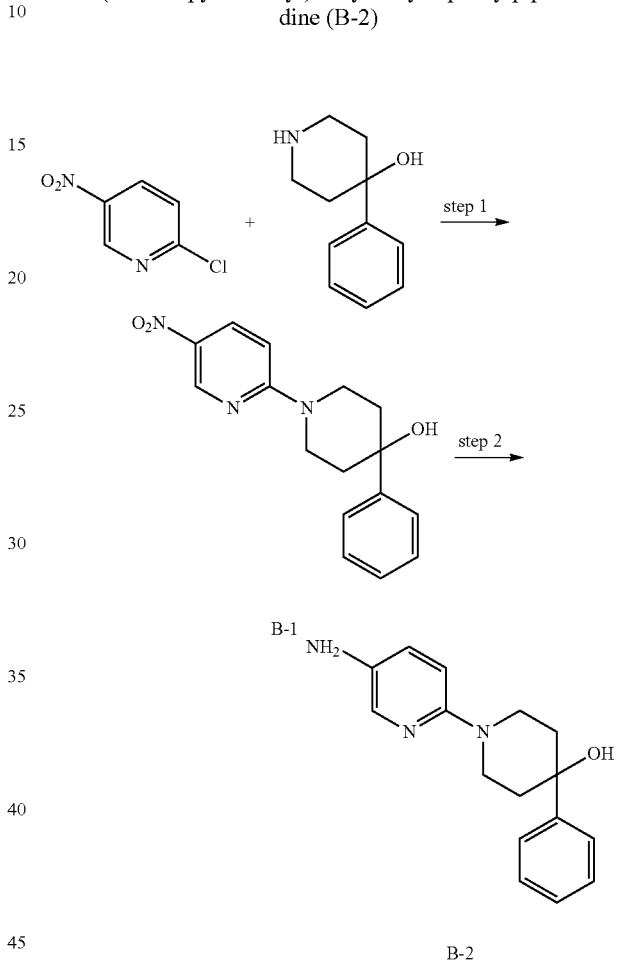

Step 1: 1-(5-nitropyridin-2-yl)-4-hydroxy-4-phenylpiperidine (B-1)

To a solution of 2-chloro-5-nitropyridine (0.9 g) in EtOH (5 mL) was added N,N-diisopropylethylamine (2.9 mL) and 4-hydroxy-4-phenylpiperidine (1.5 g). The reaction mixture was heated at 140° C. for 20 min by microwave. Then the reaction mixture was cooled to RT, diluted with EtOAc (150 mL), washed with H$_2$O (2×100 mL), saturated NH$_4$Cl (3×100 mL), brine (1×100 mL), dried over Na$_2$SO$_4$, filtered, and concentrated to give B-1.

Step 2: 1-(5-aminopyridin-2-yl)-4-hydroxy-4-phenylpiperidine (B-2)

Compound B-1 was suspended in EtOAc (50 mL) and EtOH (50 mL). The suspension was treated with 5% Pd/C (0.5 g) and stirred at RT under 1 atmosphere of H$_2$ for 16 h. The catalyst was removed by filtration over a pad of celite and concentrated to yield 1-(5-aminopyridin-2-yl)-4-hydroxy-4-phenylpiperidine (B-2) as a purple solid (1.0 g, 69% yield). LCMS (ESI) calcd for [M+1]⁺ 270.2. found 270.1.

Intermediate B-6

6-(4-phenylpiperidin-1-yl)pyridin-3-amine (B-6)

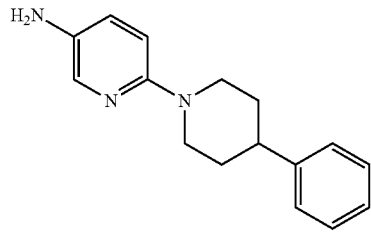

Intermediate B-6 was prepared by the general procedure for intermediate B-2, by using 2-chloro-5-nitropyridine and 4-phenylpiperidine as starting materials. LCMS (ESI) calcd for [M+1]⁺ 254.2. found 254.1.

Intermediate B-10 cyclopentyl 4-(5-aminopyridin-2-yl)-piperazine-1-carboxylate (B-10)

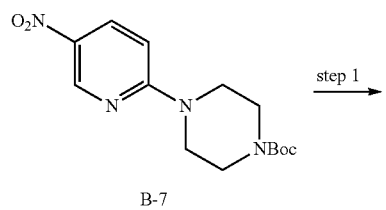

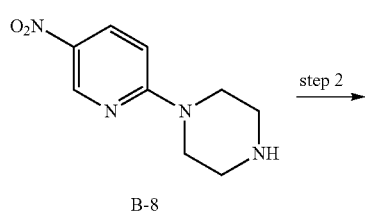

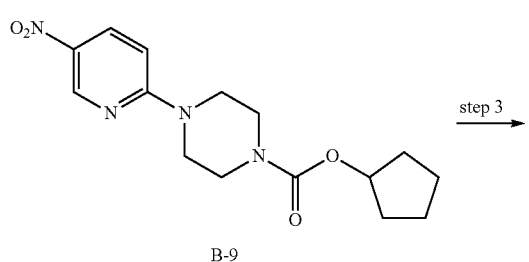

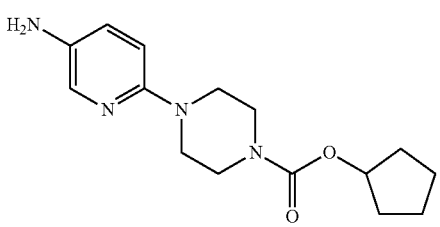

Step 1: N-(5-nitropyridin-2-yl)-piperazine (B-8)

Compound B-7 was prepared by the general procedure of the intermediate B-1. To compound B-7 (19.45 g, 0.0631 mol) dissolved in CH₂Cl₂ (250 mL) and cooled to 0° C. was added trifluoroacetic acid (50 mL). The resulting reaction mixture was stirred at RT for 16 h then concentrated. The crude product was dissolved in CH₂Cl₂ (250 mL) and made basic with the addition of 1 N aqueous NaOH (200 mL) and 3 N aqueous NaOH (100 mL). The layers were separated, and the aqueous solution extracted with CH₂Cl₂. The combined organic extract was dried (MgSO₄), filtered, and concentrated to give the product N-(5-nitropyridin-2-yl)-piperazine (B-8) as a yellow solid (13.13 g, 100% yield). MS (M+1): 209.

Step 2: cyclopentyl 4-(5-nitropyridin-2-yl)-piperazine-1-carboxylate (B-9)

To compound B-8 (6.6 g, 32 mmol) dissolved in dry THF (200 mL) was added triethylamine (8.8 mL, 63 mmol) and cyclopentyl chloroformate (5.7 g, 38 mmol). The resulting reaction mixture was stirred at RT for 16 h then concentrated. Water (150 mL) was added, and the aqueous solution was extracted with CH₂Cl₂. The combined organic extract was dried (MgSO₄), filtered, and concentrated to give a yellow solid. The solid was purified by silica gel chromatography (eluant: 2% MeOH with NH₃—CH₂Cl₂) to give cyclopentyl 4-(5-nitropyridin-2-yl)-piperazine-1-carboxylate (B-9) as a yellow solid (8.8 g, 87% yield). MS (M+1): 321.

Step 3: cyclopentyl 4-(5-aminopyridin-2-yl)-piperazine-1-carboxylate (B-10)

To compound B-9 (8.8 g, 27 mmol) suspended in ethyl acetate (100 mL) and isopropanol (100 mL) under a nitrogen atmosphere was added platinum dioxide catalyst (0.5 g). The resulting reaction mixture was stirred at RT under a hydrogen atmosphere (balloon) for 16 h. The catalyst was removed by filtration through celite and washed with isopropanol. The filtrate was concentrated to an oil which was triturated with 50% ether-hexane to give the product cyclopentyl 4-(5-aminopyridin-2-yl)piperazine-1-carboxylate (B-10) as a light purple solid (7.9 g, 99% yield). ¹H NMR (500 MHz, CDCl₃) δ 7.80 (d, 1H, J=3 Hz), 7.00 (dd, 1H, J=3, 8.5 Hz), 6.60 (d, 1H, J=8.5 Hz), 5.15 (m, 1H), 3.60 (br s, 4H), 3.35 (m, 5H), 1.90 (m, 2H), 1.75 (m, 4H), 1.60 (m, 2H).

Intermediate B-11 tert-butyl 4-(5-aminopyridin-2-yl)piperazine-1-carboxylate (B-11)

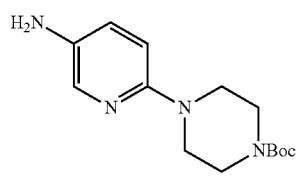

B-11

Intermediate B-11 was prepared by the general procedure for intermediate B-2, by using 2-chloro-5-nitropyridine and 1-BOC-piperazine as starting materials. LCMS (ESI) calcd for [M+1]$^+$ 279.2. found 279.2.

Intermediate B-12

6-(4-phenylpiperazin-1-yl)pyridin-3-amine (B-12)

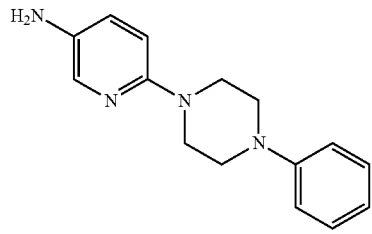

B-12

Intermediate B-12 was prepared by the general procedure for intermediate B-2, by using 2-chloro-5-nitropyridine and 1-phenylpiperazine as starting materials. LCMS (ESI) calcd for [M+1]$^+$ 255.2. found 255.1.

Intermediate B-15

4-(5-aminopyridin-2-yl)-1-benzyl-piperazin-2-one (B-15)

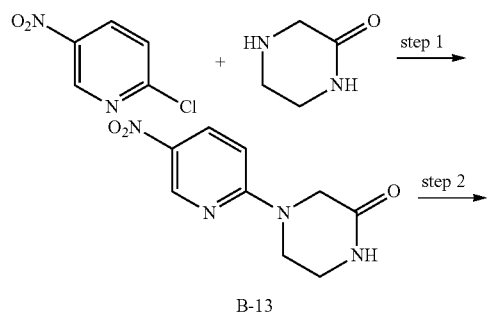

B-13

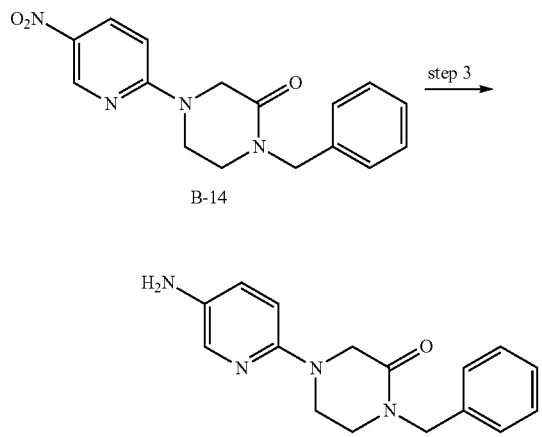

Step 1: 4-(5-nitropyridin-2-yl)piperazin-2-one (B-13)

To a solution of 2-chloro-5-nitropyridine (623 mg, 3.9 mmol) in DMF (6 mL) was added N,N-diisopropylethylamine (1.4 mL, 8.5 mmol) and 2-oxopiperazine (424 mg, 4.24 mmol). The reaction mixture was heated at 85° C. for 40 min by microwave. Then the reaction mixture was cooled to RT, and poured into water (150 mL). The precipitate was filtered, washed with water and dried under vacuum to yield 4-(5-nitropyridin-2-yl)piperazin-2-one as a solid (588 mg, 68% yield). MS (M+1): 223.3

Step 2: 1-benzyl-4-(5-nitropyridin-2-yl)piperazin-2-one (B-14)

To a solution of 4-(5-nitropyridin-2-yl)piperazin-2-one (B-13) (365 mg, 1.64 mmol) in DMF (6 mL) was added, dropwise, 1.0 M sodium bis(trimethylsilyl)amide solution in THF (1.8 mL, 1.8 mmol), followed 1 min later by benzyl bromide (215 µL, 1.8 mmol), also dropwise. After 1 h, the reaction mixture was poured into water and extracted with EtOAc. The extract was dried over Na$_2$SO$_4$, filtered, and concentrated. The crude product was purified by silica gel chromatography (eluant: gradient of EtOAc in hexanes) to give 1-benzyl-4-(5-nitropyridin-2-yl)piperazin-2-one (B-14) (329 mg, 64% yield). MS (M+1): 313.2

Step 3: 4-(5-aminopyridin-2-yl)-1-benzyl-piperazin-2-one (B-15)

The 1-benzyl-4-(5-nitropyridin-2-yl)piperazin-2-one (B-14) (195 mg, 0.63 mmol) was stirred in EtOAc (30 mL) and MeOH (15 mL). The mixture was treated with PtO$_2$ (72 mg) and stirred at RT under 1 atm of H$_2$ for 1 h 10 min. Then, the reaction mixture was filtered over a pad of celite and concentrated to yield 4-(5-aminopyridin-2-yl)-1-benzyl-piperazin-2-one (B-15) (176 mg, 100% yield). MS (M+1): 283.2

Intermediate B-16

1-(1-(5-aminopyridin-2-yl)piperidin-4-yl)-1H-benzo[d]imidazo-2(3H)-one (B-16)

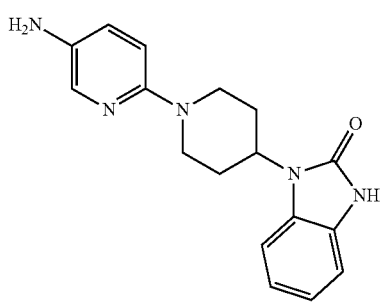

Intermediate B-16 was prepared by the general procedure for intermediate B-2, by using 2-chloro-5-nitropyridine and 1-(piperidin-4-yl)-1H-benzo[d]imidazo-2(3H)-one. MS (M+1): 310.2

Intermediate B-17

8-(5-aminopyridin-2-yl)-2-benzyl-2,8-diazaspiro[4,5]decan-1-one (B-17)

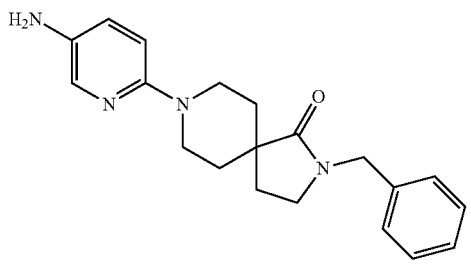

Intermediate B-17 was prepared by the general procedure for intermediate B-15, by using 2-chloro-5-nitropyridine, 2,8-diazaspiro[4,5]decan-1-one, and benzyl bromide as starting materials. MS (M+1): 337.3

Intermediate B-18

1-(1-(5-aminopyridin-2-yl)piperidin-4-O-3-benzyl-1H-benzo[d]imidazo-2(3H)-one (B-18)

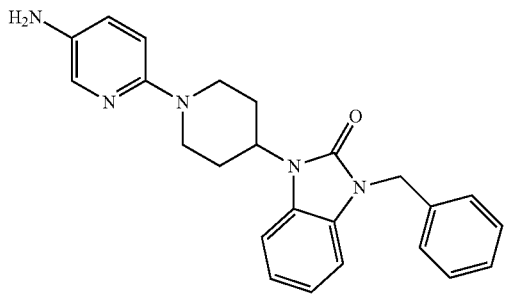

Intermediate B-18 was prepared by the general procedure for intermediate B-15, by using 2-chloro-5-nitropyridine, 1-(piperidin-4-yl)-1H-benzo[d]imidazo-2(3H)-one, and benzyl bromide as starting materials. MS (M+1): 400.3

Intermediate B-19

1-(1-(5-aminopyridin-2-yl)piperidin-4-yl)-3-methyl-1H-benzo[d]imidazo-2(3H)-one (B-19)

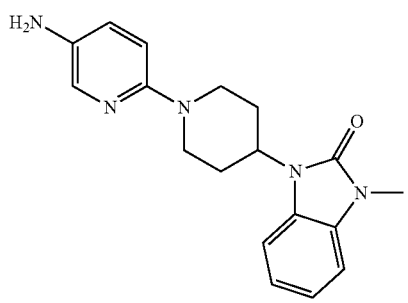

Intermediate B-19 was prepared by the general procedure for intermediate B-15, by using 2-chloro-5-nitropyridine, 1-(piperidin-4-yl)-1H-benzo[d]imidazo-2(3H)-one, and methyl iodide as starting materias. MS (M+1): 324.2

Intermediate B-20

8-(5-aminopyridin-2-yl)-2-methyl-2,8-diazaspiro[4,5]decan-1-one (B-20)

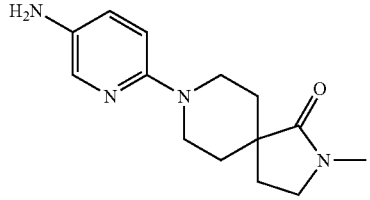

Intermediate B-20 was prepared by the general procedure for intermediate B-15, by using 2-chloro-5-nitropyridine, 2,8-diazaspiro[4,5]decan-1-one, and methyl iodide as starting materials. MS (M+1): 261.2

Intermediate B-21 tert-butyl 4-(5-aminopyridin-2-yl)homopiperazine-1-carboxylate (B-21)

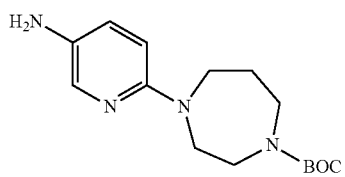

Intermediate B-21 was prepared by the general procedure for intermediate B-2, by using 2-chloro-5-nitropyridine and 1-BOC-homopiperazine as starting materials. MS (M+1): 293.

Intermediate B-22

6-(4-phenethylpiperidin-1-yl)pyridin-3-amine (B-22)

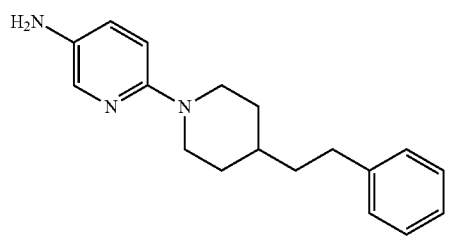

Intermediate B-22 was prepared by the general procedure for intermediate B-2, by using 2-chloro-5-nitropyridine and 4-phenethylpiperidine as starting materials. MS (M+1): 312.

Intermediate B-23

6-(4-benzyloxypiperidin-1-yl)pyridin-3-amine (B-23)

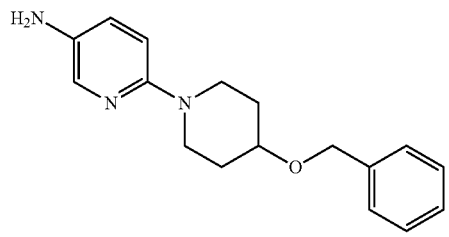

Intermediate B-23 was prepared by the general procedure for intermediate B-2, by using 2-chloro-5-nitropyridine and 4-benzyloxypiperidine as starting materials. MS (M+1): 284.

Intermediate B-24

6-(4-(hydroxyphenylmethyl)piperidin-1-yl)pyridin-3-amine (B-24)

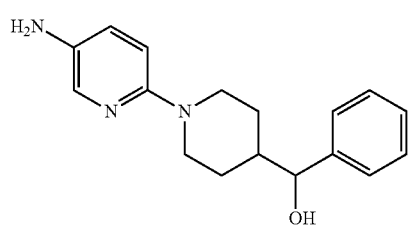

Intermediate B-24 was prepared by the general procedure for intermediate B-2, by using 2-chloro-5-nitropyridine and 4-(hydroxyphenylmethyl)piperidine as starting materials. MS (M+1): 284.

Intermediate B-25

6-[4-((phenylmethylamino)sulfonyl)piperidin-1-yl]pyridin-3-amine (B-25)

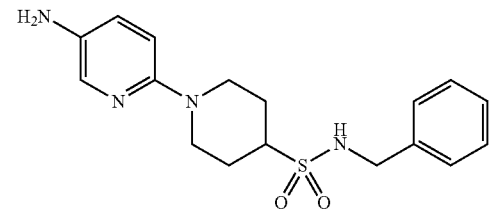

Intermediate B-25 was prepared by the general procedure for intermediate B-2, by using 2-chloro-5-nitropyridine and 4-((phenylmethylamino)sulfonyl)piperidine as starting materials. MS (M+1): 347.

Intermediate B-26

6-[hexahydro-5-oxo-4-(phenylmethyl)-1H-1,4-diazepin-1-yl]pyridin-3-amine (B-26)

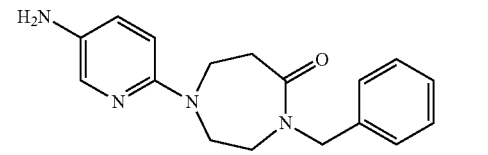

Intermediate B-26 was prepared by the general procedure for intermediate B-2, by using 2-chloro-5-nitropyridine and hexahydro-5-oxo-4-(phenylmethyl)-1H-1,4-diazepine as starting materials. MS (M+1): 297.

Intermediate B-32 methyl 4-(5-aminopyridin-2-yl)oxy-benzoate (B-32)

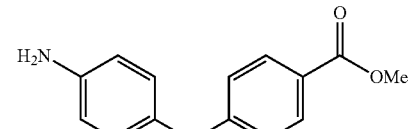

Intermediate B-32 was prepared by the general procedure for intermediate B-2, by using 2-chloro-5-nitropyridine and methyl 4-hydroxybenzoate as starting materials. MS (M+1): 245.

Intermediate B-33 tert-butyl 1-(5-aminopyridin-2-yl)piperidin-4-ylcarbamate (B-33)

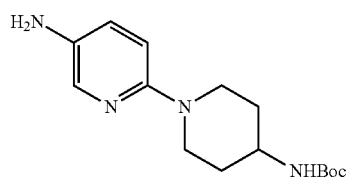

Intermediate B-33 was prepared by the general procedure for intermediate B-2, by using 2-chloro-5-nitropyridine and tert-butyl piperidin-4-ylcarbamate as the starting material. LCMS [M+1]$^+$ 293.2.

Intermediate B-34 ethyl 5-amino-1H-indole-2-carboxylate (B-34)

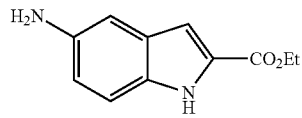

Intermediate B-34 was prepared by the general procedure for intermediate B-2, by using ethyl 5-nitro-1H-indole-2-carboxylate as the starting material. LCMS [M+1]$^+$ 205.1.

Example 1

N-[6-(4-hydroxy-4-phenylpiperidin-1-yl)pyridin-3-yl]-2-(piperidin-1-yl)-4-(trifluoromethyl)oxazole-5-carboxamide (1)

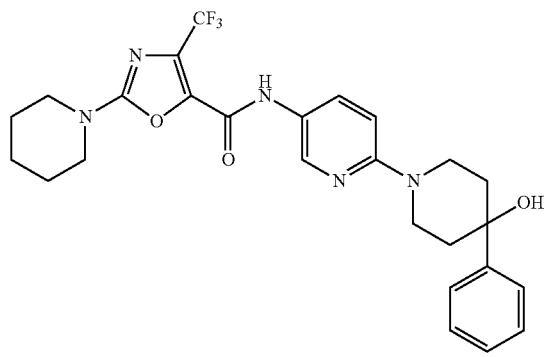

To a solution of intermediate A-4 (0.079 g) and B-2 (0.097 g) in DMF (3 mL) were added O-(7-azabenzotriazol-1-yl)-N,N,N',N'-tetramethyluronium hexafluorophosphate (0.14 g, HATU), 4-dimethylaminopyridine (0.005 mg, DMAP), and N,N-diisopropylethylamine (0.079 mL). The reaction mixture was stirred at RT for 17 h then diluted with EtOAc (50 mL), washed with H$_2$O (4×100 mL), sat. NH$_4$Cl (1×100 mL), sat. NaHCO$_3$(1×100 mL), brine (1×100 mL), dried over Na$_2$SO$_4$, filtered, and concentrated. The crude product was purified by prep-TLC (eluant: 30% CH$_3$CN in CH$_2$Cl$_2$) to yield N-(6-(4-hydroxy-4-phenylpiperidin-1-yl)pyridin-3-yl)-2-(piperidin-1-yl)-4-(trifluoromethyl)oxazole-5-carboxamide (1) as a white solid (0.15 g, 100% yield). $^1$H NMR (400 MHz, DMSO-d6) δ 10.03 (s, 1H), 8.32 (d, 1H, J=2.6 Hz), 7.79 (dd, 1H, J=9.2, 2.6 Hz), 7.46 (m, 2H), 7.32 (m, 2H), 7.21 (m, 1H), 6.91 (d, 1H, J=9.2 Hz), 5.10 (s, 1H), 4.15 (d, 2H, J=12.8 Hz), 3.61 (br s, 4H), 3.23 (dt, 2H, J=12.8, 2.2 Hz), 1.92 (dt, 2H, J=12.8, 4.0 Hz), 1.66 (d, 2H, J=12.5 Hz), 1.61 (br s, 6H). LCMS (ESI) Rt=3.32 min, [M+1]$^+$ 516.3.

Example 2

N-[6-(4-(2-hydroxyethyl)piperidin-1-yl)pyridin-3-yl]-2-(piperidin-1-yl)-4-(trifluoromethyl)oxazole-5-carboxamide (2)

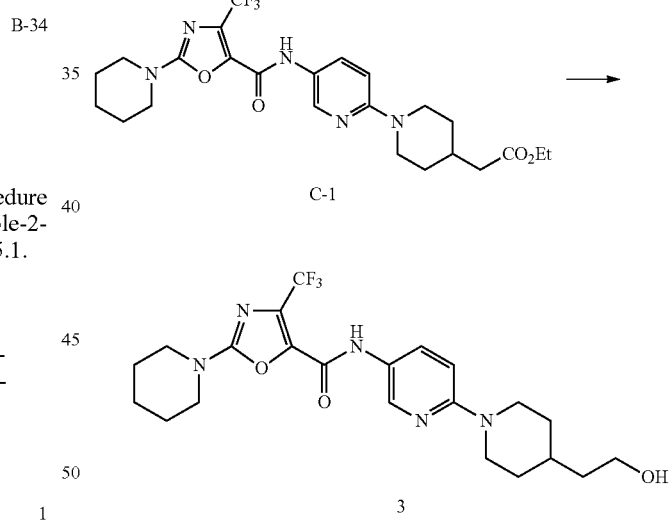

Ethyl 2-(1-(5-(2-(piperidin-1-yl)-4-(trifluoromethyl)oxazole-5-carboxamido)pyridin-2-yl)piperidin-4-yl)acetate (C-1) was prepared by the general procedure for compound 1.

To a solution of compound C-1 (51 mg) in THF (5 mL) was added a solution of LiBH$_4$ (0.36 mL, 2.0 M in THF) at RT. The reaction mixture was stirred at RT under N$_2$ for 2 h then treated with anhydrous MeOH (0.032 mL). After 18 h of additional stirring at RT under N$_2$, the reaction mixture was quenched by the addition of saturated NaHCO$_3$ (1 mL). The reaction mixture was diluted with EtOAc (10 mL), washed with saturated NaHCO$_3$ (3×10 mL), brine (1×10 mL), dried over Na$_2$SO$_4$, filtered, and concentrated. The crude product was purified by prep-TLC (eluant: 50% CH$_3$CN in CH$_2$Cl$_2$)

to yield N-[6-(4-(2-hydroxyethyl)piperidin-1-yl)pyridin-3-yl]-2-(piperidin-1-yl)-4-(trifluoromethyl)oxazole-5-carboxamide (3) as a white solid (29 mg, 62% $^1$H NMR (400 MHz, DMSO-d6) δ 10.00 (s, 1H), 8.29 (d, 1H, J=2.6 Hz), 7.75 (dd, 1H, J=9.2, 2.9 Hz), 6.83 (d, 1H, J=9.2 Hz), 4.38 (t, 1H, J=5.1 Hz), 4.23 (d, 2H, J=13.2 Hz), 3.61 (br s, 4H), 3.46 (q, 2H, J=5.2 Hz), 2.73 (dt, 2H, J=12.5, 2.2 Hz), 1.70 (m, 2H), 1.61 (br s, 6H), 1.37 (q, 2H, J=6.6 Hz), 1.10 (dq, 2H, J=12.1, 4.0 Hz). LCMS (ESI) Rt=2.95 min, [M+1]$^+$ 468.3.

Example 3

N-[6-(4-Phenyl-1-piperidinyl)-3-pyridinyl]-2-(pyrrolidin-1-yl)-4-(trifluoromethyl)-5-oxazolecarboxamide (3)

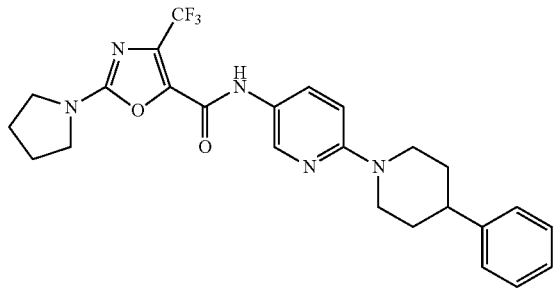

Compound 3 was prepared by the general procedure for compound 1, by using intermediates A-5 and B-6 as starting materials. $^1$H NMR (500 MHz, DMSO-d6) δ 10.25 (s, 1H), 8.75 (s, 1/2H), 8.55 (d, 1/2H, J=9.5 Hz), 8.40 (s, 1H), 8.10 (d, 1H, J=9.5 Hz), 7.55 (m, 1/2H), 7.45 (m, 1/2H), 7.30 (m, 3H), 7.20 (t, 1H, J=7.5 Hz), 4.30 (d, 2H, J=13 Hz), 3.55 (br s, 4H), 3.25 (t, 2H, J=11.5 Hz), 2.90 (t, 1H, J=11 Hz), 1.95 (m, 6H), 1.75 (q, 2H, J=9 Hz). MS (M+1): 486.

Example 4 tert-butyl 2-(2-oxo-2-(4-(5-(2-(4-phenylpiperidin-1-yl)-4-(trifluoromethyl)oxazole-5-carboxamido)pyridin-2-yl)piperazin-1-yl)ethyl)benzoate (4)

Compound 4 was prepared by the general procedure for compound 1. $^1$H NMR (500 MHz, CDCl$_3$) δ 8.21 (d, 1H, J=3 Hz), 8.04 (m, 2H), 7.91 (d, 1H, J=8 Hz), 7.63 (s, 1H), 7.45 (t, 1H, J=7.5 Hz), 7.37 (d, 1H, J=7.5 Hz), 7.34 (d, 1H, J=3 Hz), 7.32 (d, 1H, J=7.5 Hz), 7.26 (t, 3H, J=8 Hz), 6.68 (d, 1H, J=9 Hz), 4.39 (d, 2H, J=13 Hz), 4.16 (s, 2H), 3.80 (m, 2H), 3.71 (m, 2H), 3.60 (m, 2H), 3.54 (m, 2H), 3.23 (td, 2H, J=12.5, 2 Hz), 2.80 (tt, 1H, J=12, 3 Hz), 2.03 (d, 2H, J=12 Hz), 1.84 (qd, 2H, J=12.5, 4 Hz), 1.58 (s, 9H). MS (M+1): 719.3

Example 5

N-[6-(4-phenylpiperazin-1-yl)pyridin-3-yl]-2-(piperidin-1-yl)-4-(trifluoromethyl)oxazole-5-carboxamide (5)

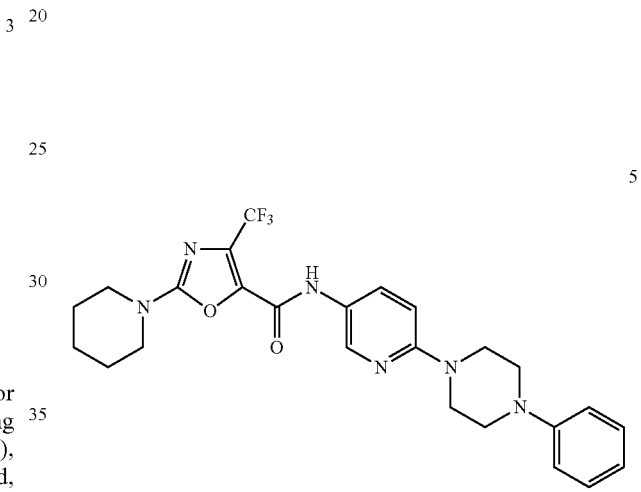

Compound 5 was prepared by the general procedure for compound 1, by using intermediates A-4 and B-12 as starting materials. $^1$H NMR (400 MHz, DMSO-d6) δ 10.07 (s, 1H), 8.37 (d, 1H, J=2.6 Hz), 7.84 (dd, 1H, J=9.2, 2.6 Hz), 7.24 (m, 2H), 7.00 (m, 2H), 6.95 (d, 1H, J=9.2 Hz), 6.81 (m, 1H), 3.61 (m, 8H), 3.24 (m, 4H), 1.61 (br s, 6H). LCMS (ESI) Rt=3.58 min, [M+1]$^+$ 501.3.

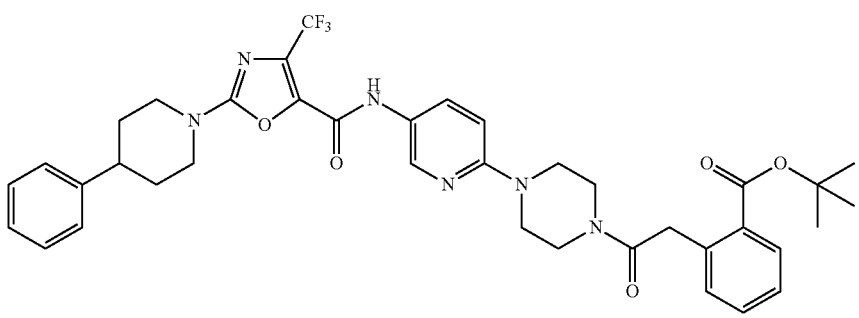

Example 6

N-[6-(4-phenylpiperidin-1-yl)pyridin-3-yl]-2-(piperidin-1-yl)-4-(trifluoromethyl)oxazole-5-carboxamide (6)

Example 7

N-[6-(4-phenyl-1-piperidinyl)-3-pyridinyl]-2-(diethylamino)-4-(trifluoromethyl)-5-oxazolecarboxamide (7)

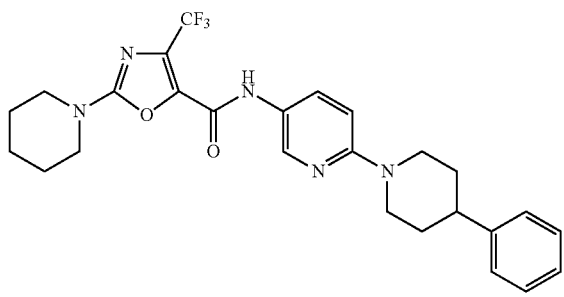

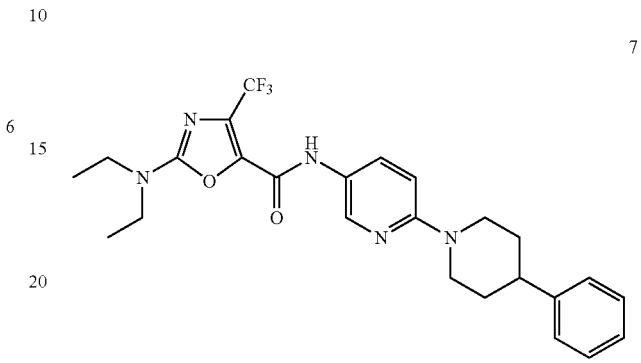

Compound 7 was prepared by the general procedure for compound 1, by using intermediates A-16 and B-6 as starting materials. $^1$H NMR (500 MHz, DMSO-d6) δ 10.25 (s, 1H), 8.40 (s, 1H), 8.10 (d, 1H, J=11 Hz), 7.45 (d, 1H, J=9.5 Hz), 7.30 (m, 4H), 7.20 (t, 1H, J=7 Hz), 4.30 (d, 2H, J=13.5 Hz), 3.60 (q, 4H, J=7 Hz), 3.25 (t, 2H, J=13.5 Hz), 2.90 (t, 1H, J=12.5 Hz), 1.95 (d, 2H, J=12 Hz), 1.75 (q, 2H, J=9.5 Hz), 1.20 (t, 6H, J=7 Hz). MS (M+1): 488.

Compound 6 was prepared by the general procedure for compound 1, by using intermediates A-4 and B-6 as starting materials. $^1$H NMR (400 MHz, DMSO-d6) δ 10.03 (s, 1H), 8.33 (d, 1H, J=2.9 Hz), 7.79 (dd, 1H, J=9.2, 2.6 Hz), 7.27 (m, 4H), 7.19 (m, 1H), 6.91 (d, 1H, J=9.2 Hz), 4.41 (d, 2H, J=12.8 Hz), 3.61 (br s, 4H), 2.86 (dt, 2H, J=12.8, 2.6 Hz), 2.77 (tt, 1H, J=12.5, 3.7 Hz), 1.84 (d, 2H J=12.5 Hz), 1.65 (dt, 2H, J=12.5, 3.0 Hz), 1.61 (s, 6H). LCMS (ESI) Rt=3.66 min, [M+1]$^+$ 500.3.

Example 8 methyl 3-((4-(5-(2-(3-methylpiperidin-1-yl)-4-(trifluoromethyl)oxazole-5-carboxamido)pyridin-2-yl)-2-oxopiperazin-1-yl)methyl)benzoate (8)

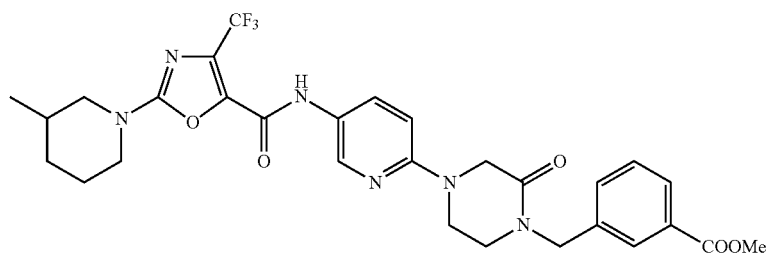

Compound 8 was prepared by the general procedure for compound 1. $^1$H NMR (500 MHz, CDCl$_3$) δ 8.35 (s, 1H), 8.19 (broad s, 1H), 8.03 (m, 1H), 8.00 (d, 1H, J=8 Hz), 7.96 (s, 1H), 7.53 (d, 1H, J=7.5 Hz), 7.45 (t, 1H, J=8 Hz), 6.67 (d, 1H, J=9 Hz), 4.74 (s, 2H), 4.25 (s, 2H), 4.16 (m, 2H), 3.94 (s, 3H), 3.92 (m, 2H), 3.44 (m, 2H), 3.05 (td, 1H, J=12.5, 2.5 Hz), 2.72 (t, 1H, J=13 Hz), 1.90 (m, 1H), 1.82 (m, 1H), 1.75 (m, 1H), 1.64 (m, 1H), 1.17 (q, 1H, J=13 Hz), 0.99 (d, 3H, J=6.5 Hz). MS (M+1): 601.

Example 9

N-[6-(4-(o-tolylsulfonyl)piperazin-1-yl)pyridin-3-yl]-2-(piperidin-1-yl)-4-(trifluoromethyl)oxazole-5-carboxamide (9)

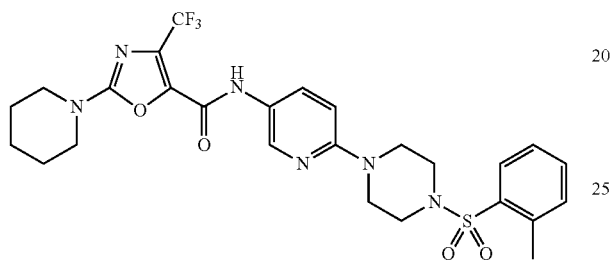

9

Compound 9 was prepared by the general procedure for compound 8, by using intermediate C-3 and o-tolylsulfonyl chloride as starting materials. $^1$H NMR (400 MHz, DMSO-d6) δ 10.05 (s, 1H), 8.33 (d, 1H, J=2.6 Hz), 7.82 (m, 2H), 7.59 (m, 1H), 7.45 (m, 2H), 6.87 (d, 1H, J=9.2 Hz), 3.60 (br s, 4H), 3.55 (m, 4H), 3.12 (m, 4H), 2.59 (s, 3H), 1.60 (br s, 6H). LCMS (ESI) Rt=3.89 min, [M+1]$^+$ 579.3.

Example 10 methyl 3-((2-oxo-4-(5-(2-(4-phenylpiperidin-1-yl)-4-(trifluoromethyl)oxazole-5-carboxamido)pyridin-2-yl)piperazin-1-yl)methyl)benzoate (10)

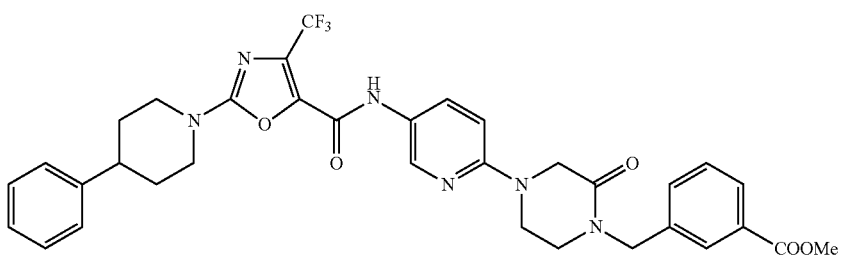

10

Compound 10 was prepared by the general procedure for compound 1. $^1$H NMR (500 MHz, CDCl$_3$) δ 8.37 (broad s, 1H), 8.23 (broad s, 1H), 8.00 (d, 1H, J=7.5 Hz), 7.95 (s, 1H), 7.52 (d, 1H, J=7.5 Hz), 7.45 (t, 1H, J=7.5 Hz), 7.35 (t, 2H, J=7.5 Hz), 7.24 (m, 3H), 6.68 (d, 1H, J=8.5 Hz), 4.73 (s, 2H), 4.45 (d, 2H, J=12.5 Hz), 4.25 (s, 2H), 3.94 (s, 3H), 3.92 (m, 2H), 3.44 (m, 2H), 3.22 (t, 2H, J=13.5 Hz), 2.79 (t, 1H, J=12 Hz), 2.02 (d, 2H, J=13 Hz), 1.83 (qd, 2H, J=12.5, 4 Hz). MS (M+1): 663.

Example 11

3-((4-(5-(2-(3-methylpiperidin-1-yl)-4-(trifluoromethyl)oxazole-5-carboxamido)pyridin-2-yl)-2-oxopiperazin-1-yl)methyl)benzoic acid (11)

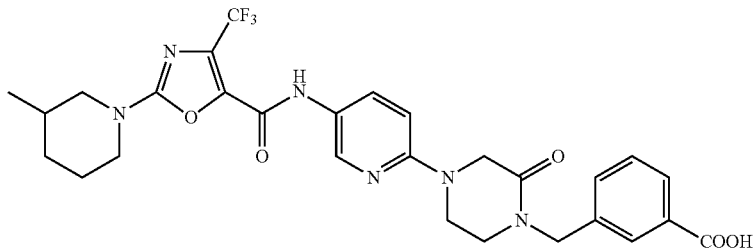

Compound 11 was prepared by the saponification of compound 8. $^1$H NMR (500 MHz, CD$_3$OD) δ 8.39 (s, 1H), 7.98 (m, 2H), 7.91 (m, 1H), 7.56 (m, 1H), 7.49 (t, 1H, J=7.5 Hz), 6.87 (d, 1H, J=9 Hz), 4.76 (s, 2H), 4.27 (s, 2H), 4.20 (m, 2H), 3.84 (m, 2H), 3.49 (m, 2H), 3.10 (t, 1H, J=13 Hz), 2.78 (t, 1H, J=13 Hz), 1.90 (m, 1H), 1.83 (m, 1H), 1.75 (m, 1H), 1.65 (m, 1H), 1.24 (q, 1H, J=11.5 Hz), 1.01 (d, 3H, J=6.5 Hz). MS (M+1): 587.

Example 12 methyl 3-((2-oxo-4-(5-(2-(4-phenylpiperidin-1-yl)-4-(trifluoromethyl)oxazole-5-carboxamido)pyridin-2-yl)piperazin-1-yl)methyl)benzoate (12)

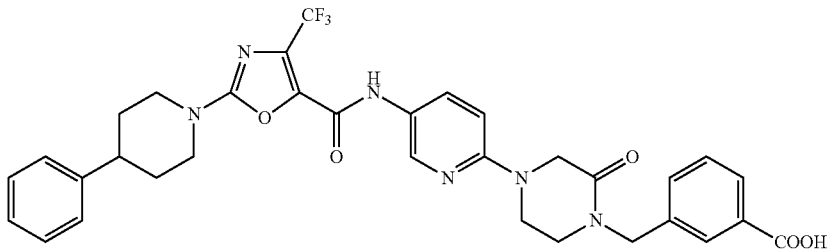

Compound 12 was prepared by the saponification of compound 10. $^1$H NMR (500 MHz, CD$_3$OD) δ 8.40 (s, 1H), 7.96 (m, 3H), 7.56 (d, 1H, J=8.5 Hz), 7.49 (t, 1H, J=8 Hz), 7.30 (m, 4H), 7.22 (m, 1H), 6.88 (d, 1H, J=9.5 Hz), 4.76 (s, 2H), 4.45 (d, 2H, J=12.5 Hz), 4.28 (s, 2H), 3.85 (m, 2H), 3.49 (m, 2H), 3.27 (t, 2H, J=12.5 Hz), 2.86 (t, 1H, J=12.5 Hz), 1.98 (d, 2H, J=13.5 Hz), 1.84 (q, 2H, J=12.5 Hz). MS (M+1): 649.

Example 13

N-[6-(4-phenyl-1-piperidinyl)-3-pyridinyl]-2-(3,5-dimethyl-1-piperidinyl)-4-(trifluoromethyl)-5-oxazolecarboxamide (13)

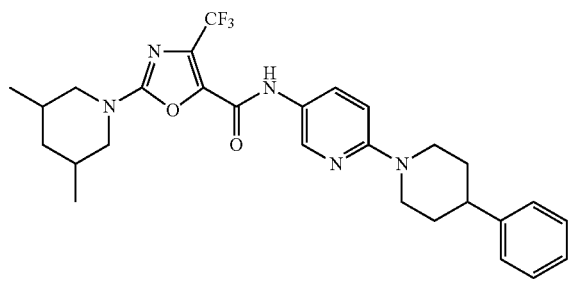

Compound 13 was prepared by the general procedure for compound 1, by using intermediates A-17 and B-6 as starting materials. $^1$H NMR (500 MHz, CDCl$_3$) δ 8.20 (s, 1H), 8.00 (d, 1H, J=9 Hz), 7.50 (s, 1H), 7.35 (m, 2H), 7.25 (m, 3H), 6.75 (d, 1H, J=9 Hz), 4.45 (d, 2H, J=13 Hz), 4.15 (d, 2H, J=12.5 Hz), 3.70 (m, 1/3H), 3.30 (m, 1/3H), 2.95 (t, 2H, J=10 Hz), 2.75 (tm, 1H, J=12.5 Hz), 2.55 (t, 2H, J=12.5 Hz), 2.10 (m, 1/3H), 1.95 (m, 2H), 1.90 (d, 1H, J=13 Hz), 1.80 (m, 4H), 1.00 (d, 6H, J=6.5 Hz). MS (M+1): 528.

Example 14

N-[6-(4-phenyl-1-piperidinyl)-3-pyridinyl]-2-(3,3-dimethyl-1-piperidinyl)-4-(trifluoromethyl)-5-oxazolecarboxamide (14)

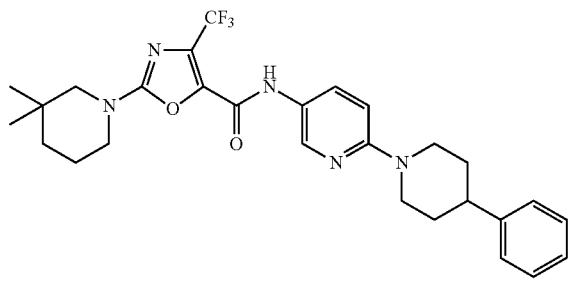

Compound 14 was prepared by the general procedure for compound 1, by using intermediates A-18 and B-6 as starting materials. $^1$H NMR (500 MHz, CDCl$_3$) δ 8.20 (s, 1H), 8.00 (d, 1H, J=9), 7.50 (s, 1H), 7.35 (m, 2H), 7.25 (m, 3H), 6.75 (d, 1H, J=9 Hz), 4.45 (d, 2H, J=13 Hz), 3.60 (m, 2H), 3.30 (s, 2H), 2.95 (t, 2H, J=10.5 Hz), 2.75 (tm, 1H, J=12.5 Hz), 1.95 (d, 2H, J=12 Hz), 1.80 (m, 4H), 1.50 (m, 2H), 1.00 (s, 6H). MS (M+1): 528.

Example 15

N-[6-(4-phenyl-1-piperidinyl)-3-pyridinyl]-2-(3,4-dihydro-1(2H)-quinolinyl)-4-(trifluoromethyl)-5-oxazolecarboxamide (15)

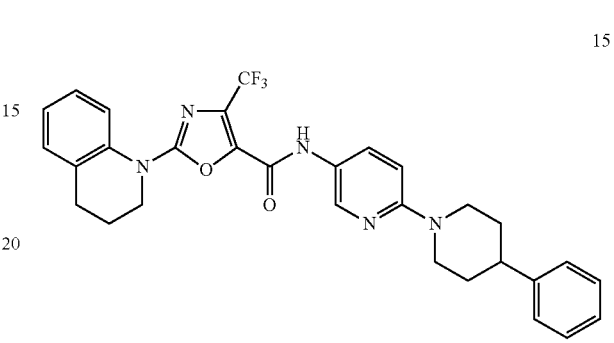

Compound 15 was prepared by the general procedure for compound 1, by using intermediates A-19 and B-6 as starting materials. $^1$H NMR (500 MHz, DMSO-d6) δ 8.85 (br s, 1H), 8.35 (s, 1H), 8.05 (d, 1H, J=8 Hz), 7.85 (d, 1H, J=8 Hz), 7.15-7.35 (m, 7H), 7.05 (t, 1H, J=7.5 Hz), 7.00 (d, 1H, J=9 Hz), 4.40 (d, 2H, J=13 Hz), 4.05 (m, 2H), 2.90 (t, 2H, J=12.5 Hz), 2.85 (t, 2H, J=7 Hz), 2.80 (t, 1H, J=12 Hz), 2.00 (t, 2H, J=6 Hz), 1.85 (d, 2H, J=13 Hz), 1.65 (q, 2H, J=12.5 Hz). MS (M+1): 548.

Example 16

N-[6-(4-phenyl-1-piperidinyl)-3-pyridinyl]-2-(2,3-dihydro-1H-indol-1-yl)-4-(trifluoromethyl)-5-oxazolecarboxamide (16)

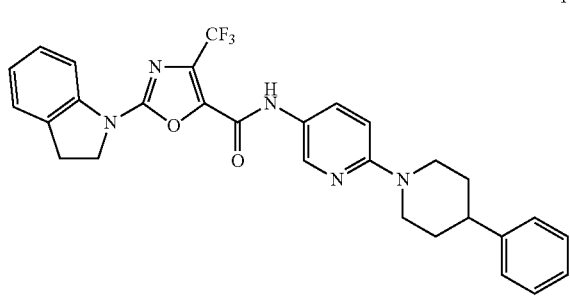

Compound 16 was prepared by the general procedure for compound 1, by using intermediates A-20 and B-6 as starting materials. $^1$H NMR (500 MHz, DMSO-d6) δ 8.85 (br s, 1H), 8.40 (s, 1H), 7.90 (d, 2H, J=8 Hz), 7.30 (m, 6H), 7.20 (t, 1H, J=7 Hz), 7.05 (t, 2H, J=7.5 Hz), 4.40 (d, 2H, J=13 Hz), 4.35 (t, 2H, J=8.5 Hz), 3.30 (t, 2H, J=8.5 Hz), 2.95 (t, 2H, J=13 Hz), 2.80 (t, 1H, J=13.5 Hz), 1.85 (d, 2H, J=13 Hz), 1.65 (q, 2H, J=9.5 Hz). MS (M+1): 534.

Example 18

N-[6-(4-phenyl-1-piperidinyl)-3-pyridinyl]-2-(3,4-dihydro-2(1H)-isoquinolinyl)-4-(trifluoromethyl)-5-oxazolecarboxamide (18)

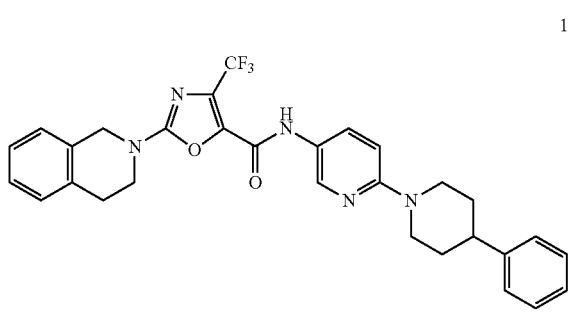

18

Compound 18 was prepared by the general procedure for compound 1, by using intermediates A-21 and B-6 as starting materials. $^1$H NMR (500 MHz, DMSO-d6) δ 8.85 (br s, 1H), 8.35 (s, 1H), 7.85 (d, 1H, J=9.5 Hz), 7.25 (m, 9H), 6.95 (d, 1H, J=9 Hz), 4.80 (s, 2H), 4.40 (d, 2H, J=12.5 Hz), 3.95 (t, 2H, J=5.5 Hz), 3.00 (t, 2H, J=6 Hz), 2.90 (t, 2H, J=13.5 Hz), 2.75 (t, 1H, J=11 Hz), 1.85 (d, 2H, J=10.5 Hz), 1.65 (q, 2H, J=9.5 Hz). MS (M+1): 548.

Example 22

N-[6-(4-phenyl-1-piperidinyl)-3-pyridinyl]-2-(4-phenylpiperidin-1-yl)-4-(trifluoromethyl)-5-oxazole-carboxamide (22)

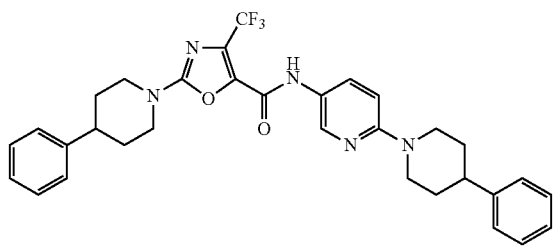

22

Compound 22 was prepared by the general procedure for compound 1, by using intermediates A-22 and B-6 as starting materials. $^1$H NMR (500 MHz, DMSO-d6) δ 10.05 (s, 1H), 8.35 (s, 1H), 7.80 (d, 1H, J=9 Hz), 7.15-7.35 (m, 10H), 6.90 (d, 1H, J=9 Hz), 4.40 (d, 2H, J=12.5 Hz), 4.35 (d, 2H, J=12.5 Hz), 3.20 (t, 2H, J=12.5 Hz), 2.85 (t, 2H, J=12.5 Hz), 2.80 (m, 2H), 1.85 (m, 4H), 1.75 (q, 2H, J=13 Hz), 1.65 (q, 2H, J=12 Hz). MS (M+1): 576.

Example 23

N-[6-(3-phenyl-1-piperidinyl)-3-pyridinyl]-2-(4-phenylpiperidin-1-yl)-4-(trifluoromethyl)-5-oxazole-carboxamide (23)

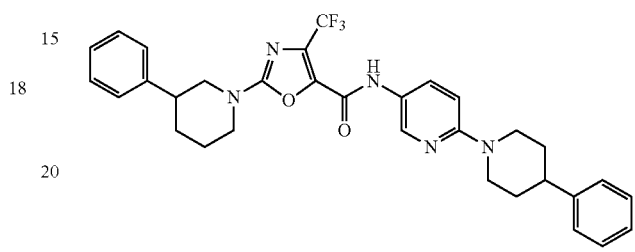

23

Compound 23 was prepared by the general procedure for compound 1, by using intermediates A-23 and B-6 as starting materials. $^1$H NMR (500 MHz, DMSO-d6) δ 10.05 (s, 1H), 8.30 (s, 1H), 7.75 (d, 1H, J=6.5 Hz), 7.15-7.40 (m, 10H), 6.90 (d, 1H, J=9 Hz), 4.40 (d, 2H, J=13 Hz), 4.25 (t, 2H, J=13 Hz), 3.20 (t, 1H, J=12 Hz), 3.15 (t, 1H, J=12 Hz), 2.85 (m, 3H), 2.75 (t, 1H, J=12 Hz), 1.95 (m, 1H), 1.85 (m, 1H), 1.85 (d, 2H, J=13.5 Hz), 1.70 (m, 4H). MS (M+1): 576.

Example 31

N-[6-[3-oxo-4-(phenylmethyl)-1-piperazinyl]-3-pyridinyl]-2-(3-methyl-1-piperidinyl)-4-(trifluoromethyl)-5-oxazolecarboxamide (31)

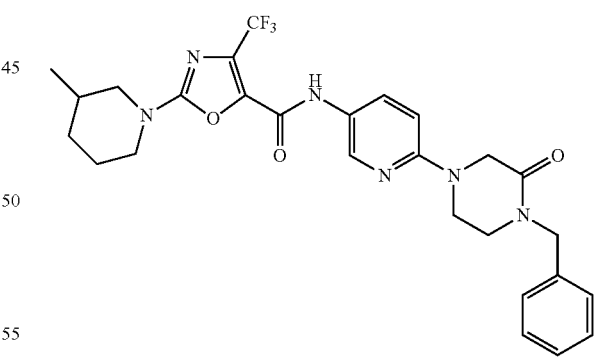

31

To a solution of intermediate B-15 (170 mg, 0.6 mmol) and intermediate A-10 (185 mg, 0.67 mmol) in DMF (8 mL) were added 1-(3-dimethylaminopropyl)-3-ethylcarbodiimide hydrochloride (173 mg, 0.9 mmol, EDCI), 1-hydroxybenzotriazole (122 mg, 0.9 mmol, HOBT), and N,N-diisopropylethylamine (200 μL, 1.2 mmol). The reaction mixture was stirred at RT for 17 h. The mixture was poured into water (150 mL). The precipitate was filtered, dissolved in DMF and purified by chromatography on a C-18 reverse phase column (eluant: acetonitrile/water gradient) to give 2-(3-methyl-1- piperidinyl)-N-[6-[3-oxo-4-(phenylmethyl)-1-piperazinyl]-3-pyridinyl]-4-(trifluoromethyl)-5-oxazolecarboxamide (31) (169 mg, 52% yield) $^1$H NMR (500 MHz, CDCl$_3$) δ 8.28 (s, 1H), 8.04 (d, 1H, J=9 Hz), 7.61 (s, 1H), 7.4-7.3 (m, 5H), 6.64 (d, 1H, J=9 Hz), 4.73 (s, 2H), 4.23 (s, 2H), 4.15 (bt, 2H), 3.88 (t, 2H, J=5.5 Hz), 3.43 (t, 2H, J=5.5 Hz), 3.08 (dt, 1H), 2.75 (t, 1H, J=12 Hz), 1.97-1.74 (m, 3H), 1.31 (bs, 1H), 1.28-1.16 (m, 2H), 1.03 (d, 3H, J=6.5 Hz). LCMS (ESI) Rt=3.83 min, 543.3 [M+1]$^+$.

Example 32

N-[6-[4-(2,3-dihydro-2-oxo-1H-benzimidazol-1-yl)-1-piperidinyl]-3-pyridinyl]-2-(3-methyl-1-piperidinyl)-4-(trifluoromethyl)-5-oxazolecarboxamide (32)

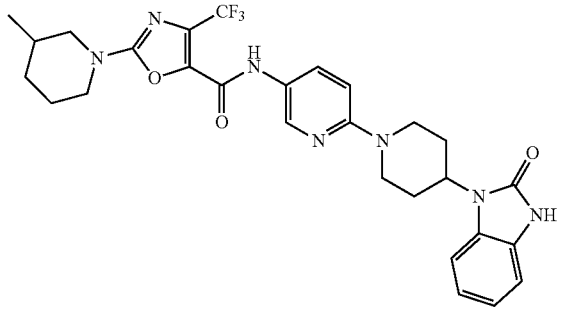

32

Compound 32 was prepared by the general procedure for compound 31, by using intermediates A-10 and B-16 as starting materials. $^1$H NMR (500 MHz, DMSO-d6) δ 10.85 (s, 1H), 10.03 (s, 1H), 8.37 (s, 1H), 7.83 (dd, 1H), 7.12 (m, 1H), 6.98 (m, 4H), 4.48 (bd, 3H, J=12.5 Hz), 4.14 (dd, 3H, J=12.5 Hz, 12.5 Hz), 3.06 (t, 1H, J=12.5 Hz), 2.97 (t, 2H, J=11 Hz), 2.76 (dd, 1H, J=11 Hz,11 Hz), 2.34 (q, 2H, J=12.5 Hz), 1.74-1.59 (m, 6H), 1.26-1.22 (m, 1H), 0.94 (d, 3H, J=6.5 Hz). LCMS (ESI) Rt=3.40 min, 570.3 [M+1]$^+$.

Example 33

N-[6-[1-oxo-2-(phenylmethyl)-2,8-diazaspiro[4.5]dec-8-yl]-3-pyridinyl]-2-(3-methyl-1-piperidinyl)-4-(trifluoromethyl)-5-oxazolecarboxamide (33)

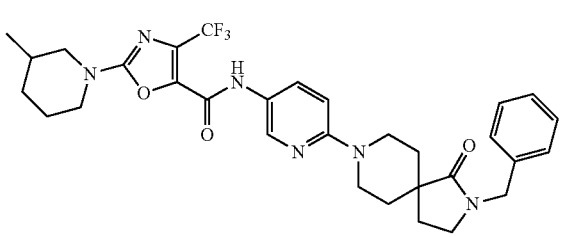

33

Compound 33 was prepared by the general procedure for compound 31, by using intermediates A-10 and B-17 as starting materials. $^1$H NMR (500 MHz, CDCl$_3$) δ 8.21 (s, 1H), 8.02 (d, 1H, J=9 Hz), 7.59 (s, 1H), 7.4-7.3 (m, 3H), 7.27 (d, 2H, J=8 Hz) 6.74 (d, 1H, J=8 Hz), 4.52 (s, 2H), 4.22 (dt, 2H J=13.5 Hz, J=4 Hz), 4.15 (bt, 2H), 3.26 (t, 2H, J=7 Hz), 3.18 (td, 2H, J=12 Hz, J=3 Hz), 3.09 (td, 1H, J=12.5 Hz, J=3 Hz), 2.78 (t, 1H, J=12 Hz), 2.14-2.02 (m, 4H), 1.98-1.62 (m, 5H), 1.56 (d, 2H, J=13.5 Hz), 1.22 (td, 1H, J=12.5 Hz, J=4 Hz), 1.04 (d, 3H, J=7 Hz). LCMS (ESI) Rt=3.51 min, 597.3 [M+1]$^+$.

Example 34

N-[6-[4-[2,3-dihydro-2-oxo-3-(phenylmethyl)-1H-benzimidazol-1-yl]-1-piperidinyl]-3-pyridinyl]-2-(3-methyl-1-piperidinyl)-4-(trifluoromethyl)-5-oxazolecarboxamide (34)

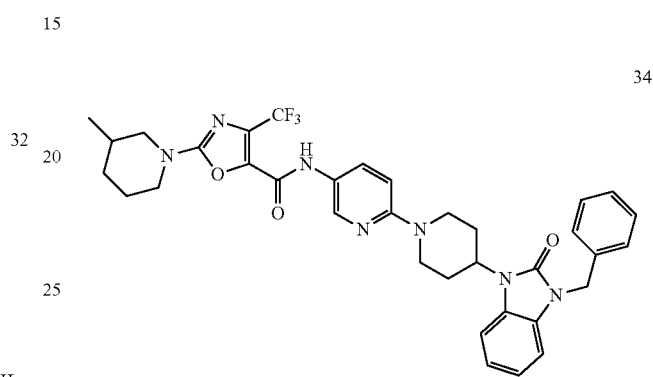

34

Compound 34 was prepared by the general procedure for compound 31, by using intermediates A-10 and B-18 as starting materials. $^1$H NMR (500 MHz, CDCl$_3$) δ 8.25 (d, 1H, J=3 Hz), 8.07 (dd, 1H, J=2.5 Hz), 7.60 (s, 1H), 7.37 (m, 4H), 7.16 (d, 1H, J=7.5 Hz), 7.05 (m, 2H), 6.95 (d, 1H, J=8.5 Hz), 6.80 (d, 1H, J=9.5 Hz), 5.13 (s, 2H), 4.72 (tt, 1H, J=12.5 Hz, J=4.5 Hz), 4.55 (d, 2H, J=13.5 Hz), 4.16 (bt, 2H, J=15.5 Hz), 3.08 (q, 3H, J=12.5 Hz), 2.77 (t, 1H, J=11 Hz), 2.53 (qd, 2H, J=12.5 Hz, 4 Hz), 2.04-1.62 (m), 1.34-1.18 (m), 1.04 (d, 3H J=11 Hz). LCMS (ESI) Rt=3.72 min, 660.4 [M+1]$^+$.

Example 35

N-[6-[4-(2,3-dihydro-3-methyl-2-oxo-1H-benzimidazol-1-yl)-1-piperidinyl]-3-pyridinyl]-2-(3-methyl-1-piperidinyl)-4-(trifluoromethyl)-5-oxazolecarboxamide (35)

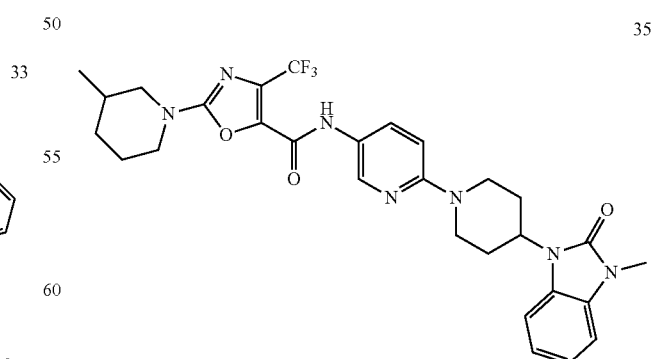

35

Compound 35 was prepared by the general procedure for compound 31, by using intermediates A-10 and B-19 as starting materials. $^1$H NMR (500 MHz, CDCl$_3$) δ 8.25 (d, 1H, J=2.5 Hz), 8.07 (dd, 1H J=9.5 Hz, J=2.5 Hz), 7.61 (s, 1H), 7.14 (t, 2H, J=8 Hz), 7.09 (t, 1H, J=8 Hz), 7.04 (d, 1H, J=8 Hz), 6.80 (d, 1H, J=9 Hz), 4.67 (tt, 1H, J=12.5 Hz, J=4 Hz), 4.53 (d, 2H, J=13 Hz), 4.16 (bt, 2H, J=16 Hz), 3.47 (s, 3H), 3.14-3.01 (m, 3H), 2.77 (t, 1H, J=13 Hz), 2.52 (qd, 1H, J=12.5 Hz, 4 Hz), 2.00-1.59 (m, 6H), 1.34-1.17 (m, 1H), 1.04 (d, 3H, J=6.5 Hz). LCMS (ESI) Rt=3.56 min, 584.3 [M+1]⁺.

Example 36

N-[6-(2-methyl-1-oxo-2,8-diazaspiro[4.5]dec-8-yl)-3-pyridinyl]-2-(4-phenyl-1-piperidinyl)-4-(trifluoromethyl)-5-oxazolecarboxamide (36)

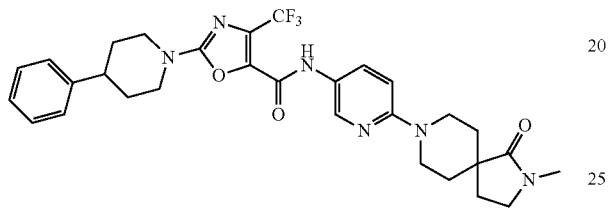

36

Compound 36 was prepared by the general procedure for compound 31, by using intermediates A-22 and B-20 as starting materials. ¹H NMR (500 MHz, CDCl₃) δ 8.20 (d, 1H, J=2.5 Hz), 8.01 (dd, 1H, J=2.5 Hz, J=9 Hz), 7.64 (s, 1H), 7.39 (t, 2H, J=7.5 Hz), 7.29 (t, 3H, J=7 Hz), 6.73 (d, 1H, J=8.5 Hz), 4.42 (bd, 2H, J=14.5 Hz), 4.21 (dt, 2H, J=13.5 Hz, J=4.5 Hz), 3.40 (t, 2H, J=7 Hz), 3.26 (td, 2H, J=13 Hz, J=2.5 Hz), 3.16 (td, 2H, J=12 Hz, J=2.5 Hz), 2.92 (s, 3H), 2.83 (tt, 1H, J=12 Hz, J=3 Hz), 2.50-1.98 (m, 6H), 1.86 (qd, 2H, J=13 Hz, J=4 Hz), 1.53 (d, 2H, J=13.5 Hz). LCMS (ESI) Rt=3.29 min, 583.3 [M+1]⁺.

Example 37

N-[6-[4-(2,3-dihydro-3-methyl-2-oxo-1H-benzimidazol-1-yl)-1-piperidinyl]-3-pyridinyl]-2-(4-phenyl-1-piperidinyl)-4-(trifluoromethyl)-5-oxazolecarboxamide (37)

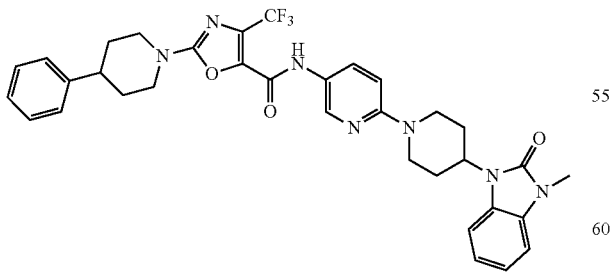

37

Compound 37 was prepared by the general procedure for compound 31, by using intermediates A-22 and B-19 as starting materials. ¹H NMR (500 MHz, CDCl₃) δ 8.25 (d, 1H, J=2.5 Hz), 8.08 (dd, 1H J=9 Hz, J=2.5 Hz), 7.64 (s, 1H), 7.40 (t, 2H, J=7.5 Hz), 7.33-7.26 (m, 2H), 7.14 (t, 2H, J=8 Hz), 7.09 (t, 1H, J=7.5 Hz), 7.04 (d, 1H, J=7.5 Hz), 6.80 (d, 1H, J=9.5 Hz), 4.67 (tt, 1H, J=12.5 Hz, J=4 Hz), 4.53 (d, 2H, J=13 Hz), 4.43 (b, 2H, J=13 Hz), 3.47 (s, 3H), 3.28 (td, 2H, J=12.5 Hz, J=2 Hz), 3.06 (t, 2H, J=12.5 Hz), 2.84 (tt, 1H, J=12 Hz, J=3.5 Hz), 2.51 (qd, 2H, J=12.5 Hz, J=3.5 Hz), 2.06 (2.07) (s(bd), 3H, J=13 Hz), 1.96 (bd, 2H, J=11 Hz), 1.89 (qd, 2H, J=12.5 Hz, J=3.5 Hz). LCMS (ESI) Rt=3.69 min, 646.4 [M+1]⁺.

Example 38 tert-butyl 4-[5-(2-(3-methylpiperidin-1-yl)-4-(trifluoromethyl)oxazole-5-carboxamido)pyridin-2-yl]homopiperazine-1-carboxylate (38)

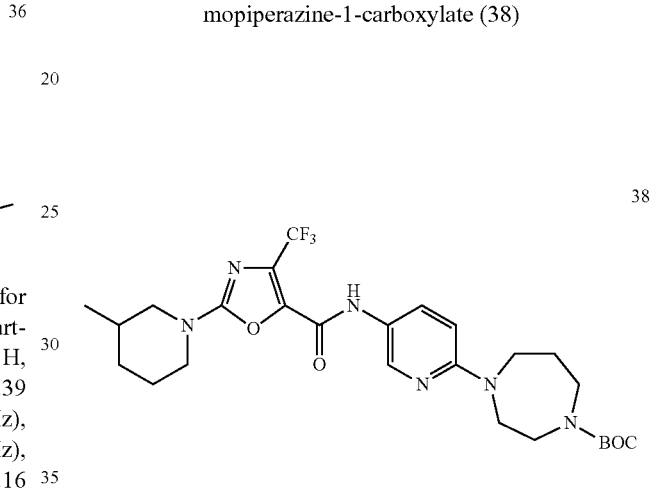

38

Compound 38 was prepared by the general procedure for compound 1, by using intermediates A-10 and B-21 as starting materials. ¹H NMR (500 MHz, CDCl₃) δ 8.15 (d, 1H, J=7 Hz), 8.50 (d, 1H, J=8.5 Hz), 7.60 (d, 1H, J=11.5 Hz), 6.55 (d, 1H, J=9 Hz), 4.15 (m, 2H), 3.80 (m, 2H), 3.65 (m, 2H), 3.60 (m, 2H), 3.35 (m, 1H), 3.25 (m, 1H), 3.05 (t, 1H, J=12.5 Hz), 2.70 (t, 1H, J=12.5), 1.60-2.05 (m, 6H), 1.45 (s, 9H), 1.20 (m, 1H), 1.00 (d, 3H, J=6.5 Hz). MS (M+1): 553.

Example 39

N-(6-(homopiperazin-1-yl)pyridin-3-yl)-2-(3-methylpiperidin-1-yl)-4-(trifluoromethyl)-oxazole-5-carboxamide (39)

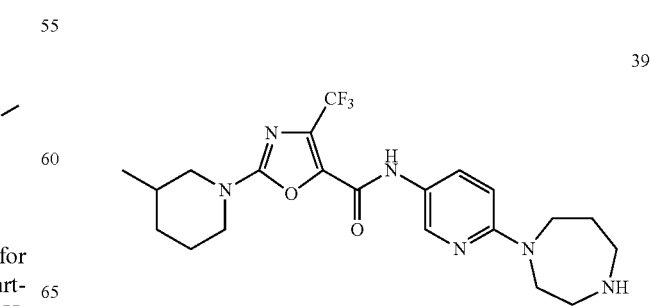

39

Compound 39 was prepared by the general procedure for intermediate C-3, by using compound 38 as starting material. MS (M+1): 453.

Example 40

4-[5-[[2-(3-methylpiperidin-1-yl)-4-(trifluoromethyl)-5-oxazolyl]carbonylamino]-2-pyridinyl]-N-(2-fluorophenyl)-1-homopiperazinecarboxamide (40)

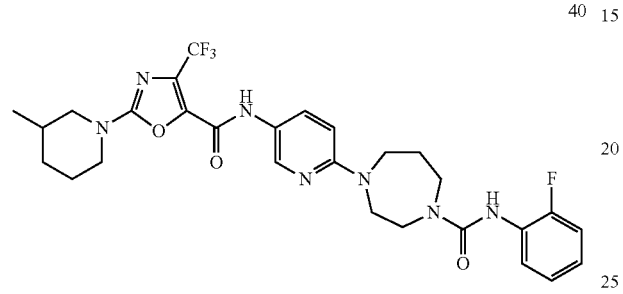

40

Compound 40 was prepared by the general procedure for compound 8, by using compound 39 and 2-fluorophenylisocyanate as starting materials. $^1$H NMR (500 MHz, CDCl$_3$) δ 8.15 (d, 1H, J=2.5 Hz), 8.10 (t, 1H, J=8 Hz), 7.90 (dd, 1H, J=2.5, 9 Hz), 7.50 (s, 1H), 7.10 (m, 2H), 7.00 (m, 1H), 6.60 (d, 1H, J=4 Hz), 6.55 (d, 1H, J=9 Hz), 4.10 (m, 2H), 3.90 (m, 2H), 3.75 (m, 4H), 3.45 (t, 2H, J=6.5 Hz), 3.05 (t, 1H, J=12 Hz), 2.75 (t, 1H, J=13 Hz), 2.10 (t, 2H, J=6 Hz), 1.90 (d, 1H, J=13 Hz), 1.80 (m, 2H), 1.65 (m, 1H), 1.20 (q, 1H, J=11.5 Hz), 1.00 (d, 3H, J=6.5 Hz). MS (M+1): 590.

Example 41

N-[6-(4-(benzylsulfonyl)homopiperazin-1-yl)pyridin-3-yl]-2-(3-methylpiperidin-1-yl)-4-(trifluoromethyl)oxazole-5-carboxamide (41)

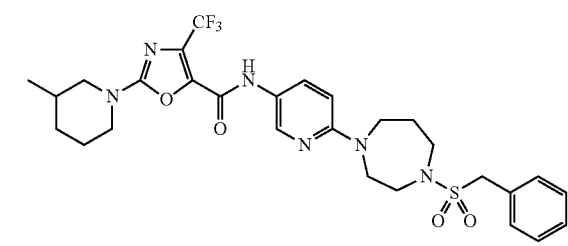

41

Compound 41 was prepared by the general procedure for compound 8, by using compound 39 and α-toluenesulfonyl chloride as starting materials. $^1$H NMR (500 MHz, CDCl$_3$) δ 8.10 (d, 1H, J=2.5 Hz), 7.85 (dd, 1H, J=2.5, 9 Hz), 7.50 (s, 1H), 7.40 (m, 3H), 7.35 (m, 2H), 6.50 (d, 1H, J=9 Hz), 4.25 (s, 2H), 4.10 (m, 2H), 3.75 (m, 4H), 3.20 (m, 2H), 3.05 (t, 1H, J=9.5 Hz), 2.95 (t, 1H, J=6 Hz), 2.75 (t, 1H, J=11 Hz), 1.60-2.00 (m, 6H), 1.20 (q, 1H, J=11 Hz), 1.00 (d, 3H, J=7 Hz). MS (M+1): 607.

Example 42

4-[5-[[2-(3-methylpiperidin-1-yl)-4-(trifluoromethyl)-5-oxazolyl]carbonylamino]-2-pyridinyl]-N-(2-fluorophenyl)-1-homopiperazinethiocarboxamide (42)

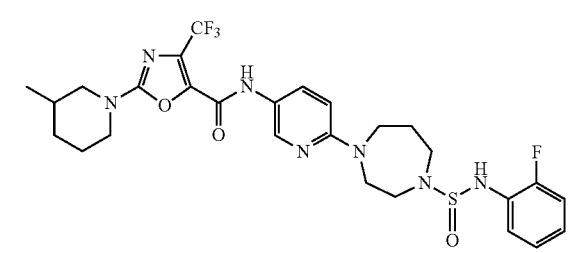

42

Compound 42 was prepared by the general procedure for compound 8, by using compound 39 and 2-fluorophenylthioisocyanate as starting materials. $^1$H NMR (500 MHz, CDCl$_3$) δ 8.20 (d, 1H, J=2.5 Hz), 7.90 (dd, 1H, J=2.5, 9 Hz), 7.80 (br s, 1H), 7.55 (s, 1H), 7.15 (m, 4H), 6.60 (d, 1H, J=9 Hz), 4.15 (m, 4H), 4.00 (br s, 2H), 3.80 (br s, 2H), 3.75 (t, 2H, J=6 Hz), 3.05 (t, 1H, J=12.5 Hz), 2.70 (t, 1H, J=11 Hz), 2.20 (t, 2H, J=6 Hz), 1.60-2.00 (m, 4H), 1.20 (q, 1H, J=11.5 Hz), 1.00 (d, 3H, J=6.5 Hz). MS (M+1): 606.

Example 43

Cyclopentyl 4-[5-(2-(3-methylpiperidin-1-yl)-4-(trifluoromethyl)oxazole-5-carboxamido)pyridin-2-yl]homopiperazine-1-carboxylate (43)

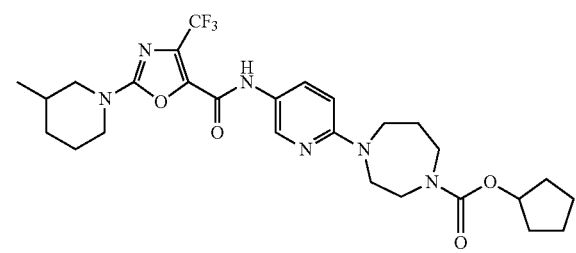

43

Compound 43 was prepared by the general procedure for compound 8, by using compound 39 and cyclopentyl chloroformate as starting materials. $^1$H NMR (500 MHz, CDCl$_3$) δ 8.10 (br s, 1H), 7.90 (d, 1H, J=9 Hz), 7.50 (s, 1H), 6.50 (d, 1H, J=9 Hz), 5.10 (br s, 1H), 4.10 (t, 2H, J=14.5 Hz), 3.80 (m, 2H), 3.60 (m, 3H), 3.40 (t, 1H, J=6 Hz), 3.25 (t, 1H, J=6 Hz), 3.05

(t, 1H, J=13 Hz), 2.70 (t, 1H, J=13 Hz), 1.55-2.00 (m, 16H), 1.20 (q, 1H, J=12.5 Hz), 1.00 (d, 3H, J=7 Hz). MS (M+1): 565.

Example 44

N-(1H-indol-5-yl)-2-(3-methyl-1-piperidinyl)-4-(trifluoromethyl)-5-oxazolecarboxamide (44)

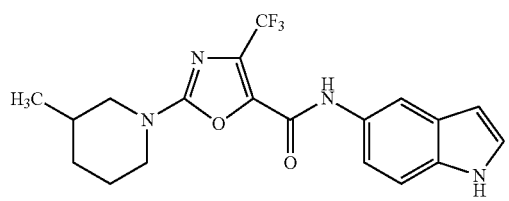

44

Compound 44 was prepared by the general procedure for compound 1, by using intermediates A-10 and 5-aminoindole as starting materials. $^1$H NMR (500 MHz, DMSO-d$_6$) δ 11.10 (br s, 1H), 10.01 (s, 1H), 7.36 (m, 2H), 7.30 (br d, 1H, J=6.8 Hz), 6.41 (s, 1H), 4.12 (m, 2H), 3.29 (br s, 1H), 3.05 (t, 1H, J=12.3 Hz), 2.74 (t, 1H, J=12.2 Hz), 1.70 (m, 3H), 1.53 (m, 1H), 1.15 (m, 1H), 0.94 (d, 3H, J=6.0 Hz). MS (M+1): 393.

Example 45

N-(2,6-dichlorophenyl)-5-[[2-(3-methyl-1-piperidinyl)-4-(trifluoromethyl)-5-oxazolyl]carbonylamino]-1H-indole-1-carboxamide (45)

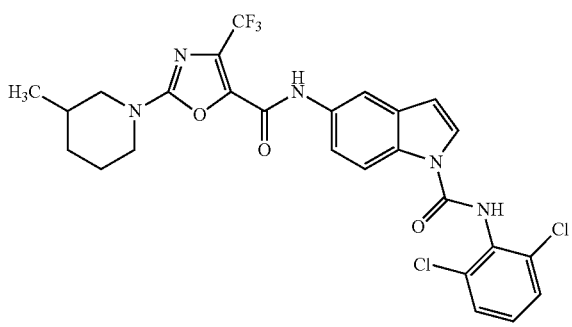

45

To a solution of compound 44 (0.050 g, 0.126 mmol) and 2,6-dichlorophenylisocyanate (0.025 g, 0.133 mmol) in anhydrous DMF (1.0 mL) at room temperature was added potassium carbonate (0.026 g, 0.189 mmol). The reaction mixture was stirred at room temperature for 72 h (eventually with addition of 2,6-dichlorophenyl isocyanate (0.025 g, 0.133 mmol) to drive the reaction to completion). The reaction mixture was then quenched with methanol (0.2 mL), stirred for 60 mins and concentrated. Purification of the crude residue by silica gel chromatography (eluant gradient: 100% methylene chloride to 100% EtOAc) followed by C$_{18}$ reverse phase chromatography (eluant: H$_2$O:CH$_3$CN gradient) gave 0.033 g (45% yield) of N-(2,6-dichlorophenyl)-5-[[2-(3-methyl-1-piperidinyl)-4-(trifluoromethyl)-5-oxazolyl]carbonylamino]-1H-indole-1-carboxamide (45) as a white solid. $^1$H NMR (500 MHz, DMSO-d$_6$) δ 10.18 (br s, 1H), 10.15 (br s, 1H), 8.18 (d, 1H, J=9.1 Hz), 8.10 (m, 2H), 7.66 (d, 2H, J=7.9 Hz), 7.48 (m, 2H), 6.84 (d, 1H, J=3.5 Hz), 4.13 (m, 2H), 3.06 (t, 1H, J=12.0 Hz), 2.76 (t, 1H, J=11.6 Hz), 1.72 (m, 3H), 1.54 (m, 1H), 1.15 (m, 1H), 0.94 (d, 3H, J=6.5 Hz). MS (M+1): 580/582.

Example 46

N-[1-[(phenylmethyl)sulfonyl]-1H-indol-5-yl]-2-(3-methyl-1-piperidinyl)-4-(trifluoromethyl)-5-oxazolecarboxamide (46)

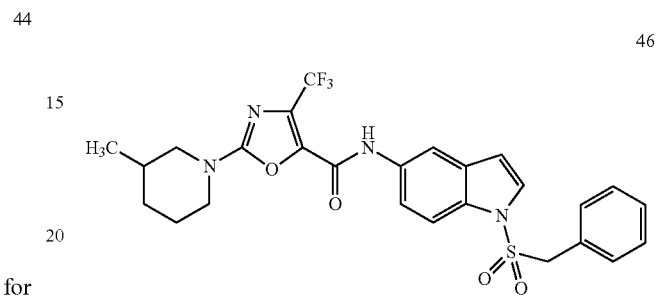

46

To a solution of compound 44 (0.050 g, 0.126 mmol) in anhydrous DMF (0.64 mL) at 0° C. under argon was added sodium hydride (60% dispersion in oil, 7.70 mg, 0.191 mmol). The reaction mixture was stirred for 20 mins and -toluenesulfonyl chloride (48.5 mg, 0.254 mmol) was added. The reaction mixture was stirred at RT for 12 h and was then diluted with methylene chloride (20 mL), quenched with an aqueous pH 7 phosphate buffer solution (10 mL). The aqueous layer was extracted with methylene chloride (2×30 mL). The combined organic extracts were then washed with brine (20 mL), dried over MgSO$_4$, filtered, and concentrated. Purification by silica gel chromatography (eluant: 100% methylene chloride to 50:50-EtOAc:methylene chloride gradient) followed by C$_{18}$ reverse phase chromatography (eluant: H$_2$O: CH$_3$CN gradient) gave 6.4 mg (10% yield) of N-[1-[(phenylmethyl)sulfonyl]-1H-indol-5-yl]-2-(3-methyl-1-piperidinyl)-4-(trifluoromethyl)-5-oxazolecarboxamide (46) as a white solid. $^1$H NMR (500 MHz, DMSO-d$_6$) δ 11.32 (br s, 1H), 7.42 (m, 6H), 7.25 (d, 1H, J=8.5 Hz), 6.84 (s, 1H), 6.45 (dm, 1H, J=8.5 Hz), 6.34 (m, 1H), 5.16 (s, 2H), 3.20 (m, 1H), 3.08 (m, 1H), 2.21 (t, 1H, J=12.0 Hz), 1.51 (m, 1H), 1.28 (m, 2H), 1.06 (m, 1H), 0.89 (m, 2H), 0.64 (d, 3H, J=6.4 Hz). MS (M+1): 547.

Example 47

5-[[2-(3-methyl-1-piperidinyl)-4-(trifluoromethyl)-5-oxazolyl]carbonylamino]-N-(2-nitrophenyl)-1H-indole-1-carboxamide (47)

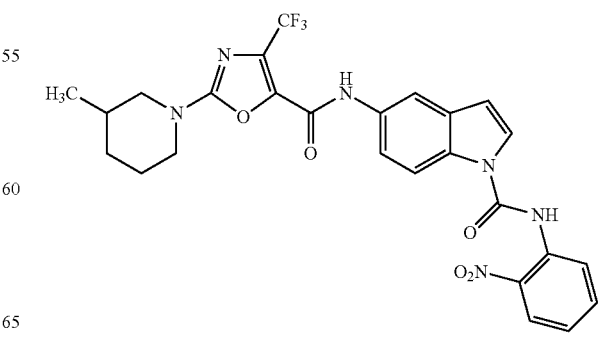

47

Compound 47 was prepared by the general procedure for compound 45, using compound 44 and 2-nitrophenyl isocyanate as starting materials. $^1$H NMR (500 MHz, DMSO-d$_6$) δ 10.55 (br s, 1H), 10.18 (br s, 1H), 8.14 (br d, 1H, J=8.5 Hz), 8.08 (br s, 1H), 8.05 (br d, 1H, J=8.5 Hz), 8.00 (br d, 1H, J=8.0 Hz), 7.79 (tm, 1H, J=7.6 Hz), 7.72 (br d, 1H, J=8.2 Hz), 7.51 (br d, 1H, J=8.2 Hz), 7.46 (m, 1H), 6.84 (m, 1H), 4.13 (m, 2H), 3.06 (br t, 1H, J=12.0 Hz), 2.76 (br t, 1H, J=11.7 Hz), 1.74 (m, 3H), 1.54 (m, 1H), 1.16 (m, 1H), 0.94 (d, 3H, J=6.3 Hz). MS (M+1): 557.

Example 48 phenyl 5-[[2-(3-methyl-1-piperidinyl)-4-(trifluoromethyl)-5-oxazolyl]carbonylamino]-1H-indole-1-acetate (48)

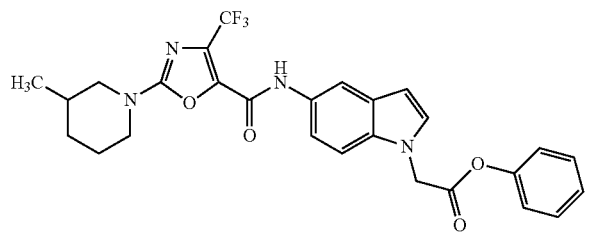

Compound 48 was prepared by the general procedure for compound 45, by using compound 44 and phenyl 2-bromoacetate as starting materials. $^1$H NMR (500 MHz, DMSO-d$_6$) δ 10.22 (br s, 1H), 8.29 (m, 1H), 8.08 (m, 1H), 7.96 (dd, 1H, J=3.5, 13.3 Hz), 7.58 (m, 1H), 7.45 (m, 1H), 7.34 (m, 2H), 7.07 (d, 1H, J=8.5 Hz), 6.99 (t, 1H, J=7.4 Hz), 6.85 (m, 1H), 4.84 (s, 2H), 4.15 (d, 1H, J=13.2 Hz), 4.10 (d, 1H, J=13.6 Hz), 3.06 (t, 1H, J=12.0 Hz), 2.76 (dd, 1H, J=11.0, 12.3 Hz), 1.71 (m, 3H), 1.54 (m, 1H), 1.15 (m, 1H); 0.94 (d, 3H, J=6.3 Hz). MS (M+1): 527.

Example 49

N-(1H-indazol-5-yl)-2-(3-methyl-1-piperidinyl)-4-(trifluoromethyl)-5-oxazolecarboxamide (49)

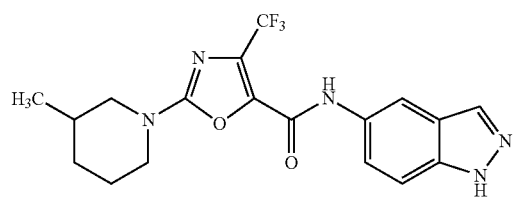

Compound 49 was prepared by the general procedure for compound 1, by using compound A-10 and 5-aminoindazole as starting materials. $^1$H NMR (500 MHz, CD$_3$OD) δ 8.10 (br s, 1H), 8.06 (br s, 1H), 7.58 (m, 2H), 4.92 (br s, 2H), 4.23 (m, 2H), 3.74 (m, 2H), 3.25 (q, 2H, J=7.5 Hz), 3.11 (dt, 1H, J=2.9, 12.6 Hz), 2.79 (t, 1H, J=11.7 Hz), 1.91 (m, 1H), 1.84 (m, 1H), 1.76 (m, 1H), 1.66 (m, 1H), 1.39 (m, 15H), 1.25 (m, 1H), 1.02 (d, 3H, J=6.6 Hz). MS (M+1): 394.

Example 50

5-[[2-(3-methyl-1-piperidinyl)-4-(trifluoromethyl)-5-oxazoly]carbonylamino]-N-phenyl-1H-indazole-1-carboxamide (50)

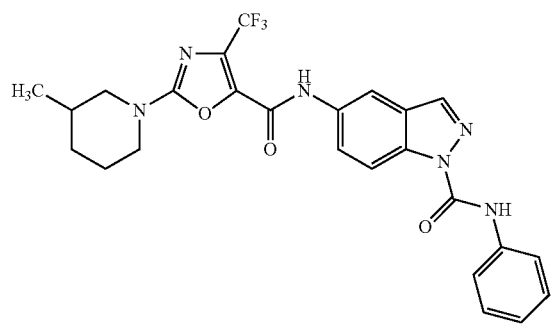

To a solution of compound 49 (0.060 g, 0.152 mmol) in anhydrous methylene chloride (1.52 mL) at room temperature under argon was added phenyl isocyanate (0.018 mL, 0.160 mmol). The reaction mixture was stirred at room temperature for 17 h and another portion of phenyl isocyanate (0.018 mL, 0.160 mmol) was added. After additional stirring at room temperature for 17 h, the reaction mixture was quenched with methanol (1.0 mL) and concentrated. Purification by silica gel chromatography (eluant: 100% methylene chloride to 100% EtOAc gradient) gave 32.7 mg (42% yield) of 5-[[2-(3-methyl-1-piperidinyl)-4-(trifluoromethyl)-5-oxazolyl]carbonylamino]-N-phenyl-1H-indazole-1-carboxamide (50) as a white solid. $^1$H NMR (500 MHz, CD$_3$OD) δ 8.31 (br d, 1H, J=8.8 Hz), 8.24 (m, 2H), 7.70 (m, 3H), 7.39 (br t, 2H, J=7.9 Hz), 7.16 (t, 1H, J=7.4 Hz), 4.90 (br s, 2H), 4.20 (m, 2H), 3.08 (td, 1H, J=12.4, 3.1 Hz), 2.75 (dd, 1H, J=12.3, 12.6 Hz), 1.89 (m, 1H), 1.82 (m, 1H), 1.74 (m, 1H), 1.65 (m, 1H), 1.23 (m, 1H), 1.01 (d, 3H, J=6.6 Hz). MS (M+1): 513.

Examples 51 and 52

N-[1-(2-methoxyethyl)-1H-indazol-5-yl]-2-(3-methyl-1-piperidinyl)-4-(trifluoromethyl)-5-oxazolecarboxamide (51) N-[2-(2-methoxyethyl)-2H-indazol-5-yl]-2-(3-methyl-1-piperidinyl)-4-(trifluoromethyl)-5-oxazolecarboxamide (52)

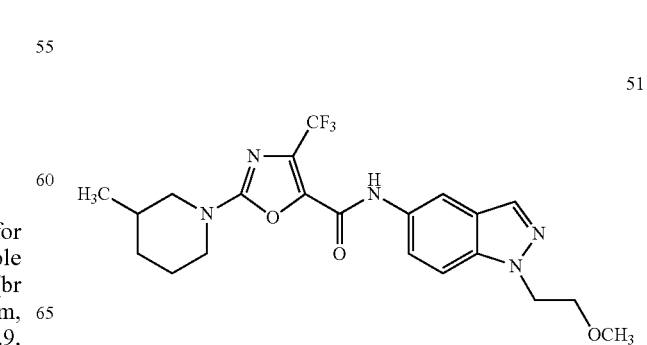

-continued

52

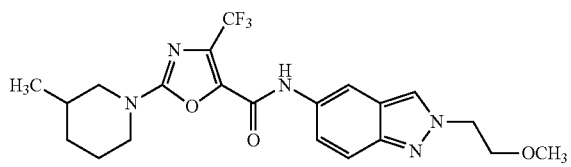

Compounds 51 and 52 were prepared by the general procedure for compound 44, by using compound 49 and 1-chloro-2-methoxyethane as starting materials.

For compound 51: $^1$H NMR (500 MHz, DMSO-d$_6$) δ 10.17 (br s, 1H), 8.10 (m, 1H), 8.07 (m, 1H), 7.68 (br d, 1H, J=8.8 Hz), 7.57 (dm, 1H, J=8.8 Hz), 4.56 (t, 2H, J=5.2 Hz), 4.12 (m, 2H), 3.76 (t, 2H, J=5.2 Hz), 3.19 (s, 3H), 3.06 (br t, 1H, J=12.0 Hz), 2.76 (t, 1H, J=11.8 Hz), 1.78 (m, 2H), 1.68 (m, 1H), 1.54 (m, 1H), 1.16 (m, 1H); 0.94 (d, 3H, J=6.6 Hz). Compound 51 was also confirmed as the N$_1$ alkylation product by the presence of $^1$H NOE between the indazole H$_8$ and NCH$_2$CH$_2$OCH$_3$. MS (M+1): 452.

For compound 52: $^1$H NMR (500 MHz, DMSO-d$_6$) δ 10.10 (br s, 1H), 8.34 (br s, 1H), 8.11 (br s, 1H), 7.61 (dm, 1H, J=9.1 Hz), 7.40 (dm, 1H, J=9.4 Hz), 4.57 (t, 2H, J=5.0 Hz), 4.12 (m, 2H), 3.83 (t, 2H, J=5.0 Hz), 3.24 (s, 3H), 3.06 (br t, 1H, J=11.8 Hz), 2.75 (t, 1H, J=11.8 Hz), 1.78 (m, 2H), 1.67 (m, 1H), 1.54 (m, 1H), 1.15 (m, 1H); 0.94 (d, 3H, J=6.6 Hz). Compound 52 was also confirmed as the N$_2$-alkylation product by the presence of strong $^1$H NOE between the indazole H$_3$ and NCH$_2$CH$_2$OCH$_3$. MS (M+1): 452.

Example 53

N-[1-[(1-methylethyl)sulfonyl]-1H-indazol-5-yl]-2-(3-methyl-1-piperidinyl)-4-(trifluoromethyl)-5-oxazolecarboxamide (53)

53

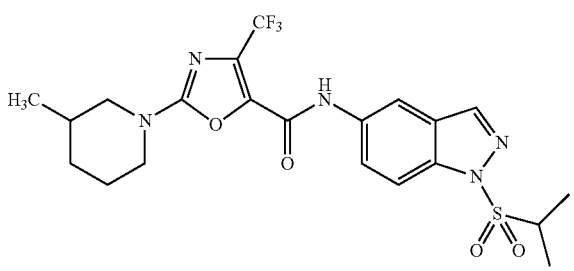

Compound 53 was prepared by the general procedure for compound 46, by using compound 49 and isopropylsulfonyl chloride as starting materials. $^1$H NMR (500 MHz, DMSO-d$_6$) δ 10.36 (br s, 1H), 8.63 (br s, 1H), 8.36 (br s, 1H), 7.97 (br d, 1H, J=9.1 Hz), 7.83 (dm, 1H, J=8.8 Hz), 4.12 (m, 2H), 3.87 (h, 1H, J=7.0 Hz), 3.07 (br t, 1H, J=13.0 Hz), 2.77 (t, 1H, J=11.8 Hz), 1.78 (m, 2H), 1.68 (m, 1H), 1.55 (m, 1H), 1.18 (d, 6H, J=7.0 Hz), 1.16 (m, 1H), 0.95 (d, 3H, J=6.6 Hz). MS (M+1): 500.

Example 54

N-[1H-pyrrolo[2,3-b]pyridin-5-yl]-2-(3-methyl-1-piperidinyl)-4-(trifluoromethyl)-5-oxazolecarboxamide (54)

54

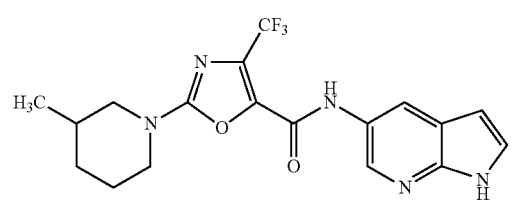

Compound 54 was prepared by the general procedure for compound 1, by using compound A-10 and 5-amino-7-azaindole as starting materials. $^1$H NMR (500 MHz, DMSO-d$_6$) δ 11.67 (s, 1H), 10.21 (s, 1H), 8.37 (s, 1H), 8.23 (s, 1H), 7.50 (s, 1H), 6.46 (m, 1H), 4.13 (m, 2H), 3.07 (m, 1H), 2.75 (t, 1H, J=11.7 Hz), 1.77 (m, 2H), 1.67 (m, 1H), 1.54 (m, 1H), 1.15 (m, 1H), 0.94 (d, 3H, J=6.3 Hz). MS (M+1): 394.

Example 55

N-[2,3-dihydro-2-oxo-1H-benzimidazol-5-yl]-2-(3-methyl-1-piperidinyl)-4-(trifluoromethyl)-5-oxazole-carboxamide (55)

55

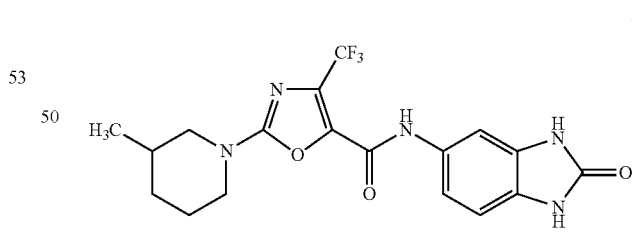

Compound 55 was prepared by the general procedure for compound 1, by using compound A-10 and 5-aminobenzimidazolone as starting materials (5-aminobenzimidazolone was prepared by reduction of 5-nitrobenzimidazolone according to Regan, J. and coll. *J. Med. Chem.* 2002, 45, 2994-3008). $^1$H NMR (500 MHz, DMSO-d$_6$) δ 10.67 (s, 1H), 10.60 (s, 1H), 10.01 (s, 1H), 7.42 (s, 1H), 7.17 (br d, 1H, J=8.2 Hz), 6.89 (d, 1H, J=8.5 Hz), 4.10 (m, 2H), 3.04 (br t, 1H, J=12.5 Hz), 2.74 (m, 1H), 1.77 (m, 2H), 1.67 (m, 1H), 1.53 (m, 1H), 1.15 (m, 1H), 0.93 (d, 3H, J=6.6 Hz). MS (M+1): 410.

Example 56 methyl 3-((1-(5-(2-(3-methylpiperidin-1-yl)-4-(trifluoromethyl)oxazole-5-carboxamido)pyridin-2-yl)piperidine-4-sulfonamido)methyl)benzoate (56)

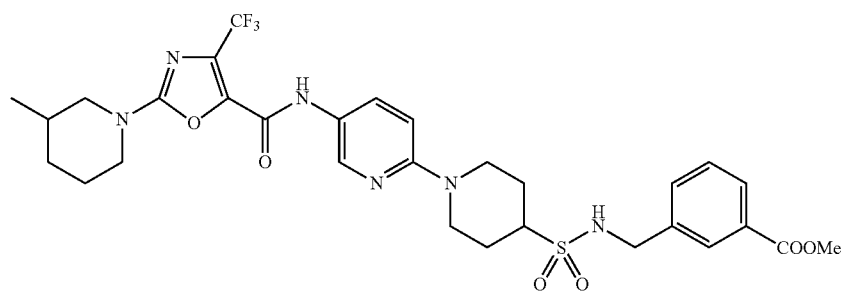

56

Compound 56 was prepared by the general procedure for compound 1. $^1$H NMR (500 MHz, DMSO-d6) δ 10.02 (s, 1H), 8.34 (s, 1H), 7.99 (s, 1H), 7.87 (d, 1H, J=7 Hz), 7.81 (m, 2H), 7.62 (d, 1H, J=8 Hz), 7.51 (t, 1H, J=8 Hz), 6.91 (d, 1H, J=9 Hz), 4.38 (d, 2H, J=13.5 Hz), 4.27 (d, 2H, J=6 Hz), 4.12 (d, 1H, J=12.5 Hz), 4.07 (d, 1H, J=13 Hz), 3.87 (s, 3H), 3.24 (t, 1H, J=12 Hz), 3.06 (t, 1H, J=12.5 Hz), 2.81 (t, 2H, J=12 Hz), 2.75 (t, 1H, J=12.5 Hz), 2.02 (d, 2H, J=11.5 Hz), 1.77 (m, 2H), 1.67 (m, 1H), 1.56 (m, 3H), 1.15 (q, 1H, J=11.5 Hz), 0.93 (d, 3H, J=6.5 Hz). MS (M+1): 665.

Example 57

3-((1-(5-(2-(3-methylpiperidin-1-yl)-4-(trifluoromethyl)oxazole-5-carboxamido)pyridin-2-yl)piperidine-4-sulfonamido)methyl)benzoic acid (57)

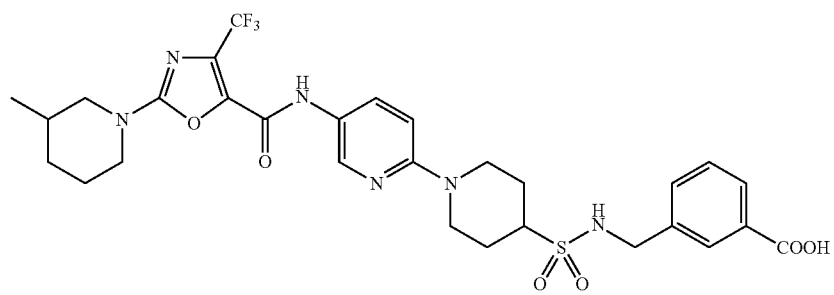

57

Compound 57 was prepared by the saponification of compound 56. $^1$H NMR (500 MHz, DMSO-d6) δ 10.08 (s, 1H), 8.36 (s, 1H), 7.98 (s, 1H), 7.86 (m, 2H), 7.82 (t, 1H, J=6.5 Hz), 7.58 (d, 1H, J=8 Hz), 7.48 (t, 1H, J=7.5 Hz), 7.02 (d, 1H, J=9 Hz), 4.36 (d, 2H, J=13 Hz), 4.26 (d, 2H, J=6 Hz), 4.12 (d, 1H, J=13 Hz), 4.07 (d, 1H, J=12.5 Hz), 3.25 (t, 1H, J=12 Hz), 3.06 (t, 1H, J=11.5 Hz), 2.87 (t, 2H, J=12.5 Hz), 2.75 (t, 1H, J=11.5

Hz), 2.04 (d, 2H, J=12 Hz), 1.77 (m, 2H), 1.60 (m, 4H), 1.15 (q, 1H, J=11 Hz), 0.94 (d, 3H, J=6.5 Hz). MS (M+1): 651.

Example 58

N-[6-(4-phenyl-1-piperazinyl)-3-pyridinyl]-2-(1-piperidinyl)-4-(trifluoromethyl)-5-thiazolecarboxamide (58)

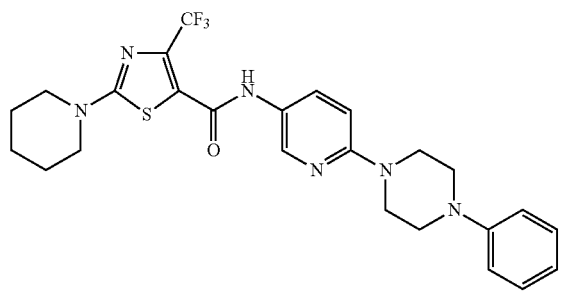

Compound 58 was prepared by the general procedure for compound 1, by using intermediates A-33 and B-12 as starting materials. $^1$H NMR (500 MHz, CDCl$_3$) δ 8.23 (d, 1H, J=2.5 Hz), 7.93-7.91 (m, 1H), 7.61 (m, 1H), 7.34-7.31 (m, 2H), 7.02-7.01 (m, 2H), 6.94-6.91 (m, 1H), 6.74 (d, 1H, J=9.0 Hz), 6.72-6.71 (m, 4H), 3.55 (m, 4H), 3.34-3.32 (m, 4H), 1.72 (m, 6H); LCMS (ESI) [M+1]$^+$ 517.3.

Example 59

N-[6-(4-phenyl-1-piperidinyl)-3-pyridinyl]-2-(1-piperidinyl)-4-(trifluoromethyl)-5-thiazolecarboxamide (59)

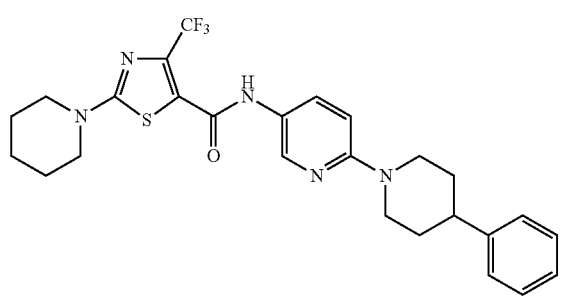

Compound 59 was prepared by the general procedure for compound 1, by using intermediates A-33 and B-6 as starting materials. $^1$H NMR (500 MHz, CDCl$_3$) δ 8.21 (d, 1H, J=2.5 Hz), 7.89-7.87 (m, 1H), 7.59 (m, 1H), 7.36-7.22 (m, 5H), 6.74 (d, 1H, J=9.0 Hz), 4.45-4.42 (m, 2H), 3.55 (m, 4H), 2.99-2.93 (m, 2H), 2.81-2.74 (m, 1H), 1.99-1.96 (m, 2H), 1.85-1.76 (m, 2H), 1.72 (m, 6H); LCMS (ESI) [M+1]$^+$ 516.3.

Example 60

N-[6-(4-hydroxy-4-phenyl-1-piperidinyl)-3-pyridinyl]-2-(1-piperidinyl)-4-(trifluoromethyl)-5-thiazolecarboxamide (60)

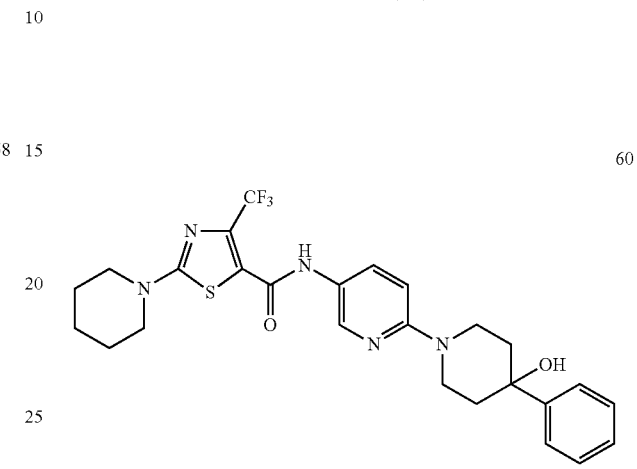

Compound 60 was prepared by the general procedure for compound 1, by using intermediates A-33 and B-2 as starting materials. $^1$H NMR (500 MHz, CDCl$_3$) δ 8.21 (d, 1H, J=2.5 Hz), 7.89-7.87 (m, 1H), 7.60 (m, 1H), 7.52-7.52 (m, 2H), 7.41-7.38 (m, 2H), 7.32-7.29 (m, 1H), 6.76 (d, 1H, J=9.0 Hz), 4.44-4.20 (m, 2H), 3.55 (m, 4H), 3.44-3.39 (m, 2H), 2.21-2.15 (m, 2H), 1.89-1.86 (m, 2H), 1.72 (m, 6H); LCMS (ESI) [M+1]$^+$ 532.3.

Example 61

2-(1-piperidinyl)-N-[6-(2-thienyl)-3-pyridinyl]-4-(trifluoromethyl)-5-thiazolecarboxamide (61)

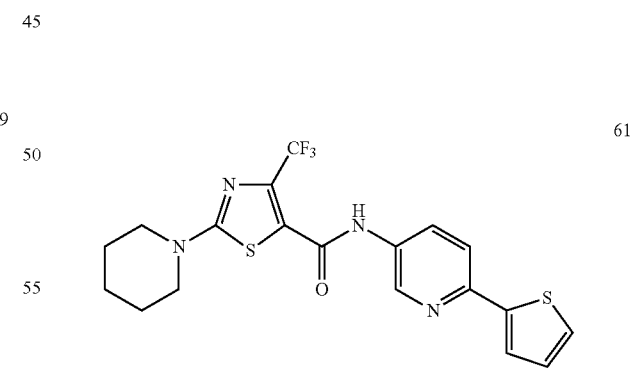

Compound 61 was prepared by the general procedure for compound 1, by using intermediates A-33 and 5-amino-2-(2-thiophenyl)-pyridine as starting materials. $^1$H NMR (500 MHz, CDCl$_3$) δ 8.55 (d, 1H, J=2.5 Hz), 8.23-8.21 (m, 1H), 7.84-7.83 (m, 1H), 7.68 (d, 1H, J=8.5 Hz), 7.57-7.56 (m, 1H), 7.41-7.40 (m, 1H), 7.14-7.12 (m, 1H), 3.57-3.56 (m, 4H), 1.73 (m, 6H); LCMS (ESI) [M+1]$^+$ 439.3.

Example 62

N-(6-phenyl-3-pyridinyl)-2-(1-piperidinyl)-4-(trifluoromethyl)-5-thiazolecarboxamide (62)

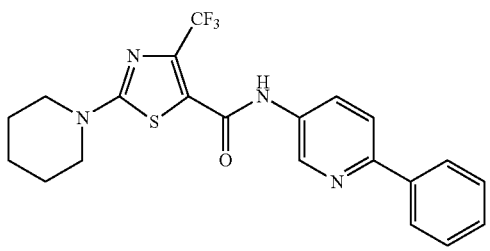

62

Compound 62 was prepared by the general procedure for compound 1, by using intermediates A-33 and 5-amino-2-phenyl-pyridine as starting materials. $^1$H NMR (500 MHz, CDCl$_3$) δ 8.68 (d, 1H, J=2.5 Hz), 8.28-8.26 (m, 1H), 8.00-7.99 (m, 2H), 7.88 (m, 1H), 7.77 (d, 1H, J=8.5 Hz), 7.51-7.41 (m, 3H), 3.58-3.57 (m, 4H), 1.73 (m, 6H); LCMS (ESI) [M+1]$^+$ 433.3.

Example 63

N-[6-(4-phenethylpiperidin-1-yl)pyridin-3-yl]-2-(3-methylpiperidin-1-yl)-4-(trifluoromethyl)oxazole-5-carboxamide (63)

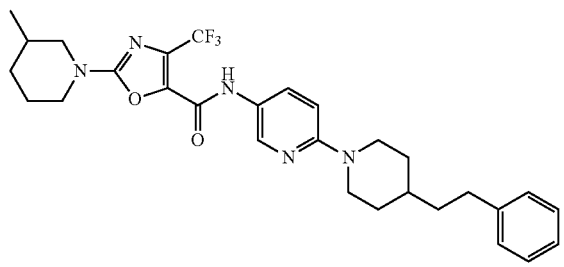

63

Compound 63 was prepared by the general procedure for compound 1, by using intermediates A-10 and B-22 as starting materials. $^1$H NMR (500 MHz, CDCl$_3$) δ 8.15 (m, 1H), 7.98-7.95 (m, 1H), 7.22-7.19 (m, 2H), 6.67-6.64 (m, 1H), 4.26 (d, 2H, J=12.9 Hz), 4.14-4.08 (m, 2H), 3.07-3.01 (m, 1H), 2.85-2.80 (m, 2H), 2.71-2.65 (m, 2H), 1.92-1.51 (m, 10H), 1.34-1.26 (m, 2H), 1.23-1.13 (m, 1H), 1.01 (d, 3H, J=6.6 Hz). LCMS (ESI): 542.3 [M+1]$^+$.

Example 64

N-[6-(4-benzyloxypiperidin-1-yl)pyridin-3-yl]-2-(3-methylpiperidin-1-yl)-4-(trifluoromethyl)oxazole-5-carboxamide (64)

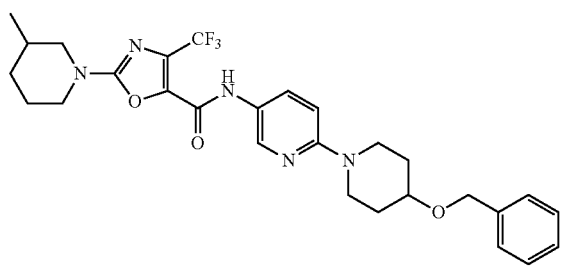

64

Compound 64 was prepared by the general procedure for compound 1, by using intermediates A-10 and B-23 as starting materials. $^1$H NMR (500 MHz, CDCl$_3$) δ 8.15 (m, 1H), 7.98-7.95 (m, 1H), 7.61 (s, 1H), 7.39-7.35 (m, 4H), 7.1-7.28 (m, 1H), 6.69 (d, 1H, J=9.14 Hz), 5.32 (s, 1H), 4.61 (s, 2H), 4.17 (m, 3H), 3.99 (m, 2H), 3.66 (m, 1H), 3.23 (m, 2H), 3.03 (m, 1H), 2.71 (m, 1H), 2.06 (m, 5H), 1.90-1.60 (m, 9H), 1.26 (m, 2H), 1.16 (m, 1H), 0.98 (d, 3H, J=9.14 Hz). LCMS (ESI): 544 [M+1]$^+$.

Example 65

N-[6-(4-(hydroxyphenylmethyl)piperidin-1-yl)pyridin-3-yl]-2-(3-methylpiperidin-1-yl)-4-(trifluoromethyl)oxazole-5-carboxamide (65)

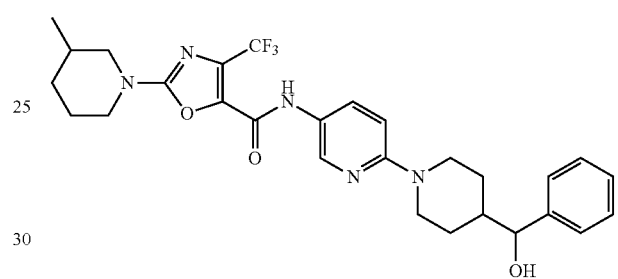

65

Compound 65 was prepared by the general procedure for compound 1, by using intermediates A-10 and B-24 as starting materials. $^1$H NMR (500 MHz, CDCl$_3$) δ 8.14 (m, 1H), 7.95 (m, 1H), 7.48 (m, 1H), 7.40-7.28 (m, 7H), 6.67 (m, 1H), 4.41-4.08 (m, 5H), 3.03 (m, 1H), 2.85-2.70 (m, 3H), 2.13 (m, 1H), 1.87-1.75 (m, 4H), 1.60 (m, 4H), 1.46-1.16 (m, 4H), 0.90 (d, 3H, J=6.62 Hz). LCMS (ESI): 544 [M+1]$^+$.

Example 66

N-[6-(4-((phenylmethylamino)sulfonyl)piperidin-1-yl)pyridin-3-yl]-2-(3-methylpiperidin-1-yl)-4-(trifluoromethyl)oxazole-5-carboxamide (66)

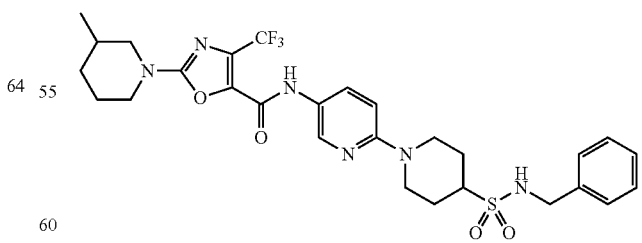

66

Compound 66 was prepared by the general procedure for compound 1, by using intermediates A-10 and B-25 as starting materials. $^1$H NMR (500 MHz, CDCl$_3$) δ 10.01 (s, 1H), 8.33 (s, 1H), 7.78-7.71 (m, 2H), 7.34-7.27 (m, 4H), 4.36 (m, 2H), 4.17-4.04 (m, 4H), 3.34 (s, 4H), 3.18-3.04 (m, 2H), 2.74

(m, 3H), 2.49 (m, 5H), 1.97 (m, 2H), 1.80-1.51 (m, 6H), 1.13 (m, 1H), 0.93 (d, 3H, J=6.3 Hz). LCMS (ESI): 607 [M+1]⁺.

Example 67

N-[6-[hexahydro-5-oxo-4-(phenylmethyl)-1H-1,4-diazepin-1-yl]pyridin-3-yl]-2-(3-methylpiperidin-1-yl)-4-(trifluoromethyl)oxazole-5-carboxamide (67)

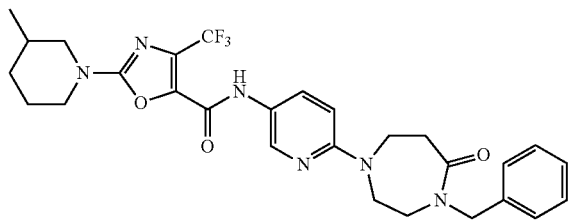

Compound 67 was prepared by the general procedure for compound 1, by using intermediates A-10 and B-26 as starting materials. ¹H NMR (500 MHz, CDCl₃) δ 8.16 (s, 1H), 7.95 (m, 1H), 7.62 (s, 1H), 7.34-7.28 (m, 5H), 6.60 (d, 1H, J=9.14 Hz), 4.65 (s, 2H), 4.10 (m, 2H), 3.81 (m, 2H), 3.66 (m, 2H), 3.43 (m, 2H), 3.04 (m, 1H), 2.83 (m, 2H), 2.69 (m, 1H), 1.98-1.61 (m, 5H), 1.16 (m, 1H), 0.98 (d, 3H, J=6.6 Hz). LCMS (ESI): 557 [M+1]⁺.

Example 68

N-[6-[hexahydro-5-oxo-4-(phenylmethyl)-1H-1,4-diazepin-1-yl]pyridin-3-yl]-2-(4-phenylpiperidin-1-yl)-4-(trifluoromethyl)oxazole-5-carboxamide (68)

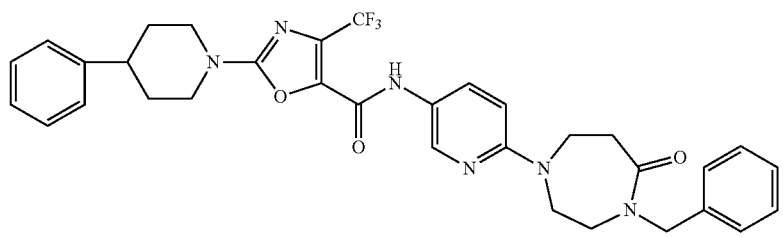

Compound 68 was prepared by the general procedure for compound 1, by using intermediates A-22 and B-26 as starting materials. ¹H NMR (500 MHz, CDCl₃) δ 8.17 (s, 1H), 7.98-7.95 (m, 1H), 7.57 (s, 1H), 7.39-7.23 (m, 10H), 6.61 (d, 1H, J=9.14 Hz), 4.66 (s, 2H), 4.37 (m, 2H), 3.83 (m, 2H), 3.66 (m, 2H), 3.46 (m, 2H), 3.23 (m, 2H), 2.84-2.77 (m, 3H), 2.01 (m, 2H), 1.82 (m, 2H). LCMS (ESI): 619 [M+1]⁺.

Example 69

N-[6-(4-((phenylmethylamino)sulfonyl)piperidin-1-yl)pyridin-3-yl]-2-(4-phenylpiperidin-1-yl)-4-(trifluoromethyl)oxazole-5-carboxamide (69)

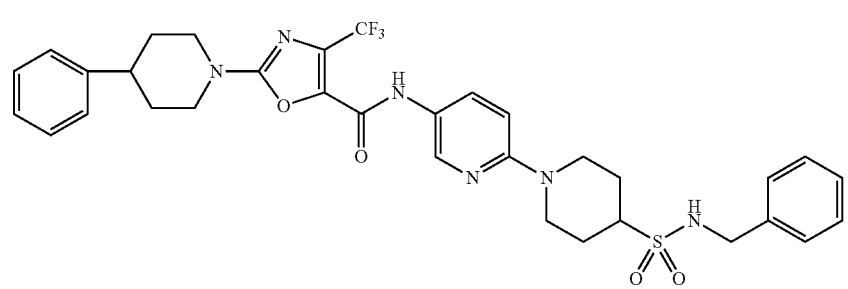

Compound 69 was prepared by the general procedure for compound 1, by using intermediates A-22 and B-25 as starting materials. $^1$H NMR (500 MHz, CDCl$_3$) δ 8.19 (s, 1H), 7.98-7.95 (m, 1H), 7.56 (s, 1H), 7.39-7.24 (m, 9H), 6.69 (d, 1H, J=9.14 Hz), 4.42-4.36 (m, 7H), 3.24 (m, 2H), 3.00 (m, 1H), 2.79 (m, 3H), 2.18 (m, 2H), 2.02 (m, 2H), 1.82 (m, 2H). LCMS (ESI): 669 [M+1]$^+$.

Example 70

N-[6-(4-benzyloxypiperidin-1-yl)pyridin-3-yl]-2-(4-phenylpiperidin-1-yl)-4-(trifluoromethyl)oxazole-5-carboxamide (70)

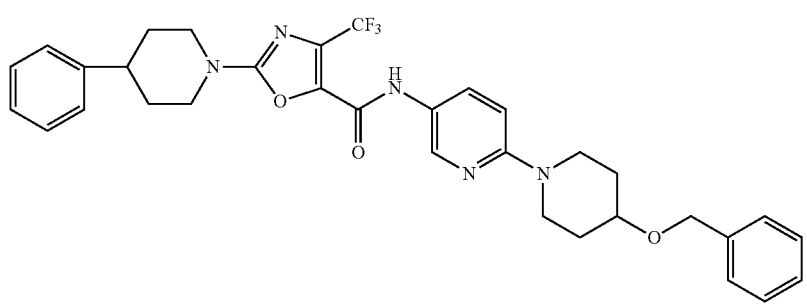

70

Compound 70 was prepared by the general procedure for compound 1, by using intermediates A-22 and B-23 as starting materials. $^1$H NMR (500 MHz, CDCl$_3$) δ 8.17 (s, 1H), 7.98-7.95 (m, 1H), 7.57 (s, 1H), 7.39-7.24 (m, 10H), 6.69 (d, 1H, J=9.14 Hz), 4.61 (s, 2H), 4.37 (m, 2H), 3.96 (m, 2H), 3.68 (m, 2H), 3.23 (m, 4H), 2.78 (m, 1H). LCMS (ESI): 606 [M+1]$^+$.

Example 71

N-[1-(3-(2-fluorophenylamino)-3-oxopropyl)-1H-indol-5-yl]-2-(3-methylpiperidin-1-yl)-4-(trifluoromethyl)oxazole-5-carboxamide (71)

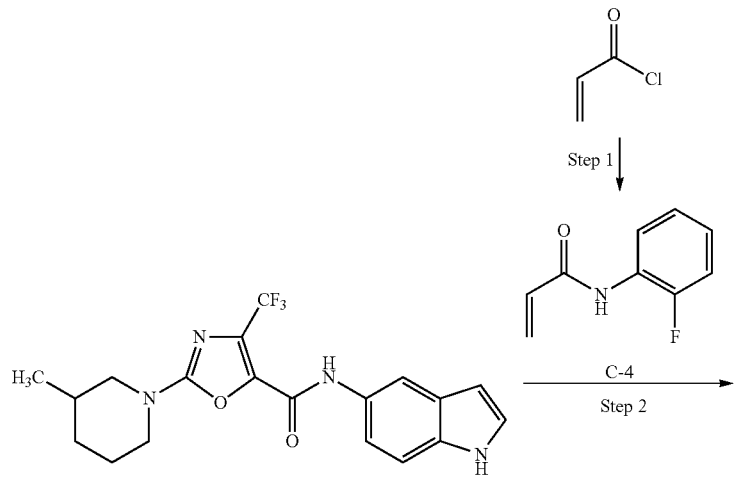

44

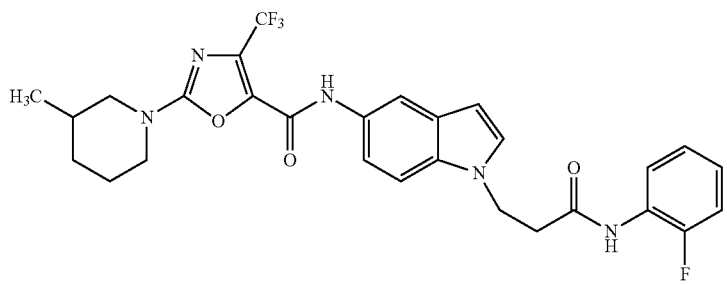

71

Step 1: N-(2-fluorophenyl)acrylamide (C-4)

To a solution of acryloyl chloride (0.70 mL, 8.63 mmol) and sodium phosphate dibasic (2.45 g, 17.26 mmol) in anhydrous methylene chloride (18.0 mL) at 0° C. was added dropwise 2-fluoroaniline (0.834 mL, 8.63 mmol). The reaction mixture was stirred at room temperature for 12 h. It was then filtered over a celite pad, washed with methylene chloride (50 mL) and concentrated to afford N-(2-fluorophenyl)acrylamide (C-4) as a white solid (0.959 g, 68% yield). MS (M+1): m/e 166. This material was used for the next step with no additional purification.

Step 2: N-[1-(3-(2-fluorophenylamino)-3-oxopropyl)-1H-indol-5-yl]-2-(3-methylpiperidin-1-yl)-4-(trifluoromethyl)oxazole-5-carboxamide (71)

To a solution of compound 44 (0.080 g, 0.204 mmol) and cesium carbonate (0.133 g, 0.408 mmol) in anhydrous acetonitrile (1.0 mL) at room temperature was added N-(2-fluorophenyl)acrylamide (C-4) (0.101 g, 0.612 mmol) in one portion. The reaction mixture was stirred at room temperature for 30 h, then additional N-(2-fluorophenyl)acrylamide (C-4) (0.168 g, 1.02 mmol) was added, and the reaction mixture was heated at 50° C. for 24 h. The reaction mixture was filtered over a celite pad, washed with methylene chloride (50 mL) and concentrated. Purification of the crude residue by silica gel chromatography (eluant gradient: 100% methylene chloride to 100% EtOAc) followed by $C_{18}$ reverse phase chromatography ($H_2O:CH_3CN$ eluant gradient) gave 8.7 mg (6.8% yield) of N-[1-(3-(2-fluorophenylamino)-3-oxopropyl)-1H-indol-5-yl]-2-(3-methylpiperidin-1-yl)-4-(trifluoromethyl)oxazole-5-carboxamide (71) as a white solid. $^1$H NMR (500 MHz, DMSO-$d_6$) δ 10.05 (br s, 1H), 10.05 (br s, 1H), 9.82 (br s, 1H), 7.88 (m, 1H), 7.85 (m, 1H), 7.53 (d, 1H, J=9.1 Hz), 7.37 (m, 1H), 7.24 (m, 1H), 7.15 (m, 2H), 6.42 (m, 1H), 4.49 (br t, 2H, J=6.6 Hz), 4.12 (m, 2H), 3.05 (t, 1H, J=11.5 Hz), 2.92 (t, 2H, J=6.6 Hz), 2.74 (t, 1H, J=11.9 Hz), 1.78 (m, 3H), 1.54 (m, 1H), 1.16 (m, 1H), 0.94 (d, 3H, J=6.3 Hz). MS (M+1): 558.

Example 72

Ethyl 2-((5-(2-(3-methylpiperidin-1-yl)-4-(trifluoromethyl)oxazole-5-carboxamido)-1H-indazol-1-yl)methyl)cyclopropanecarboxylate (72)

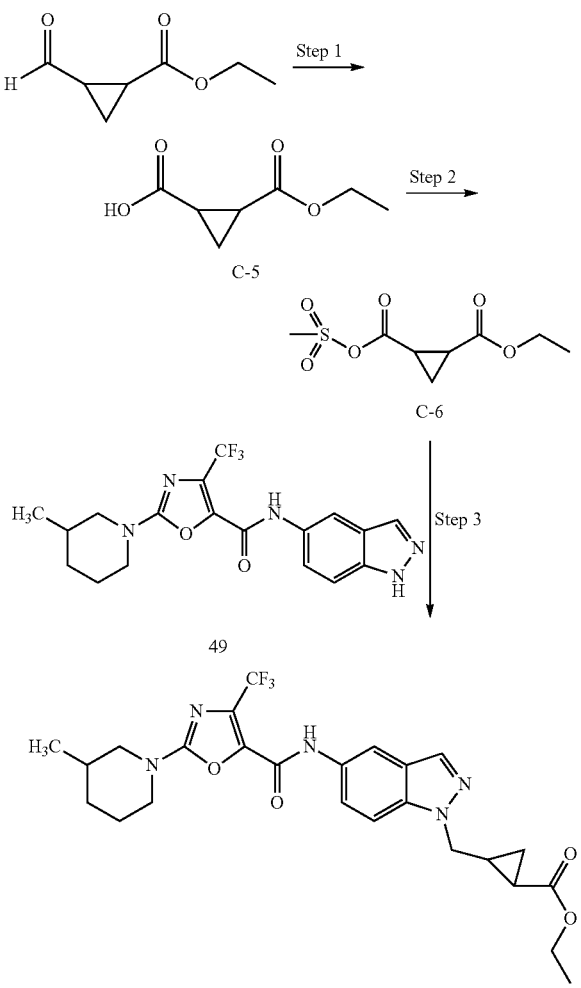

Step 1: Ethyl 2-(hydroxymethyl)cyclopropanecarboxylate (C-5)

To a solution of ethyl 2-formylcyclopropanecarboxylate (2.00 g, 13.68 mmol) in absolute ethanol (55.0 mL) at room temperature and under an anhydrous atmosphere was added sodium borohydride (0.776 g, 20.53 mmol) in one portion. The reaction mixture was stirred at room temperature for 5 h then quenched with an aqueous pH 7 phosphate buffer solution (100 mL) and the ethanol was removed under reduced pressure. The aqueous layer was mixed with methylene chloride (100 mL), decanted, then extracted with methylene chloride (2×100 mL). The combined organic extracts were then successively washed with an aqueous pH 7 phosphate buffer solution (70 mL) and brine (70 mL), dried over MgSO$_4$, filtered, and concentrated to give ethyl 2-(hydroxymethyl)cyclopropanecarboxylate (C-5) as a light yellow oil (1.334 g, 68% yield), which was used for the next step without additional purification. MS (M+1): m/e 145.

Step 2: Ethyl 2-((methylsulfonyloxy)methyl)cyclopropanecarboxylate (C-6)

To a solution of alcohol C-5 (0.50 g, 3.47 mmol) and triethylamine (1.45 mL, 10.41 mmol) in anhydrous methylene chloride (12.0 mL) at 0° C. was added methanesulfonic anhydride (0.908 g, 5.21 mmol) in one portion. The reaction mixture was then stirred at room temperature for 1 h, diluted with diethyl ether (50 mL) and quenched with an aqueous pH 7 phosphate buffer solution (30 mL). The aqueous layer was extracted with diethyl ether (2×50 mL). The combined organic extracts were then successively washed with an aqueous pH 7 phosphate buffer solution (70 mL) and brine (70 mL), dried over MgSO$_4$, filtered, and concentrated to give ethyl 2-((methylsulfonyloxy)methyl)cyclopropanecarboxylate (C-6) as a colorless oil (0.698 g, 91% yield). This material was immediately placed under argon and dissolved with anhydrous DMF (1.57 mL) to give a 2.0 M stock solution, which was used as such for the next step.

Step 3: Ethyl 2-((5-(2-(3-methylpiperidin-1-yl)-4-(trifluoromethyl)oxazole-5-carboxamido)-1H-indazol-1-yl)methyl)cyclopropanecarboxylate (72)

To a solution of indazole 49 (0.100 g, 0.255 mmol) and anhydrous potassium carbonate (70.5 mg, 0.510 mmol) in anhydrous DMF (0.90 mL) at room temperature was added mesylate C-6 (0.383 mL of 2.0 M solution, 0.765 mmol). After stirring at room temperature for 24 h, additional mesylate C-6 (0.383 mL of 2.0 M solution, 0.765 mmol) was added and the mixture was heated at 60° C. for 24 h. After cooling down to room temperature, the reaction mixture was diluted with anhydrous DMF (0.9 mL) and sodium hydride (60% dispersion in oil, 12.2 mg, 0.306 mmol) was added. The reaction mixture was stirred at room temperature for 17 h. It was then diluted with methylene chloride (20 mL), quenched with an aqueous pH 7 phosphate buffer solution (15 mL). The aqueous layer was extracted with methylene chloride (3×20 mL). The combined organic extracts were then successively washed with an aqueous pH 7 phosphate buffer solution (30 mL) and brine (30 mL), dried over MgSO$_4$, filtered, and concentrated. Purification of the crude residue by silica gel chromatography (eluant gradient: 100% methylene chloride to 100% EtOAc), followed by C$_{18}$ reverse phase chromatography (H$_2$O:CH$_3$CN eluant gradient) gave 6.50 mg (5% yield) of ethyl 2-((5-(2-(3-methylpiperidin-1-yl)-4-(trifluoromethyl)oxazole-5-carboxamido)-1H-indazol-1-yl)methyl)cyclopropanecarboxylate (72) as a white solid. $^1$H NMR (500 MHz, DMSO-d$_6$) δ 10.11 (br s, 1H), 8.38 (br s, 1H), 8.13 (br s, 1H), 7.62 (d, 1H, J=9.2 Hz), 7.41 (d, 1H, J=9.2 Hz), 4.41 (d, 2H, J=6.9 Hz), 4.12 (m, 2H), 4.03 (m, 2H), 3.06 (t, 1H, J=12.0 Hz), 2.75 (t, 1H, J=11.4 Hz), 1.89 (m, 2H), 1.78 (m, 1H), 1.68 (m, 1H), 1.54 (m, 1H), 1.26 (m, 1H), 1.16 (t, 3H, J=7.0 Hz), 1.11 (t, 2H, J=6.8 Hz), 0.94 (d, 3H, J=6.6 Hz), 0.86 (br t, 1H, J=7.8 Hz). MS (M+1): m/e 520.

Example 73

Phenyl 2-(5-(2-(3-methylpiperidin-1-yl)-4-(trifluoromethyl)oxazole-5-carboxamido)-1H-pyrrolo[2,3-b]pyridin-1-l)acetate (73):

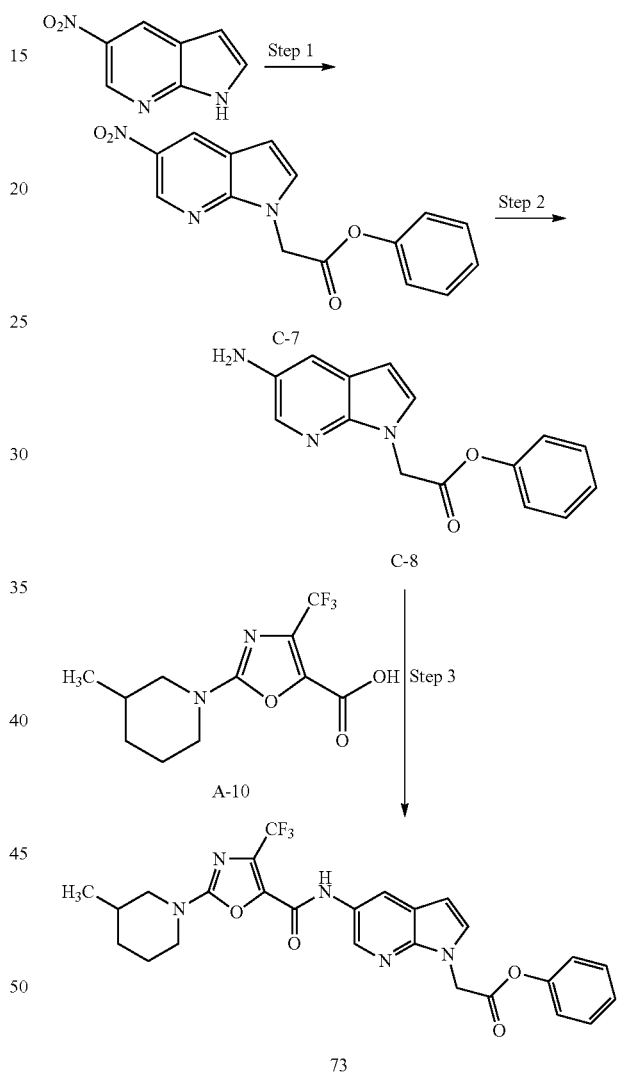

Step 1: Phenyl 2-(5-nitro-1H-pyrrolo[2,3-b]pyridin-1-yl)acetate (C-7)

To a solution of 5-nitro-1H-pyrrolo[2,3-b]pyridine (0.200 g, 1.226 mmol) and anhydrous potassium carbonate (254.2 mg, 1.839 mmol) in anhydrous DMF (6.0 mL) at room temperature was added phenyl 2-bromoacetate (0.755 mg, 3.678 mmol). After 20 h stirring at room temperature, additional phenyl 2-bromoacetate (1.256 g, 6.13 mmol) was added and the mixture was stirred at room temperature for 24 h. The reaction mixture was diluted with methylene chloride (70 mL), quenched with an aqueous pH 7 phosphate buffer solution (30 mL). The aqueous layer was extracted with methylene chloride (3×50 mL). The combined organic extracts were then successively washed with an aqueous pH 7 phosphate buffer solution (50 mL) and brine (50 mL), dried over $MgSO_4$, filtered, and concentrated. The crude residue was purified by $C_{18}$ reverse phase chromatography ($H_2O$:$CH_3CN$ eluant gradient) to give phenyl 2-(5-nitro-1H-pyrrolo[2,3-b]pyridin-1-yl)acetate (C-7) as a beige solid (50.0 mg, 13% yield). MS (M+1): m/e 298.

Step 2: Phenyl 2-(5-amino-1H-pyrrolo[2,3-b]pyridin-1-yl)acetate (C-8)

A solution of C-7 (0.050 g, 0.16 mmol) in 1:1 isopropanol:ethyl acetate (1.60 mL) was placed in an atmosphere of hydrogen (balloon, 1 atm) in the presence of platinum oxide (5.0 mg) and was vigorously stirred at room temperature for 17 h. The reaction mixture was filtered over a celite pad, washed with ethanol and ethyl acetate (10 mL each), and the filtrate concentrated. The light brown oil obtained (44.0 mg) was used for the next step without additional purification. MS (M+1): m/e 268.

Step 3: Phenyl 2-(5-(2-(3-methylpiperidin-1-yl)-4-(trifluoromethyl)oxazole-5-carboxamido)-1H-pyrrolo[2,3-b]pyridin-1-yl)acetate (73)

Compound 73 was prepared by the general procedure for compound 1, by using intermediates A-10 and C-8 as starting materials. $^{1}$H NMR (500 MHz, DMSO-$d_6$) δ 10.27 (br s, 1H), 8.45 (d, 1H, J=1.9 Hz), 8.29 (d, 1H, J=1.9 Hz), 7.67 (d, 1H, J=3.5 Hz), 7.44 (t, 2H, J=7.7 Hz), 7.29 (t, 1H, J=7.7 Hz), 7.18 (d, 2H, J=8.2 Hz), 6.57 (d, 1H, J=3.5 Hz), 5.45 (s, 2H), 4.15 (br d, 1H, J=12.6 Hz), 4.10 (br d, 1H, J=11.8 Hz), 3.07 (t, 1H, J=12.0 Hz), 2.76 (t, 1H, J=11.5 Hz), 1.78 (m, 2H), 1.68 (m, 1H), 1.55 (m, 1H), 1.16 (m, 1H), 0.94 (d, 3H, J=6.6 Hz). MS (M+1): m/e 528.

Example 74

N-[6-(4-(2-(2-fluorophenylamino)-3,4-dioxocyclobut-1-enyl)piperazin-1-yl)pyridin-3-yl]-2-(3-methylpiperidin-1-yl)-4-(trifluoromethyl)oxazole-5-carboxamide (74)

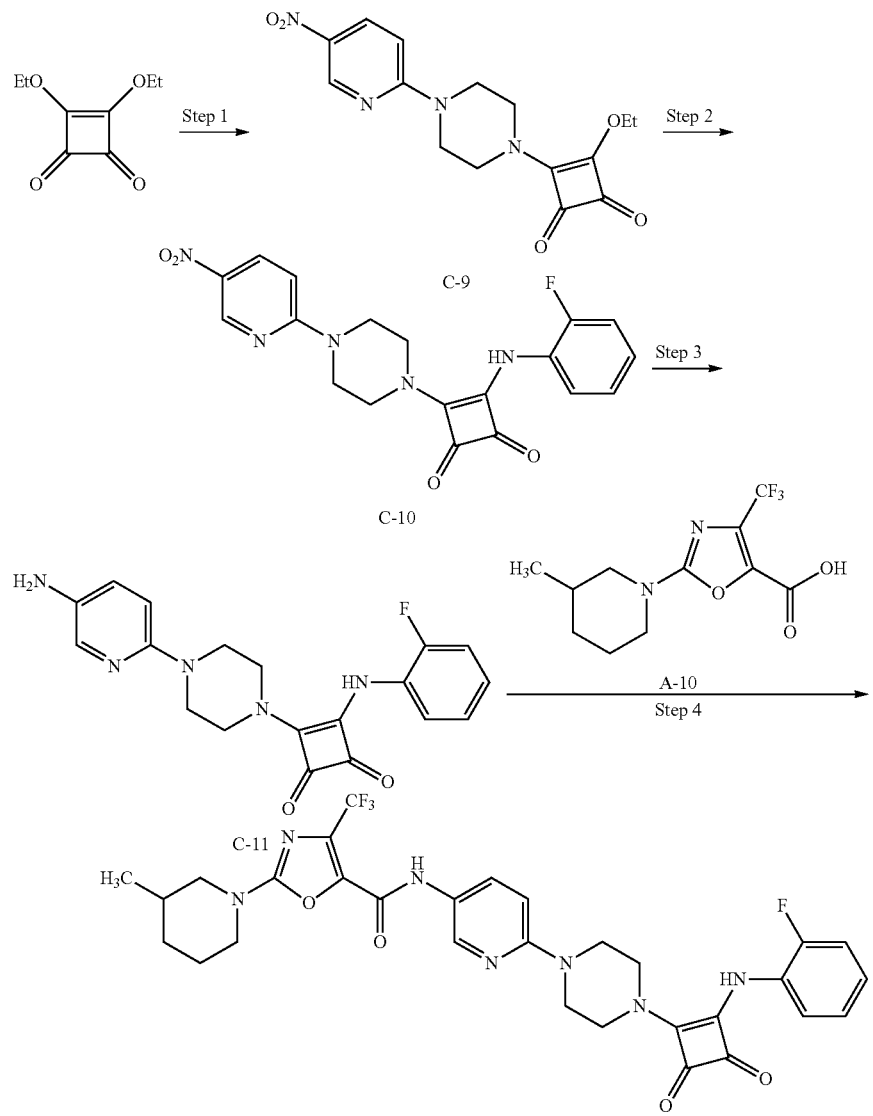

Step 1: 3-Ethoxy-4-(4-(5-nitropyridin-2-yl)piperazin-1-yl)cyclobut-3-ene-1,2-dione (C-9)

To 3,4-diethoxycyclobut-3-ene-1,2-dione (1.20 mL, 8.10 mmol) in anhydrous DMF (10.0 mL) at room temperature was added a solution of 1-(5-nitropyridin-2-yl)piperazine (B-8) (1.926 g, 9.26 mmol) in anhydrous DMF (14.0 mL). The reaction mixture was stirred at room temperature for 3 h, and then diluted with absolute ethanol (40 mL) and methanol (30 mL). The yellow precipitate formed was filtered and washed with methanol (25 mL). The alcoholic filtrate was discarded, and the solid residue was dissolved in methylene chloride. The solution obtained was concentrated to give 3-ethoxy-4-(4-(5-nitropyridin-2-yl)piperazin-1-yl)cyclobut-3-ene-1,2-dione (C-9) as a yellow solid (1.93 g, 72% yield). MS (M+1): m/e 333. Nota: The presence of 1 equivalent 2-fluoroaniline or 2,6-dichloroaniline in the reaction mixture does not affect the course of the reaction in those conditions.

Step 2: 3-(2-Fluorophenylamino)-4-(4-(5-nitropyridin-2-yl)piperazin-1-yl)cyclobut-3-ene-1,2-dione (C-10)

Compound C-9 (0.500 g, 1.50 mmol), 2-fluoroaniline (0.155 mL, 1.58 mmol) and diisopropylethylamine (0.522 mL, 3.0 mmol) were dissolved in anhydrous DMF (5.0 mL) at room temperature and stirred for 48 h. The reaction mixture was then heated to 100° C. for 2 h and cooled to room temperature. In a separate flame-dried flask, sodium hydride (60% dispersion in oil, 84.0 mg, 2.10 mmol) was added in one portion to 2-fluoroaniline (0.216 mL, 2.25 mmol) in anhydrous DMF (1.0 mL) at room temperature. After 15 min, the resulting suspension was added to the reaction mixture, which was stirred at room temperature for 4 h. Another portion of sodium (2-fluorophenyl)amide (2.25 mmol) was prepared as indicated above and added to the reaction mixture, followed by 2 h additional stirring at room temperature. The reaction mixture was diluted with ethyl acetate (200 mL) and quenched with an aqueous pH 7 phosphate buffer solution (100 mL). The aqueous layer was extracted with ethyl acetate (3×100 mL). The combined organic extracts were then successively washed with 1 N aqueous solution of HCl (150 mL), water (2×100 mL) and brine (100 mL), dried over MgSO₄, filtered, and concentrated. Purification of the crude residue by silica gel chromatography (eluant gradient: 100% methylene chloride to 100% EtOAc) gave 3-(2-fluorophenylamino)-4-(4-(5-nitropyridin-2-yl)piperazin-1-yl)cyclobut-3-ene-1,2-dione (C-10) as a yellow solid (170.0 mg of 85% pure material used as such for next step, ca. 24% yield). MS (M+1): m/e 398.

Step 3: 3-(4-(5-Aminopyridin-2-yl)piperazin-1-yl)-4-(2-fluorophenylamino)cyclobut-3-ene-1,2-dione (C-11)

Compound C-10 (0.170 g, ca. 0.360 mmol), ammonium formate (0.140 g, 2.18 mmol) and palladium on carbon (5% Pd, 80 mg) were refluxed in absolute ethanol (12.0 mL) for 1 h. The reaction mixture was cooled to room temperature, filtered over a celite pad, washed with absolute ethanol (10.0 mL,) and the filtrate concentrated. The crude residue (176.7 mg) was used for next step without additional purification. MS (M+1): m/e 368.

Step 4: N-[6-(4-(2-(2-fluorophenylamino)-3,4-dioxocyclobut-1-enyl)piperazin-1-yl)pyridin-3-yl]-2-(3-methylpiperidin-1-yl)-4-(trifluoromethyl)oxazole-5-carboxamide (74)

Compound 74 was prepared by the general procedure for compound 1, by using intermediates A-10 and C-11 as starting materials. ¹H NMR (500 MHz, DMSO-d₆) δ 10.08 (br s, 1H), 9.58 (br s, 1H), 8.39 (br s, 1H), 7.85 (d, 1H, J=8.8 Hz), 7.28 (m, 2H), 7.18 (m, 2H), 6.98 (d, 1H, J=8.6 Hz), 4.13 (dm, 1H, J=12.0 Hz), 4.07 (dm, 1H, J=12.0 Hz), 3.86 (br s, 4H), 3.66 (br s, 4H), 3.05 (t, 1H, J=12.6 Hz), 2.75 (t, 1H, J=12.0 Hz), 1.77 (m, 2H), 1.67 (m, 1H), 1.53 (m, 1H), 1.17 (m, 1H), 0.93 (d, 3H, J=6.9 Hz). MS (M+1): m/e 628.

Example 75

N-(6-(8-(2-fluorophenylcarbamoyl)-2,8-diazaspiro[4,5]decan-2-yl)pyridin-3-yl)-2-(methylpiperidin-1-yl)-4-(trifluoromethyl)oxazole-5-carboxamide (75)

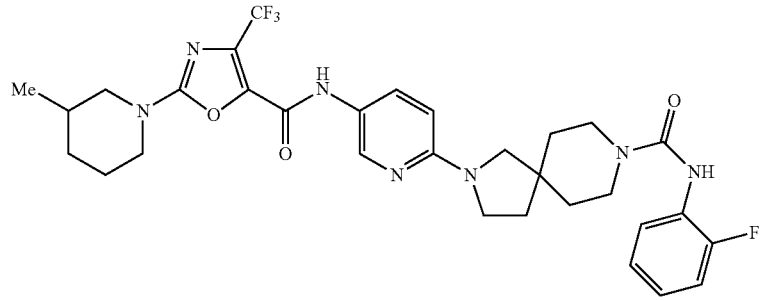

Compound 75 was prepared by the general procedure for compound 1. ¹H NMR (400 MHz, CDCl₃) δ 8.15 (d, 1H, J=2.5 Hz), 8.09 (t, 1H, J=8.2 Hz), 8.00 (dd, 1H, J=9.1, 2.5 Hz), 7.60 (s, 1H), 7.14-6.98 (m, 3H), 6.66 (d, 1H, J=9.1 Hz), 6.42 (d, 1H, J=3.8 Hz), 4.16-4.10 (m, 2H), 3.70-3.65 (m, 2H), 3.56 (t, 2H, J=6.9 Hz), 3.50-3.44 (m, 4H), 3.05 (m, 1H), 2.72 (m, 1H), 1.98 (t, 2H, J=6.9 Hz), 1.93-1.60 (m, 8H), 1.22-1.12 (m, 1H), 1.00 (d, 3H, J=6.6 Hz); LCMS (ESI) Rt=3.65 min, [M+1]⁺ 630.3.

Example 76

N-(6-(2-(2-fluorophenylcarbamoyl)-2,8-diazaspiro[4.5]decan-8-yl)pyridin-3-yl)-2-(3-methylpiperidin-1-yl)-4-(trifluoromethyl)oxazole-5-carboxamide (76)

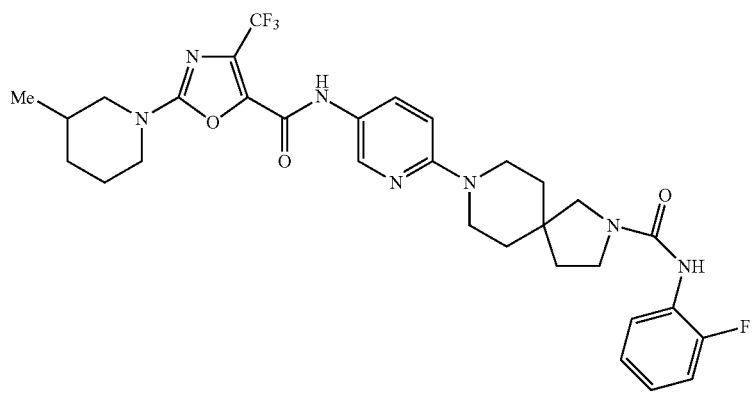

Compound 76 was prepared by the general procedure for compound 1. $^1$H NMR (400 MHz, CDCl$_3$) δ 8.23-8.18 (m, 2H), 8.03 (dd, 1H, J=9.5, 2.8 Hz), 7.60 (s, 1H), 7.16-6.95 (m, 3H), 6.71 (d, 1H, J=9.1 Hz), 6.44 (d, 1H, J=3.8 Hz), 4.18-4.08 (m, 2H), 3.72-3.59 (m, 4H), 3.52-3.42 (m, 4H), 3.05 (m, 1H), 2.72 (m, 1H), 2.18-1.60 (m, 10H), 1.23-1.12 (m, 1H), 1.00 (d, 3H, J=6.6 Hz); LCMS (ESI) Rt=3.59 min, [M+1]$^+$ 630.3.

Example 77

N-(6-(5-(2-fluorophenylcarbamoyl)hexahydropyrrolo[3,4-c]pyrrol-2(1H)-yl)pyridin-3-yl)-2-(3-methylpiperidin-1-yl)-4-(trifluoromethyl)oxazole-5-carboxamide (77)

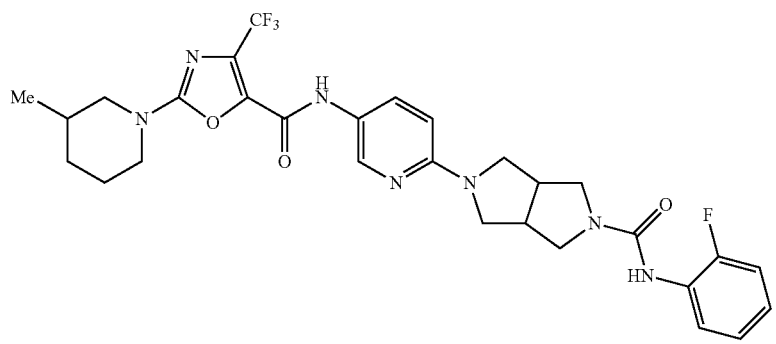

Compound 77 was prepared by the general procedure for compound 1. $^1$H NMR (400 MHz, DMSO-d6) δ 10.02 (bs, 1H), 8.30 (s, 1H), 7.90 (s, 1H), 7.78 (bs, 1H), 7.53 (m, 1H), 7.22-7.08 (m, 3H), 7.55 (bs, 1H), 4.16-4.04 (m, 2H), 3.74-3.63 (m, 4H), 3.42 (m, 2H), 3.12-3.00 (m, 3H), 2.74 (t, 1H, J=12 Hz), 1.82-1.45 (m, 4H), 1.28-1.10 (m, 3H), 0.95 (d, 3H, J=6.0 Hz); LCMS (ESI) Rt=3.47 min, [M+1]$^+$ 602.3.

Example 78

Cyclopentyl 8-(5-(2-(3-methylpiperidin-1-yl)-4-(trifluoromethyl)oxazole-5-carboxamido)pyridin-2-yl)-2,8-diazaspiro[4.5]decane-2-carboxylate (78)

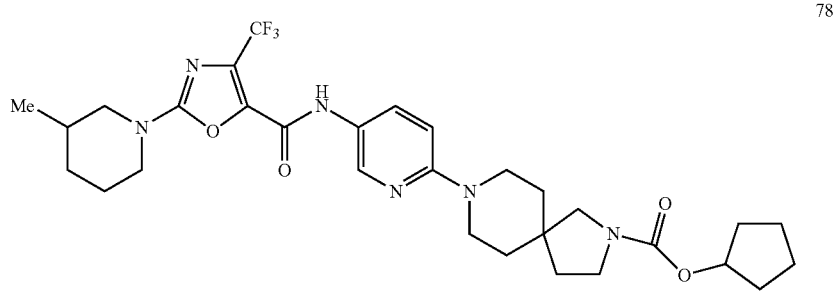 [SMILES: CC1CCCN(c2nc(C(F)(F)F)c(C(=O)Nc3ccc(N4CCC5(CCN(C(=O)OC6CCCC6)C5)CC4)nc3)o2)C1]

Compound 78 was prepared by the general procedure for compound 1. $^1$H NMR (400 MHz, CDCl$_3$) δ 8.20 (s, 1H), 8.02 (d, 1H, J=9.5 Hz), 7.78 (d, 1H, J=11 Hz), 6.71 (dd, 1H, J=9.1, 4.1 Hz), 5.12 (bs, 1H), 4.17-4.08 (m, 2H), 3.71-3.59 (m, 2H), 3.52-3.21 (m, 6H), 3.08-3.01 (m, 1H), 2.75-2.68 (m, 1H), 1.92-1.57 (m, 18H), 1.22-1.13 (m, 1H), 0.99 (d, 3H, J=6.6 Hz); LCMS (ESI) Rt=3.88 min, [M+1]$^+$ 605.3.

Example 79

Cyclopentyl 5-(5-(2-(3-methylpiperidin-1-yl)-4-(trifluoromethyl)oxazole-5-carboxamido)pyridin-2-yl)hexahydropyrrolo[3,4-c]pyrrole-2(1H)-carboxylate (79)

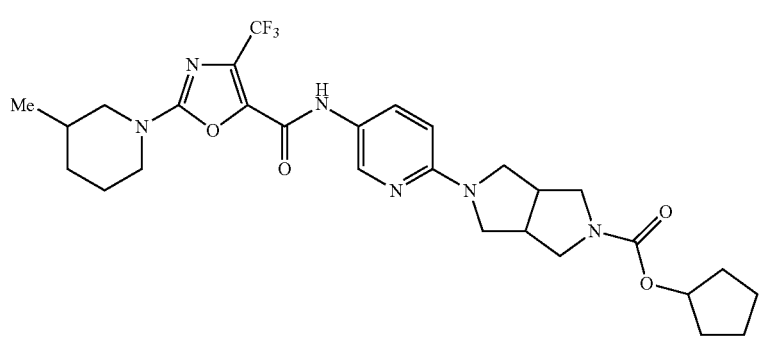

Compound 79 was prepared by the general procedure for compound 1. $^1$H NMR (400 MHz, CDCl$_3$) δ 8.14 (d, 1H, J=2.5 Hz), 7.98 (dd, 1H, J=9.1, 2.2 Hz), 7.64 (s, 1H), 6.39 (d, 1H, J=9.1 Hz), 5.11 (bs, 1H), 4.15-4.08 (m, 2H), 3.76-3.64 (m, 4H), 3.44-3.28 (m, 4H), 3.08-3.00 (m, 3H), 2.72 (t, 1H, J=11 Hz)), 1.95-1.56 (m, 12H), 1.22-1.12 (m, 1H), 1.02 (d, 3H, J=6.6 Hz); LCMS (ESI) Rt=3.62 min, [M+1]$^+$ 577.3.

Example 80

Cyclopentyl 2-(5-(2-(3-methylpiperidin-1-yl)-4-(trifluoromethyl)oxazole-5-carboxamido)pyridin-2-yl)-2,8-diazaspiro[4.5]decane-8-carboxylate (80)

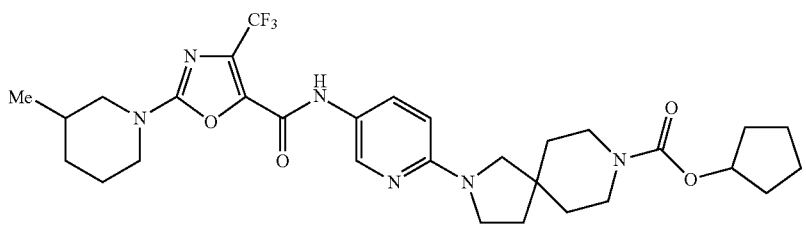

Compound 80 was prepared by the general procedure for compound 1. ¹H NMR (400 MHz, CDCl₃) δ 8.11 (dd, 1H, J=2.5 Hz), 8.03 (dd, 1H, J=9.1, 2.2 Hz), 7.69 (s, 1H), 6.45 (d, 1H, J=9.5 Hz), 5.15-5.11 (m, 1H), 4.20-4.09 (m, 2H), 3.64-3.52 (m, 4H), 3.46-3.35 (m, 4H), 3.09-3.01 (m, 1H), 2.76-2.69 (m, 1H), 2.00-1.58 (m, 18H), 1.22-1.13 (m, 1H), 1.00 (d, 3H, J=6.6 Hz); LCMS (ESI) Rt=3.83 min, [M+1]⁺ 605.3.

Example 81 tert-Butyl 4-(5-(2-(piperidin-1-yl)-4-(trifluoromethyl)oxazole-5-carboxamido)pyridin-2-yl)-1,4-diazepane-1-carboxylate (81)

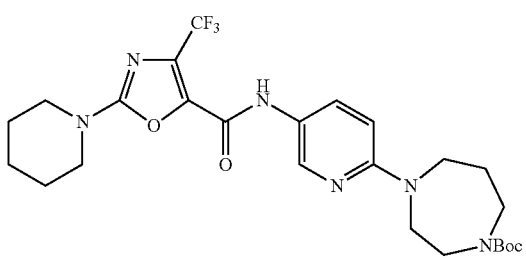

Compound 81 was prepared by the general procedure for compound 1, by using compound A-4 and B-21 as starting materials. ¹H NMR (400 MHz, DMSO-d6) δ 9.96 (s, 1H), 8.26 (m, 1H), 7.73 (m, 1H), 6.69 (d, 1H, J=8.8 Hz), 3.70 (m, 2H), 3.61 (m, 6H), 3.47 (m, 2H), 3.21 (m, 2H), 1.88 (m, 2H), 1.60 (br s, 6H), 1.26-1.33 (m, 9H); LCMS (ESI) Rt=3.36 min, [M+1]⁺ 539.3.

Example 82 tert-Butyl 4-(5-(2-(4-phenylpiperidin-1-yl)-4-(trifluoromethyl)oxazole-5-carboxamido)pyridin-2-yl)-1,4-diazepane-1-carboxylate (82)

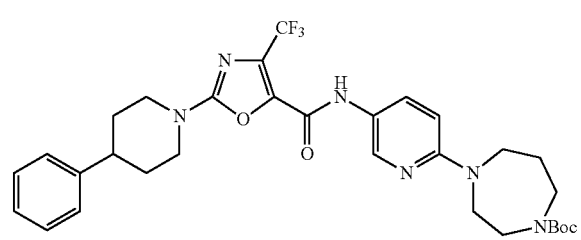

Compound 82 was prepared by the general procedure for compound 1, by using compound A-22 and B-21 as starting materials. ¹H NMR (400 MHz, DMSO-d6) δ 10.00 (s, 1H), 8.27 (m, 1H), 7.74 (m, 1H), 7.28-7.33 (m, 4H), 7.21 (m, 1H), 6.70 (d, 1H, J=9.5 Hz), 4.33 (m, 2H), 3.70 (m, 2H), 3.61 (m, 2H), 3.48 (m, 2H), 3.17-3.26 (m, 4H), 2.80 (m, 1H), 1.71-1.89 (m, 6H), 1.26-1.33 (m, 9H); LCMS (ESI) Rt=3.79 min, [M+1]⁺ 615.3.

Example 83

N-(6-(1,4-diazepan-1-yl)pyridin-3-yl)-2-(piperidin-1-yl)-4-(trifluoromethyl)oxazole-5-carboxamide (83)

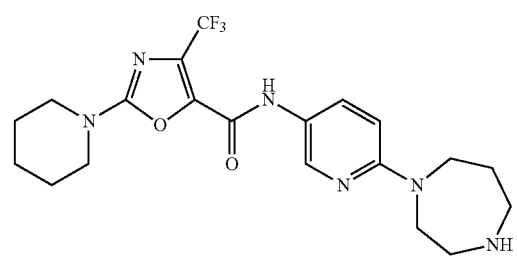

Compound 83 was prepared by the general procedure for compound C-3, by using compound 81 as the starting material. LCMS (ESI) [M+1]⁺ 439.2.

Example 84

N-(6-(1,4-diazepan-1-yl)pyridin-3-yl)-2-(4-phenylpiperidin-1-yl)-4-(trifluoromethyl)oxazole-5-carboxamide (84)

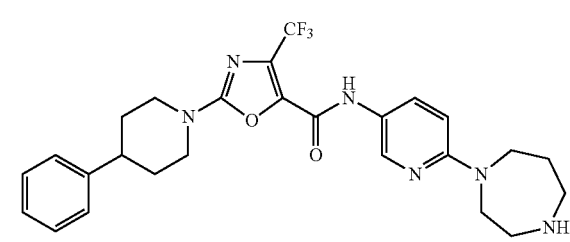

Compound 84 was prepared by the general procedure for compound C-3, by using compound 82 as the starting material. LCMS (ESI) [M+1]+ 515.3.

Examples 85-105

Compounds 175-195 were prepared by the method for amide combinatorial library synthesis described below:

Using a shaker with a capacity of 24 cartridges, the following reactions were run. To each cartridge were added 49.2 mg of EDC resin (3 eq.@ 1.39 mmol/g), 1 mL solution of compounds 39, 83, or 84 and HOBt in 3:1 CH$_3$CN:THF (10.0 mg of 39, 83, or 84 and 4.6 mg of HOBt for each cartridge), and 45.64 of each carboxylic acid (1 M solution in DMF). The cartridges were stoppered and shaken overnight. Then, to each cartridge was added 30.7 mg of Trisamine resin (6 eq.@ 4.46 mmol/g), 46.9 mg of ICN resin (3 eq.@ 1.46 mmol/g), and an additional 500 μL of 3:1 CH$_3$CN:THF. The cartridges were re-stoppered and shaken overnight. The cartridges were filtered into pre-weighed bar-coded vials, and the resins were washed with CH$_3$CN (6×500 μL). Upon concentration of the filtrates, the amides listed below were obtained as products.

| | STRUCTURE | LCMS (ESI) |
|---|---|---|
| 85 | | Rt = 3.00 min, [M + 1]+ 535.3 |
| 86 | | Rt = 3.04 min, [M + 1]+ 535.3 |
| 87 | | Rt = 3.23 min, [M + 1]+ 549.3 |

-continued
| STRUCTURE | LCMS (ESI) |
|---|---|
| 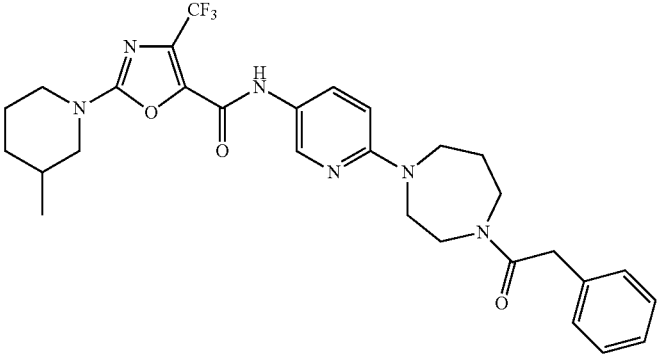<br>88 | Rt = 3.20 min, [M + 1]+ 571.3 |
| 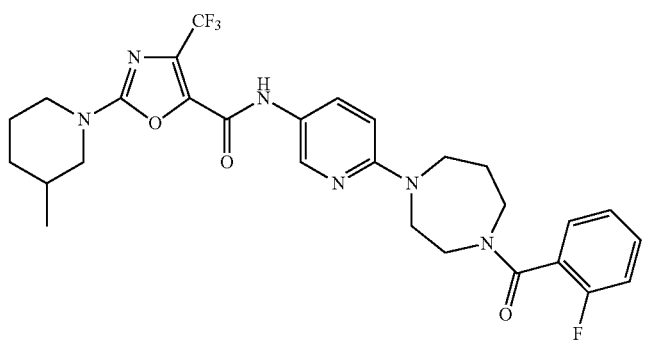<br>89 | Rt = 3.21 min, [M + 1]+ 575.3 |
| 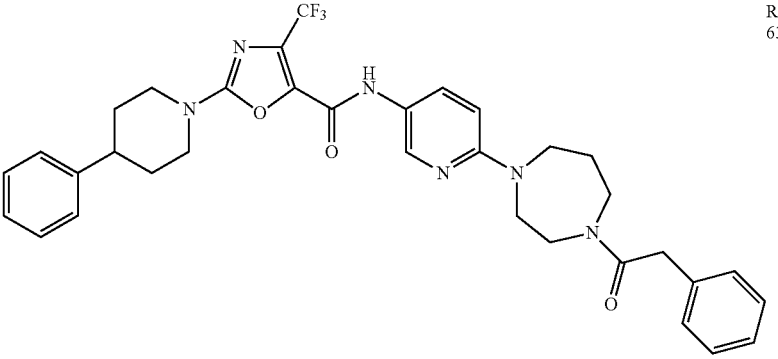<br>90 | Rt = 3.51 min, [M + 1]+ 633.3 |
| 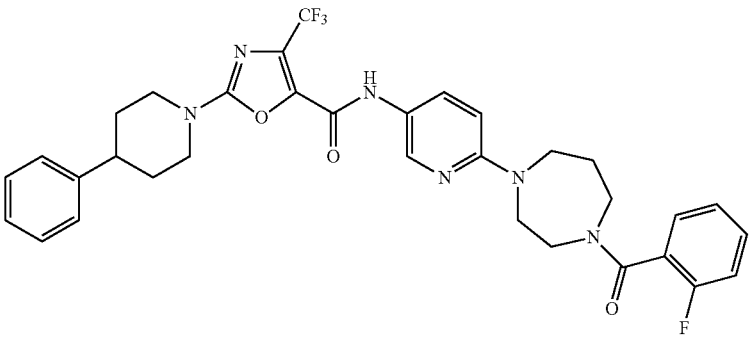<br>91 | Rt = 3.54 min, [M + 1]+ 637.4 |

| STRUCTURE | LCMS (ESI) |
|---|---|
| 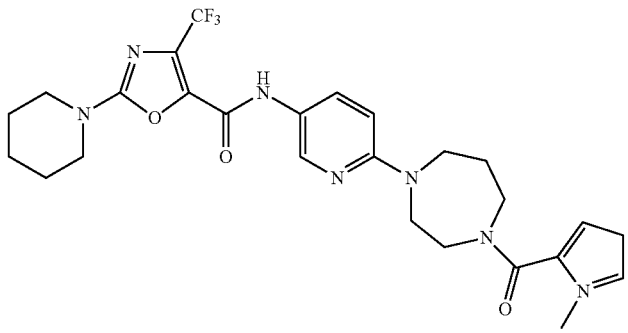<br>92 | Rt = 3.07 min, [M + 1]+ 546.3 |
| 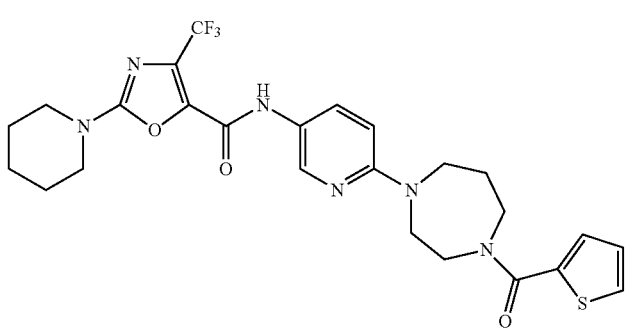<br>93 | Rt = 3.06 min, [M + 1]+ 549.3 |
| 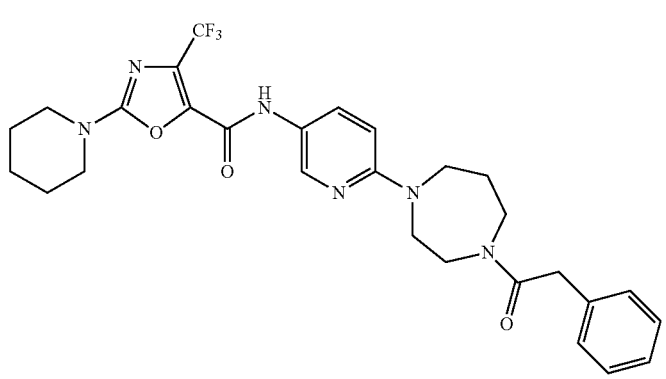<br>94 | Rt = 3.10 min, [M + 1]+ 557.3 |
| 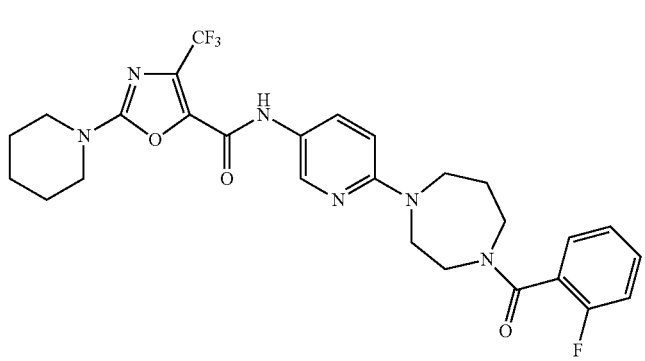<br>95 | Rt = 3.12 min, [M + 1]+ 561.3 |

| STRUCTURE | LCMS (ESI) |
|---|---|
| 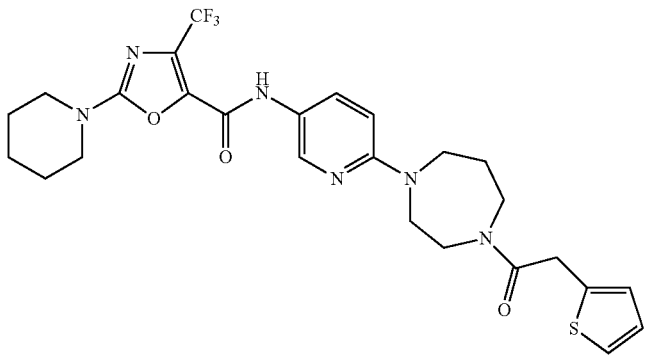<br>96 | Rt = 3.06 min, [M + 1]⁺ 563.3 |
| 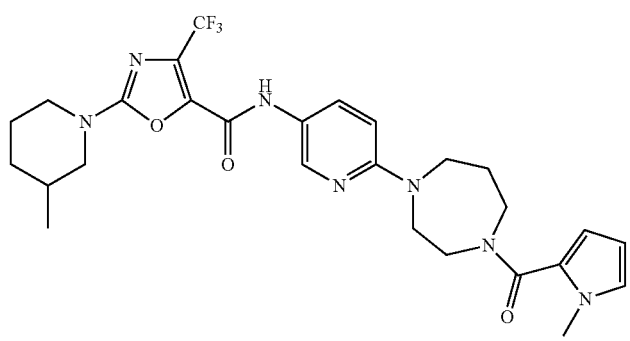<br>97 | Rt = 3.27 min, [M + 1]⁺ 560.3 |
| 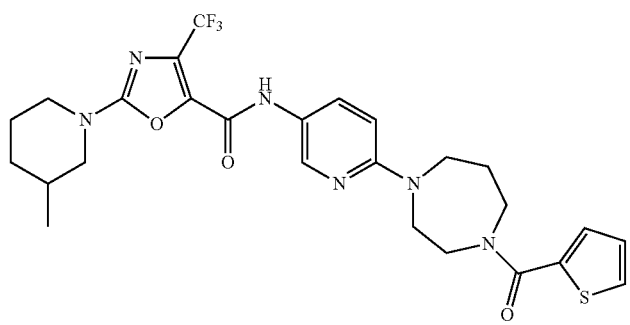<br>98 | Rt = 3.27 min, [M + 1]⁺ 563.3 |
| 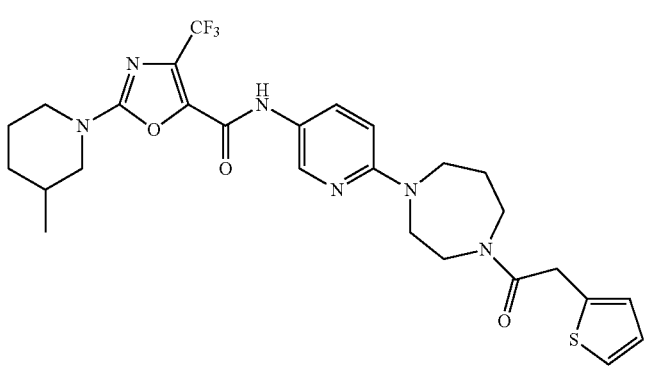<br>99 | Rt = 3.27 min, [M + 1]⁺ 577.3 |

| STRUCTURE | LCMS (ESI) |
|---|---|
| 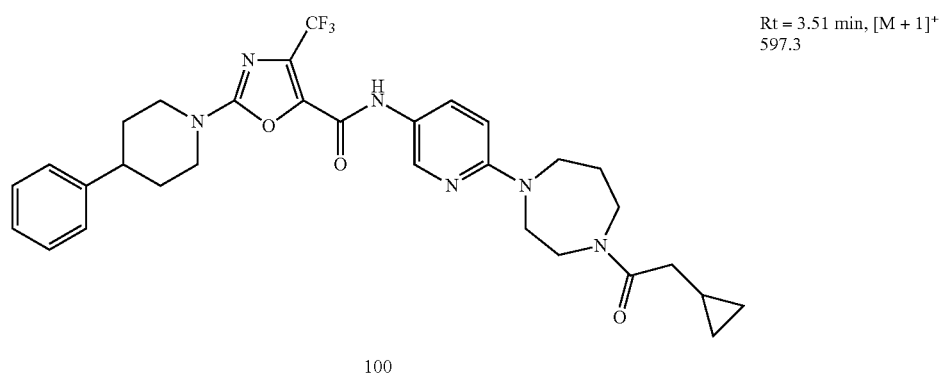<br>100 | Rt = 3.51 min, [M + 1]<sup>+</sup> 597.3 |
| 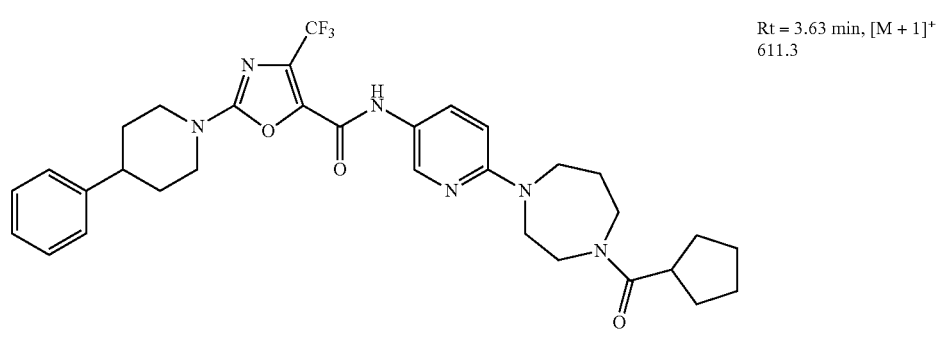<br>101 | Rt = 3.63 min, [M + 1]<sup>+</sup> 611.3 |
| 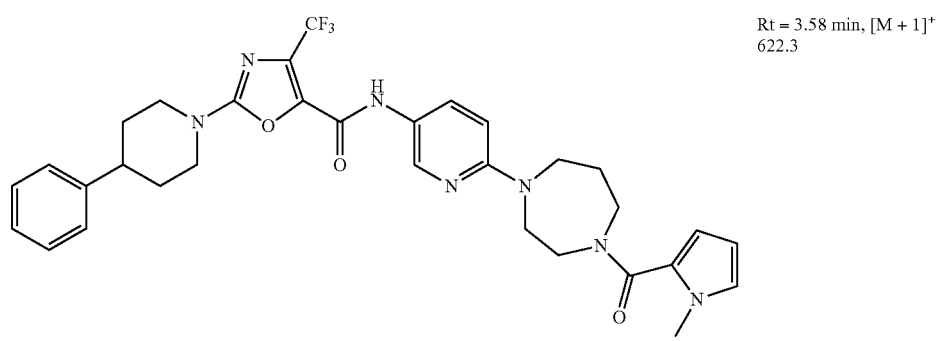<br>102 | Rt = 3.58 min, [M + 1]<sup>+</sup> 622.3 |
| 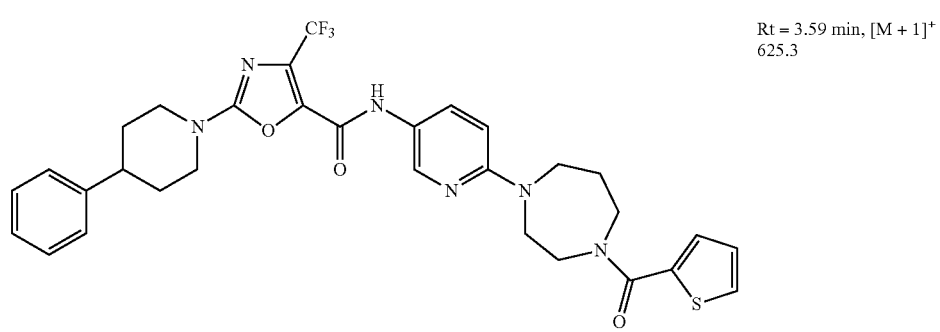<br>103 | Rt = 3.59 min, [M + 1]<sup>+</sup> 625.3 |

| STRUCTURE | LCMS (ESI) |
|---|---|
| 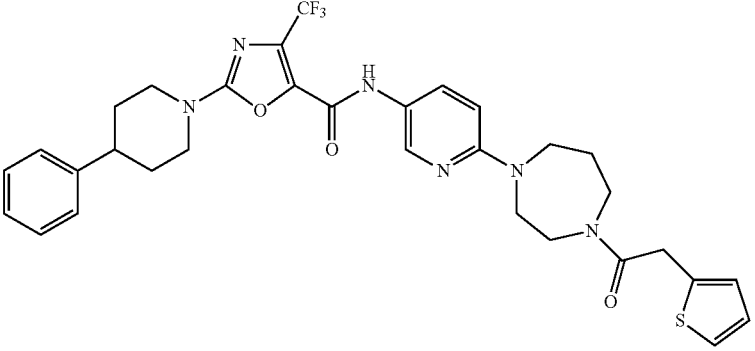<br>104 | Rt = 3.58 min, [M + 1]+<br>639.4 |
| 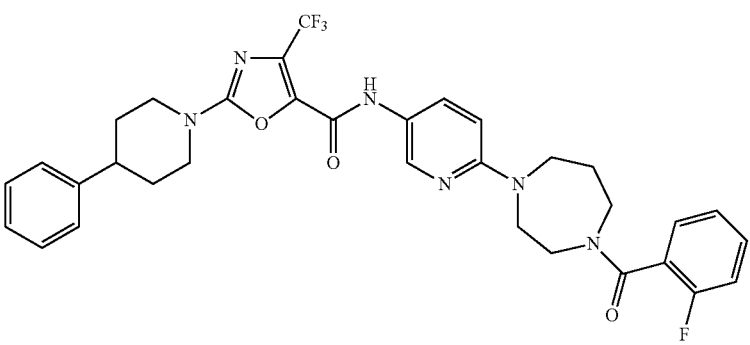<br>105 | Rt = 3.79 min, [M + 1]+<br>687.4 |

Examples 106-151

Compounds 106-151 were prepared by the method for amide combinatorial library synthesis described below using 39, 83, or 84 as starting materials. Using a shaker with a capacity of 24 cartridges, the following reactions were run. To each cartridge were added 1 mL of the solution of compound 39, 83, or 84 in DCE (10 mg of 39, 83, or 84 for each cartridge), and 45.6 µL of each isocyanate, chloroformate, or sulfonyl chlorides (1 M solution in DCE). The cartridges were stoppered and shaken overnight. Then, to the each cartridge was added 31.7 mg of Trisamine resin (6 eq.@ 4.46 mmol/g), 48.4 mg of ICN resin (3 eq.@ 1.46 mmol/g), and an additional 500 µL of DCE. The cartridges were re-stoppered and shaken overnight. The cartridges were filtered into pre-weighed vials, and the resins were washed with acetonitrile (6×500 µL). Upon concentration of the filtrates, the ureas listed below were obtained as products.

| STRUCTURE | LCMS (ESI) |
|---|---|
| 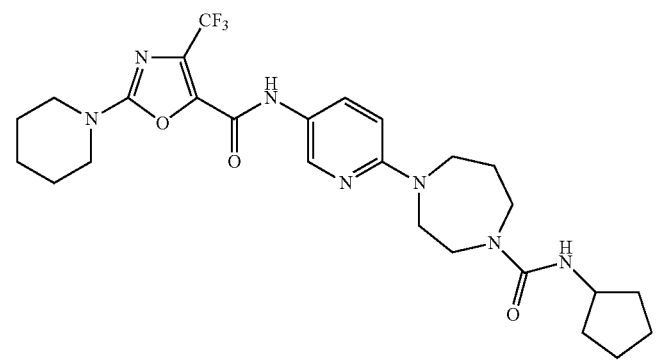<br>106 | Rt = 2.93 min, [M + 1]+<br>550.3 |

| STRUCTURE | LCMS (ESI) |
|---|---|
| 107 | Rt = 2.98 min, [M + 1]+ 572.3 |
| 108 | Rt = 2.88 min, [M + 1]+ 583.3 |
| 109 | Rt = 2.92 min, [M + 1]+ 594.3 |
| 110 | Rt = 3.01 min, [M + 1]+ 626.3 |

| STRUCTURE | LCMS (ESI) |
|---|---|
| 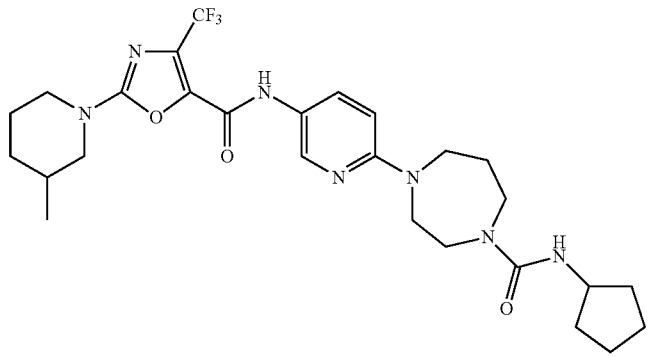<br>111 | Rt = 3.14 min, [M + 1]+ 564.3 |
| 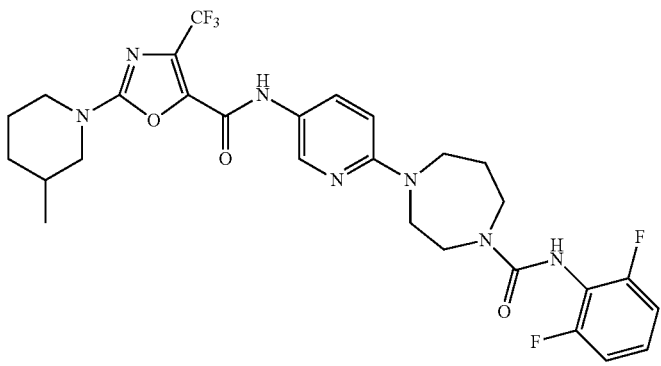<br>112 | Rt = 3.10 min, [M + 1]+ 608.3 |
| 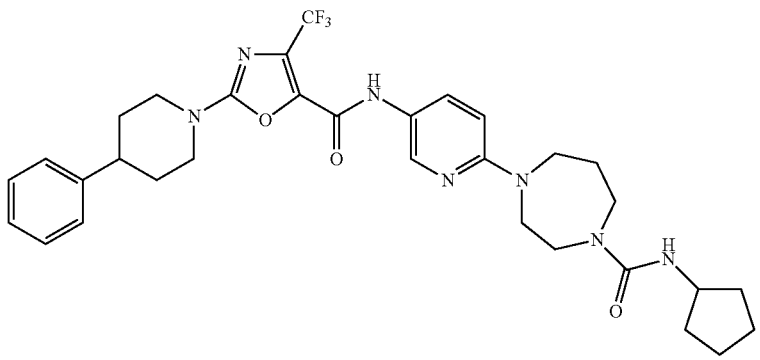<br>113 | Rt = 3.46 min, [M + 1]+ 626.3 |

| STRUCTURE | LCMS (ESI) |
|---|---|
| 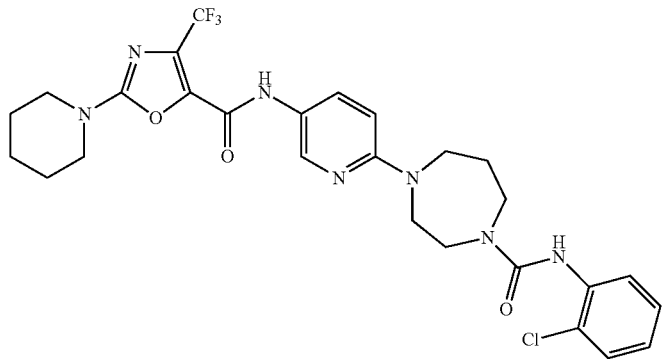<br>114 | Rt = 3.18 min, [M + 1]+ 592.3 |
| 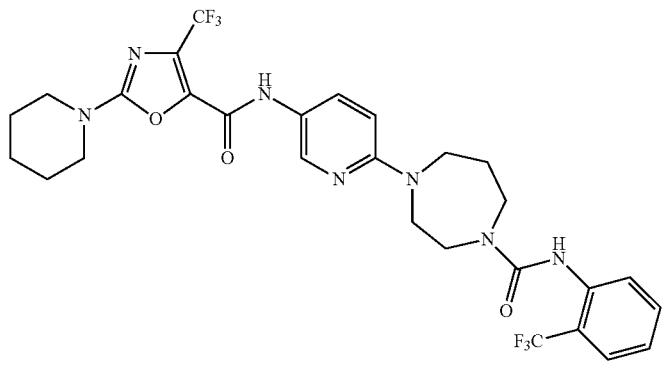<br>115 | Rt = 3.20 min, [M + 1]+ 626.3 |
| 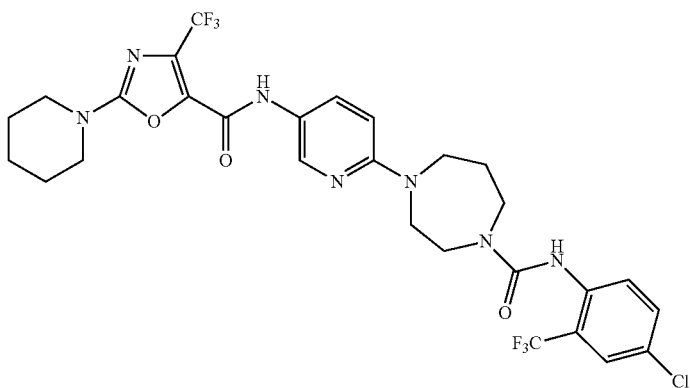<br>116 | Rt = 3.42 min, [M + 1]+ 660.4 |

-continued
| STRUCTURE | LCMS (ESI) |
|---|---|
| 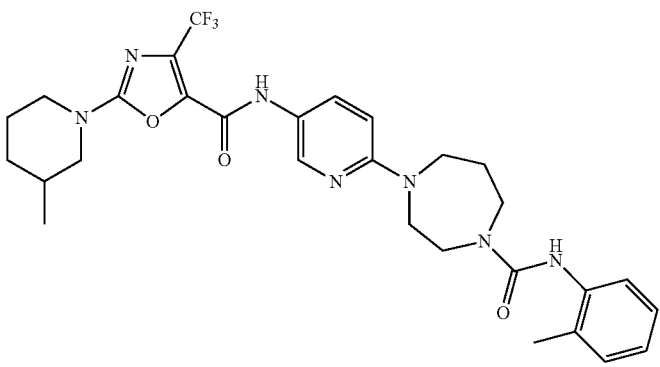<br>117 | Rt = 3.31 min, [M + 1]+ 586.3 |
| 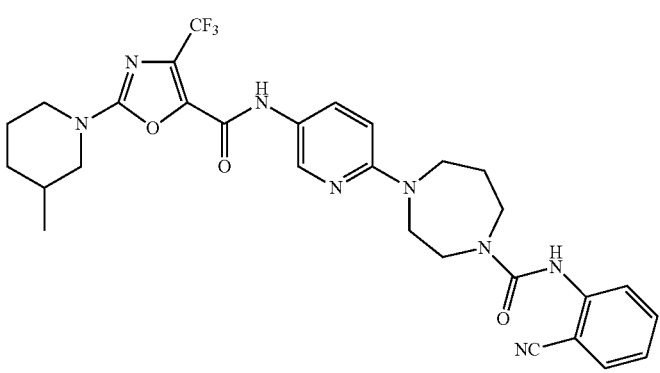<br>118 | Rt = 3.22 min, [M + 1]+ 597.3 |
| 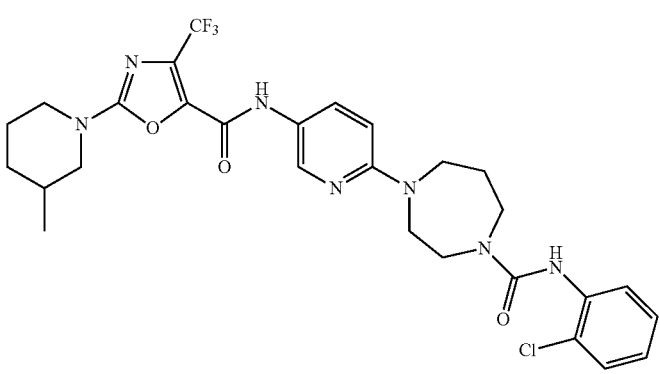<br>119 | Rt = 3.38 min, [M + 1]+ 606.3 |
| 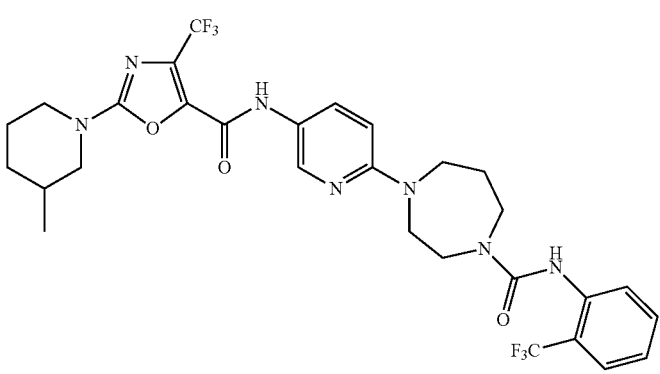<br>120 | Rt = 3.39 min, [M + 1]+ 641.4 |

-continued
| STRUCTURE | LCMS (ESI) |
|---|---|
| 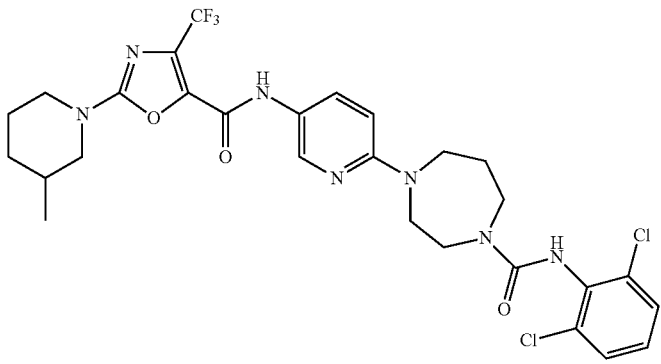 121 | Rt = 3.33 min, [M + 1]+ 642.4 |
| 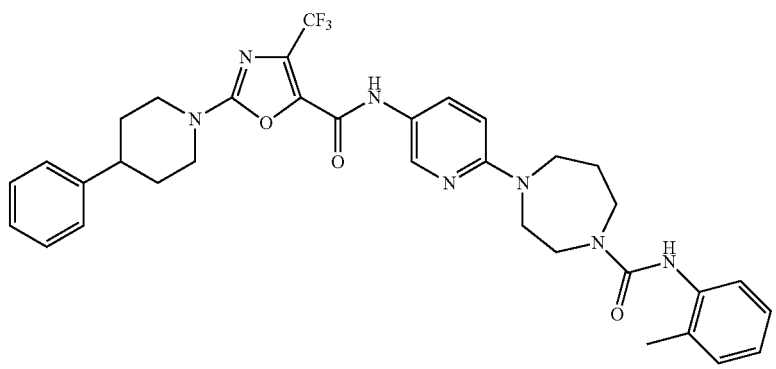 122 | Rt = 3.61 min, [M + 1]+ 648.4 |
| 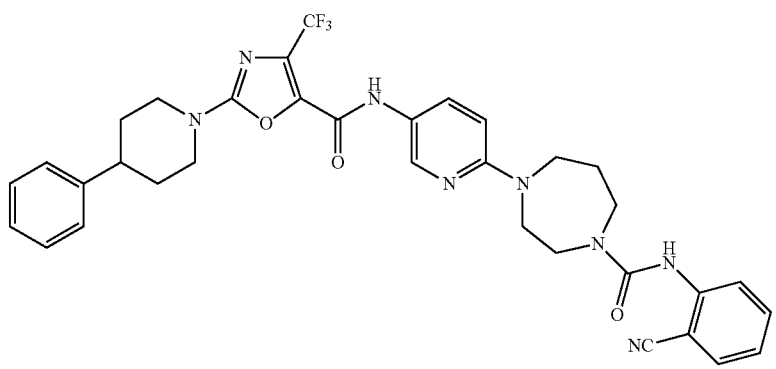 123 | Rt = 3.53 min, [M + 1]+ 660.4 |

-continued
| STRUCTURE | LCMS (ESI) |
|---|---|
| 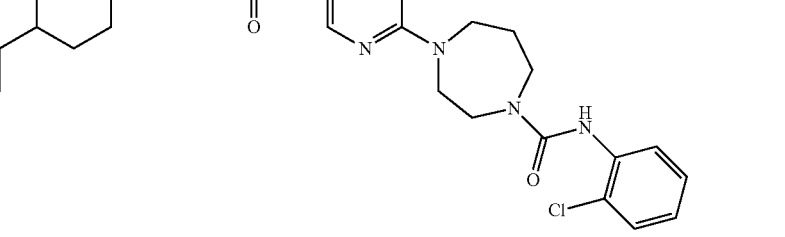<br>124 | Rt = 3.67 min, [M + 1]$^+$ 668.4 |
| 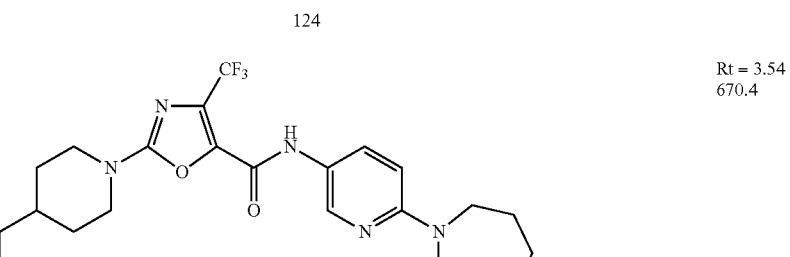<br>125 | Rt = 3.54 min, [M + 1]$^+$ 670.4 |
| 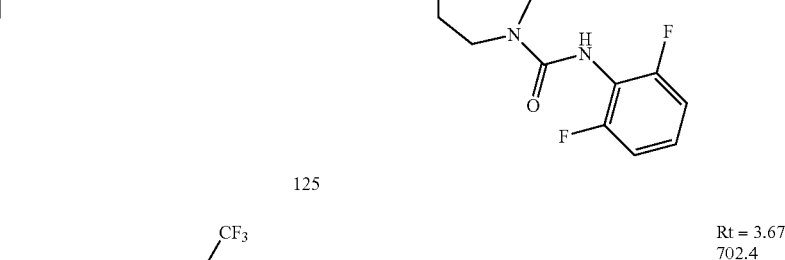<br>126 | Rt = 3.67 min, [M + 1]$^+$ 702.4 |
| 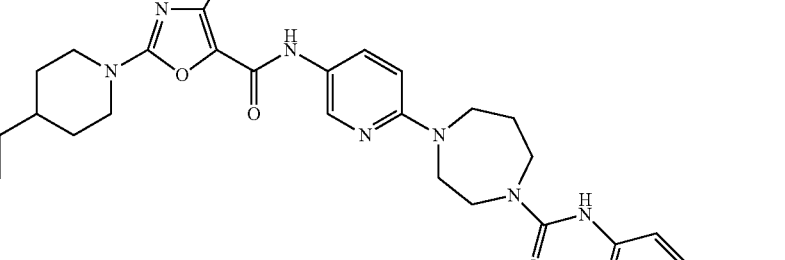<br>127 | Rt = 3.63 min, [M + 1]$^+$ 704.4 |

| STRUCTURE | LCMS (ESI) |
|---|---|
| 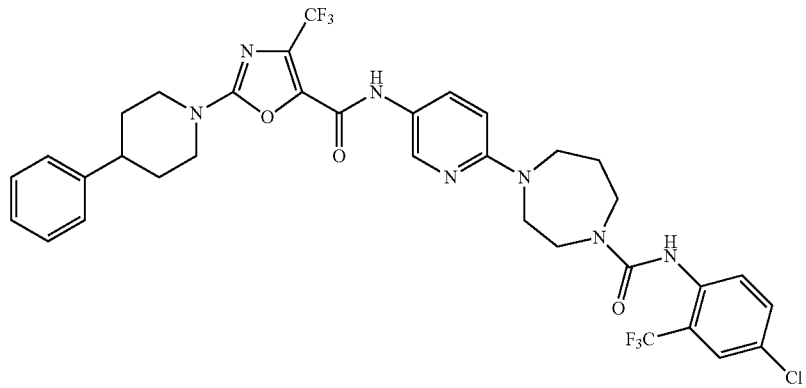<br>128 | Rt = 3.86 min, [M + 1]+<br>736.4 |
| 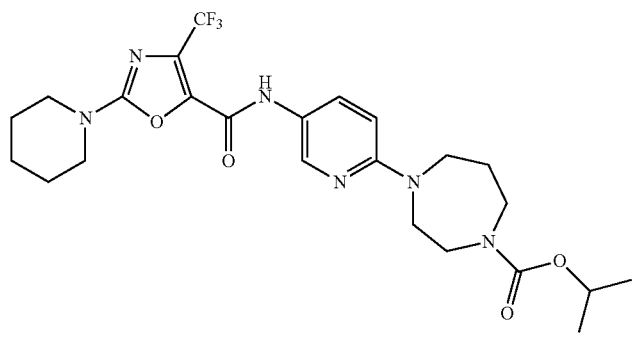<br>129 | Rt = 3.03 min, [M + 1]+<br>525.3 |
| 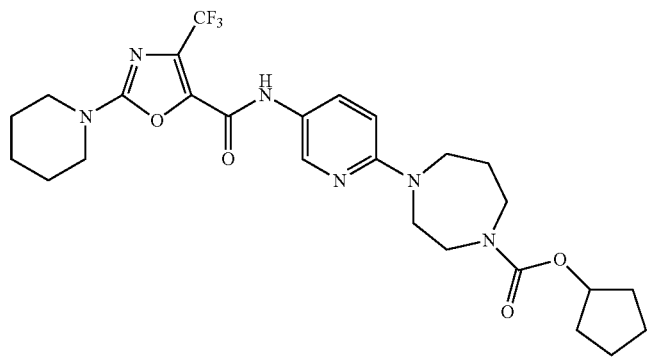<br>130 | Rt = 3.25 min, [M + 1]+<br>551.3 |

-continued
| STRUCTURE | LCMS (ESI) |
|---|---|
| 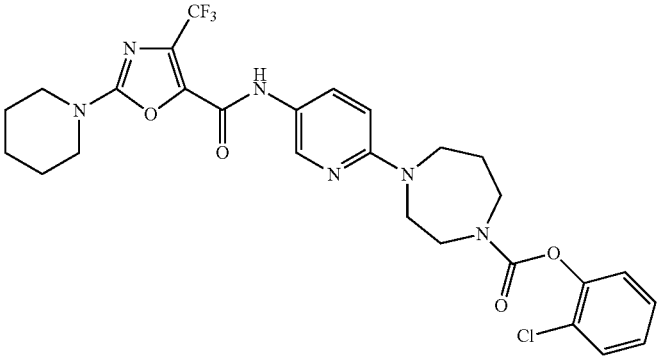<br>131 | Rt = 3.34 min, [M + 1]+ 593.3 |
| 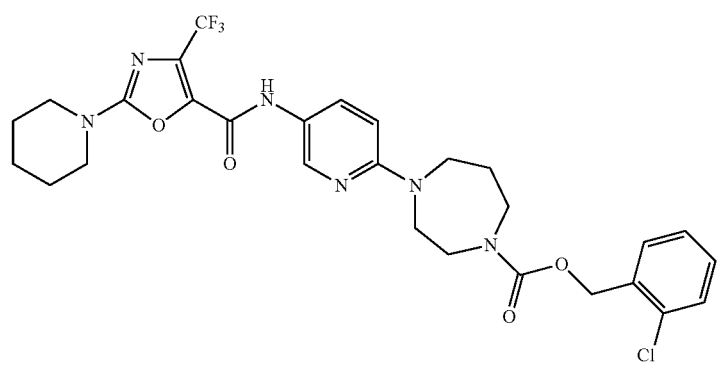<br>132 | Rt = 3.43 min, [M + 1]+ 607.3 |
| 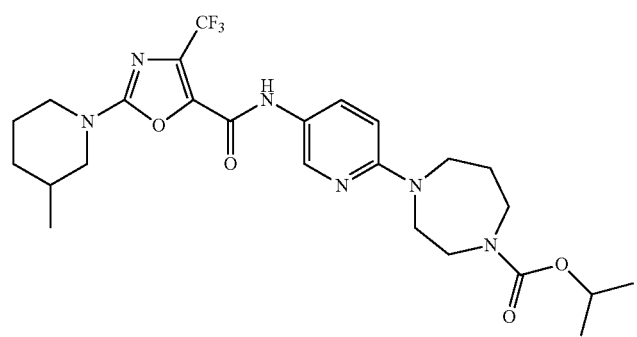<br>133 | Rt = 3.26 min, [M + 1]+ 539.3 |
| 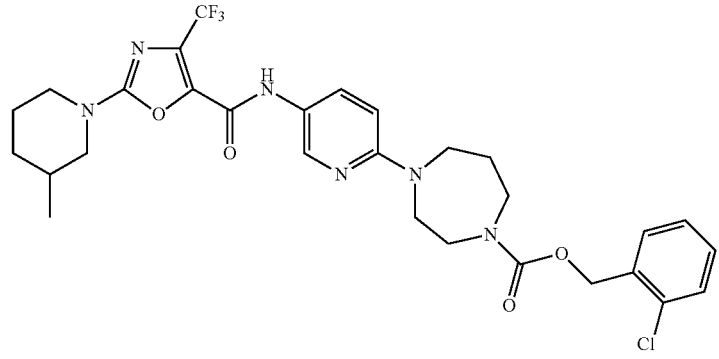<br>134 | Rt = 3.60 min, [M + 1]+ 621.3 |

-continued
| STRUCTURE | LCMS (ESI) |
|---|---|
| 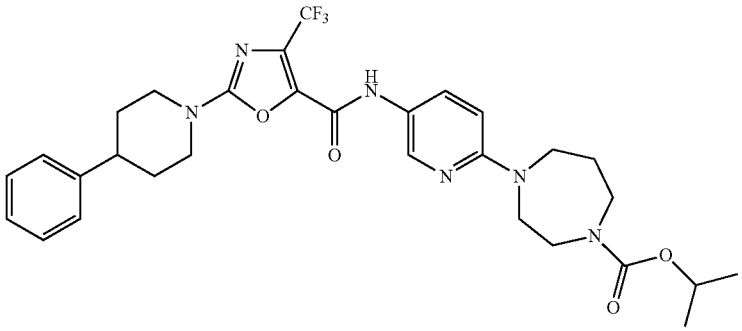<br>135 | Rt = 3.56 min, [M + 1]+<br>601.3 |
| 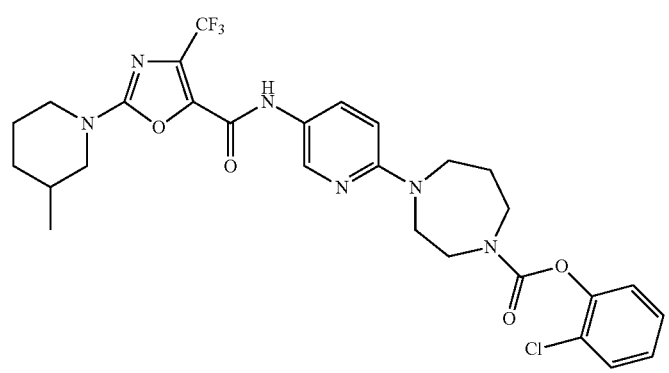<br>136 | Rt = 3.63 min, [M + 1]+<br>607.3 |
| 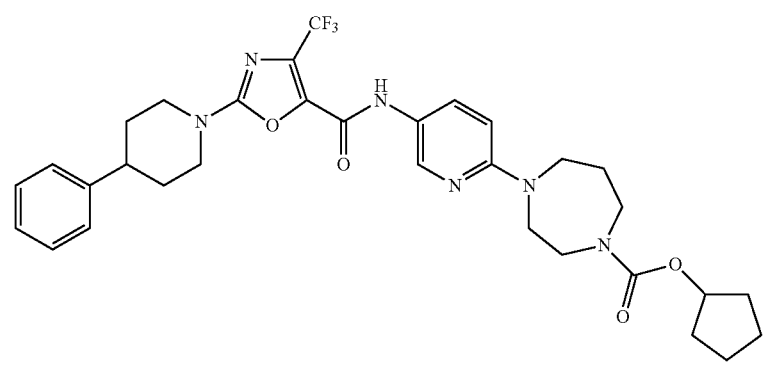<br>137 | Rt = 3.81 min, [M + 1]+<br>627.3 |
| 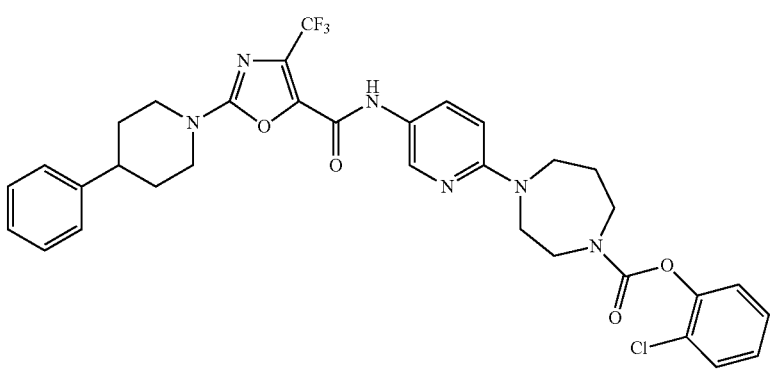<br>138 | Rt = 3.89 min, [M + 1]+<br>669.4 |

| STRUCTURE | LCMS (ESI) |
|---|---|
| 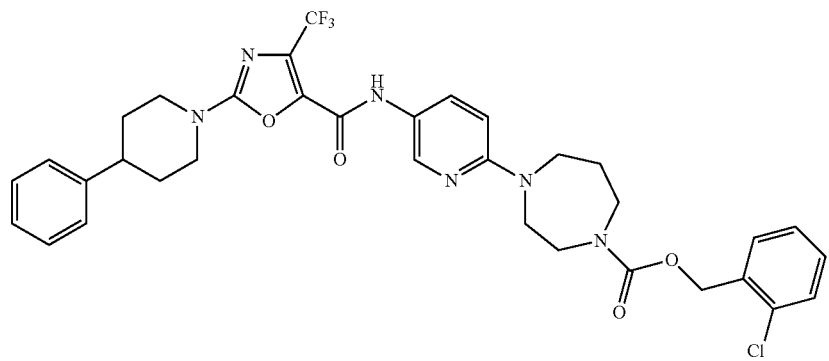<br>139 | Rt = 3.97 min, [M + 1]⁺ 683.4 |
| 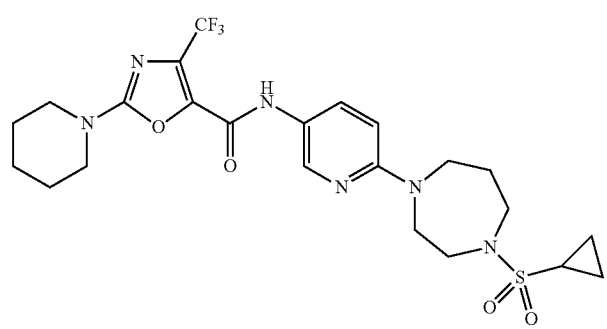<br>140 | Rt = 2.94 min, [M + 1]⁺ 543.3 |
| 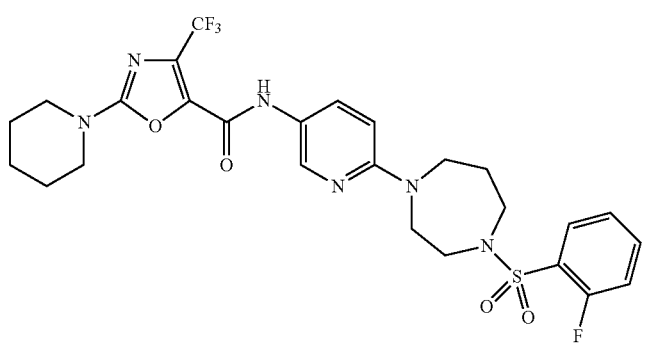<br>141 | Rt = 3.30 min, [M + 1]⁺ 597.3 |
| 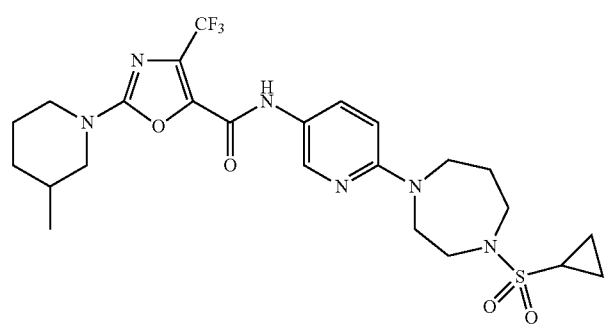<br>142 | Rt = 3.16 min, [M + 1]⁺ 557.3 |

| STRUCTURE | LCMS (ESI) |
|---|---|
| 143 | Rt = 3.49 min, [M + 1]+ 611.3 |
| 144 | Rt = 3.47 min, [M + 1]+ 613.3 |
| 145 | Rt = 3.49 min, [M + 1]+ 659.4 |
| 146 | Rt = 3.65 min, [M + 1]+ 627.3 |

-continued
| STRUCTURE | LCMS (ESI) |
|---|---|
| 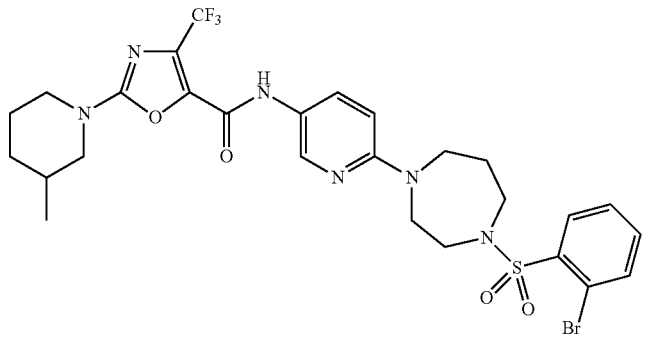<br>147 | Rt = 3.67 min, [M + 1]+ 673.4 |
| 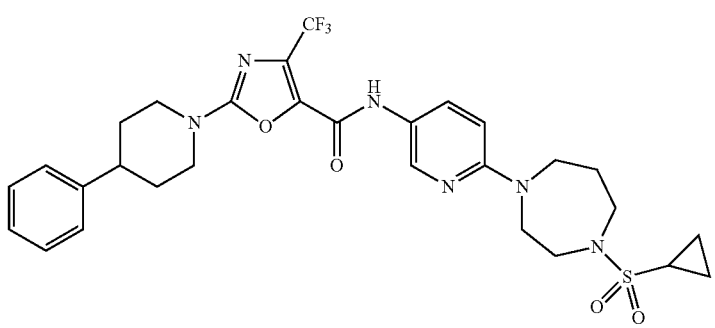<br>148 | Rt = 3.59 min, [M + 1]+ 619.3 |
| 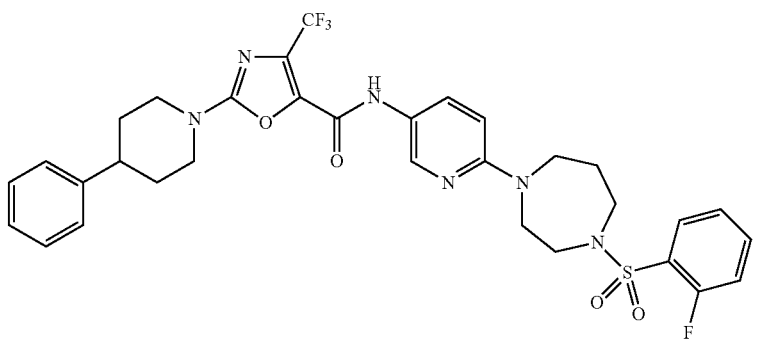<br>149 | Rt = 3.85 min, [M + 1]+ 673.4 |
| 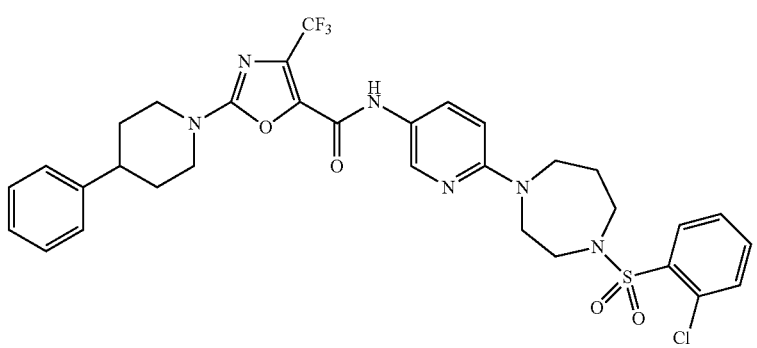<br>150 | Rt = 3.91 min, [M + 1]+ 689.4 |

| STRUCTURE | LCMS (ESI) |
|---|---|
| 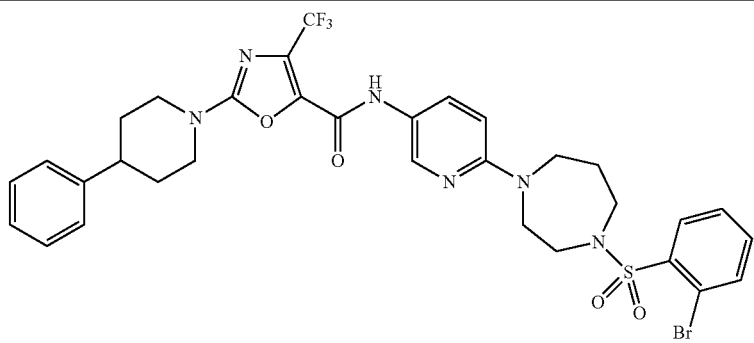 151 | Rt = 3.93 min, [M + 1]+ 733.4 |

Example 152

2-(Piperidin-1-yl)-N-(6-(4-(2,4,6-trichlorophenylsulfonyl)piperazin-1-yl)pyridin-3-yl)-4-(trifluoromethyl)oxazole-5-carboxamide (152)

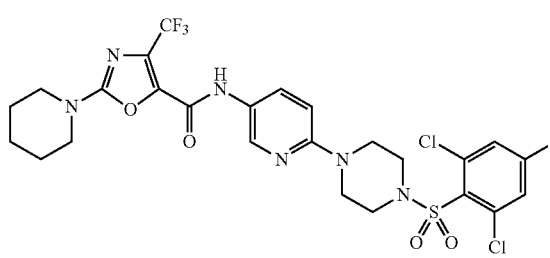

Compound 152 was prepared by the general procedure for compound 8, by using compound C-3 and 2,4,6-trichlorophenylsulfonyl chloride as the starting materials. LCMS (ESI) Rt=4.56 min, [M+1]+ 669.4.

Example 153 tert-Butyl 6-(2-(piperidin-1-yl)-4-(trifluoromethyl)oxazole-5-carboxamido)-3,4-dihydroisoquinoline-2(1H)-carboxylate (153)

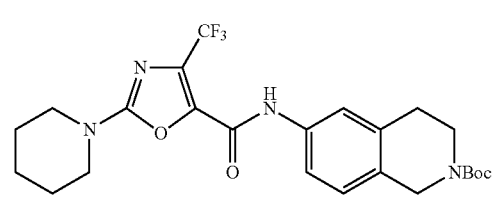

Compound 153 was prepared by the general procedure for compound 1, by using compound A-4 and tert-butyl 6-amino-3,4-dihydroisoquinoline-2(1H)-carboxylate as the starting materials. $^1$H NMR (400 MHz, DMSO-d6) δ 10.06 (s, 1H), 7.54 (s, 1H), 7.47 (d, 1H, J=8.4 Hz), 7.15 (d, 1H, J=8.4 Hz), 4.47 (s, 2H), 3.61 (m, 4H), 3.55 (t, 2H, J=5.9 Hz), 2.77 (t, 2H, J=5.9 Hz), 1.61 (m, 6H), 1.43 (s, 9H); LCMS (ESI) Rt=5.47 min, [M+1]+ 495.3.

Example 154

2-(Piperidin-1-yl)-N-(1,2,3,4-tetrahydroisoquinolin-6-yl)-4-(trifluoromethyl)oxazole-5-carboxamide (154)

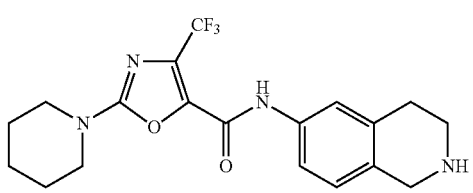

Compound 154 was prepared by the general procedure for compound C-3, by using compound 153 as the starting material. $^1$H NMR (400 MHz, DMSO-d6) δ 9.98 (s, 1H), 7.37-7.41 (m, 2H), 6.98 (d, 1H, J=8.1 Hz), 3.79 (s, 2H), 3.61 (m, 4H), 2.92 (t, 2H, J=5.9 Hz), 2.66 (t, 2H, J=5.9 Hz), 1.61 (m, 6H); LCMS (ESI) Rt=3.00 min, [M+1]+ 395.2.

Example 155

Ethyl 2-(6-(2-(piperidin-1-yl)-4-(trifluoromethyl)oxazole-5-carboxamido)-3,4-dihydroisoquinolin-2(1H)-yl)acetate (155)

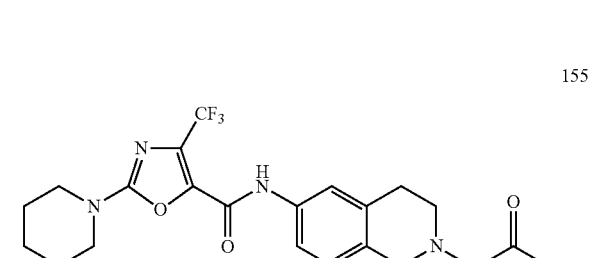

To a suspension of compound 154 (0.098 g, 0.25 mmol) and K$_2$CO$_3$ (0.5 g) in CH$_3$CN (5 mL) was added ethyl iodoacetate (0.036 mL). After 19 h of stirring at RT, the reaction mixture was diluted in EtOAc (50 mL) and filtered. The fitrate was washed with sat NaHCO₃ (2×50 mL), dried over Na₂SO₄, filtered, and concentrated. The crude materials were purified by prep-TLC using 25% CH₃CN in CH₂Cl₂ as eluents to yield compound 155 as a white solid (0.064 g, 54% yield). ¹H NMR (400 MHz, DMSO-d6) δ 10.02 (s, 1H), 7.47 (d, 1H, J=2.2 Hz), 7.41 (dd, 1H, J=8.0, 2.2 Hz), 7.02 (d, 1H, J=8.4 Hz), 4.11 (q, 2H, J=7.3 Hz), 3.66 (s, 2H), 3.61 (m, 4H), 3.41 (s, 2H), 2.80 (s, 4H), 1.61 (m, 6H), 1.21 (t, 3H, J=7.3 Hz); LCMS (ESI) Rt=3.21 min, [M+1]⁺ 481.3.

Example 156

Ethyl 5-(2-(piperidin-1-yl)-4-(trifluoromethyl)oxazole-5-carboxamido)-1H-indole-2-carboxylate (156)

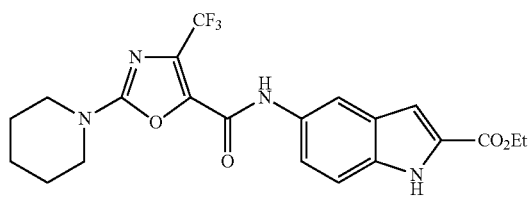

156

Compound 156 was prepared by the general procedure for compound 1, by using compounds A-4 and B-34 as the starting materials. ¹H NMR (400 MHz, DMSO-d6) δ 11.93 (s, 1H), 10.11 (s, 1H), 8.03 (m, 1H), 7.48 (dd, 1H, J=8.8, 1.8 Hz), 7.42 (d, 1H, J=9.2 Hz), 7.15 (m, 1H), 4.34 (q, 2H, J=7.0 Hz), 3.62 (m, 4H), 1.61 (m, 6H), 1.34 (t, 3H, J=7.0 Hz); LCMS (ESI) Rt=4.92 min, [M+1]⁺ 451.2.

Example 2157

5-(2-(Piperidin-1-yl)-4-(trifluoromethyl)oxazole-5-carboxamido)-1H-indole-2-carboxylic acid (157)

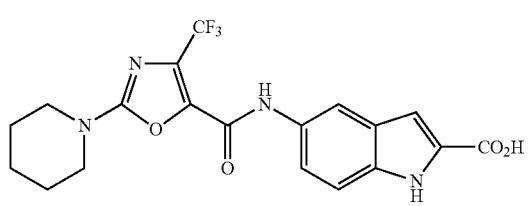

157

Compound 157 was prepared by saponification of compound 156. ¹H NMR (400 MHz, DMSO-d6) δ 11.81 (m, 1H), 10.09 (s, 1H), 8.01 (d, 1H, J=1.8 Hz), 7.45 (dd, 1H, J=8.8, 1.8 Hz), 7.40 (m, 1H), 7.08 (m, 1H), 3.62 (m, 4H), 1.61 (s, 6H); LCMS (ESI) Rt=4.14 min, [M+1]⁺ 423.2.

Example 158

2-(3-Methylpiperidin-1-yl)-N-(6-(4-phenylpiperidin-1-yl)pyridin-3-yl)-4-(trifluoromethyl)oxazole-5-carboxamide (158)

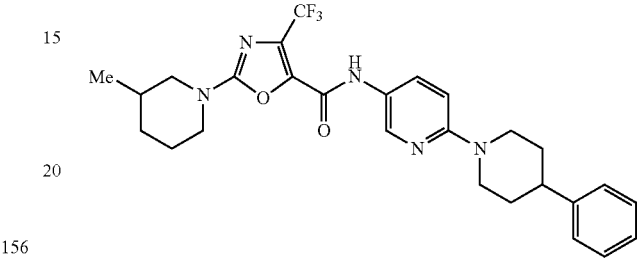

158

Compound 158 was prepared by the general procedure for compound 1, by using intermediates A-10 and B-6 as the starting materials. ¹H NMR (400 MHz, CDCl₃) δ 8.16 (d, 1H, J=2.7 Hz), 8.00 (dd, 1H, J=9.1, 2.6 Hz), 7.49 (s, 1H), 7.32 (t, 2H, J=7.4 Hz), 7.27-7.20 (m, 3H), 6.73 (d, 1H, J=9.2 Hz), 4.16 (d, 2H, J=12.8 Hz), 4.11 (t, 2H, J=19.9 Hz), 3.04 (dt, 1H, J=12.5, 3.0 Hz), 2.94 (dt, 2H, J=12.8, 2.5 Hz), 2.81-2.66 (m, 2H), 1.96 (d, 2H, J=12.2 Hz), 1.91-1.72 (m, 4H), 1.68-1.59 (m, 3H), 1.23-1.11 (m, 1H), 0.98 (d, 3H, J=6.6 Hz); LCMS (ESI) Rt=4.02 min, [M+1]⁺ 514.3.

Example 159

2-(3-Methylpiperidin-1-yl)-N-(6-(4-phenylpiperazin-1-yl)pyridin-3-yl)-4-(trifluoromethyl)oxazole-5-carboxamide (159)

159

Compound 159 was prepared by the general procedure for compound 1, by using intermediates A-10 and B-12 as the starting materials. ¹H NMR (400 MHz, CDCl₃-d3) δ 8.19 (d, 1H, J=2.5 Hz), 8.06 (dd, 1H, J=9.2, 2.6 Hz), 7.57 (s, 1H), 7.30 (t, 2H, J=8.7 Hz), 7.00 (d, 2H, J=7.7 Hz), 6.90 (t, 1H, J=7.3 Hz), 6.73 (d, 1H, J=9.2 Hz), 4.13 (t, 2H, J=15.0 Hz), 3.70 (t, 4H, J=5.0 Hz), 3.310 (t, 4H, J=5.4 Hz), 3.04 (dt, 1H, J=12.5, 3.7 Hz), 2.71 (t, 1H, J=11.7 Hz), 1.94-1.55 (m, 4H), 1.17 (dq, 1H, J=13.2, 6.6 Hz), 0.99 (d, 3H, J=6.6 Hz); LCMS (ESI) Rt=3.96 min, [M+1]$^+$ 515.3.

Example 160

N-(6-(4-hydroxy-4-phenylpiperidin-1-yl)pyridin-3-yl)-2-(3-methylpiperidin-1-yl)-4-(trifluoromethyl)oxazole-5-carboxamide (160)

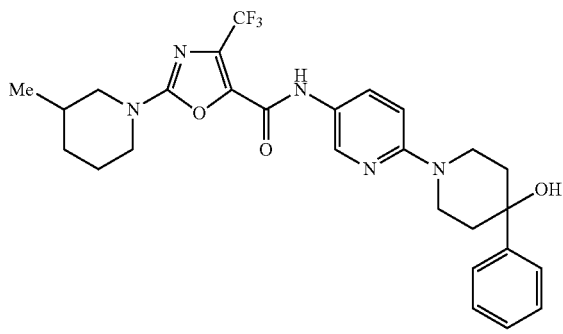

160

Compound 160 was prepared by the general procedure for compound 1, by using intermediates A-10 and B-2 as the starting materials. $^1$H NMR (400 MHz, CDCl$_3$-d3) δ 8.17 (d, 1H, J=2.6 Hz), 8.00 (dd, 1H, J=9.1, 2.9 Hz), 7.52-7.48 (m, 2H), 7.40-7.35 (m, 2H), 7.31-7.28 (m, 1H), 6.75 (d, 1H, J=9.5 Hz), 4.20 (dt, 2H, J=13.6, 3.3 Hz), 4.15-4.05 (m, 2H), 3.39 (dt, 2H, J=13.2, 3.3 Hz), 3.04 (dt, 1H, J=12.2, 3.0 Hz), 2.71 (dd, 1H J=12.8, 11.1 Hz), 2.16 (dt, 2H, J=16.5, 7.0 Hz), 1.94-1.69 (m, 6H), 1.24-1.11 (m, 1H), 0.98 (d, 3H, J=6.6 Hz); LCMS (ESI) Rt=3.71 min, [M+1]$^+$ 530.3.

Example 161

N-(6-(4-(3-chloropyridin-2-yl)piperazin-1-yl)pyridin-3-yl)-2-(piperidin-1-yl)-4-(trifluoromethyl)oxazole-5-carboxamide (161)

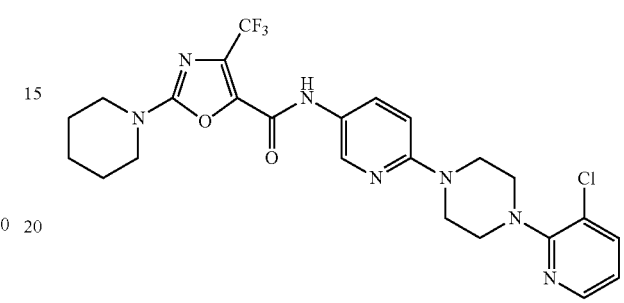

161

To a solution of compound C-3 (16 mg, 0.038 mmol) dissolved in 2-methyltetrahydrofuran (2 mL) was added 2,3-dichloropyridine (7.9 mg, 0.053 mmol), Pd$_2$ dba$_3$ (3.3 mg, 0.0036 mmol), BINAP (4.3 mg, 0.015 mmol) and sodium tert-butoxide (13.8 mg, 0.14 mmol). The reaction mixture was heated in a microwave reactor at 120° C. for 30 min. Dichloromethane and water was added. The organic layer was washed with water and brine. The organic layer was dried over anhydrous sodium sulfate. The organic solvent was evaporated under reduced pressure. The crude product was purified by flash column chromatography to yield compound 161 (6 mg, 29% yield). $^1$H NMR (400 MHz, CDCl$_3$) δ 8.20-8.23 (m, 2H), 8.06 (dd, 1H, J=9.2, 2.8 Hz), 7.64 (m, 1H), 7.55 (s, 1H), 6.89 (m, 1H), 6.74 (d, 1H, J=9.2 Hz), 3.70 (m, 4H), 3.64 (s, 4H), 3.51 (m, 4H), 1.72 (s, 6H); LCMS (ESI) Rt=3.46 min, [M+1]$^+$ 536.3.

Example 162

N-(6-(2-(3-(2-fluorophenyl)-2-oxoimidazolidin-1-yl)ethylamino)pyridin-3-yl)-2-(4-phenylpiperidin-1-yl)-4-(trifluoromethyl)oxazole-5-carboxamide (162)

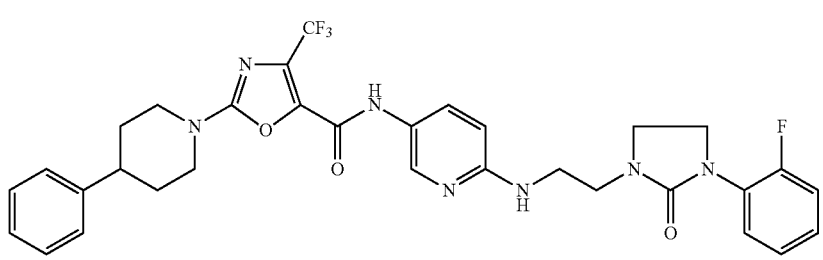

162

Compound 162 was prepared by the general procedure for compound 1. $^1$H NMR (500 MHz, CDCl$_3$) δ 8.15 (s, 1H), 7.85 (s, 1H), 7.79 (m, 1H), 7.45 (m, 1H), 7.24 (m, 4H), 7.23 (m, 3H), 6.44 (m, 2H), 5.08 (s, 1H), 4.36 (m, 2H), 3.83 (m, 2H), 3.58 (m, 6H), 3.18 (m, 2H), 2.77 (m, 1H), 2.00 (m, 2H), 1.80 (m, 4H). MS (M+1): 638

Example 163

N-(6-(2-(3-(2-fluorophenyl)-2-oxoimidazolidin-1-yl)ethylamino)pyridin-3-yl)-2-(3-methylpiperidin-1-yl)-4-(trifluoromethyl)oxazole-5-carboxamide (163)

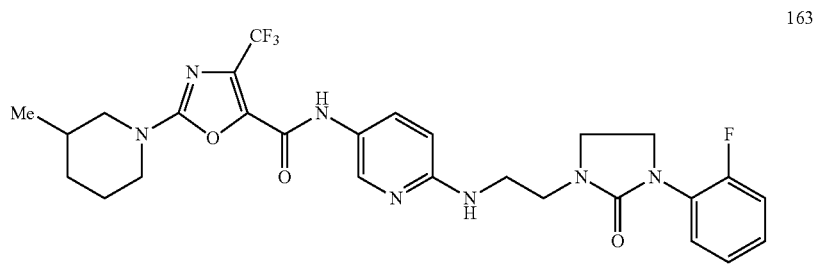 [SMILES: CC1CCCN(c2nc(C(F)(F)F)c(C(=O)Nc3ccc(NCCN4CCN(c5ccccc5F)C4=O)nc3)o2)C1]

163

Compound 163 was prepared by the general procedure for compound 1. $^1$H NMR (500 MHz, CDCl$_3$) δ 8.15 (m, 1H), 7.79 (m, 1H), 7.62 (s, 1H), 7.47 (m, 1H), 7.13 (m, 3H), 6.48 (m, 1H), 5.05 (s, 1H), 4.10 (m, 2H), 3.84 (m, 2H), 3.57 (m, 6H), 3.03 (m, 1H), 2.70 (m, 1H), 1.71 (m, 7H), 1.16 (m, 1H), 1.00 (m, 3H). MS (M+1): 576

Example 164

N-(6-(4-(2-fluorophenyl)piperazin-1-yl)pyridin-3-yl)-2-(3-methylpiperidin-1-yl)-4-(trifluoromethyl)oxazole-5-carboxamide (164)

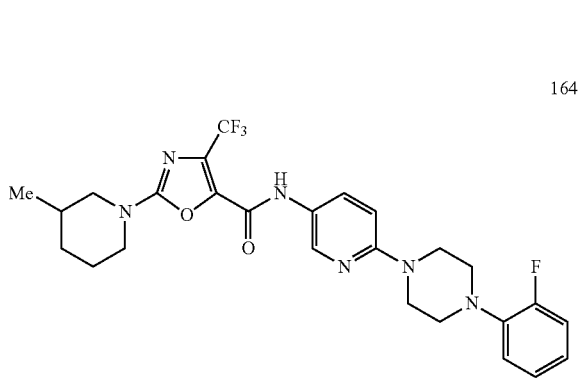 [SMILES: CC1CCCN(c2nc(C(F)(F)F)c(C(=O)Nc3ccc(N4CCN(c5ccccc5F)CC4)nc3)o2)C1]

164

Compound 164 was prepared by the general procedure for compound 1. $^1$H NMR (500 MHz, CDCl$_3$) δ 8.22 (d, J=3.0 Hz, 1H), 8.05 (dd, J=3.0, 9.0 Hz, 1H), 7.54 (s, 1H), 7.13-6.98 (m, 4H), 6.74 (d, J=9.0 Hz, 1H), 4.16-4.09 (m, 2H), 3.73-3.71 (m, 4H), 3.24-3.22 (m, 4H), 3.09-3.04 (m, 1H), 2.76-2.71 (m, 1H), 1.93-1.69 (m, 3H), 1.68-1.64 (m, 1H), 1.23-1.15 (m, 1H), 1.01 (d, J=6.5 Hz, 3H); MS (ESI) [M+1]$^+$ 533.

Example 165

N-(6-(4-(bis(4-fluorophenyl)methyl)piperazin-1-yl)pyridin-3-yl)-2-(3-methylpiperidin-1-yl)-4-(trifluoromethyl)oxazole-5-carboxamide (165)

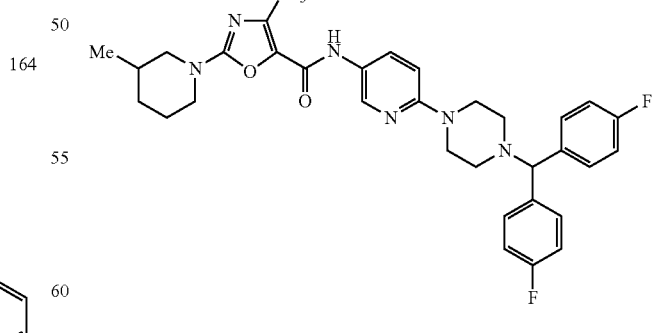

165

Compound 165 was prepared by the general procedure for compound 1. $^1$H NMR (500 MHz, DMSO-d$_6$) δ 10.03 (s, 1H), 8.32 (d, J=2.5 Hz, 1H), 7.78 (dd, J=2.5, 9.0 Hz, 1H), 7.50-7.47 (m, 4H), 7.17-7.14 (m, 4H), 6.82 (d, J=9.0 Hz, 1H), 4.42 (s, 1H), 4.13-4.05 (m, 2H), 3.47 (m, 4H), 3.07-3.02 (m, 1H), 2.76-2.72 (m, 1H), 2.42-2.39 (m, 4H), 1.80-1.49 (m, 4H), 1.19-1.11 (m, 1H), 0.93 (d, J=7.0 Hz, 3H); MS (ESI) [M+1]+ 641.

Example 166

N-(6-(5-fluoro-3,4-dihydroisoquinolin-2(1H)-yl)pyridin-3-yl)-2-(3-methylpiperidin-1-yl)-4-(trifluoromethyl)oxazole-5-carboxamide (166)

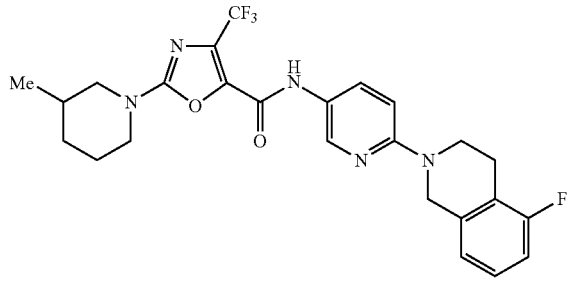

Compound 166 was prepared by the general procedure for compound 1. $^1$H NMR (500 MHz, CDCl$_3$) δ 8.21 (d, J=3.0 Hz, 1H), 8.04 (dd, J=3.0, 9.0 Hz, 1H), 7.52 (s, 1H), 7.21-7.17 (m, 1H), 7.02 (d, J=7.5 Hz, 1H), 6.93 (t, J=9.0 Hz, 1H), 6.75 (d, J=9.0 Hz, 1H), 4.73 (s, 2H), 4.16-4.09 (m, 2H), 3.88 (t, J=6.0 Hz, 2H), 3.09-3.03 (m, 1H), 2.97 (t, J=6.0 Hz, 2H), 2.73 (dd, J=7.5, 13.0 Hz, 1H), 1.92-1.62 (m, 4H), 1.23-1.16 (m, 1H), 1.01 (d, J=6.0 Hz, 3H); MS (ESI) [M+1]+ 504.

Example 167 methyl 2-(5-(2-(3-methylpiperidin-1-yl)-4-(trifluoromethyl)oxazole-5-carboxamido)pyridin-2-yl)-1,2,3,4-tetrahydroisoquinoline-5-carboxylate (167)

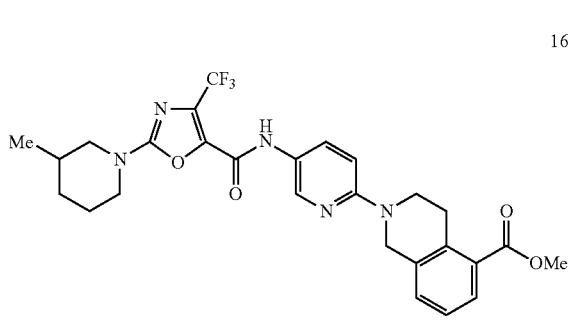 [SMILES: CC1CCCN(c2nc(C(F)(F)F)c(C(=O)Nc3ccc(N4CCc5c(cccc5C(=O)O)C4)nc3)o2)C1]

Compound 167 was prepared by the general procedure for compound 1. $^1$H NMR (500 MHz, DMSO-d$_6$) δ 10.04 (s, 1H), 8.37 (d, J=2.5 Hz, 1H), 7.84 (dd, J=2.0, 9.0 Hz, 1H), 7.71 (d, J=8.0 Hz, 1H), 7.51 (d, J=8.0 Hz, 1H), 7.34 (t, J=8.0 Hz, 1H), 6.96 (d, J=6.0 Hz, 1H), 4.74 (s, 2H), 4.14-4.05 (m, 2H), 3.84 (s, 3H), 3.78 (t, J=6.0 Hz, 2H), 3.20-3.18 (m, 2H), 3.08-3.02 (m, 1H), 2.77-2.72 (m, 1H), 1.80-1.49 (m, 4H), 1.19-1.11 (m, 1H), 0.94 (d, J=6.0 Hz, 3H); MS (ESI) [M+1]+ 544.

Example 168

2-(5-(2-(3-methylpiperidin-1-yl)-4-(trifluoromethyl)oxazole-5-carboxamido)pyridin-2-yl)-1,2,3,4-tetrahydroisoquinoline-5-carboxylic acid (168)

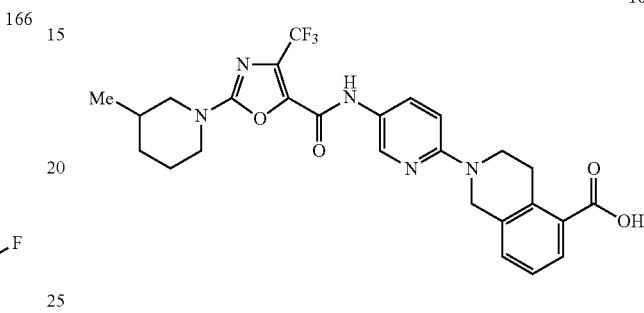

Compound 168 was prepared by the saponification of compound 167. $^1$H NMR (500 MHz, DMSO-d$_6$) δ 12.92 (s, 1H), 10.03 (s, 1H), 8.37 (d, J=2.5 Hz, 1H), 7.83 (dd, J=2.5, 9.0 Hz, 1H), 7.72 (d, J=7.5 Hz, 1H), 7.47 (d, J=7.5 Hz, 1H), 7.31 (t, J=8.0 Hz, 1H), 6.94 (d, J=9.0 Hz, 1H), 4.74 (s, 2H), 4.13-4.06 (m, 2H), 3.76 (t, J=6.0 Hz, 2H), 3.22 (t, J=6.0 Hz, 2H), 3.08-3.02 (m, 1H), 2.77-2.72 (m, 1H), 1.80-1.48 (m, 4H), 1.89-1.11 (m, 1H), 0.94 (d, J=6.5 Hz, 3H); MS (ESI) [M+1]+ 530.

Example 169

2-(3-methylpiperidin-1-yl)-N-(6-(4-(pyridin-2-yl)piperazin-1-yl)pyridin-3-yl)-4-(trifluoromethyl)oxazole-5-carboxamide (169)

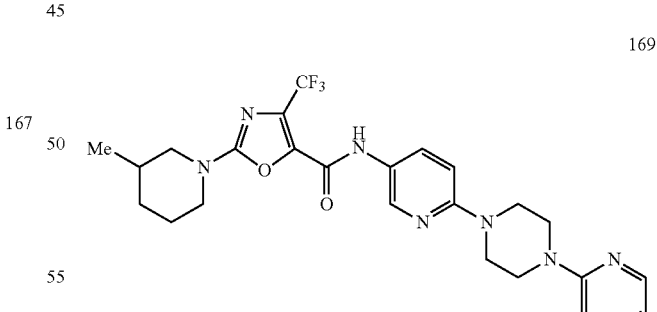

Compound 169 was prepared by the general procedure for compound 1. $^1$H NMR (500 MHz, DMSO-d$_6$) δ 10.05 (s, 1H), 8.38 (d, J=2.0 Hz, 1H), 8.15-8.14 (m, 1H), 7.84 (dd, J=2.0, 9.0 Hz, 1H), 7.59-7.55 (m, 1H), 6.94 (d, J=9.0 Hz, 1H), 6.90 (d, J=9.0 Hz, 1H), 6.69-6.65 (m, 1H), 4.14-4.06 (m, 2H), 3.61-3.60 (m, 4H), 3.08-3.03 (m, 1H), 2.77-2.69 (m, 1H), 2.51-2.50 (m, 4H), 1.80-1.52 (m, 4H), 1.19-1.12 (m, 1H), 0.94 (d, J=6.0 Hz, 3H); MS (ESI) [M+1]+ 516.

Example 170

2-(3-methylpiperidin-1-yl)-N-(6-(5-(phenylcarbamoyl)-3,4-dihydroisoquinolin-2(1H)-yl)pyridin-3-yl)-4-(trifluoromethyl)oxazole-5-carboxamide (170)

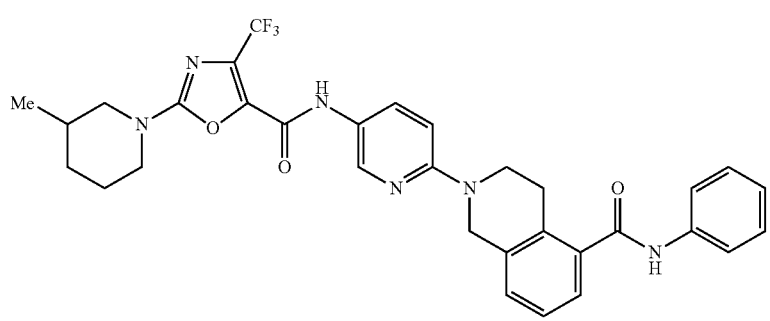

170

Compound 170 was prepared by the general procedure for compound 1. $^1$H NMR (500 MHz, DMSO-d$_6$) δ 10.34 (s, 1H), 10.03 (s, 1H), 8.36 (d, J=2.5 Hz, 1H), 7.83 (dd, J=2.5, 9.0 Hz, 1H), 7.75 (d, J=8.0 Hz, 2H), 7.42-7.31 (m, 5H), 7.11-7.08 (m, 1H), 6.95 (d, J=9.5 Hz, 1H), 4.77 (s, 2H), 4.14-4.06 (m, 2H), 3.80 (t, J=6.0 Hz, 2H), 3.17 (d, J=4.5 Hz, 2H), 3.02-3.00 (m, 1H), 2.77-2.72 (m, 1H), 1.81-1.64 (m, 3H), 1.58-1.50 (m, 1H), 1.19-1.11 (m, 1H), 0.94 (d, J=6.0 Hz, 3H); MS (ESI) [M+1]$^+$ 605.

Example 171

N-(6-(4-(2-hydroxyphenyl)piperazin-1-yl)pyridin-3-yl)-2-(3-methylpiperidin-1-yl)-4-(trifluoromethyl)oxazole-5-carboxamide (171)

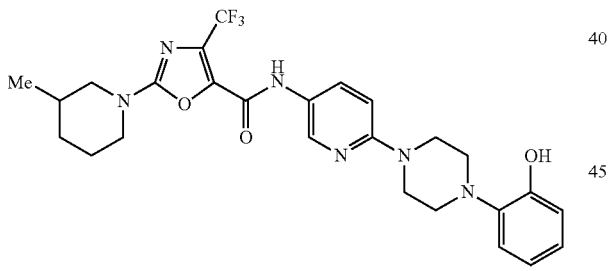

171

Compound 171 was prepared by the general procedure for compound 1. $^1$H NMR (500 MHz, DMSO-d$_6$) δ 10.04 (s, 1H), 9.02 (s, 1H), 8.37 (d, J=2.0 Hz, 1H), 7.82 (dd, J=2.0, 9.0 Hz, 1H), 6.93-6.74 (m, 5H), 4.14-4.06 (m, 2H), 3.63-3.62 (m, 4H), 3.08-3.02 (m, 5H), 2.75 (t, J=12.0 Hz, 1H), 1.80-1.49 (m, 4H), 1.92-1.11 (m, 1H), 0.94 (d, J=6.0 Hz, 3H); MS (ESI) [M+1]$^+$ 531.

Example 172

N-(6-(5-(2-fluorophenylcarbamoyl)-3,4-dihydroisoquinolin-2(1H)-yl)pyridin-3-yl)-2-(3-methylpiperidin-1-yl)-4-(trifluoromethyl)oxazole-5-carboxamide (172)

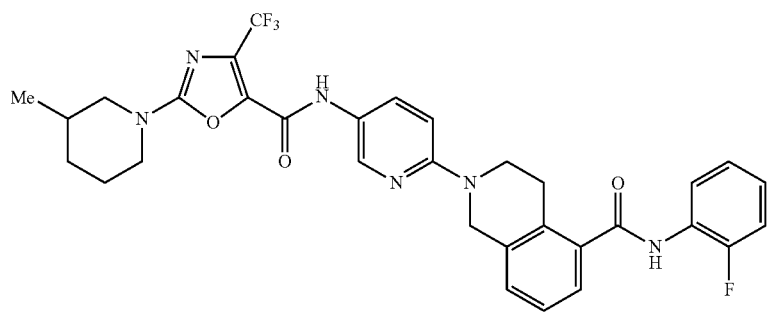

172

Compound 172 was prepared by the general procedure for compound 1. ¹H NMR (500 MHz, CDCl₃) δ 8.52-8.49 (m, 1H), 8.22 (d, J=3.0 Hz, 1H), 8.03 (dd, J=3.0, 9.0 Hz, 1H), 7.75 (m, 1H), 7.51-7.32 (m, 4H), 7.25-7.13 (m, 3H), 6.72 (d, J=9.0 Hz, 1H), 4.80 (s, 2H), 4.16-4.10 (m, 2H), 3.83 (t, J=6.0 Hz, 2H), 3.26 (t, J=6.0 Hz, 2H), 3.09-3.04 (m, 1H), 2.76-2.71 (m, 1H), 1.95-1.58 (m, 4H), 1.24-1.18 (m, 1H), 1.01 (d, J=6.0 Hz, 3H); MS (ESI) [M+1]⁺ 623.

Example 173

2-(4-(2-fluorophenyl)piperazin-1-yl)-N-(6-(4-(pyridin-2-yl)piperazin-1-yl)pyridin-3-yl)-4-(trifluoromethyl)oxazole-5-carboxamide (173)

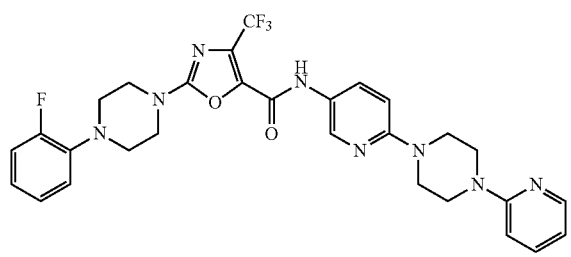

173

Compound 173 was prepared by the general procedure for compound 1. ¹H NMR (500 MHz, DMSO-d₆) δ 10.13 (s, 1H), 8.39 (d, J=2.5 Hz, 1H), 8.15-8.14 (m, 1H), 7.86 (dd, J=2.5, 9.0 Hz, 1H), 7.59-7.55 (m, 1H), 7.21-7.03 (m, 4H), 6.95 (d, J=9.0 Hz, 1H), 6.90 (d, J=9.0 Hz, 1H), 6.69-6.65 (m, 1H), 3.82-3.81 (m, 4H), 3.61-3.60 (m, 8H), 3.18-3.15 (m, 4H); MS (ESI) [M+1]⁺ 597.

Example 174

N-(6-(5-(2-fluorophenylamino)-3,4-dihydroisoquinolin-2(1H)-yl)pyridin-3-yl)-2-(3-methylpiperidin-1-yl)-4-(trifluoromethyl)oxazole-5-carboxamide (174)

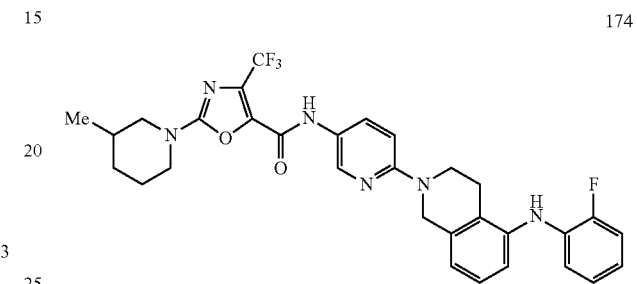

174

Compound 174 was prepared by the general procedure for compound 1. ¹H NMR (500 MHz, DMSO-d₆) δ 10.02 (s, 1H), 8.36 (d, J=2.0 Hz, 1H), 7.82 (dd, J=2.0, 9.0 Hz, 1H), 7.26 (s, 1H), 7.19-7.11 (m, 2H), 7.03-6.80 (m, 6H), 4.70 (s, 2H), 4.16-4.06 (m, 2H), 3.80 (t, J=6.0 Hz, 2H), 3.08-3.03 (m, 1H), 2.77-2.73 (m, 3H), 1.81-1.52 (m, 4H), 1.18-1.12 (m, 1H), 0.94 (d, J=6.5 Hz, 3H); MS (ESI) [M+1]⁺ 595.

Example 175

2-(4-(2-fluorophenylcarbamoyl)piperazin-1-yl)-N-(6-(4-phenylpiperidin-1-yl)pyridin-3-yl)-4-(trifluoromethyl)oxazole-5-carboxamide (175)

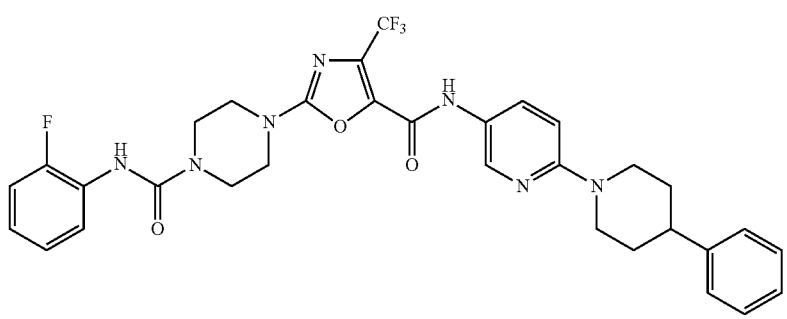

175

Compound 175 was prepared by the general procedure for compound 1. $^1$H NMR (500 MHz, DMSO-d$_6$) δ 10.09 (s, 1H), 8.51 (s, 1H), 8.35 (d, J=2.5 Hz, 1H), 7.81 (dd, J=2.5, 9.0 Hz, 1H), 7.47-7.43 (m, 1H), 7.32-7.12 (m, 8H), 6.93 (d, J=9.0 Hz, 1H), 4.42 (d, J=13.0 Hz, 2H), 3.70-3.62 (m, 8H), 2.91-2.76 (m, 3H), 1.87-1.61 (m, 4H); MS (ESI) [M+1]$^+$ 638.

Example 176 methyl 2-(3-(5-(2-(3-methylpiperidin-1-yl)-4-(trifluoromethyl)oxazole-5-carboxamido)pyridin-2-yl)-3-azaspiro[5.5]undecan-9-yl)acetate (176)

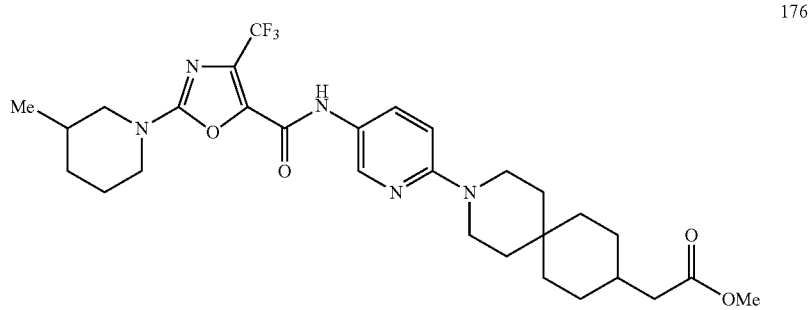 [SMILES: COC(=O)CC1CCC2(CC1)CCN(c1ccc(NC(=O)c3oc(N4CCCC(C)C4)nc3C(F)(F)F)cn1)CC2]

Compound 176 was prepared by the general procedure for compound 1. $^1$H NMR (500 MHz, CDCl$_3$) δ 8.15 (d, J=2.5 Hz, 1H), 7.98 (dd, J=2.5, 9.0 Hz, 1H), 7.49 (s, 1H), 6.67 (d, J=9.0 Hz, 1H), 4.15-4.08 (m, 2H), 3.70 (s, 3H), 3.52-3.48 (m, 4H), 3.09-3.03 (m, 1H), 2.73 (dd, J=11.0, 12.5 Hz, 1H), 2.27 (d, J=7.0 Hz, 2H), 1.92-1.73 (m, 6H), 1.62-1.58 (m, 5H), 1.48-1.46 (m, 2H), 1.26-1.15 (m, 5H), 1.01 (d, J=6.0 Hz, 3H); MS (ESI) [M+1]$^+$ 578.

Example 177

2-(3-methylpiperidin-1-yl)-N-(1-((2-(o-tolylcarbamoyl)cyclopropyl)-methyl)indolin-5-yl)-4-(trifluoromethyl)oxazole-5-carboxamide (177)

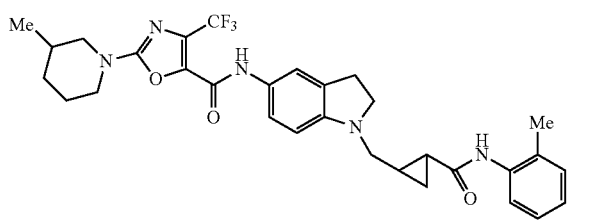

Compound 177 was prepared by the general procedure for compound 72. $^1$H NMR (500 MHz, DMSO-d6) δ 9.86 (s, 1H), 9.55 (s, 1H), 7.42 (d, 1H, J=7.3 Hz), 7.39 (s, 1H), 7.26 (d, 1H, J=7.9 Hz), 7.21 (d, 1H, J=7.4 Hz), 7.14 (t, 1H, J=8.0 Hz), 7.06 (t, 1H, J=8.0 Hz), 6.56 (d, 1H, J=8.5 Hz), 4.11 (d, 1H, J=12.9 Hz), 4.06 (dd, 1H, J=3.6, 12.9 Hz), 3.44 (q, 2H, J=8.5 Hz), 3.18 (dd, 1H, J=6.1, 12.9 Hz), 3.03 (t, 1H, J=12.3 Hz), 2.97 (dd, 1H, J=7.4, 13.4 Hz), 2.92 (t, 2H, J=8.0 Hz), 2.73 (t, 1H, J=11.7 Hz), 2.21 (s, 3H), 1.90-1.84 (m, 1H), 1.82-1.70 (m, 2H), 1.70-1.61 (m, 1H), 1.58-1.47 (m, 1H), 1.47-1.40 (m, 1H), 1.14 (q, 1H, J=11.0 Hz), 1.09-1.02 (m, 1H), 0.93 (d, 3H, J=6.8 Hz), 0.88-0.81 (m, 1H). MS (M+1): 582.4.

Example 178

2-(3-methylpiperidin-1-yl)-N-(1-(2-(3-phenylureido)acetyl)indolin-5-yl)-4-(trifluoromethyl)oxazole-5-carboxamide (178)

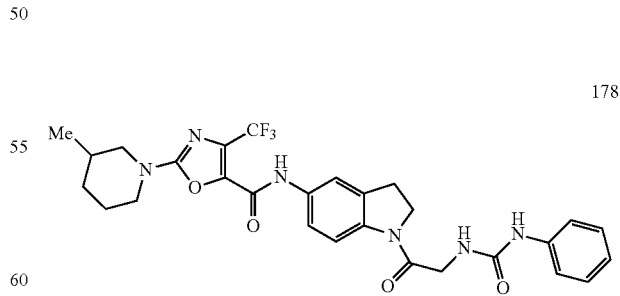

$^1$H NMR (500 MHz, DMSO-d6) δ 10.09 (s, 1H), 8.92 (s, 1H), 8.04 (d, 1H, J=7.9 Hz), 7.66 (s, 1H), 7.42 (d, 3H, J=7.6 Hz), 7.24 (t, 2H, J=7.6 Hz), 6.91 (t, 1H, J=7.6 Hz), 6.46 (t, 1H, J=4.7 Hz), 4.14 (t, 2H, J=8.4 Hz), 4.11-4.05 (m, 4H), 3.20 (t, 2H, J=8.2 Hz), 3.05 (t, 1H, J=12.1 Hz), 2.73 (t, 1H, J=11.5

Hz), 1.82-1.78 (m, 2H), 1.70-1.62 (m, 1H), 1.58-1.47 (m, 1H), 1.15 (q, 1H, J=11.2 Hz), 0.94 (d, 3H, J=6.7 Hz). MS (M+1): 571.3.

Example 179

2-(3-methylpiperidin-1-yl)-N-(1-(3-(3-phenylureido) propanoyl)indolin-5-yl)-4-(trifluoromethyl)oxazole-5-carboxamide (179)

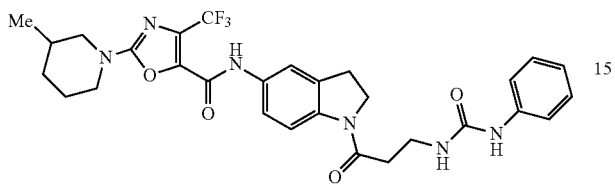

179

¹H NMR (500 MHz, DMSO-d6) δ 10.06 (s, 1H), 8.64 (s, 1H), 8.09 (d, 1H, J=8.5 Hz), 7.63 (s, 1H), 7.44 (d, 1H, J=8.0 Hz), 7.38 (d, 2H, J=7.7 Hz), 7.21 (t, 2H, J=7.7 Hz), 6.88 (t, 1H, J=7.2 Hz), 6.31 (t, 1H, J=5.5 Hz), 4.16-4.05 (m, 4H), 3.41 (q, 2H, J=5.5 Hz), 3.16 (t, 2H, J=8.4 Hz), 3.05 (t, 1H, J=12.3 Hz), 2.74 (t, 1H, J=11.6 Hz), 2.66 (t, 2H, J=6.2 Hz), 1.82-1.71 (m, 2H), 1.71-1.62 (m, 1H), 1.58-1.47 (m, 1H), 1.15 (q, 1H, J=11.3 Hz), 0.94 (d, 3H, J=6.7 Hz). MS (M+1): 585.3.

Example 180

N-(6-(4-(2-fluorophenylcarbamoyl)piperazin-1-yl) pyridin-3-yl)-N-methyl-2-(4-phenylpiperidin-1-yl)-4-(trifluoromethyl)oxazole-5-carboxamide (180)

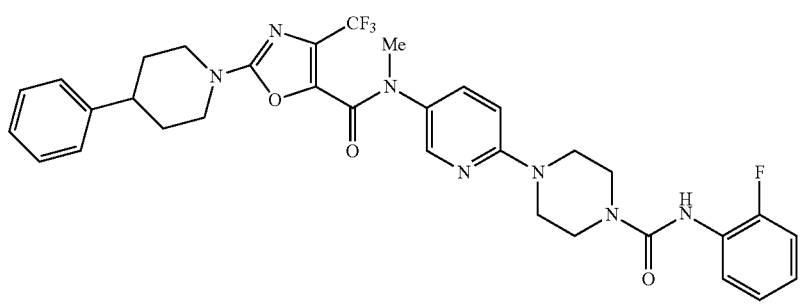

180

¹H NMR (500 MHz, DMSO-d6) δ 8.36 (s, 1H), 8.01 (s, 1H), 7.57 (dd, 1H, J=2.4, 9.0 Hz), 7.47-7.41 (m, 1H), 7.28 (t, 2H, J=7.6 Hz), 7.23-7.11 (m, 6H), 6.92 (d, 1H, J=9.1 Hz), 3.70-3.63 (m, 2H), 3.47 (br s, 4H), 3.42 (br s, 4H), 3.28 (s, 3H), 3.00 (t, 2H, J=12.9 Hz), 2.72 (t, 1H, J=11.0 Hz), 1.71 (d, 2H, J=11.8 Hz), 1.43-1.32 (m, 2H). MS (M+1): 652.4.

Example 181

N-(6-(4-(2-fluorophenylcarbamothioyl)piperazin-1-yl)pyridin-3-yl)-2-(4-phenylpiperidin-1-yl)-4-(trifluoromethyl)oxazole-5-carboxamide (181)

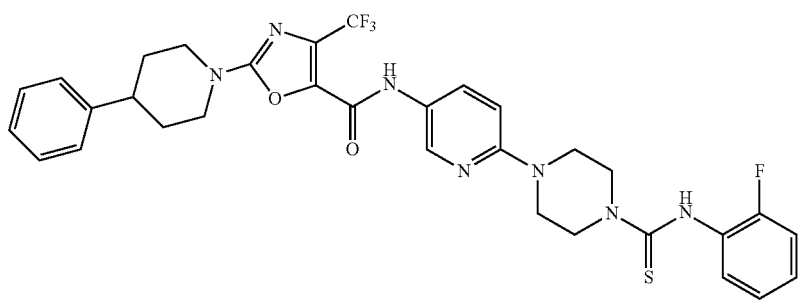

181

¹H NMR (500 MHz, DMSO-d6) δ 10.10 (s, 1H), 9.24 (s, 1H), 8.39 (s, 1H), 7.87 (d, 1H, J=8.4 Hz), 7.39-7.13 (m, 9H), 6.91 (d, 1H, J=8.4 Hz), 4.36 (d, 2H, J=12.3 Hz), 4.06 (s, 4H), 3.63 (s, 4H), 3.22 (t, 2H, J=12.5 Hz), 2.81 (t, 1H, J=12.5 Hz), 1.93-1.84 (m, 2H), 1.80-1.68 (m, 2H). MS (M+1): 654.4.

Example 182

(Z)—N-(6-(4-((cyanoimino)(pyrrolidin-1-yl)methyl)piperazin-1-yl)pyridin-3-yl)-2-(4-phenylpiperidin-1-yl)-4-(trifluoromethyl)oxazole-5-carboxamide (182)

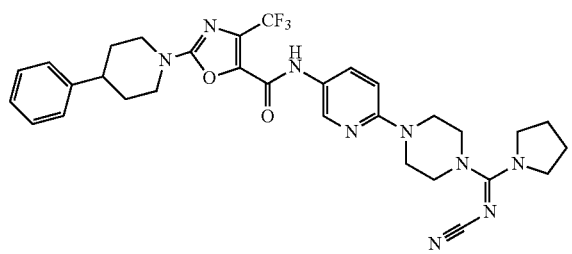

182

¹H NMR (500 MHz, DMSO-d6) δ 10.10 (s, 1H), 8.39 (d, 1H, J=2.5 Hz), 7.86 (dd, 1H, J=2.8, 8.8 Hz), 7.35-7.29 (m, 4H), 7.24-7.20 (m, 1H), 6.94 (d, 1H, J=9.1 Hz), 4.35 (d, 2H, J=12.7 Hz), 3.60-3.56 (m, 4H), 3.49-3.41 (m, 8H), 3.22 (br t, 2H, J=12.3 Hz), 2.82 (br t, 1H, J=12.2 Hz), 1.93-1.86 (m, 2H), 1.85-1.80 (m, 4H), 1.79-1.69 (m, 2H). MS (M+1): 622.3.

Example 183

Cyclopentyl 4-(5-(2-(3-methylpiperidin-1-yl)-4-(trifluoromethyl)oxazole-5-carboxamido)pyridin-2-yl)piperazine-1-carboxylate (183)

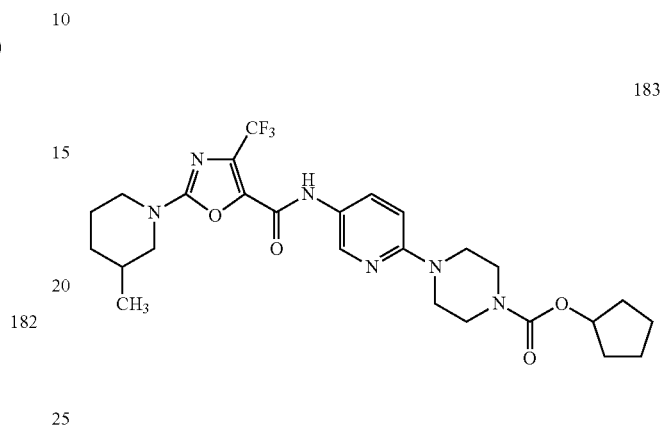

183

Compound 183 was prepared by the general procedure for compound 1. ¹H NMR (500 MHz, CDCl₃) δ 8.43 (s, 1H), 8.27 (m, 1H), 7.97 (s, 1H), 7.34 (d, 1H, J=9.2 Hz), 5.17 (m, 1H), 4.13 (m, 2H), 3.65 (m, 4H), 3.15 (m, 4H), 3.04 (m, 1H), 2.71 (m, 1H), 1.75 (m, 12H), 1.18 (m, 1H), 1.05 (d, 3H, J=6.6 Hz). MS (M+1): 551.3

Example 184

Cyclopentyl 4-(5-(2-(4-phenylpiperidin-1-yl)-4-(trifluoromethyl)oxazole-5-carboxamido)pyridin-2-yl)piperazine-1-carboxylate (184)

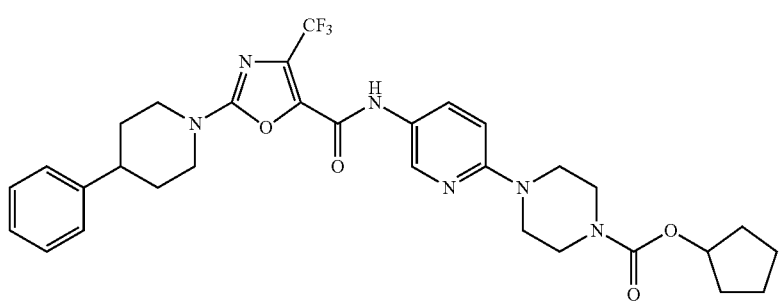

184

Compound 184 was prepared by the general procedure for compound 1. ¹H NMR (500 MHz, CDCl₃) δ 8.35 (s, 1H), 8.27 (d, 1H, J=8.5 Hz), 7.98 (s, 1H), 7.36 (m, 3H), 7.26 (m, 3H), 5.17 (m, 1H), 4.39 (m, 2H), 3.65 (m, 4H), 3.23 (m, 2H), 3.16 (m, 4H), 2.80 (m, 1H), 1.75 (m, 12H). MS (M+1): 613.3

Example 185

(1s,4s)-4-(4-(5-(2-(3-Methylpiperidin-1-yl)-4-(trifluoromethyl)oxazole-5-carboxamido)pyridin-2-yl)-1,4-diazepane-1-carbonyl)cyclohexanecarboxylic acid (185)

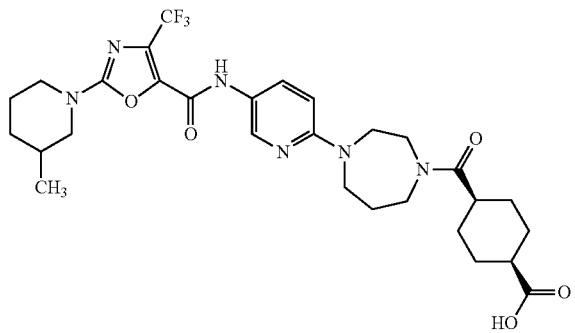

185

Compound 185 was prepared by the general procedure for compound 85. ¹H NMR (500 MHz, CD₃OD) δ 8.60 (s, 1H), 8.52 (m, 1H), 7.38 (d, 1H, J=9.8 Hz), 4.20 (m, 2H), 3.87 (m, 6H), 3.72 (m, 2H), 3.15 (m, 2H), 2.80 (m, 1H), 2.61 (m, 1H), 1.77 (m, 15H), 1.02 (d, 3H, J=6.6 Hz). MS (M+1): 607.3

Example 186

(1R,4R)-4-(4-(5-(2-(3-Methylpiperidin-1-yl)-4-(trifluoromethyl)oxazole-5-carboxamido)pyridin-2-yl)-1,4-diazepane-1-carbonyl)cyclohexanecarboxylic acid (186)

186

Compound 186 was prepared by the general procedure for compound 85. ¹H NMR (500 MHz, CD₃OD) δ 8.60 (s, 1H), 8.15 (m, 1H), 7.37 (d, 1H, J=9.8 Hz), 4.20 (m, 2H), 3.87 (m, 6H), 3.72 (m, 2H), 3.12 (m, 2H), 2.80 (m, 1H), 2.61 (m, 1H), 1.77 (m, 15H), 1.02 (d, 3H, J=6.6 Hz). MS (M+1): 607.3

Example 187

(1R,2R)-2-(4-(5-(2-(3-methylpiperidin-1-yl)-4-(trifluoromethyl)oxazole-5-carboxamido)pyridin-2-yl-1,4-diazepane-1-carbonyl)cyclopentanecarboxylic acid (187)

187

Compound 187 was prepared by the general procedure for compound 85. ¹H NMR (500 MHz, CD₃OD) δ 8.59 (s, 1H), 8.13 (m, 1H), 7.33 (d, 1H, J=10.1 Hz), 4.21 (m, 2H), 3.92 (m, 6H), 3.61 (m, 2H), 3.28 (m, 2H), 3.12 (m, 1H), 2.80 (m, 1H), 1.80 (m, 12H), 1.26 (m, 1H), 1.02 (d, 3H, J=6.6 Hz). MS (M+1): 594.3

Example 188

1-(4-(5-(2-(3-methylpiperidin-1-yl)-4-(trifluoromethyl)oxazole-5-carboxamido)pyridin-2-yl)-1,4-diazepane-1-carbonyl)cyclobutanecarboxylic acid (188)

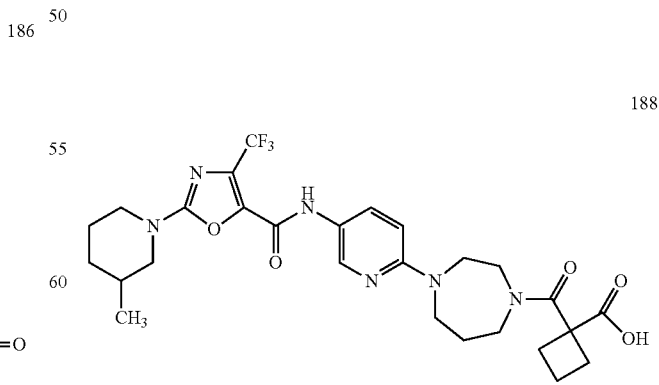

188

Compound 188 was prepared by the general procedure for compound 85. ¹H NMR (500 MHz, CD₃OD) δ 8.57 (s, 1H), 8.14 (d, 1H, J=10.0 Hz), 7.35 (d, 1H, J=9.5 Hz), 4.20 (m, 2H), 3.93 (m, 3H), 3.82 (m, 2H), 3.63 (m, 1H), 3.49 (m, 1H), 3.42 (m, 1H), 3.12 (m, 1H), 2.78 (m, 1H), 2.53 (m, 4H), 1.84 (m, 8H), 1.25 (m, 1H), 1.02 (d, 3H, J=6.6 Hz). MS (M+1): 579.3

Example 189

5-(4-(5-(2-(3-methylpiperidin-1-yl)-4-(trifluoromethyl)oxazole-5-carboxamido)pyridin-2-yl)-1,4-diazepane-1-carbonyl)nicotinic acid (189)

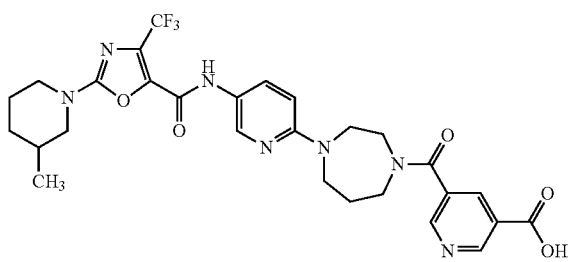

189

Compound 189 was prepared by the general procedure for compound 85. ¹H NMR (500 MHz, CD₃OD) δ 9.23 (s, 1H), 8.77 (s, 1H), 8.54 (s, 1H), 8.12 (m, 2H), 7.24 (d, 1H, J=9.8 Hz), 4.18 (m, 3H), 3.92 (m, 5H), 3.78 (m, 1H), 3.60 (m, 1H), 3.12 (t, 1H, J=12.6 Hz), 2.80 (t, 1H, J=11.7 Hz), 2.15 (s, 1H), 1.78 (m, 5H), 1.27 (m, 1H), 1.02 (d, 3H, J=6.6 Hz). MS (M+1): 602.3

Example 190

3-(4-(5-(2-(3-methylpiperidin-1-yl)-4-(trifluoromethyl)oxazole-5-carboxamido)pyridin-2-yl)-1,4-diazepane-1-carbonyl)benzoic acid (190)

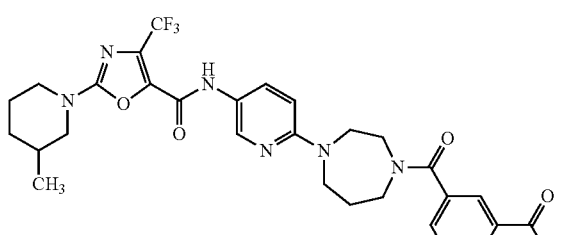

190

Compound 190 was prepared by the general procedure for compound 85. ¹H NMR (500 MHz, CD₃OD) δ 8.50 (s, 1H), 8.15 (m, 2H), 7.72 (s, 1H), 7.59 (m, 2H), 7.20 (d, 1H, J=9.8 Hz), 4.22 (m, 2H), 4.11 (m, 1H), 3.88 (m, 5H), 3.76 (m, 1H), 3.57 (m, 1H), 3.13 (m, 1H), 2.80 (m, 1H), 2.12 (s, 1H), 1.78 (m, 5H), 1.26 (m, 1H), 1.03 (d, 3H, J=6.6 Hz). MS (M+1): 601.3

Example 191

2-(3-methylpiperidin-1-yl)-N-(6-(4-(3,3,3-trifluoro-2-hydroxypropanoyl)-1,4-diazepan-1-yl)pyridin-3-yl)-4-(trifluoromethyl)oxazole-5-carboxamide (191)

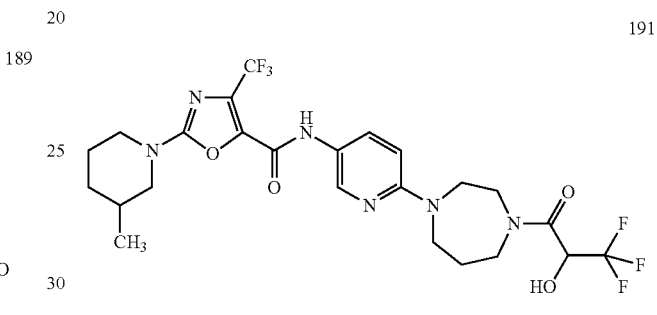

191

Compound 191 was prepared by the general procedure for compound 85. ¹H NMR (500 MHz, CD₃OD) δ 8.35 (s, 1H), 7.85 (d, 1H, J=9.1 Hz), 6.83 (d, 1H, J=9.1 Hz), 4.90 (m, 1H), 4.20 (m, 2H), 3.92 (m, 7H), 3.35 (m, 1H), 3.10 (t, 1H, J=12.6 Hz), 2.78 (t, 1H, J=12.0), 1.85 (m, 6H), 1.25 (m, 1H), 1.01 (d, 3H, J=6.6 Hz). MS (M+1): 579.3

Example 192

N-(6-(4-((R)-2-cyclohexyl-2-hydroxyacetyl)-1,4-diazepan-1-yl)pyridin-3-yl)-2-(3-methylpiperidin-1-yl)-4-(trifluoromethyl)oxazole-5-carboxamide (192)

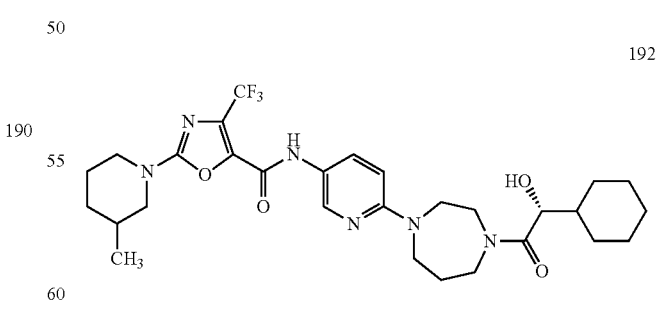

192

Compound 192 was prepared by the general procedure for compound 85. ¹H NMR (500 MHz, CD₃OD) δ 8.39 (s, 1H), 7.89 (d, 1H, J=9.1 Hz), 6.87 (d, 1H, J=9.1 Hz), 4.24 (m, 2H), 3.84 (m, 8H), 3.10 (m, 1H), 2.88 (m, 1H), 1.71 (m, 11H), 1.18 (m, 7H), 1.02 (d, 3H, J=6.6 Hz). MS (M+1): 593.3

Example 193

N-(6-(4-((R)-2-hydroxy-2-phenylacetyl)-1,4-diazepan-1-yl)pyridin-3-yl)-2-(3-methylpiperidin-1-yl)-4-(trifluoromethyl)oxazole-5-carboxamide (193)

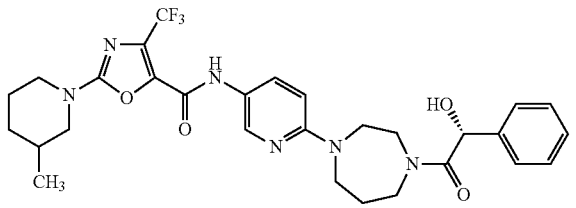

193

Compound 193 was prepared by the general procedure for compound 85. $^1$H NMR (500 MHz, CD$_3$OD) δ 8.52 (s, 1H), 8.13 (d, 1H, J=9.8 Hz), 7.38 (d, 1H, J=7.6 Hz), 7.30 (m, 3H), 7.18 (d, 1H, J=10 Hz), 7.17 (d, 1H, J=7.3 Hz), 5.42 (d, 1H, J=32 Hz), 4.22 (m, 3H), 3.92 (m, 1H), 3.71 (m, 5H), 3.50 (m, 1H), 3.13 (m, 1H), 2.81 (m, 1H), 1.83 (m, 5H), 1.35 (m, 2H), 1.02 (d, 3H, J=6.6 Hz). MS (M+1): 587.3

Example 194

2-(3-methylpiperidin-1-yl)-N-(6-(4-(3,3,3-trifluoro-2-hydroxypropanoyl)piperazin-1-yl)pyridin-3-yl)-4-(trifluoromethyl)oxazole-5-carboxamide (194)

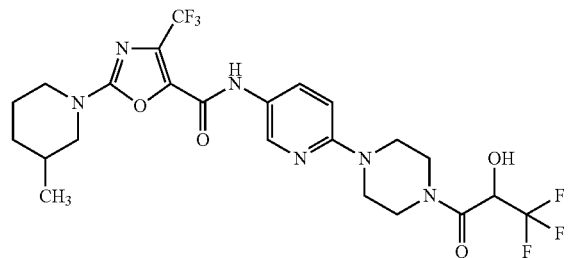

194

Compound 194 was prepared by the general procedure for compound 85. $^1$H NMR (500 MHz, CD$_3$OD) δ 8.55 (d, 1H, J=2.5 Hz), 8.08 (m, 1H), 7.22 (d, 1H, J=9.5 Hz), 5.12 (m, 1H), 4.21 (m, 2H), 3.80 (m, 8H), 3.11 (m, 1H), 2.79 (m, 1H), 1.77 (m, 4H), 1.25 (m, 1H), 1.02 (d, 3H, J=6.6 Hz). MS (M+1): 565.3

Example 195

N-(6-(4-(2-(3,4-difluorophenyl)-2-hydroxyacetyl)piperazin-1-yl)pyridin-3-yl)-2-(3-methylpiperidin-1-yl)-4-(trifluoromethyl)oxazole-5-carboxamide (195)

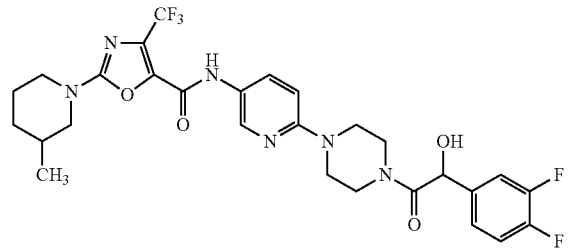

195

Compound 195 was prepared by the general procedure for compound 85. $^1$H NMR (500 MHz, CD$_3$OD) δ 8.54 (d, 1H, J=2.5 Hz), 8.08 (m, 1H), 7.40 (m, 1H), 7.30 (m, 2H), 7.21 (d, 1H, J=9.5 Hz), 5.53 (s, 1H), 4.19 (m, 2H), 3.56 (m, 8H), 3.11 (m, 1H), 2.78 (m, 1H), 1.78 (m, 4H), 1.25 (m, 1H), 1.02 (d, 3H, J=6.6 Hz). MS (M+1): 609.3

Example 196

N-(6-(4-((R)-2-cyclohexyl-2-hydroxyacetyl)piperazin-1-yl)pyridin-3-yl)-2-(3-methylpiperidin-1-yl)-4-(trifluoromethyl)oxazole-5-carboxamide (196)

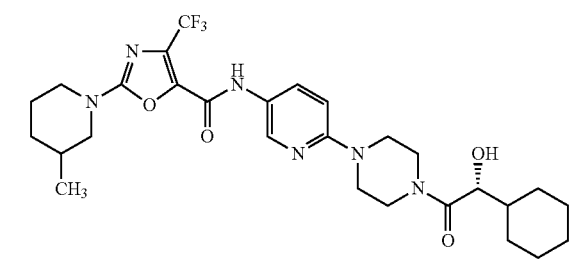

196

Compound 196 was prepared by the general procedure for compound 85. $^1$H NMR (500 MHz, CD$_3$OD) δ 8.61 (d, 1H, J=2.5 Hz), 8.15 (m, 1H), 7.34 (d, 1H, J=9.8 Hz), 4.21 (m, 3H), 3.80 (m, 8H), 3.12 (m, 1H), 2.79 (m, 1H), 1.76 (m, 10H), 1.24 (m, 6H), 1.02 (d, 3H, J=6.6 Hz). MS (M+1): 579.3

Example 197

N-(6-(4-(2-(3,4-difluorophenyl)-2-hydroxyacetyl)-1,4-diazepan-1-yl)pyridin-3-yl)-2-(3-methylpiperidin-1-yl)-4-(trifluoromethyl)oxazole-5-carboxamide (197)

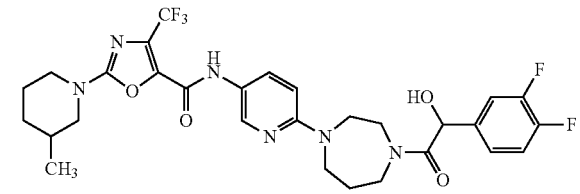

197

Compound 197 was prepared by the general procedure for compound 85. $^1$H NMR (500 MHz, CD$_3$OD) δ 8.25 (s, 1H), 7.78 (d, 1H, J=9.5 Hz), 7.20 (m, 3H), 6.67 (d, 1H, J=9.5 Hz), 5.34 (s, 1H), 4.21 (m, 2H), 3.96 (m, 1H), 3.64 (m, 7H), 3.08 (m, 1H), 2.78 (m, 1H), 1.82 (m, 6H), 1.31 (m, 1H), 1.01 (d, 3H, J=6.6 Hz). MS (M+1): 623.3

Example 198

N-(6-(4-((R)-2-hydroxy-2-phenylacetyl)piperazin-1-yl)pyridin-3-yl)-2-(3-methylpiperidin-1-yl)-4-(trifluoromethyl)oxazole-5-carboxamide (198)

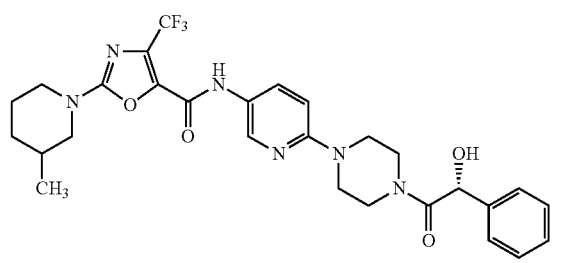

Compound 198 was prepared by the general procedure for compound 85. $^1$H NMR (500 MHz, CD$_3$OD) δ 8.48 (d, 1H, J=2.5 Hz), 8.01 (m, 1H), 7.41 (m, 5H), 7.10 (d, 1H, J=9.5 Hz), 5.53 (s, 1H), 4.20 (m, 2H), 3.64 (m, 7H), 3.12 (m, 2H), 2.78 (m, 1H), 1.76 (m, 4H), 1.23 (m, 1H), 1.01 (d, 3H, J=6.6 Hz). MS (M+1): 573.3

Example 199

(R)—N-(6-(4-(2-hydroxy-2-phenylacetyl)-1,4-diazepan-1-yl)pyridin-3-yl)-2-(4-phenylpiperidin-1-yl)-4-(trifluoromethyl)oxazole-5-carboxamide (199)

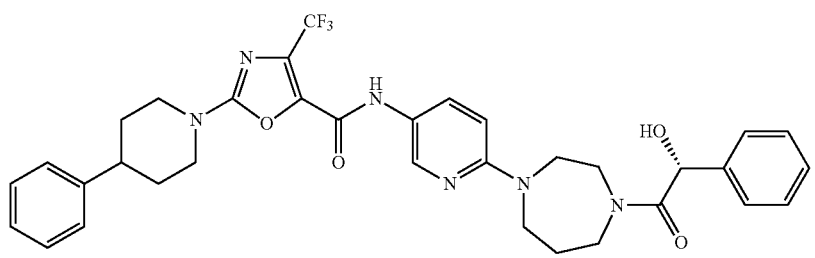

Compound 199 was prepared by the general procedure for compound 85. $^1$H NMR (500 MHz, CD$_3$OD) δ 8.54 (s, 1H), 8.12 (m, 1H), 7.28 (m, 1H), 5.42 (d, 1H. J=34 Hz), 4.48 (m, 2H), 4.23 (m, 1H), 3.80 (m, 6H), 3.46 (m, 2H), 3.29 (m, 2H), 2.87 (m, 1H), 1.92 (m, 5H). MS (M+1): 649.4

Example 200

(R)—N-(6-(4-(2-hydroxy-2-phenylacetyl)piperazin-1-yl)pyridin-3-yl)-2-(4-phenylpiperidin-1-yl)-4-(trifluoromethyl)oxazole-5-carboxamide (200)

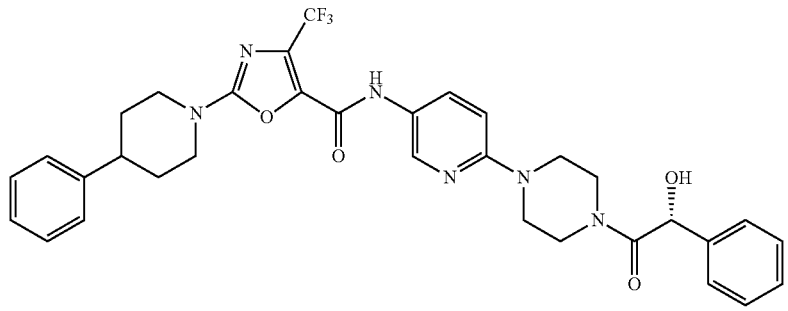

Compound 200 was prepared by the general procedure for compound 85. $^1$H NMR (500 MHz, CD$_3$OD) δ 8.35 (s, 1H), 7.88 (d, 1H, J=9.1 Hz), 7.36 (m, 9H), 7.21 (t, 1H, J=7.3 Hz), 6.83 (d, 1H, J=9.1 Hz), 5.52 (s, 1H), 4.44 (m, 2H), 3.83 (m, 1H), 3.61 (m, 4H), 3.39 (m, 2H), 3.25 (m, 2H), 2.99 (m, 1H), 2.85 (m, 1H), 1.97 (m, 2H), 1.83 (m, 2H). MS (M+1): 635.3

Example 201

N-(6-(4-(2-(3,5-difluorophenyl)-2-hydroxyacetyl)piperazin-1-yl)pyridin-3-yl)-2-(4-phenyl piperidin-1-yl)-4-(trifluoromethyl)oxazole-5-carboxamide (201)

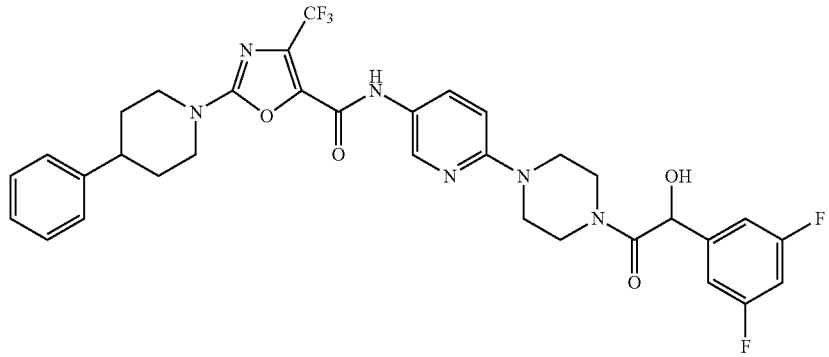

Compound 201 was prepared by the general procedure for compound 85. $^1$H NMR (500 MHz, CDCl$_3$) δ 8.53 (s, 1H), 7.29 (m, 6H), 6.91 (m, 2H), 6.81 (m, 2H), 5.27 (s, 1H), 4.53 (m, 2H), 3.64 (m, 8H), 3.20 (m, 2H), 2.77 (m, 1H), 1.99 (m, 2H), 1.83 (m, 2H). MS (M+1): 671.4

Example 202

N-(6-(4-(2-(3,5-difluorophenyl)-2-hydroxyacetyl)-1,4-diazepan-1-yl)pyridin-3-yl)-2-(4-phenylpiperidin-1-yl)-4-(trifluoromethyl)oxazole-5-carboxamide (202)

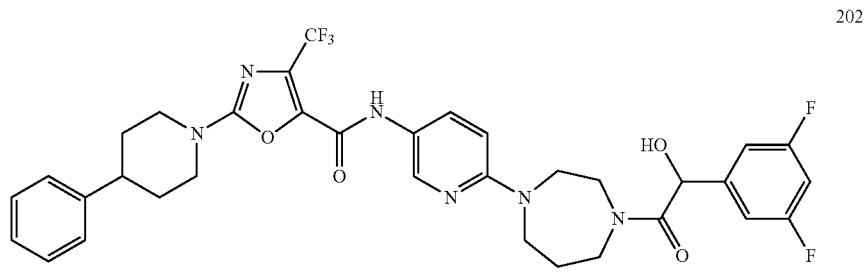 [SMILES: O=C(Nc1ccc(N2CCCN(C(=O)C(O)c3cc(F)cc(F)c3)CC2)nc1)c1oc(N2CCC(c3ccccc3)CC2)nc1C(F)(F)F]

Compound 202 was prepared by the general procedure for compound 85. $^1$H NMR (500 MHz, CD$_3$OD) δ 8.47 (s, 1H), 8.02 (m, 1H), 7.22 (m, 6H), 6.90 (m, 3H), 5.42 (s, 1H), 4.46 (m, 2H), 3.77 (m, 8H), 3.28 (m, 3H), 2.85 (m, 1H), 1.90 (m, 5H). MS (M+1): 685.4

Example 203

(R)—N-(6-(4-(2-cyclohexyl-2-hydroxyacetyl)-1,4-diazepan-1-yl)pyridin-3-yl)-2-(4-phenylpiperidin-1-yl)-4-(trifluoromethyl)oxazole-5-carboxamide (203)

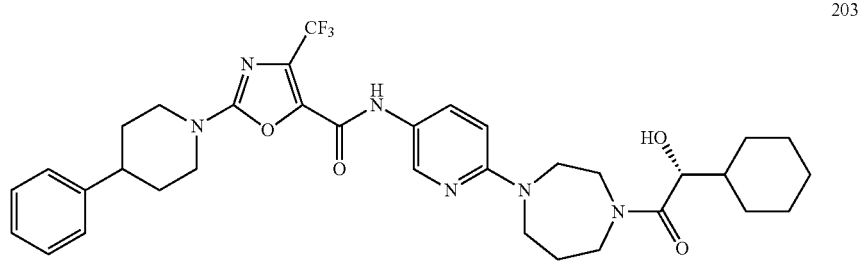 [SMILES: O=C(Nc1ccc(N2CCCN(C(=O)[C@H](O)C3CCCCC3)CC2)nc1)c1oc(N2CCC(c3ccccc3)CC2)nc1C(F)(F)F]

Compound 203 was prepared by the general procedure for compound 85. $^1$H NMR (500 MHz, CD$_3$OD) δ 8.52 (s, 1H), 8.05 (d, 1H, J=9.8 Hz), 7.20 (m, 6H), 4.45 (m, 2H), 3.84 (m, 8H), 3.28 (m, 2H), 2.86 (m, 1H), 1.75 (m, 11H), 1.20 (m, 6H). MS (M+1): 655.4

Example 204

(R)—N-(6-(4-(2-cyclohexyl-2-hydroxyacetyppiper-azin-1-yl)pyridin-3-yl)-2-(4-phenylpiperidin-1-yl)-4-(trifluoromethyl)oxazole-5-carboxamide (204)

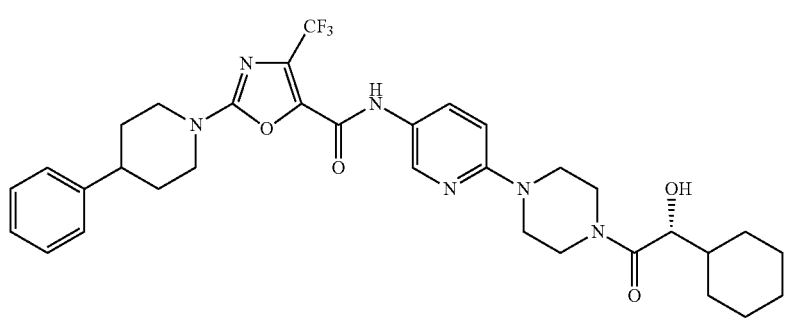

Compound 204 was prepared by the general procedure for compound 85. $^1$H NMR (500 MHz, CD$_3$OD) δ 8.40 (s, 1H), 7.92 (d, 1H, J=9.1 Hz), 7.31 (m, 4H), 7.21 (m, 1H), 6.92 (d, 1H, J=9.1 Hz), 4.45 (m, 2H), 4.27 (m, 1H), 3.67 (m, 8H), 3.27 (m, 1H), 2.87 (m, 1H), 1.83 (m, 10H), 1.24 (m, 5H). MS (M+1): 641.4

Example 205

N-(6-(4-(2-(2,5-dimethylphenyl)-2-hydroxyacetyl)piperazin-1-yl)pyridin-3-yl)-2-(4-phenylpiperidin-1-yl)-4-(trifluoromethyl)oxazole-5-carboxamide (205)

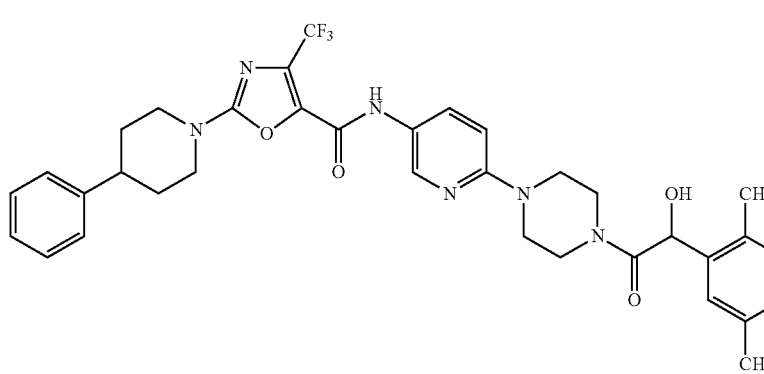

Compound 205 was prepared by the general procedure for compound 85. $^1$H NMR (500 MHz, CD$_3$OD) δ 8.36 (s, 1H), 7.88 (m, 1H), 7.30 (m, 4H), 7.21 (m, 2H), 7.15 (d, 1H, J=7.6 Hz), 7.06 (d, 1H, J=7.6 Hz), 6.82 (d, 1H, J=9.1 Hz), 5.65 (s, 1H), 4.44 (m, 2H), 3.96 (s, 1H), 3.68 (m, 2H), 3.34 (m, 6H), 2.87 (m, 2H), 2.45 (s, 3H), 2.28 (s, 3H), 1.96 (m, 2H), 1.82 (m, 2H). MS (M+1): 663.4

Example 206

N-(6-(4-(2-(2,5-dimethylphenyl)-2-hydroxyacetyl)piperazin-1-yl)pyridin-3-yl)-2-(3-methyl piperidin-1-yl)-4-(trifluoromethyl)oxazole-5-carboxamide (206)

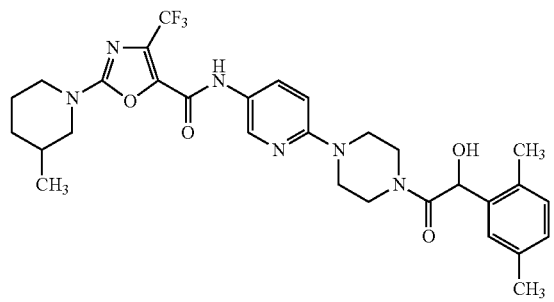

Compound 206 was prepared by the general procedure for compound 85. $^1$H NMR (500 MHz, CD$_3$OD) δ 8.39 (s, 1H), 7.92 (m, 1H), 7.12 (m, 3H), 6.93 (d, 1H, J=9.1 Hz), 5.58 (s, 1H), 4.19 (m, 2H), 3.97 (m, 1H), 3.72 (m, 2H), 3.46 (m, 3H), 3.27 (m, 1H), 3.10 (m, 1H), 2.96 (m, 1H), 2.77 (m, 1H), 2.45 (s, 3H), 2.36 (s, 3H), 1.78 (m, 4H), 1.23 (m, 1H), 0.99 (d, 3H, J=6.6 Hz). MS (M+1): 601.3

Example 207

2-(3-(3-chlorophenyl)pyrrolidin-1-yl)-N-(6-(4-((R)-2-hydroxy-2-phenylacetyl)piperazin-1-yl)pyridin-3-yl)-4-(trifluoromethyl)oxazole-5-carboxamide (207)

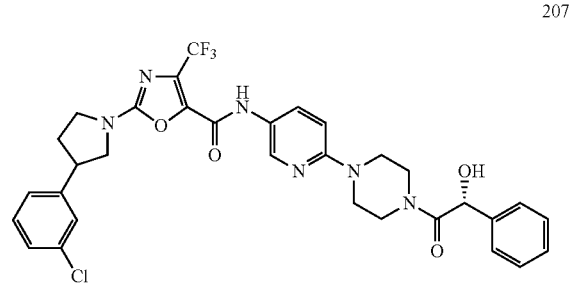 [SMILES: O=C(Nc1ccc(N2CCN(C(=O)[C@H](O)c3ccccc3)CC2)nc1)c1oc(N2CCC(c3cccc(Cl)c3)C2)nc1C(F)(F)F]

Compound 207 was prepared by the general procedure for compound 85. $^1$H NMR (500 MHz, CD$_3$OD) δ 8.36 (d, 1H, J=2.5 Hz), 7.88 (m, 1H), 7.36 (m, 9H), 6.85 (d, 1H, J=9.1 Hz), 5.51 (s, 1H), 4.13 (m, 1H), 3.88 (m, 2H), 3.60 (m, 7H), 3.38 (m, 2H), 3.01 (m, 1H), 2.47 (s, 1H), 2.23 (s, 1H). MS (M+1): 655.4

Example 208

2-(3-(3-chlorophenyl)pyrrolidin-1-yl)-N-(6-(4-(2-(3,5-difluorophenyl)-2-hydroxyacetyl)piperazin-1-yl)pyridin-3-yl)-4-(trifluoromethyl)oxazole-5-carboxamide (208)

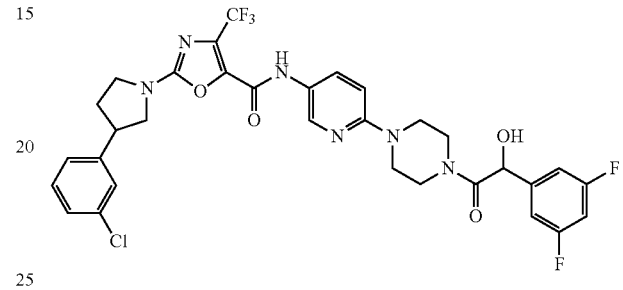

Compound 208 was prepared by the general procedure for compound 85. $^1$H NMR (500 MHz, CD$_3$OD) δ 8.39 (d, 1H, J=2.5 Hz), 7.89 (m, 1H), 7.36 (m, 4H), 7.10 (m, 2H), 6.94 (m, 1H), 6.88 (d, 1H, J=9.5 Hz), 5.56 (s, 1H), 4.13 (m, 1H), 3.93 (m, 1H), 3.60 (m, 11H), 2.48 (m, 1H), 2.22 (s, 1H). MS (M+1): 691.4

Example 209

2-(3-(3-fluorophenyl)pyrrolidin-1-yl)-N-(6-(4-(3,3,3-trifluoro-2-hydroxypropanoyl)piperazin-1-yl)pyridin-3-yl)-4-(trifluoromethyl)oxazole-5-carboxamide (209)

Compound 209 was prepared by the general procedure for compound 85. $^1$H NMR (500 MHz, CD$_3$OD) δ 8.42 (d, 1H, J=2.5 Hz), 7.93 (m, 1H), 7.39 (m, 1H), 7.17 (m, 2H), 7.02 (m, 1H), 6.96 (d, 1H, J=9.1 Hz), 5.11 (m, 1H), 4.13 (m, 1H), 3.77 (m, 12H), 2.48 (m, 1H), 2.22 (s, 1H). MS (M+1): 631.3

Example 210

N-(6-(4-((R)-2-cyclohexyl-2-hydroxyacetyl)piperazin-1-yl)pyridin-3-yl)-2-(3-(3-fluorophenyl)pyrrolidin-1-yl)-4-(trifluoromethyl)oxazole-5-carboxamide (210)

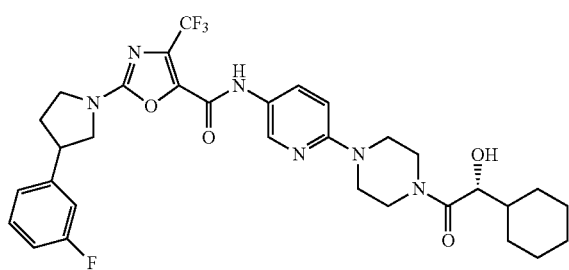

Compound 210 was prepared by the general procedure for compound 85. ¹H NMR (500 MHz, CD₃OD) δ 8.42 (d, 1H, J=2.8 Hz), 7.93 (m, 1H), 7.39 (m, 1H), 7.20 (m, 1H), 7.14 (m, 1H), 7.02 (m, 1H), 6.96 (d, 1H, J=9.1 Hz), 4.27 (m, 1H), 4.13 (m, 1H), 3.93 (m, 1H), 3.68 (m, 11H), 2.28 (m, 1H), 2.31 (m, 1H), 1.73 (m, 6H), 1.23 (m, 5H). MS (M+1): 645.4

Example 211

2-(3-(3-fluorophenyl)pyrrolidin-1-yl)-N-(6-(4-((R)-2-hydroxy-2-phenylacetyl)piperazin-1-yl)pyridin-3-yl)-4-(trifluoromethyl)oxazole-5-carboxamide (211)

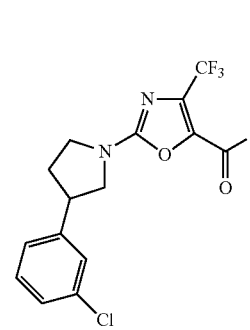

Compound 211 was prepared by the general procedure for compound 85. ¹H NMR (500 MHz, CD₃OD) δ 8.36 (d, 1H, J=2.5 Hz), 7.90 (m, 1H), 7.41 (m, 6H), 7.16 (m, 2H), 7.01 (m, 1H), 6.88 (d, 1H, J=9.1 Hz), 5.54 (s, 1H), 4.13 (m, 1H), 3.92 (m, 1H), 3.83 (m, 1H), 3.62 (m, 7H), 3.38 (m, 2H), 3.01 (m, 1H), 2.47 (s, 1H), 2.23 (s, 1H). MS (M+1): 639.4

Example 212

2-(3-(3-chlorophenyl)pyrrolidin-1-yl)-N-(6-(4-(3,3,3-trifluoro-2-hydroxypropanoyl)piperazin-1-yl)pyridin-3-yl)-4-(trifluoromethyl)oxazole-5-carboxamide (212)

Compound 212 was prepared by the general procedure for compound 85. ¹H NMR (500 MHz, CD₃OD) δ 8.42 (d, 1H, J=2.5 Hz), 7.93 (m, 1H), 7.35 (m, 4H), 6.96 (d, 1H, J=9.1 Hz), 5.11 (m, 1H), 4.13 (m, 1H), 3.77 (m, 12H), 2.48 (m, 1H), 2.22 (s, 1H). MS (M+1): 647.4

Example 213

N-(6-(4-((R)-2-cyclohexyl-2-hydroxyacetyl)piperazin-1-yl)pyridin-3-yl)-2-(3-(3-chlorophenyl)pyrrolidin-1-yl)-4-(trifluoromethyl)oxazole-5-carboxamide (213)

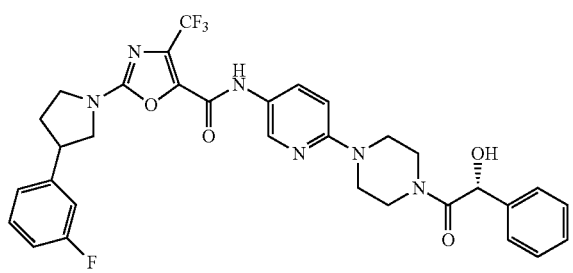

Compound 213 was prepared by the general procedure for compound 85. ¹H NMR (500 MHz, CD₃OD) δ 8.42 (s, 1H), 7.93 (m, 1H), 7.36 (m, 4H), 6.96 (d, 1H, J=9.1 Hz), 4.27 (m, 1H), 4.13 (m, 1H), 3.93 (m, 1H), 3.68 (m, 11H), 2.48 (m, 1H), 2.23 (m, 1H), 1.73 (m, 6H), 1.23 (m, 5H). MS (M+1): 661.4

Example 214

N-(6-(4-(2-(2,5-dimethylphenyl)-2-hydroxyacetyl)piperazin-1-yl)pyridin-3-yl)-2-(3-(3-fluorophenyl)pyrrolidin-1-yl)-4-(trifluoromethyl)oxazole-5-carboxamide (214)

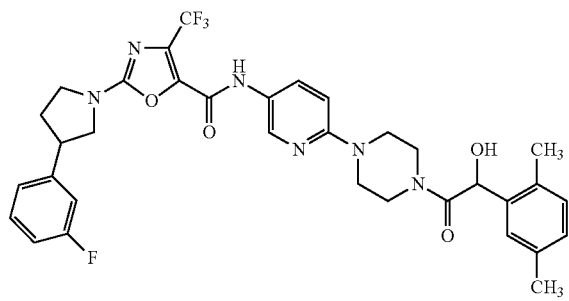

214

Compound 214 was prepared by the general procedure for compound 85. $^1$H NMR (500 MHz, CD$_3$OD) δ 8.36 (s, 1H), 7.88 (m, 1H), 7.38 (m, 1H), 7.13 (m, 6H), 6.85 (d, 1H, J=9.1 Hz), 5.57 (s, 1H), 4.13 (m, 1H), 3.92 (m, 1H), 3.70 (m, 5H), 3.42 (m, 4H), 3.26 (m, 1H), 2.90 (s, 1H), 2.34 (s, 8H). MS (M+1): 667.4

Example 215

N-(2-chloro-6-methylphenyl)hexahydro-4-[5-[[[2-(3-methyl-1-piperidinyl)-4-(trifluoromethyl)-5-oxazolyl]carbonyl]amino]-2-pyridinyl]-1H-1,4-diazepine-1-carboxamide (215)

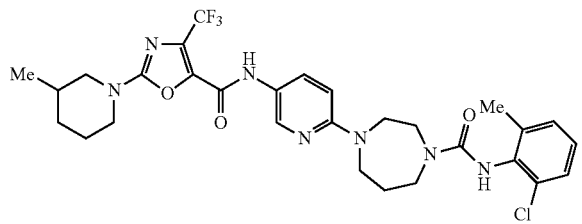

215

Compound 39 HCl salt (53 mg, 0.1 mmol) in DMF (2 mL) was mixed with diisopropylethylamine (0.037 mL) and 2-chloro-6-methylphenyl isocyanate (0.016 mL, 0.22 mmol). The mixture was stirred at r.t. for 15 h then purified by Gilson HPLC to give 58 mg of the product 221. $^1$H NMR (500 MHz, DMSO-d6) δ 10.20 (s, 1H), 8.37 (s, 1H), 8.03 (s, 1H), 7.99 (m, 1H), 7.28 (d, 1H, J=7.6 Hz), 7.15 (m, 2H), 4.10 (m, 2H), 3.78 (m, 6H), 3.49 (s, 2H), 3.07 (m, 1H), 2.76 (m, 1H), 2.05 (s, 3H), 1.95 (m, 2H), 1.78 (m, 2H), 1.68 (m, 1H), 1.54 (m, 1H), 1.16 (m, 1H), 0.94 (d, 3H, J=6.6 Hz). MS (M+1): 620.3

Example 216

Ethyl 5,6,7,8-tetrahydro-7-[5-[[[2-(4-phenyl-1-piperidinyl)-4-(trifluoromethyl)-5-oxazolyl]carbonyl]amino]-2-pyridinyl]-1,2,4-triazolo[4,3-a]pyrazine-3-carboxylate (216)

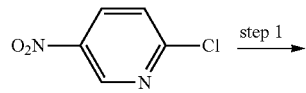

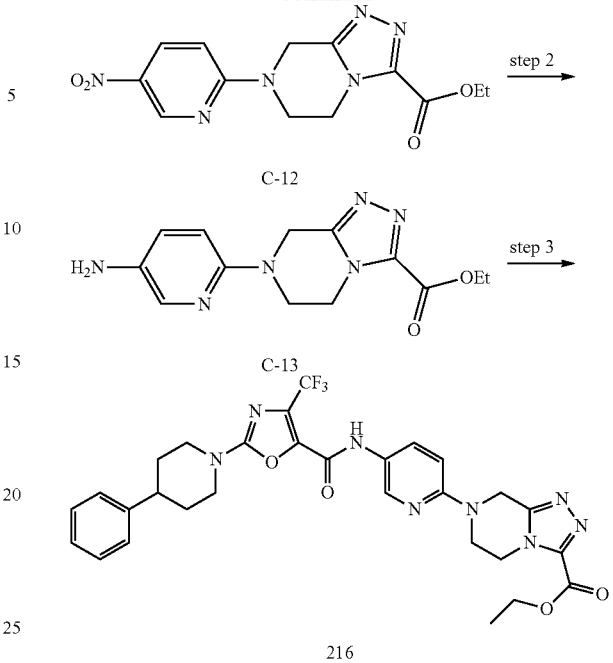

Step 1: ethyl 7-(5-nitropyridin-2-yl)-5,6,7,8-tetrahydro-[1,2,4]triazolo[4,3-a]pyrazine-3-carboxylate (C-12)

2-Chloro-5-nitropyridine (0.97 g, 5.5 mmol), ethyl 5,6,7,8-tetrahydro-[1,2,4]triazolo[4,3-a]pyrazine-3-carboxylate (1.0 g, 5.1 mmol), and diisopropylethylamine (2 mL) were mixed in acetonitrile (5 mL), and heated to 80° C. for one h. The mixture was poured into water, and the precipitate was collected by filtration. The precipitate was washed with water, then by ether, and dried in a vacuum oven overnight to give 1.2 gram of product C-12 (75% yield).

Step 2: ethyl 7-(5-aminopyridin-2-yl)-5,6,7,8-tetrahydro-[1,2,4]triazolo[4,3-a]pyrazine-3-carboxylate (C-13)

Compound C-12 (1.1 g) was reduced by stirring with PtO$_2$ (20 mg) in 3:1 EtOAc:MeOH (40 mL) under a balloon of hydrogen at r.t. overnight. The solid was filtered off, and the filtrate was concentrated to give 1.0 gram of the aminopyridine product C-13 which was used in the next step without further purification.

Step 3: ethyl 5,6,7,8-tetrahydro-7-[5-[[[2-(4-phenyl-1-piperidinyl)-4-(trifluoromethyl)-5-oxazolyl]carbonyl]amino]-2-pyridinyl]-1,2,4-triazolo[4,3-a]pyrazine-3-carboxylate (216)

Compound C-13 (60 mg, 0.21 mmol) was mixed with compound A-22 (70 mg, 0.2 mmol), diisopropylethylamine (0.1 mL), and HATU (100 mg, 0.26 mmol) in dry DMF (3 mL). The mixture was stirred at room temperature overnight, diluted with 3 mL of DMF, and then purified by prep Gilson HPLC to give 101 mg of the product 216 as pale solid. $^1$H NMR (500 MHz, DMSO-d6) δ 10.15 (s, 1H), 8.44 (d, 1H, J=2.5 Hz), 7.93 (m, 1H), 7.31 (m, 4H), 7.22 (m, 1H), 7.15 (d, 1H, J=9.1), 5.77 (s, 1H), 4.96 (s, 2H), 4.36 (m, 6H), 4.05 (t, 2H, J=5.5 Hz), 3.22 (t, 2H, J=12.6 Hz), 2.82 (t, 1H, J=12.1 Hz), 1.89 (m, 2H), 1.74 (m, 2H), 1.34 (t, 3H, J=6.9 Hz). MS (M+1): 611.3

Example 217

Ethyl 5,6,7,8-tetrahydro-7-[5-[[[2-(3-methyl-1-piperidinyl)-4-(trifluoromethyl)-5-oxazolyl]carbonyl]amino]-2-pyridinyl]-1,2,4-triazolo[4,3-a]pyrazine-3-carboxylate (217)

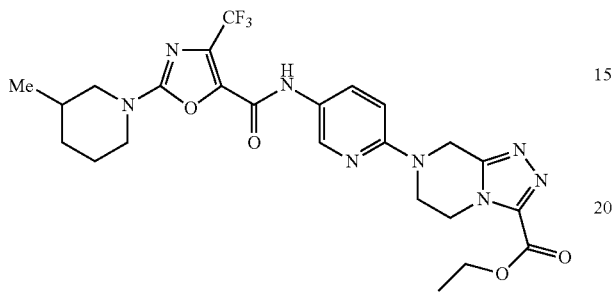

217

Compound 217 was prepared by the general procedure for compound 216. ¹H NMR (500 MHz, DMSO-d6) δ 10.10 (s, 1H), 8.43 (d, 1H, J=2.5 Hz), 7.92 (m, 1H), 7.15 (d, 1H, J=9.1), 4.96 (s, 2H), 4.37 (m, 4H), 4.08 (m, 5H), 3.05 (m, 1H), 2.75 (t, 1H, J=11.8 Hz), 1.72 (m, 3H), 1.34 (t, 3H, J=7.1 Hz), 1.18 (m, 1H), 0.93 (d, 3H, J=6.6 Hz). MS (M+1): 549.3

Example 218

N-[6-(5,6-dihydro-1,2,4-triazolo[4,3-a]pyrazin-7(8H)-yl)-3-pyridinyl]-2-(3-methyl-1-piperidinyl)-4-(trifluoromethyl)-5-oxazolecarboxamide (218)

218

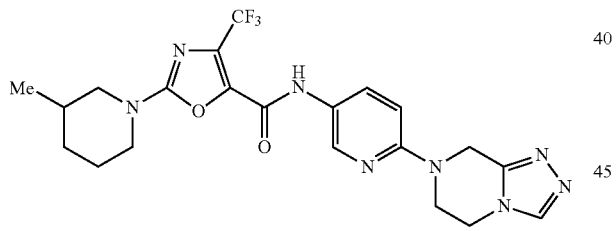

Compound 217 (64 mg) in 4:1:1 THF:MeOH:H₂O (3 mL) was mixed with LiOH (15 mg), and stirred at r.t. overnight. The mixture was concentrated and purified by prep Gilson HPLC to give the decarboxylation product 218 (25 mg as a pale solid). ¹H NMR (500 MHz, DMSO-d6) δ 10.08 (s, 1H), 8.49 (s, 1H), 8.42 (d, 1H, J=2.5 Hz), 7.89 (m, 1H), 7.11 (d, 1H, J=9.1), 4.86 (s, 2H), 4.10 (m, 6H), 3.05 (m, 1H), 2.75 (t, 1H, J=11.7 Hz), 1.77 (m, 2H), 1.67 (m, 1H), 1.53 (m, 1H), 1.15 (m, 1H), 0.94 (d, 3H, J=6.6 Hz). MS (M+1): 477.3

Example 219

N-[6-(5,6-dihydro-1,2,4-triazolo[4,3-a]pyrazin-7(8H)-yl)-3-pyridinyl]-2-(4-phenyl-1-piperidinyl)-4-(trifluoromethyl)-5-oxazolecarboxamide (219)

219

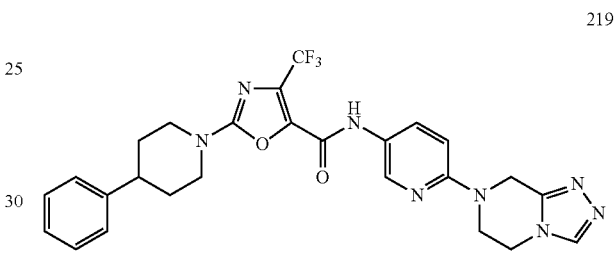

Compound 219 was prepared by the general procedure for compound 218. ¹H NMR (500 MHz, DMSO-d6) δ 10.13 (s, 1H), 8.49 (s, 1H), 8.43 (d, 1H, J=2.5 Hz), 7.91 (m, 1H), 7.31 (m, 4H), 7.22 (m, 1H), 7.11 (d, 1H, J=9.1 Hz), 4.86 (s, 2H), 4.35 (d, 2H, J=12.9 Hz), 4.16 (t, 2H, J=5.3 Hz), 4.03 (t, 2H, J=5.4 Hz), 3.21 (m, 2H), 2.81 (m, 1H), 1.89 (m, 2H), 1.74 (m, 2H). MS (M+1): 539.3

Example 220

N-(6-(3-(3-(2-fluorophenyl)ureido)azetidin-1-yl)pyridin-3-yl)-2-(4-phenyl piperidin-1-yl)-4-(trifluoromethyl)oxazole-5-carboxamide (220)

220

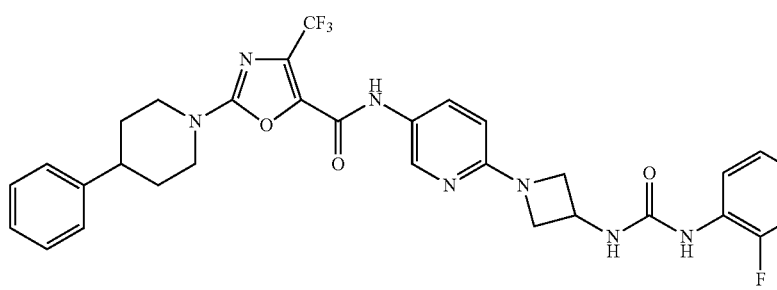

Compound 220 was prepared by the general procedure for compound 1. ¹H NMR (500 MHz, DMSO-d6) δ 10.07 (s, 1H), 8.30 (s, 2H), 8.08 (t, 1H, J=8 Hz), 7.80 (d, 1H, J=6.5 Hz), 7.30 (m, 5H), 7.20 (m, 2H), 7.10 (t, 1H, J=8 Hz), 6.95 (m, 1H), 6.48 (d, 1H, J=8.5 Hz), 4.57 (m, 1H), 4.35 (d, 2H, J=12.5 Hz), 4.25 (t, 2H, J=8.5 Hz), 3.73 (t, 2H, J=8 Hz), 3.22 (t, 2H, J=12 Hz), 2.80 (t, 1H, J=12 Hz), 1.88 (d, 2H, J=12.5 Hz), 1.75 (q, 2H, J=12.5 Hz). MS (M+1): 624.4

Example 221

N-(6-(3-(3-(2-fluorophenyl)ureido)azetidin-1-yl)pyridin-3-yl)-2-(3-methylpiperidin-1-yl)-4-(trifluoromethyl)oxazole-5-carboxamide (221)

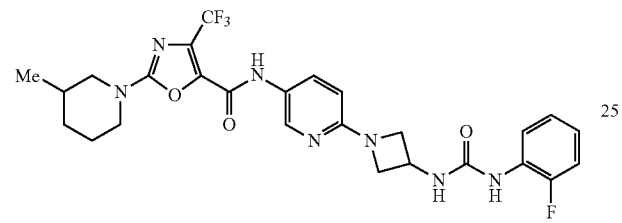

Compound 221 was prepared by the general procedure for compound 1. ¹H NMR (500 MHz, DMSO-d6) δ 10.03 (s, 1H), 8.30 (d, 2H, J=10 Hz), 8.08 (t, 1H, J=8 Hz), 7.78 (d, 1H, J=9 Hz), 7.28 (d, 1H, J=7 Hz), 7.20 (t, 1H, J=8 Hz), 7.10 (t, 1H, J=7.5 Hz), 6.95 (m, 1H), 6.47 (d, 1H, J=8.5 Hz), 4.58 (m, 1H), 4.25 (t, 1H, J=7.5 Hz), 4.12 (d, 1H, J=11 Hz), 4.07 (d, 1H, J=13 Hz), 3.73 (t, 2H, J=6 Hz), 3.05 (t, 1H, J=11.5 Hz), 2.75 (t, 1H, J=12 Hz), 1.77 (m, 2H), 1.67 (m, 1H), 1.52 (m, 1H), 1.15 (q, 1H, J=11 Hz), 0.93 (d, 3H, J=6.5 Hz). MS (M+1): 562.3

Example 222

N-(6-(1-(2-fluorophenylcarbamoyl)azetidin-3-ylamino)pyridin-3-yl)-2-(4-phenylpiperidin-1-yl)-4-(trifluoromethyl)oxazole-5-carboxamide (222)

Compound 222 was prepared by the general procedure for compound 1. ¹H NMR (500 MHz, DMSO-d6) δ 10.02 (s, 1H), 8.20 (d, 2H, J=6.5 Hz), 7.68 (d, 1H, J=9 Hz), 7.60 (t, 1H, J=7.5 Hz), 7.30 (m, 4H), 7.22 (m, 3H), 7.10 (m, 2H), 6.53 (d, 1H, J=9 Hz), 4.53 (m, 1H), 4.35 (d, 2H, J=13 Hz), 4.29 (t, 2H, J=8 Hz), 3.80 (dd, 2H, J=5, 8.5 Hz), 3.22 (t, 2H, J=12 Hz), 2.80 (t, 1H, J=11.5 Hz), 1.88 (d, 2H, J=12 Hz), 1.75 (q, 2H, J=12.5 Hz). MS (M+1): 624.3

Example 223

N-(6-(1-(2-fluorophenylcarbamoyl)azetidin-3-ylamino)pyridin-3-yl)-2-(3-methylpiperidin-1-yl)-4-(trifluoromethyl)oxazole-5-carboxamide (223)

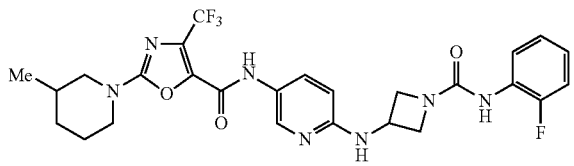

Compound 223 was prepared by the general procedure for compound 1. ¹H NMR (500 MHz, DMSO-d6) δ 9.97 (s, 1H), 8.20 (s, 2H), 7.67 (d, 1H, J=9 Hz), 7.60 (t, 1H, J=8 Hz), 7.20 (m, 2H), 7.10 (m, 2H), 6.53 (d, 1H, J=8.5 Hz), 4.53 (m, 1H), 4.28 (t, 1H, J=8 Hz), 4.12 (d, 1H, J=14 Hz), 4.07 (d, 1H, J=10.5 Hz), 3.80 (t, 1H, J=5 Hz), 3.05 (t, 1H, J=12.5 Hz), 2.73 (t, 1H, J=13 Hz), 1.73 (m, 3H), 1.52 (m, 1H), 1.15 (q, 1H, J=10 Hz), 0.93 (d, 3H, J=6.5 Hz). MS (M+1): 562.2

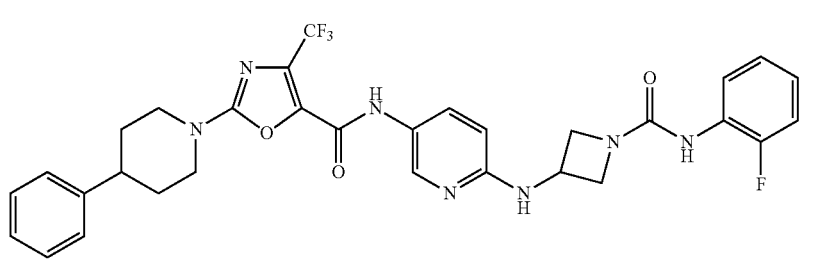

Example 224 cyclopentyl 4-(5-(2-(4-phenylpiperidin-1-yl)-4-(trifluoromethyl)oxazole-5-carboxamido)pyridin-2-yl)piperazine-1-carboxylate (224)

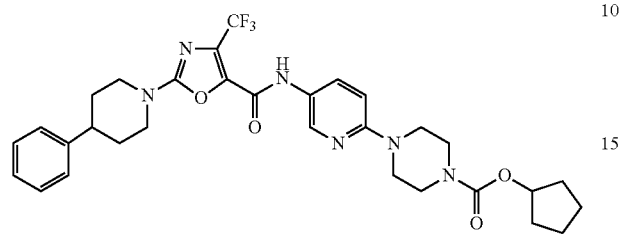

224

Compound 224 was prepared by the general procedure for compound 1. $^1$H NMR (500 MHz, DMSO-d6) δ 10.09 (s, 1H), 8.42 (s, 1H), 8.37 (s, 1H), 7.84 (dd, 1H, J=9.5, 2.5 Hz), 7.31 (m, 4H), 7.22 (t, 1H, J=6.5 Hz), 6.89 (d, 1H, J=9 Hz), 5.02 (m, 1H), 4.35 (d, 2H, J=12.5 Hz), 3.46 (s, 8H), 3.56 (m, 4H), 3.22 (t, 2H, J=12 Hz), 2.81 (t, 1H, J=12 Hz), 1.89 (d, 2H, J=12 Hz), 1.78 (m, 4H), 1.65 (m, 4H), 1.55 (m, 2H). MS (M+1): 613.3

Example 225

N-(6-(4-(2-(2-fluorophenyl)acetyl)piperazin-1-yl)pyridin-3-yl)-2-(4-phenylpiperidin-1-yl)-4-(trifluoromethyl)oxazole-5-carboxamide (225)

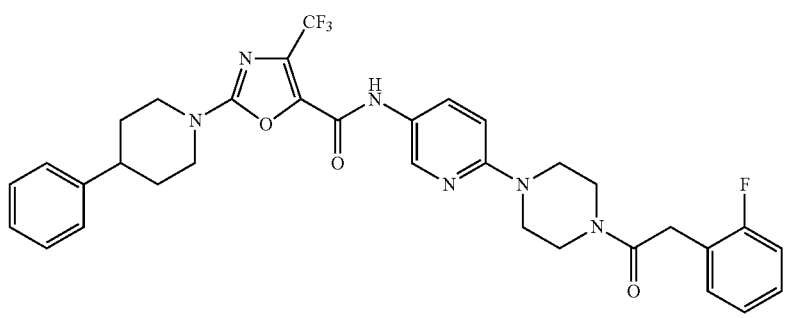

225

Compound 225 was prepared by the general procedure for compound 85. $^1$H NMR (500 MHz, DMSO-d6) δ 10.10 (s, 1H), 8.38 (d, 1H, J=2.5 Hz), 7.85 (dd, 1H, J=9, 2.5 Hz), 7.31 (m, 6H), 7.22 (m, 1H), 7.15 (q, 2H, J=8 Hz), 6.91 (d, 1H, J=9.5 Hz), 4.35 (d, 2H, J=11.5 Hz), 3.80 (s, 2H), 3.67 (m, 2H), 3.60 (m, 2H), 3.53 (m, 2H), 3.48 (m, 2H), 3.22 (t, 2H, J=12.5 Hz), 2.82 (t, 1H, J=12.5 Hz), 1.89 (d, 2H, J=12 Hz), 1.75 (qd, 2H, J=12.5, 4 Hz). MS (M+1): 637.3

Example 226

N-(6-(4-(2-(2-hydroxyphenyl)acetyl)piperazin-1-yl)pyridin-3-yl)-2-(4-phenylpiperidin-1-yl)-4-(trifluoromethyl)oxazole-5-carboxamide (226)

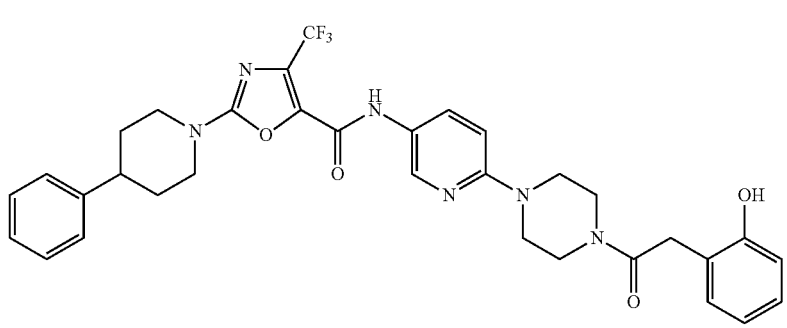

226

Compound 226 was prepared by the general procedure for compound 85. ¹H NMR (500 MHz, DMSO-d6) δ 10.09 (s, 1H), 9.55 (s, 1H), 8.36 (d, 1H, J=2.5 Hz), 7.84 (dd, 1H, J=9, 3 Hz), 7.31 (m, 4H), 7.22 (t, 1H, J=7 Hz), 7.06 (m, 2H), 6.89 (d, 1H, J=9 Hz), 6.81 (d, 1H, J=7.5 Hz), 6.74 (t, 1H, J=7.5 Hz), 4.35 (d, 2H, J=13 Hz), 3.61 (m, 4H), 3.44 (m, 4H), 3.21 (t, 2H, J=11 Hz), 2.81 (t, 1H, J=12.5 Hz), 1.89 (d, 2H, J=11 Hz), 1.75 (qd, 2H, J=13, 4 Hz). MS (M+1): 635.3

Example 227

N-(6-(4-(2-(phenyl)acetyl)piperazin-1-yl)pyridin-3-yl)-2-(4-phenylpiperidin-1-yl)-4-(trifluoromethyl)oxazole-5-carboxamide (227)

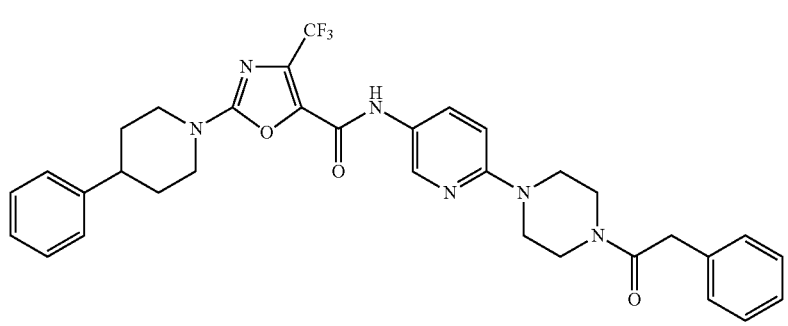

227

Compound 227 was prepared by the general procedure for compound 85. ¹H NMR (500 MHz, DMSO-d6) δ 10.09 (s, 1H), 8.36 (d, 1H, J=2.5 Hz), 7.85 (dd, 1H, J=9, 2.5 Hz), 7.31 (m, 6H), 7.25 (d, 2H, J=7.5 Hz), 7.22 (d, 2H, J=7 Hz), 6.90 (d, 1H, J=9 Hz), 4.35 (d, 2H, J=13 Hz), 3.61 (m, 4H), 3.45 (m, 2H), 3.41 (m, 2H), 3.22 (t, 2H, J=11 Hz), 2.81 (t, 1H, J=12.5 Hz), 1.89 (d, 2H, J=12 Hz), 1.74 (qd, 2H, J=12.5, 4 Hz). MS (M+1): 619.3

Example 228

2-(4-phenylpiperidin-1-yl)-N-(6-(4-(2-o-tolylacetyl)piperazin-1-yl)pyridin-3-yl)-4-(trifluoromethyl)oxazole-5-carboxamide (228)

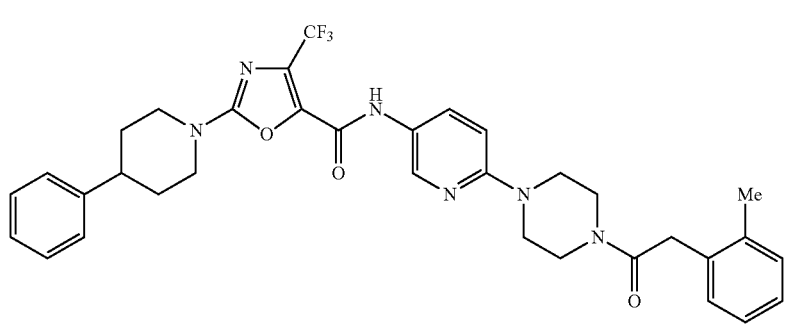

228

Compound 228 was prepared by the general procedure for compound 85. $^1$H NMR (500 MHz, DMSO-d6) δ 10.10 (s, 1H), 8.38 (d, 1H, J=2.5 Hz), 7.85 (dd, 1H, J=9, 2.5 Hz), 7.31 (m, 4H), 7.22 (t, 1H, J=6.5 Hz), 7.14 (m, 4H), 6.91 (d, 1H, J=9.5 Hz), 4.35 (d, 2H, J=13.5 Hz), 3.75 (s, 2H), 3.62 (m, 4H), 3.49 (m, 4H), 3.22 (t, 2H, J=11 Hz), 2.82 (t, 1H, J=12 Hz), 2.21 (s, 3H), 1.89 (d, 2H, J=12 Hz), 1.75 (qd, 2H, J=12.5, 4 Hz). MS (M+1): 633.4

Example 229

N-(6-(4-(2-(2,6-difluorophenyl)acetyl)piperazin-1-yl)pyridin-3-yl)-2-(4-phenylpiperidin-1-yl)-4-(trifluoromethyl)oxazole-5-carboxamide (229)

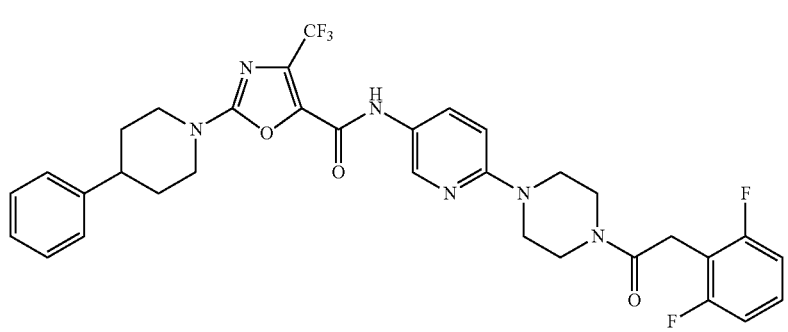

229

Compound 229 was prepared by the general procedure for compound 85. $^1$H NMR (500 MHz, DMSO-d6) δ 10.10 (s, 1H), 8.39 (d, 1H, J=2.5 Hz), 7.86 (dd, 1H, J=8.5, 2.5 Hz), 7.37 (t, 1H, J=8 Hz), 7.31 (m, 4H), 7.22 (t, 1H, J=6.5 Hz), 7.08 (t, 2H, J=7.5 Hz), 6.92 (d, 1H, J=9.5 Hz), 4.36 (d, 2H, J=12.5 Hz), 3.74 (m, 2H), 3.59 (m, 4H), 3.49 (m, 2H), 3.22 (t, 2H, J=11.5 Hz), 2.82 (t, 1H, J=12 Hz), 1.89 (d, 2H, J=12.5 Hz), 1.75 (qd, 2H, J=13, 4.5 Hz). MS (M+1): 655.3

Example 230

N-(6-(4-(2-(2-chlorophenyl)acetyl)piperazin-1-yl)pyridin-3-yl)-2-(4-phenylpiperidin-1-yl)-4-(trifluoromethyl)oxazole-5-carboxamide (230)

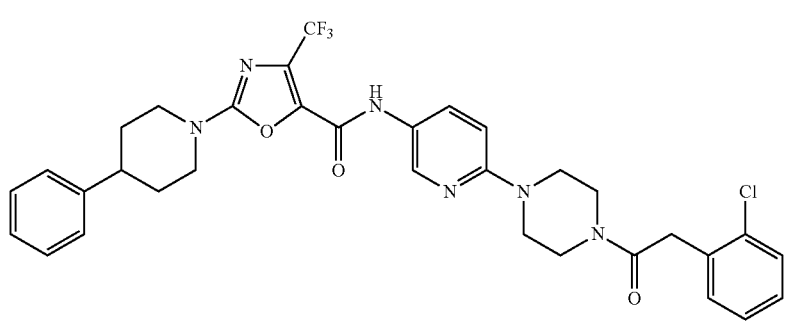

230

Compound 230 was prepared by the general procedure for compound 85. $^1$H NMR (500 MHz, DMSO-d6) δ 10.10 (s, 1H), 8.38 (d, 1H, J=2.5 Hz), 7.85 (dd, 1H, J=9, 2.5 Hz), 7.44 (m, 1H), 7.31 (m, 7H), 7.22 (t, 1H, J=6 Hz), 6.91 (d, 1H, J=9 Hz), 4.35 (d, 2H, J=13 Hz), 3.68 (m, 2H), 3.61 (m, 2H), 3.54 (m, 2H), 3.49 (m, 2H), 3.22 (t, 2H, J=12 Hz), 2.82 (t, 1H, J=12 Hz), 1.89 (d, 2H, J=11.5 Hz), 1.75 (qd, 2H, J=12.5, 4 Hz). MS (M+1): 653.3

Example 231

N-(6-(4-(2-(2-nitrophenyl)acetyl)piperazin-1-yl)pyridin-3-yl)-2-(4-phenylpiperidin-1-yl)-4-(trifluoromethyl)oxazole-5-carboxamide

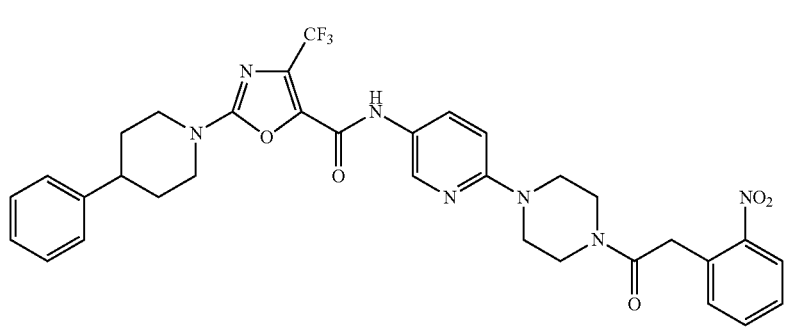

231

Compound 231 was prepared by the general procedure for compound 85. $^1$H NMR (500 MHz, DMSO-d6) δ 10.11 (s, 1H), 8.40 (d, 1H, J=2.5 Hz), 8.06 (d, 1H, J=7.5 Hz), 7.87 (dd, 1H, J=9, 2.5 Hz), 7.70 (t, 1H, J=7.5 Hz), 7.55 (t, 1H, J=8 Hz), 7.50 (d, 1H, J=7.5 Hz), 7.31 (m, 4H), 7.22 (t, 1H, J=6 Hz), 6.94 (d, 1H, J=9.5 Hz), 4.36 (d, 2H, J=12 Hz), 3.73 (m, 2H), 3.62 (m, 2H), 3.58 (m, 2H), 3.47 (m, 2H), 3.22 (t, 2H, J=10.5 Hz), 2.82 (t, 1H, J=12 Hz), 1.89 (d, 2H, J=11.5 Hz), 1.75 (qd, 2H, J=12, 3.5 Hz). MS (M+1): 664.3

Example 232

N-(6-(4-(2-(2-aminophenyl)acetyl)piperazin-1-yl)pyridin-3-yl)-2-(4-phenylpiperidin-1-yl)-4-(trifluoromethyl)oxazole-5-carboxamide (232)

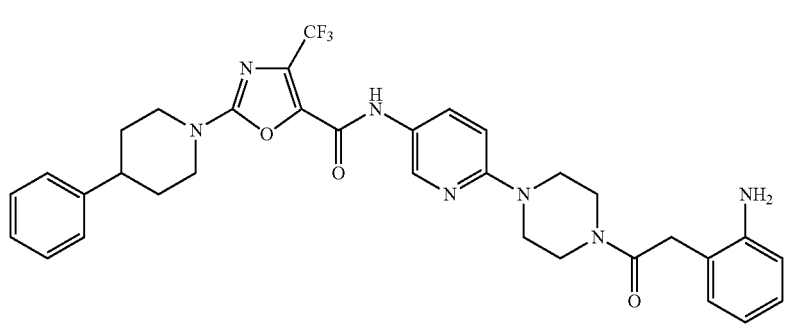

232

Compound 232 was prepared by the general procedure for compound C-13. ¹H NMR (500 MHz, DMSO-d6) δ 10.08 (s, 1H), 8.36 (d, 1H, J=3 Hz), 7.83 (dd, 1H, J=9, 2.5 Hz), 7.31 (m, 4H), 7.22 (t, 1H, J=7 Hz), 6.98 (d, 1H, J=7.5 Hz), 6.94 (t, 1H, J=7.5 Hz), 6.88 (d, 1H, J=9.5 Hz), 6.65 (d, 1H, J=8.5 Hz), 6.53 (t, 1H, J=7.5 Hz), 5.09 (s, 2H), 4.35 (d, 2H, J=13 Hz), 3.60 (m, 4H), 3.45 (m, 2H), 3.40 (m, 2H), 3.22 (t, 2H, J=11 Hz), 2.81 (t, 1H, J=11.5 Hz), 1.89 (d, 2H, J=11.5 Hz), 1.75 (qd, 2H, J=13, 4 Hz). MS (M+1): 634.3

Example 233

2-(3-methylpiperidin-1-yl)-N-(1-(trans-2-(o-tolylcarbamoyl)cyclopropanecarbonyl)indolin-5-yl)-4-(trifluoromethyl)oxazole-5-carboxamide (233)

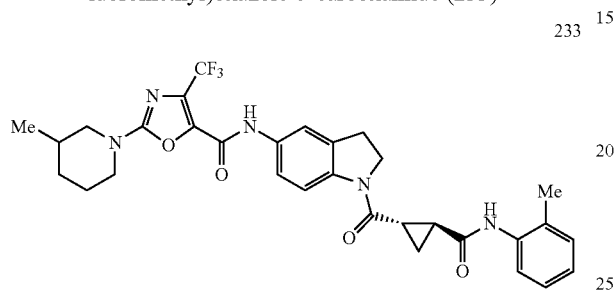

233

Compound 233 was prepared by the general procedure for compound 1. ¹H NMR (500 MHz, DMSO-d6) δ 10.08 (s, 1H), 9.72 (s, 1H), 8.02 (d, 1H, J=8.5 Hz), 7.65 (s, 1H), 7.47 (d, 1H, J=8 Hz), 7.42 (d, 1H, J=8.5 Hz), 7.22 (d, 1H, J=7.5 Hz), 7.15 (t, 1H, J=7.5 Hz), 7.08 (t, 1H, J=7.5 Hz), 4.40 (q, 1H, J=9.5 Hz), 4.28 (q, 1H, J=9.5 Hz), 4.10 (m, 2H), 3.20 (t, 2H, J=8.5 Hz), 3.05 (t, 1H, J=11 Hz), 2.75 (t, 1H, J=11 Hz), 2.33 (m, 1H), 1.73 (m, 3H), 1.53 (m, 1H), 1.35 (m, 2H), 1.15 (m, 2H), 0.94 (d, 3H, J=6 Hz). MS (M+1): 596.3

Example 234

2-(4-phenylpiperidin-1-yl)-N-(7-(o-tolylcarbamoyl)-9H-fluoren-2-yl)-4-(trifluoromethyl)oxazole-5-carboxamide (234)

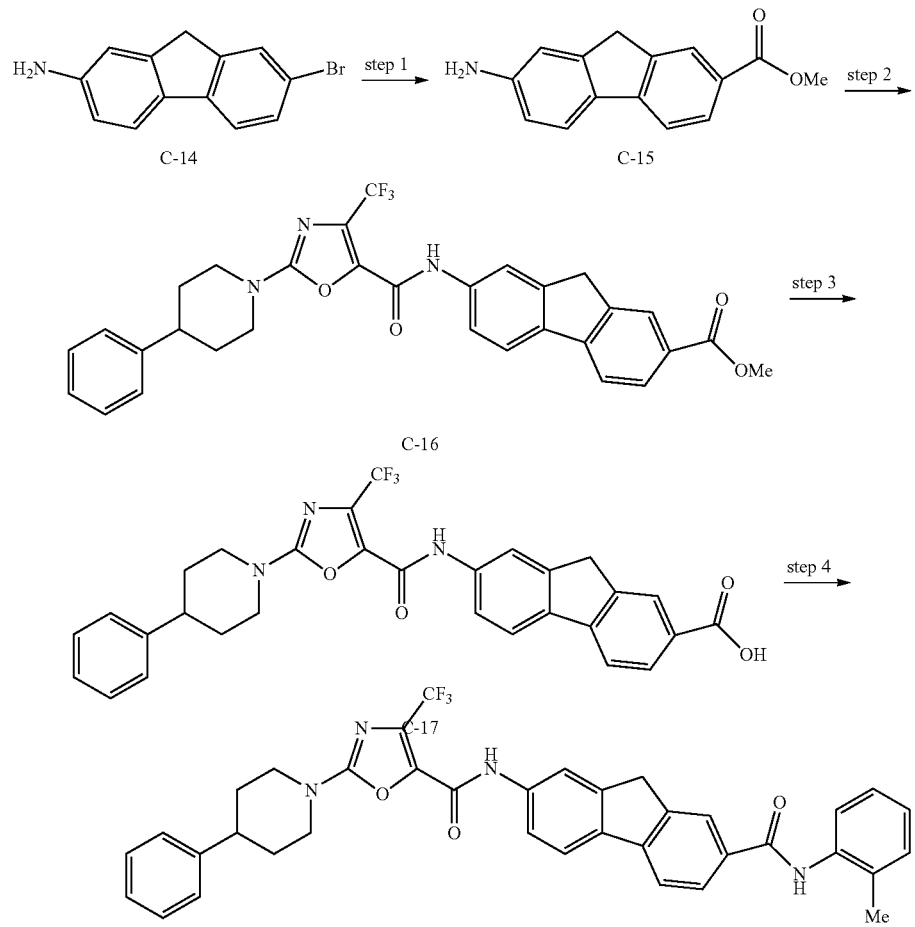

234

Step 1: methyl 7-amino-9H-fluorene-2-carboxylate (C-15)

7-Bromo-9H-fluoren-2-amine (C-14) (2.10 g, 8307 mmol), triethylamine (1.23 g, 1.7 mL, 12.1 mmol), and palladium(BINAP)dichloride (0.32 g, 0.404 mmol) were combined in MeOH (30 mL) in a steel bomb which was pressured to 45 psi with carbon monoxide and heated at 100° C. for 48 h. The reaction mixture was cooled and concentrated. Water (50 mL) was added and extracted with $CH_2Cl_2$. The combined extracts were dried ($MgSO_4$), filtered, and concentrated. Purification by silica gel chromatography (eluant: $CH_2Cl_2$ to 3% EtOAc—$CH_2Cl_2$) gave the product C-15 (1.50 g, 78% yield) as a white solid. MS (M+1): 240

Step 2: methyl 7-(2-(4-phenylpiperidin-1-yl)-4-(trifluoromethyl)oxazole-5-carboxamido)-9H-fluorene-2-carboxylate (C-16)

Compound C-16 was prepared by the general procedure of compound 216. MS (M+1): 562

Step 3: 7-(2-(4-phenylpiperidin-1-yl)-4-(trifluoromethyl)oxazole-5-carboxamido)-9H-fluorene-2-carboxylic acid (C-17)

Compound C-16 (380 mg, 0.677 mmol) and lithium hydroxide (57 mg, 1.35 mmol) were combined in THF (5 mL), MeOH (5 mL), and water (3 mL) and heated at reflux for 20 h. The reaction mixture was cooled and concentrated. 1 N HCl (20 mL) was added and extracted with 10% EtOH in $CH_2Cl_2$ (by volume). The combined extracts were dried ($MgSO_4$), filtered, and concentrated to give the product C-17 (323 mg, 87% yield). MS (M+1): 548

Step 4: 2-(4-phenylpiperidin-1-yl)-N-(7-(o-tolylcarbamoyl)-9H-fluoren-2-yl)-4-(trifluoromethyl)oxazole-5-carboxamide (234)

Compound 234 was prepared by the general procedure for compound 216. $^1$H NMR (500 MHz, DMSO-d6) δ 10.30 (s, 1H), 9.91 (s, 1H), 8.20 (s, 1H), 8.10 (s, 1H), 8.04 (d, 1H, J=8.5 Hz), 8.00 (d, 2H, J=7.5 Hz), 7.74 (d, 1H, J=8 Hz), 7.37 (d, 1H, J=8 Hz), 7.32 (m, 5H), 7.23 (m, 2H), 7.18 (t, 1H, J=7.5 Hz), 4.38 (d, 2H, J=10.5 Hz), 4.05 (s, 2H), 3.25 (t, 2H, J=13 Hz), 2.83 (t, 1H, J=12.5 Hz), 2.27 (s, 3H), 1.90 (d, 2H, J=11.5 Hz), 1.75 (q, 2H, J=12.5 Hz). MS (M+1): 637.3

Example 235

2-(3-methylpiperidin-1-yl)-N-(7-(o-tolylcarbamoyl)-9H-fluoren-2-yl)-4-(trifluoromethyl)oxazole-5-carboxamide (235)

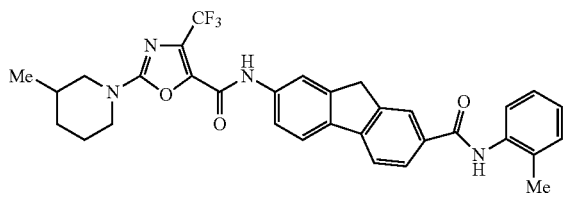

235

Compound 235 was prepared by the general procedure for compound 234. $^1$H NMR (500 MHz, DMSO-d6) δ 10.25 (s, 1H), 9.91 (s, 1H), 8.20 (s, 1H), 8.08 (s, 1H), 8.04 (d, 1H, J=8 Hz), 8.00 (d, 2H, J=8.5 Hz), 7.73 (d, 1H, J=8.5 Hz), 7.37 (d, 1H, J=8 Hz), 7.29 (d, 1H, J=8 Hz), 7.24 (t, 1H, J=7.5 Hz), 7.18 (t, 1H, J=7.5 Hz), 4.15 (d, 1H, J=14 Hz), 4.10 (d, 1H, J=13 Hz), 4.05 (s, 2H), 3.07 (t, 1H, J=12.5 Hz), 2.77 (t, 1H, J=12 Hz), 2.27 (s, 3H), 1.78 (m, 2H), 1.68 (m, 1H), 1.55 (q, 1H, J=11.5 Hz), 1.17 (q, 1H, J=12 Hz), 0.95 (d, 3H, J=6 Hz). MS (M+1): 575.3

Example 236

N-(6-(4-(benzo[d]oxazol-2-yl)piperazin-1-yl)pyridin-3-yl-2-(4-phenylpiperidin-1-yl)-4-(trifluoromethyl)oxazole-5-carboxamide (236)

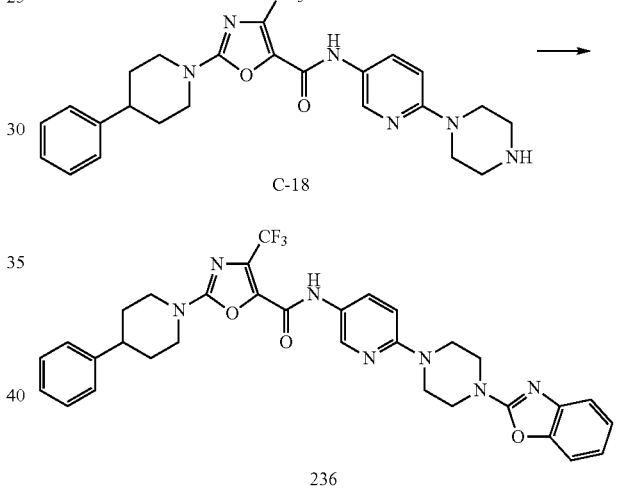

Compound C-18 was prepared by the general procedure for compound 84. Compound C-18 (150 mg, 0.30 mmol), Hunigs base (78 mg, 0.10 mL, 0.60 mmol), and 2-chlorobenzoxazole (92 mg, 0.60 mmol) in dry DMF (3 mL) was heated at 100° C. for 24 h. The reaction mixture was cooled and concentrated. Water (15 mL) was added, and the aqueous solution was extracted with $CH_2Cl_2$. The combined extracts were dried ($MgSO_4$), filtered, and concentrated. Purification by silica gel chromatography (eluant:10-30% EtOAc—$CH_2Cl_2$) gave the product 236 (77 mg, 42% yield) as a beige foam.

$^1$H NMR (500 MHz, DMSO-d6) δ 10.10 (s, 1H), 8.40 (d, 1H, J=2.5 Hz), 7.88 (dd, 2H, J=9, 2.5 Hz), 7.43 (d, 1H, J=8 Hz), 7.31 (m, 5H), 7.22 (t, 1H, J=7 Hz), 7.17 (t, 1H, J=7.5 Hz), 7.04 (t, 1H, J=7.5 Hz), 6.97 (d, 1H, J=9.5 Hz), 4.35 (d, 2H, J=13 Hz), 3.73 (m, 4H), 3.66 (m, 4H), 3.22 (t, 2H, J=11 Hz), 2.82 (t, 1H, J=12 Hz), 1.89 (d, 2H, J=11.5 Hz), 1.75 (qd, 2H, J=13, 4 Hz). MS (M+1): 618.3

Example 237

N-(6-(4-(1H-benzo[d]imidazol-2-yl)piperazin-1-yl)pyridin-3-yl)-2-(4-phenylpiperidin-1-yl)-4-(trifluoromethyl)oxazole-5-carboxamide (237)

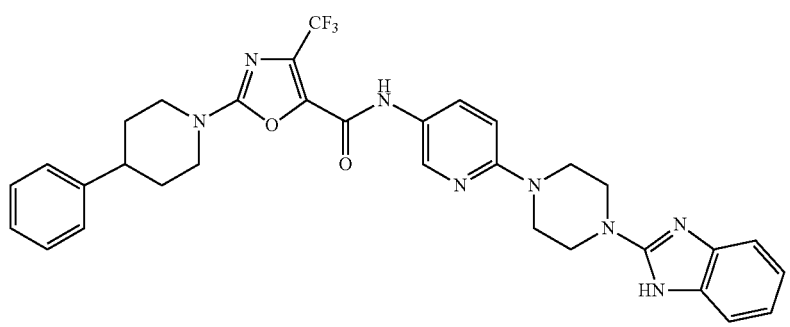

Compound 237 was prepared by the general procedure for compound 236. $^1$H NMR (500 MHz, DMSO-d6) δ 10.10 (s, 1H), 8.40 (d, 1H, J=2.5 Hz), 7.88 (d, 1H, J=2.5 Hz), 7.86 (d, 1H, J=2.5 Hz), 7.31 (m, 4H), 7.22 (m, 3H), 6.99 (d, 1H, J=9.5 Hz), 6.96 (m, 2H), 4.35 (d, 2H, J=13 Hz), 3.34 (m, 8H), 3.22 (t, 2H, J=12 Hz), 2.82 (t, 1H, J=12.5 Hz), 1.90 (d, 2H, J=13 Hz), 1.75 (q, 2H, J=12 Hz). MS (M+1): 617.3

Example 238

N-(6-(4-(5-methylbenzo[d]oxazol-2-yl)piperazin-1-yl)pyridin-3-yl)-2-(4-phenylpiperidin-1-yl)-4-(trifluoromethyl)oxazole-5-carboxamide (238)

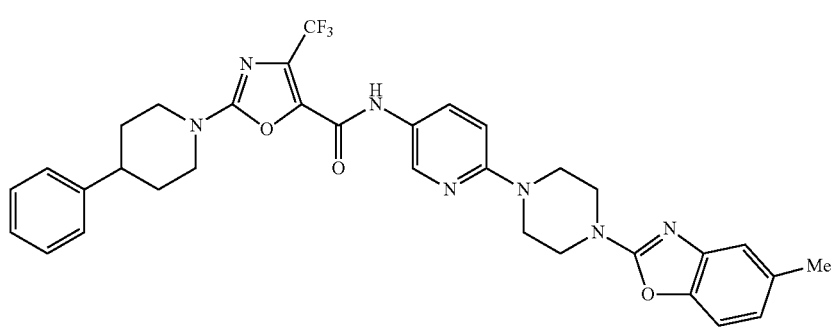

Compound 238 was prepared by the general procedure for compound 236. $^1$H NMR (500 MHz, DMSO-d6) δ 10.11 (s, 1H), 8.40 (s, 1H), 7.88 (dd, 2H, J=9, 2.5 Hz), 7.31 (m, 5H), 7.22 (t, 1H, J=6.5 Hz), 7.13 (s, 1H), 6.96 (d, 1H, J=9 Hz), 6.84 (d, 1H, J=8 Hz), 4.36 (d, 2H, J=13 Hz), 3.71 (m, 4H), 3.65 (m, 4H), 3.22 (t, 2H, J=11.5 Hz), 2.81 (t, 1H, J=12.5 Hz), 2.34 (s, 3H), 1.89 (d, 2H, J=12 Hz), 1.75 (q, 2H, J=12.5 Hz). MS (M+1): 632.3

Example 239

N-(6-(4-(1H-indole-2-carbonyl)piperazin-1-yl)pyridin-3-yl)-2-(4-phenylpiperidin-1-yl)-4-(trifluoromethyl)oxazole-5-carboxamide (239)

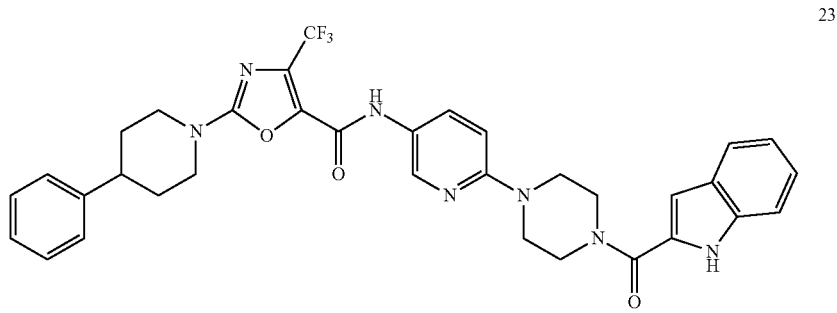

239

Compound 239 was prepared by the general procedure for compound 85. $^1$H NMR (500 MHz, DMSO-d6) δ 11.63 (s, 1H), 10.11 (s, 1H), 8.40 (s, 1H), 7.87 (dd, 1H, J=9.5, 2.5 Hz), 7.63 (d, 1H, J=8 Hz), 7.44 (d, 1H, J=8 Hz), 7.31 (m, 4H), 7.20 (t, 2H, J=7.5 Hz), 7.06 (t, 1H, J=7.5 Hz), 6.92 (d, 1H, J=9.5 Hz), 6.87 (s, 1H), 4.35 (d, 2H, J=9.5 Hz), 3.90 (m, 4H), 3.62 (m, 4H), 3.22 (t, 2H, J=10.5 Hz), 2.82 (t, 1H, J=11.5 Hz), 1.89 (d, 2H, J=11 Hz), 1.75 (q, 2H, J=12 Hz). MS (M+1): 644.3

Example 240

N-(6-(4-(indoline-2-carbonyl)piperazin-1-yl)pyridin-3-yl)-2-(4-phenylpiperidin-1-yl)-4-(trifluoromethyl)oxazole-5-carboxamide (240)

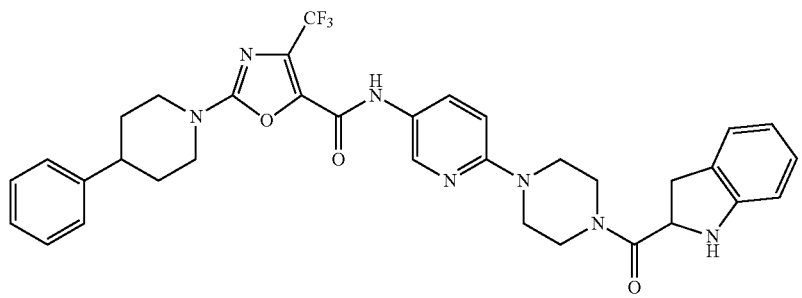

240

Compound 240 was prepared by the general procedure for compound 85. $^1$H NMR (500 MHz, DMSO-d6) δ 10.10 (s, 1H), 8.38 (d, 1H, J=3 Hz), 7.86 (dd, 1H, J=9.5, 2.5 Hz), 7.31 (m, 4H), 7.22 (m, 1H), 7.00 (d, 1H, J=7 Hz), 6.93 (m, 2H), 6.59 (d, 1H, J=8 Hz), 6.56 (t, 1H, J=7 Hz), 4.70 (dd, 1H, J=11, 6 Hz), 4.36 (d, 2H, J=13 Hz), 3.60 (m, 8H), 3.22 (t, 2H, J=13.5 Hz), 3.13 (dd, 1H, J=16, 5.5 Hz), 2.82 (t, 1H, J=12 Hz), 1.89 (d, 2H, J=11.5 Hz), 1.75 (qd, 2H, J=13, 4.5 Hz). MS (M+1): 646.3

Example 241

2-(4-phenylpiperidin-1-yl)-N-(6-(4-(1,2,3,4-tetrahydroquinoline-2-carbonyl)piperazin-1-yl)pyridin-3-yl)-4-(trifluoromethyl)oxazole-5-carboxamide (241)

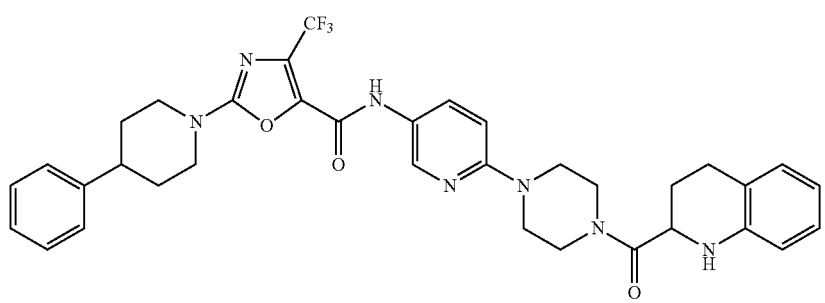

241

Compound 241 was prepared by the general procedure for compound 85. $^1$H NMR (500 MHz, DMSO-d6) δ 10.10 (s, 1H), 8.39 (s, 1H), 7.86 (dd, 1H, J=9, 2.5 Hz), 7.31 (m, 4H), 7.22 (m, 1H), 6.92 (d, 1H, J=9 Hz), 6.87 (t, 1H, J=7 Hz), 6.84 (d, 1H, J=7.5 Hz), 6.57 (d, 1H, J=8 Hz), 6.44 (t, 1H, J=7 Hz), 5.58 (s, 1H), 4.36 (m, 3H), 3.68 (m, 3H), 3.53 (m, 5H), 3.22 (t, 2H, J=11 Hz), 2.82 (m, 1H), 2.64 (m, 1H), 1.99 (m, 1H), 1.90 (d, 2H, J=12 Hz), 1.73 (m, 3H). MS (M+1): 660.4

Example 242

2-(4-phenylpiperidin-1-yl)-N-(6-(4-(1,2,3,4-tetrahydroisoquinoline-1-carbonyl)piperazin-1-yl)pyridin-3-yl)-4-(trifluoromethyl)oxazole-5-carboxamide (242)

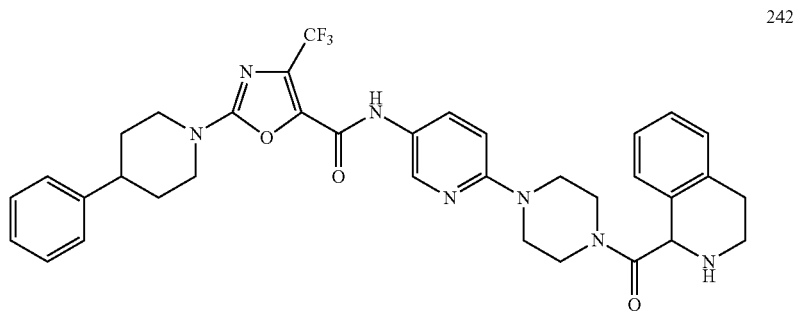 [SMILES: O=C(Nc1ccc(N2CCN(C(=O)C3NCCc4ccccc43)CC2)nc1)c1oc(N2CCC(c3ccccc3)CC2)nc1C(F)(F)F]

242

Compound 242 was prepared by the general procedure for compound 85. $^1$H NMR (500 MHz, DMSO-d6) δ 10.09 (s, 1H), 8.36 (d, 1H, J=3 Hz), 7.84 (dd, 1H, J=9.5, 2.5 Hz), 7.31 (m, 4H), 7.22 (t, 1H, J=6.5 Hz), 7.13 (m, 3H), 6.94 (d, 1H, J=7 Hz), 6.89 (d, 1H, J=9 Hz), 4.99 (s, 1H), 4.35 (d, 2H, J=13.5 Hz), 3.73 (m, 4H), 3.55 (m, 3H), 3.43 (m, 1H), 3.27 (m, 1H), 3.22 (t, 2H, J=12.5 Hz), 3.12 (m, 1H), 2.80 (m, 2H), 2.66 (m, 1H), 1.89 (d, 2H, J=11.5 Hz), 1.75 (qd, 2H, J=12.5, 4 Hz). MS (M+1): 600.3

Example 243

N-(6-(4-(1-phenylcyclopropanecarbonyl)piperazin-1-yl)pyridin-3-yl)-2-(4-phenylpiperidin-1-yl)-4-(trifluoromethyl)oxazole-5-carboxamide (243)

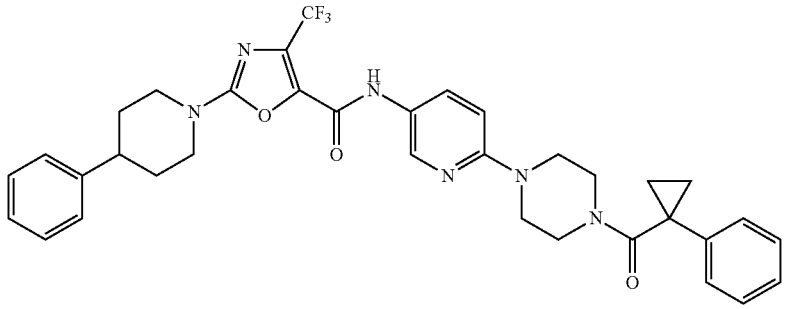

243

Compound 243 was prepared by the general procedure for compound 85. $^1$H NMR (500 MHz, DMSO-d6) δ 10.07 (s, 1H), 8.34 (d, 1H, J=2.5 Hz), 7.81 (dd, 1H, J=9, 2.5 Hz), 7.32 (m, 6H), 7.22 (d, 2H, J=7 Hz), 7.19 (d, 2H, J=7.5 Hz), 6.84 (d, 1H, J=9.5 Hz), 4.34 (d, 2H, J=13.5 Hz), 3.53 (m, 6H), 3.21 (m, 2H), 3.21 (t, 2H, J=12.5 Hz), 2.81 (t, 1H, J=12 Hz), 1.89 (d, 2H, J=12 Hz), 1.74 (qd, 2H, J=13, 4.5 Hz), 1.34 (dd, 2H, J=7, 4.5 Hz), 1.20 (dd, 2H, J=7, 5 Hz). MS (M+1): 645.3

Example 244

N-(6-(4-(2,3-dihydro-1H-indene-2-carbonyl)piperazin-1-yl)pyridin-3-yl)-2-(4-phenylpiperidin-1-yl)-4-(trifluoromethyl)oxazole-5-carboxamide (244)

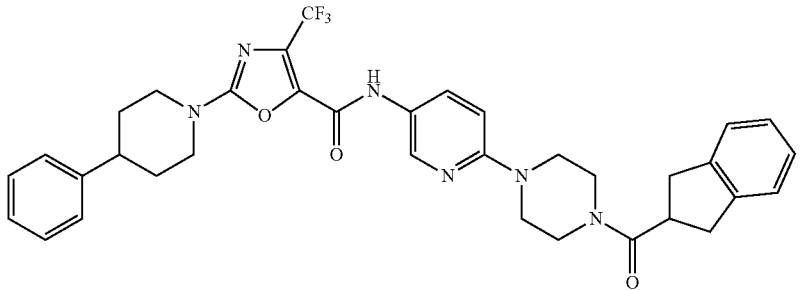

244

Compound 244 was prepared by the general procedure for compound 85. $^1$H NMR (500 MHz, DMSO-d6) δ 10.10 (s, 1H), 8.39 (d, 1H, J=3 Hz), 7.86 (dd, 1H, J=9.5, 3 Hz), 7.31 (m, 4H), 7.21 (m, 3H), 7.13 (dd, 2H, J=5, 3 Hz), 6.92 (d, 1H, J=9 Hz), 4.35 (d, 2H, J=12.5 Hz), 3.70 (m, 3H), 3.62 (m, 2H), 3.56 (m, 2H), 3.48 (m, 2H), 3.22 (t, 2H, J=12.5 Hz), 3.14 (d, 4H, J=8.5 Hz), 2.82 (t, 1H, J=12 Hz), 1.89 (d, 2H, J=12.5 Hz), 1.75 (qd, 2H, J=12.5, 4 Hz). MS (M+1): 645.3

Example 245

N-(6-(4-(2-(2,4-difluorophenyl)acetyl)piperazin-1-yl)pyridin-3-yl)-2-(4-phenylpiperidin-1-yl)-4-(trifluoromethyl)oxazole-5-carboxamide (245)

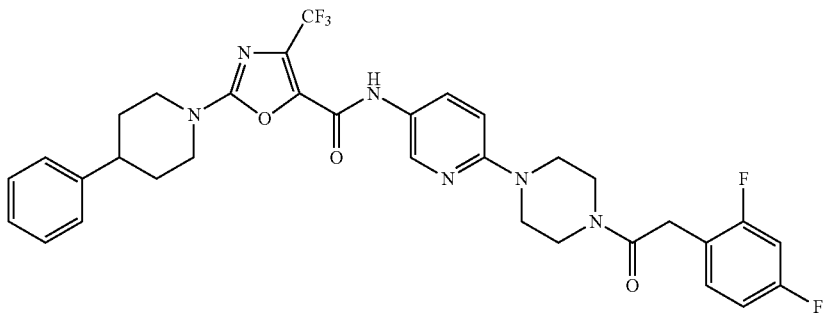

Compound 245 was prepared by the general procedure for compound 85. $^1$H NMR (500 MHz, DMSO-d6) δ 10.10 (s, 1H), 8.38 (d, 1H, J=3 Hz), 7.85 (dd, 1H, J=9, 2.5 Hz), 7.31 (m, 5H), 7.22 (t, 1H, J=7.5 Hz), 7.20 (td, 1H, J=9.5, 2.5 Hz), 7.03 (td, 1H, J=8.5, 2.5 Hz), 6.91 (d, 1H, J=9 Hz), 4.35 (d, 2H, J=12.5 Hz), 3.80 (s, 2H), 3.67 (m, 2H), 3.59 (m, 2H), 3.55 (m, 2H), 3.48 (m, 2H), 3.22 (t, 2H, J=11 Hz), 2.82 (t, 1H, J=12.5 Hz), 1.89 (d, 2H, J=11 Hz), 1.75 (qd, 2H, J=12.5, 4 Hz). MS (M+1): 655.2

Example 246

N-(6-(4-(2-(2,5-difluorophenyl)acetyl)piperazin-1-yl)pyridin-3-yl)-2-(4-phenylpiperidin-1-yl)-4-(trifluoromethyl)oxazole-5-carboxamide (246)

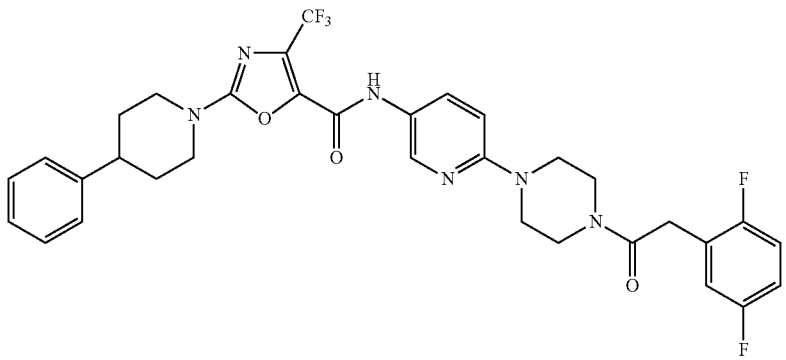

Compound 246 was prepared by the general procedure for compound 85. $^1$H NMR (500 MHz, DMSO-d6) δ 10.10 (s, 1H), 8.38 (d, 1H, J=2.5 Hz), 7.85 (dd, 1H, J=9, 2.5 Hz), 7.31 (m, 4H), 7.22 (m, 2H), 7.16 (m, 2H), 6.92 (d, 1H, J=9 Hz), 4.35 (d, 2H, J=12.5 Hz), 3.82 (s, 2H), 3.68 (m, 2H), 3.60 (m, 2H), 3.56 (m, 2H), 3.48 (m, 2H), 3.22 (t, 2H, J=13 Hz), 2.82 (t, 1H, J=12 Hz), 1.89 (d, 2H, J=11 Hz), 1.75 (qd, 2H, J=12.5, 4 Hz). MS (M+1): 655.2

Example 247
N-(6-(4-(2-(2,3-difluorophenyl)acetyl)piperazin-1-yl)pyridin-3-yl)-2-(4-phenylpiperidin-1-yl)-4-(trifluoromethyl)oxazole-5-carboxamide (247)
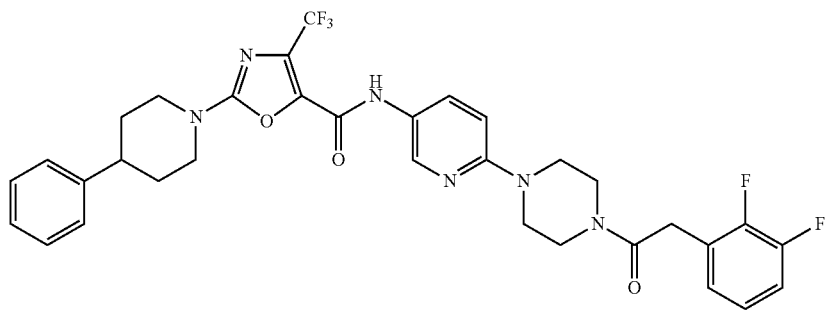
Compound 247 was prepared by the general procedure for compound 85. $^1$H NMR (500 MHz, DMSO-d6) δ 10.10 (s, 1H), 8.38 (d, 1H, J=2.5 Hz), 7.86 (dd, 1H, J=9.5, 2.5 Hz), 7.31 (m, 5H), 7.22 (t, 1H, J=6.5 Hz), 7.16 (td, 1H, J=6.5, 3 Hz), 7.11 (t, 1H, J=6.5 Hz), 6.92 (d, 1H, J=9.5 Hz), 4.35 (d, 2H, J=12.5 Hz), 3.89 (s, 2H), 3.68 (m, 2H), 3.60 (m, 2H), 3.56 (m, 2H), 3.49 (m, 2H), 3.22 (t, 2H, J=13 Hz), 2.82 (t, 1H, J=11.5 Hz), 1.89 (d, 2H, J=11.5 Hz), 1.75 (qd, 2H, J=12.5, 4 Hz). MS (M+1): 655.3
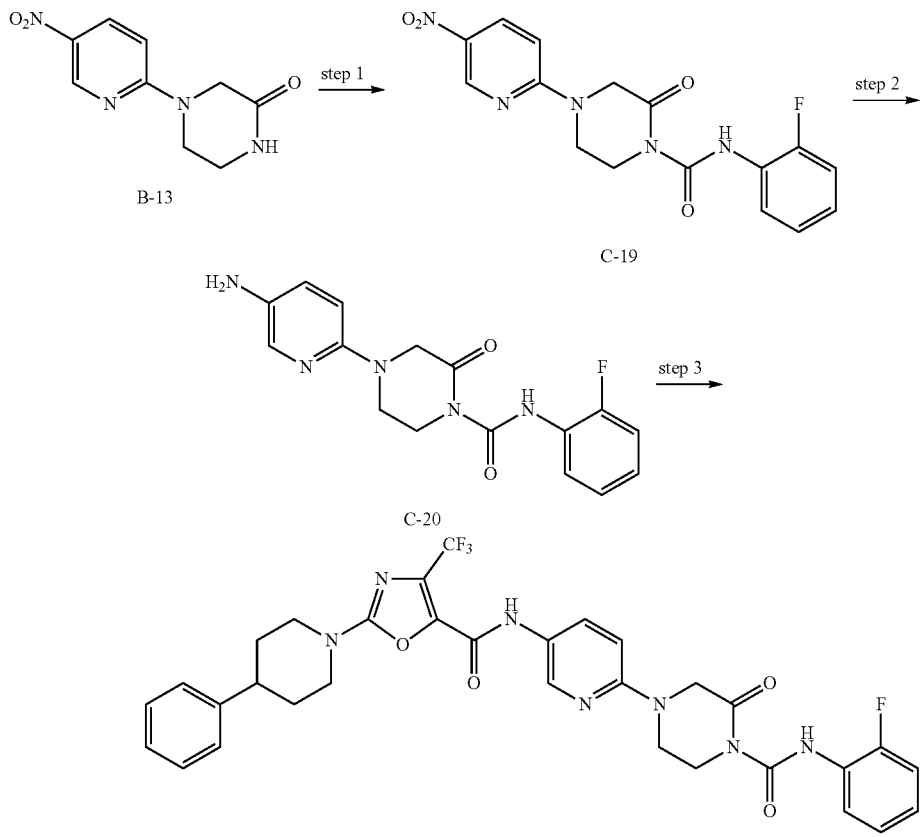

Example 248

N-(6-(4-(2-fluorophenylcarbamoyl)-3-oxopiperazin-1-yl)pyridin-3-yl)-2-(4-phenylpiperidin-1-yl)-4-(trifluoromethyl)oxazole-5-carboxamide (248)

Step 1: N-(2-fluorophenyl)-4-(5-nitropyridin-2-yl)-2-oxopiperazine-1-carboxamide (C-19)

To compound B-13 (0.60 g, 2.70 mmol) and 2-fluorophenylisocyanate (0.44 g, 3.24 mmol) in toluene (20 mL) was added 2 drops of 4 N HCl in dioxane. The mixture was heated at reflux for 16 h then cooled to 0° C. The precipitate was isolated by filtration, washed with diethyl ether, and dried to give the product C-19 (0.88 g, 91% yield). MS (M+1): 360

Step 2: 4-(5-aminopyridin-2-yl)-N-(2-fluorophenyl)-2-oxopiperazine-1-carboxamide (C-20)

Compound C-20 was prepared by the general procedure for compound C-13. MS (M+1): 330

Step 3: N-(6-(4-(2-fluorophenylcarbamoyl)-3-oxopiperazin-1-yl)pyridin-3-yl)-2-(4-phenylpiperidin-1-yl)-4-(trifluoromethyl)oxazole-5-carboxamide (248)

Compound 248 was prepared by the general procedure for compound 216. $^1$H NMR (500 MHz, DMSO-d6) δ 11.63 (s, 1H), 10.11 (s, 1H), 8.40 (d, 1H, J=2.5 Hz), 8.16 (t, 1H, J=8.5 Hz), 7.90 (dd, 1H, J=9, 2.5 Hz), 7.31 (m, 5H), 7.23 (m, 3H), 7.17 (m, 1H), 6.88 (d, 1H, J=9.5 Hz), 4.45 (s, 2H), 4.36 (d, 2H, J=12.5 Hz), 4.01 (m, 2H), 3.82 (m, 2H), 3.22 (t, 2H, J=13 Hz), 2.82 (t, 1H, J=12 Hz), 1.89 (d, 2H, J=12 Hz), 1.75 (qd, 2H, J=13, 4.5 Hz). MS (M+1): 652.2

Example 249 methyl 3-((1-(5-(2-(3-methylpiperidin-1-yl)-4-(trifluoromethyl)oxazole-5-carboxamido)pyridin-2-yl)piperidin-4-yloxy)methyl)benzoate (249)

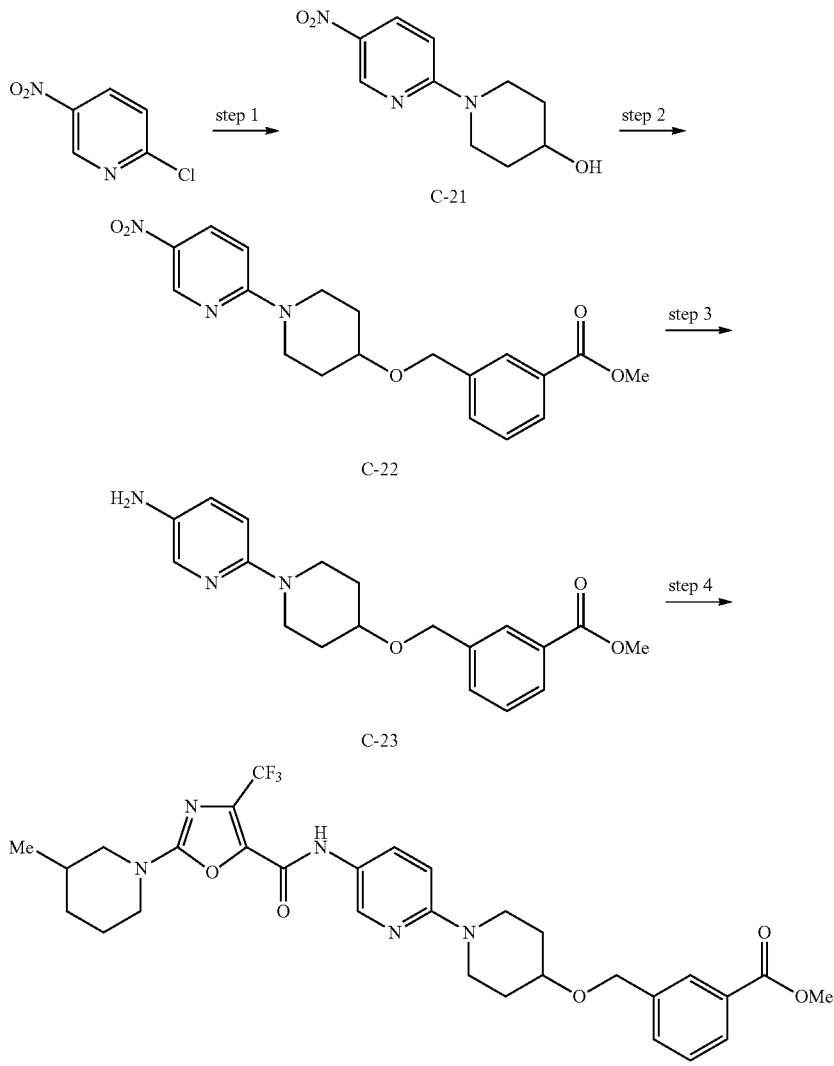

247

Step 1: 1-(5-nitropyridin-2-yl)piperidin-4-ol (C-21)

Compound C-21 was prepared by the general procedure for compound B-1. MS (M+1): 224

Step 2: methyl 3-((1-(5-nitropyridin-2-yl)piperidin-4-yloxy)methyl)benzoate (C-22)

To compound C-21 (1.00 g, 4.48 mmol) in dry THF (20 mL) under nitrogen was added sodium hydride (0.215 g of 60 wt % in oil, 5.38 mmol). The mixture was stirred at room temperature for 20 mins then added 3-(bromomethyl)benzoate (1.54 g, 6.72 mmol) and tetrabutylammonium iodide (0.41 g, 1.12 mmol). The reaction mixture was heated at reflux for 4 h then cooled and concentrated. Water (50 mL) was added, and the aqueous solution was extracted with $CH_2Cl_2$. The combined extracts were dried ($MgSO_4$), filtered, and concentrated. Purification by silica gel chromatography (eluant: $CH_2Cl_2$ to 6% EtOAc—$CH_2Cl_2$) gave the product C-22 (0.96 g, 58% yield) as a yellow oil. MS (M+1): 372

Step 3: methyl 3-((1-(5-aminopyridin-2-yl)piperidin-4-yloxy)methyl)benzoate (C-23)

Compound C-23 was prepared by the general procedure for compound C-13. MS (M+1): 342.5

248

Step 4: methyl 3-((1-(5-(2-(3-methylpiperidin-1-yl)-4-(trifluoromethyl)oxazole-5-carboxamido)pyridin-2-yl)piperidin-4-yloxy)methyl)benzoate (249)

Compound 249 was prepared by the general procedure for compound 216. $^1$H NMR (500 MHz, CDCl$_3$) δ 8.17 (d, 1H, J=2.5 Hz), 8.05 (s, 1H), 7.99 (m, 2H), 7.60 (d, 1H, J=8 Hz), 7.54 (s, 1H), 7.46 (t, 1H, J=7.5 Hz), 6.70 (d, 1H, J=9.5 Hz), 4.65 (s, 2H), 4.12 (m, 2H), 3.99 (m, 2H), 3.95 (s, 3H), 3.68 (m, 1H), 3.25 (td, 2H, J=9.5, 3.5 Hz), 3.05 (td, 1H, J=13, 3.5 Hz), 2.73 (t, 1H, J=11 Hz), 2.02 (m, 2H), 1.91 (d, 2H, J=13 Hz), 1.83 (dt, 1H, J=13.5, 3.5 Hz), 1.74 (m, 3H), 1.65 (dt, 1H, J=13, 4 Hz), 1.19 (qd, 1H, J=12.5, 3 Hz), 1.00 (d, 3H, J=6.5 Hz). MS (M+1): 602.2

Example 250 methyl 4-((1-(5-(2-(3-methylpiperidin-1-yl)-4-(trifluoromethyl)oxazole-5-carboxamido)pyridin-2-yl)piperidin-4-yloxy)methyl)benzoate (250)

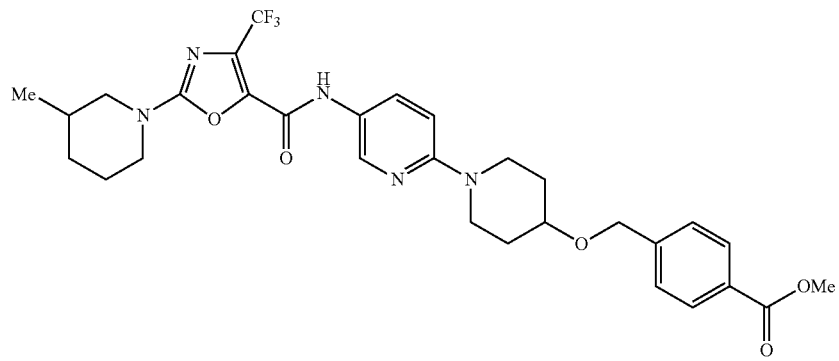

250

Compound 250 was prepared by the general procedure for compound 249. ¹H NMR (500 MHz, CDCl₃) δ 8.17 (d, 1H, J=3 Hz), 8.04 (m, 2H), 7.98 (dd, 1H, J=9, 2.5 Hz), 7.56 (s, 1H), 7.45 (d, 1H, J=8 Hz), 6.70 (d, 1H, J=9 Hz), 4.67 (s, 2H), 4.10 (dm, 2H, J=13.5 Hz), 3.99 (m, 2H), 3.94 (s, 3H), 3.68 (m, 1H), 3.25 (td, 2H, J=9.5, 3.5 Hz), 3.06 (td, 1H, J=13, 3.5 Hz), 2.72 (t, 1H, J=11.5 Hz), 2.02 (m, 2H), 1.90 (d, 2H, J=12 Hz), 1.83 (dt, 1H, J=13.5, 3.5 Hz), 1.75 (m, 3H), 1.63 (m, 1H), 1.19 (qd, 1H, J=12.5, 4 Hz), 1.00 (d, 3H, J=7 Hz). MS (M+1): 602.3

Example 251 methyl 2-((1-(5-(2-(3-methylpiperidin-1-yl)-4-(trifluoromethyl)oxazole-5-carboxamido)pyridin-2-yl)piperidin-4-yloxy)methyl)benzoate (251)

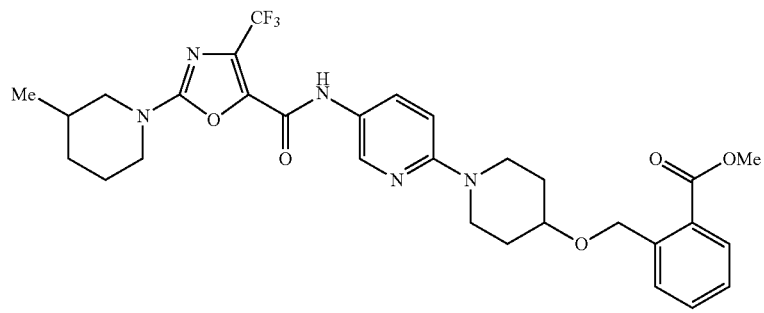

251

Compound 251 was prepared by the general procedure for compound 249. ¹H NMR (500 MHz, CDCl₃) δ 8.17 (d, 1H, J=2.5 Hz), 7.99 (dd, 1H, J=9.5, 2.5 Hz), 7.96 (d, 1H, J=7.5 Hz), 7.76 (d, 1H, J=8 Hz), 7.56 (td, 1H, J=7.5, 1.5 Hz), 7.53 (s, 1H), 7.35 (t, 1H, J=7.5 Hz), 6.71 (d, 1H, J=9.5 Hz), 5.00 (s, 2H), 4.12 (t, 2H, J=16 Hz), 3.98 (m, 2H), 3.92 (s, 3H), 3.73 (m, 1H), 3.28 (td, 2H, J=9, 3.5 Hz), 3.06 (td, 1H, J=12.5, 3.5 Hz), 2.73 (t, 1H, J=11 Hz), 2.05 (m, 2H), 1.90 (d, 1H, J=12 Hz), 1.78 (m, 4H), 1.66 (m, 1H), 1.19 (q, 1H, J=12.5 Hz), 1.00 (d, 3H, J=6.5 Hz). MS (M+1): 602.3

Example 252 methyl 3-((1-(5-(2-(4-phenylpiperidin-1-yl)-4-(trifluoromethyl)oxazole-5-carboxamido)pyridin-2-yl)piperidin-4-yloxy)methyl)benzoate (252)

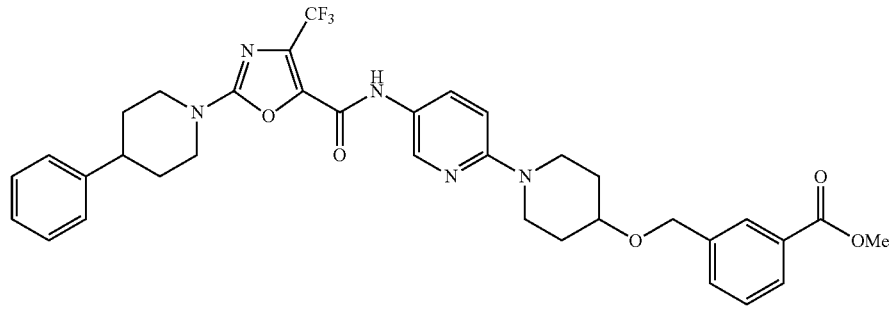

252

Compound 252 was prepared by the general procedure for compound 249. ¹H NMR (500 MHz, CDCl₃) δ 8.17 (d, 1H, J=2.5 Hz), 8.04 (s, 1H), 7.99 (m, 2H), 7.60 (m, 2H), 7.45 (t, 1H, J=7.5 Hz), 7.36 (t, 2H, J=7 Hz), 7.25 (t, 3H, J=7.5 Hz), 6.70 (d, 1H, J=9 Hz), 4.65 (s, 2H), 4.39 (d, 2H, J=13.5 Hz), 4.00 (m, 2H), 3.95 (s, 3H), 3.68 (m, 1H), 3.25 (m, 4H), 2.80 (m, 1H), 2.02 (m, 4H), 1.85 (m, 2H), 1.75 (m, 2H). MS (M+1): 664.3

Example 253

4-((1-(5-(2-(3-methylpiperidin-1-yl)-4-(trifluoromethyl)oxazole-5-carboxamido)pyridin-2-yl)piperidin-4-yloxy)methyl)benzoic acid (253)

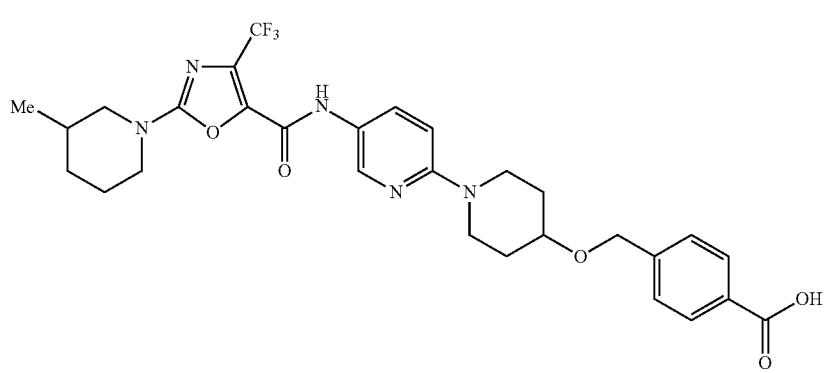

253

Compound 253 was prepared by hydrolysis of compound 250. ¹H NMR (500 MHz, DMSO-d6) δ 12.90 (s, 1H), 10.00 (s, 1H), 8.33 (s, 1H), 7.93 (d, 2H, J=8 Hz), 7.77 (d, 1H, J=9 Hz), 7.47 (d, 2H, J=8 Hz), 6.89 (d, 1H, J=9.5 Hz), 4.67 (s, 2H), 4.64 (s, 2H), 4.12 (d, 1H, J=12.5 Hz), 4.07 (d, 1H, J=13 Hz), 3.95 (d, 2H, J=13.5 Hz), 3.66 (m, 1H), 3.16 (t, 2H, J=10.5 Hz), 3.04 (t, 1H, J=10 Hz), 2.74 (t, 1H, J=11.5 Hz), 1.95 (m, 2H), 1.77 (m, 2H), 1.66 (m, 1H), 1.52 (d, 3H, J=9.5 Hz), 1.15 (q, 1H, J=11.5 Hz), 0.93 (d, 3H, J=6.5 Hz). MS (M+1): 588.3

Example 254

3-((1-(5-(2-(3-methylpiperidin-1-yl)-4-(trifluoromethyl)oxazole-5-carboxamido)pyridin-2-yl)piperidin-4-yloxy)methyl)benzoic acid (254)

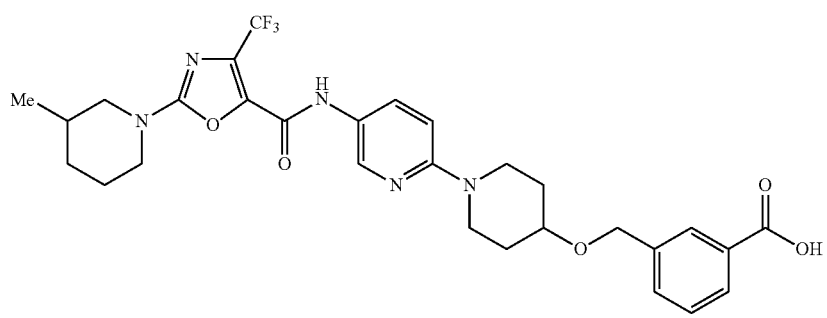

254

Compound 254 was prepared by hydrolysis of compound 249. ¹H NMR (500 MHz, DMSO-d6) δ 12.99 (broad s, 1H), 10.01 (s, 1H), 8.32 (d, 1H, J=2 Hz), 7.94 (s, 1H), 7.86 (d, 1H, J=8 Hz), 7.79 (d, 1H, J=9.5 Hz), 7.60 (d, 1H, J=7.5 Hz), 7.49 (t, 1H, J=7.5 Hz), 6.91 (d, 1H, J=9 Hz), 4.63 (s, 2H), 4.12 (d, 1H, J=13 Hz), 4.07 (d, 1H, J=14 Hz), 3.95 (d, 2H, J=13 Hz), 3.67 (m, 1H), 3.17 (t, 2H, J=10 Hz), 3.05 (t, 1H, J=12.5 Hz), 2.74 (t, 1H, J=12 Hz), 1.95 (m, 2H), 1.77 (m, 2H), 1.66 (m, 1H), 1.54 (m, 3H), 1.16 (t, 1H, J=14 Hz), 0.93 (d, 3H, J=6 Hz). MS (M+1): 588.2

Example 255

2-((1-(5-(2-(3-methylpiperidin-1-yl)-4-(trifluoromethyl)oxazole-5-carboxamido)pyridin-2-yl)piperidin-4-yloxy)methyl)benzoic acid (255)

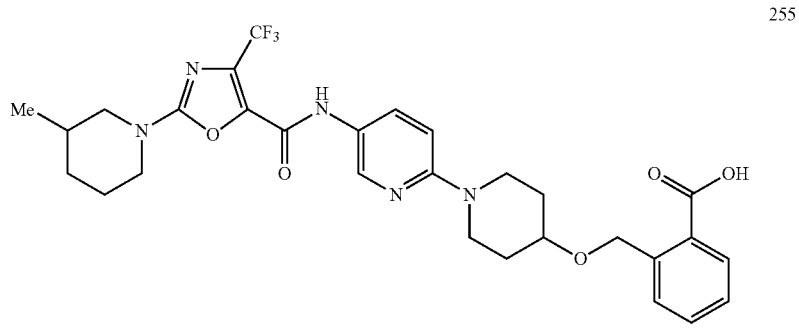 [SMILES: CC1CCCN(c2nc(C(F)(F)F)c(C(=O)Nc3ccc(N4CCC(OCc5ccccc5C(=O)O)CC4)nc3)o2)C1]

255

Compound 255 was prepared by hydrolysis of compound 251. ¹H NMR (500 MHz, DMSO-d6) δ 12.95 (s, 1H), 10.00 (s, 1H), 8.32 (d, 1H, J=2.5 Hz), 7.84 (d, 1H, J=8 Hz), 7.77 (dd, 1H, J=9.5, 2 Hz), 7.65 (d, 1H, J=7.5 Hz), 7.57 (t, 1H, J=7.5 Hz), 7.38 (t, 1H, J=7.5 Hz), 6.89 (d, 1H, J=9.5 Hz), 4.89 (s, 2H), 4.12 (d, 1H, J=11.5 Hz), 4.07 (d, 1H, J=13.5 Hz), 3.95 (m, 2H), 3.67 (m, 1H), 3.31 (m, 1H), 3.19 (t, 2H, J=9.5 Hz), 3.05 (t, 1H, J=12 Hz), 2.75 (t, 1H, J=12.5 Hz), 1.95 (m, 2H), 1.77 (m, 2H), 1.67 (m, 1H), 1.54 (m, 2H), 1.15 (t, 1H, J=14 Hz), 0.93 (d, 3H, J=6.5 Hz). MS (M+1): 588.2

Example 256

3-((1-(5-(2-(4-phenylpiperidin-1-yl)-4-(trifluoromethyl)oxazole-5-carboxamido)pyridin-2-yl)piperidin-4-yloxy)methyl)benzoic acid (256)

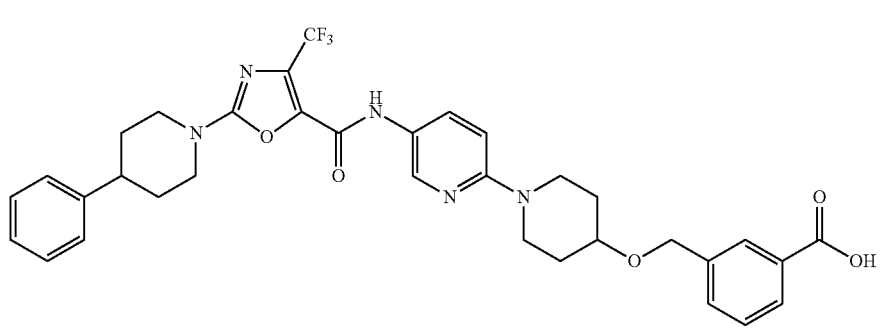

256

255

Compound 256 was prepared by hydrolysis of compound 252. ¹H NMR (500 MHz, DMSO-d6) δ 10.05 (s, 1H), 8.34 (d, 1H, J=2.5 Hz), 7.94 (s, 1H), 7.86 (d, 1H, J=8 Hz), 7.79 (dd, 1H, J=9, 3 Hz), 7.60 (d, 1H, J=7.5 Hz), 7.48 (t, 1H, J=7.5 Hz), 7.31 (m, 4H), 7.22 (t, 1H, J=7 Hz), 6.89 (d, 1H, J=9 Hz), 4.63 (s, 2H), 4.35 (d, 2H, J=13 Hz), 3.96 (dm, 2H, J=13.5 Hz), 3.66 (m, 1H), 3.22 (t, 2H, J=11 Hz), 3.16 (t, 2H, J=10 Hz), 2.81 (t, 1H, J=12 Hz), 1.95 (m, 2H), 1.89 (d, 2H, J=12 Hz), 1.74 (qd, 2H, J=13, 3.5 Hz), 1.52 (qm, 2H, J=9 Hz). MS (M+1): 650.3

Example 257 methyl 3-((1-(5-(2-(3-methylpiperidin-1-yl)-4-(trifluoromethyl)oxazole-5-carboxamido)pyridin-2-yl)piperidin-4-yl)methoxy)benzoate (257)

256

Step 1: (1-(5-nitropyridin-2-yl)piperidin-4-yl)methanol (C-24)

Compound C-24 was prepared by the general procedure for compound B-1. MS (M+1): 238

Step 2: (1-(5-nitropyridin-2-yl)piperidin-4-yl)methyl methanesulfonate (C-25)

To compound C-24 (1.00 g, 4.21 mmol) in CH₂Cl₂ (30 mL) and cooled to 0° C. was added triethylamine (0.85 g, 1.2 mL, 8.43 mmol) and mesyl chloride (0.60 g, 0.41 mL, 5.27 mmol). The reaction mixture was stirred at 0° C. for 15 mins then at room temperature for 60 mins. Water (50 mL) was added, and the aqueous solution was extracted with CH₂Cl₂. The com-

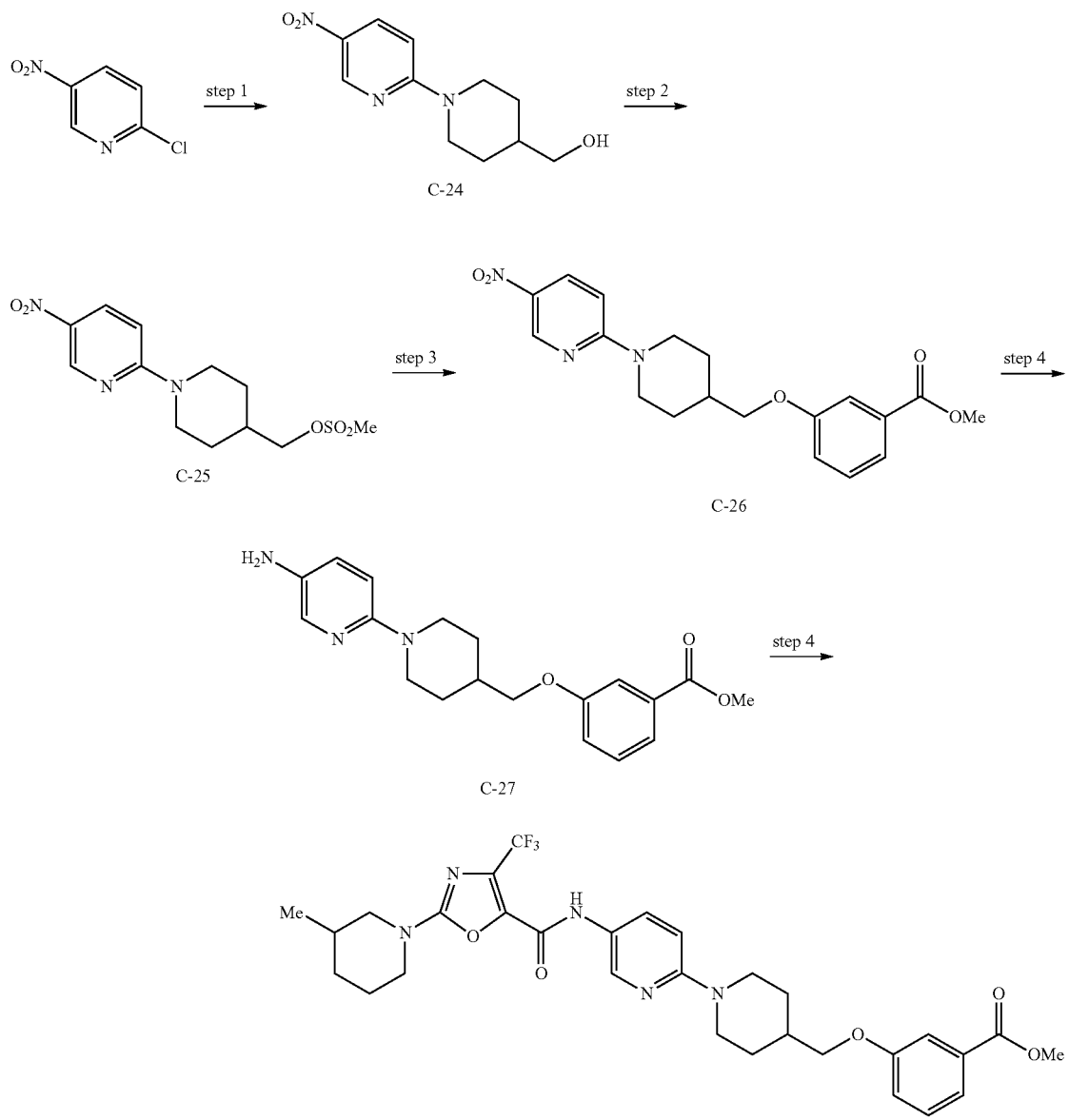

bined extracts were dried (MgSO$_4$), filtered, and concentrated to give the product C-25 (1.33 g, 100% yield). MS (M+1): 316

Step 3: methyl 3-((1-(5-nitropyridin-2-yl)piperidin-4-yl)methoxy)benzoate (C-26)

To methyl 3-hydroxybenzoate (0.96 g, 6.28 mmol) in dry DMF (20 mL) under nitrogen was added sodium hydride (0.25 g of 60 wt % in oil, 6.28 mmol). The mixture was stirred at room temperature for 15 mins then added compound C-25 (1.32 g, 4.19 mmol) in dry DMF (10 mL). The resulting mixture was heated at 50° C. for 5 h then cooled and concentrated. Water (50 mL) was added, and the aqueous solution was extracted with CH$_2$Cl$_2$. The combined extracts were dried (MgSO$_4$), filtered, and concentrated. Purification by silica gel chromatography (eluant: 5% EtOAc—CH$_2$Cl$_2$) gave the product C-26 (1.22 g, 78% yield). MS (M+1): 372

Step 4: methyl 3-((1-(5-aminopyridin-2-yl)piperidin-4-yl)methoxy)benzoate (C-27)

Compound C-27 was prepared by the general procedure for compound C-13. MS (M+1): 342

Step 5: methyl 3-((1-(5-(2-(3-methylpiperidin-1-yl)-4-(trifluoromethyl)oxazole-5-carboxamido)pyridin-2-yl)piperidin-4-yl)methoxy)benzoate (257)

Compound 257 was prepared by the general procedure for compound 216. $^1$H NMR (500 MHz, CDCl$_3$) δ 8.18 (d, 1H, J=2.5 Hz), 8.00 (dd, 1H, J=9, 2.5 Hz), 7.65 (d, 1H, J=7.5 Hz), 7.57 (m, 1H), 7.53 (s, 1H), 7.36 (t, 1H, J=8 Hz), 7.12 (dd, 1H, J=8, 2.5 Hz), 6.71 (d, 1H, J=9 Hz), 4.34 (d, 2H, J=13 Hz), 4.12 (tm, 2H, J=13 Hz), 3.94 (s, 3H), 3.90 (d, 2H, J=6.5 Hz), 3.06 (td, 1H, J=12.5, 3.5 Hz), 2.91 (td, 1H, J=12.5, 2 Hz), 2.73 (t, 1H, J=11 Hz), 2.10 (m, 1H), 1.97 (d, 2H, J=12.5 Hz), 1.91 (d, 1H, J=12 Hz), 1.83 (dt, 1H, J=14, 3.5 Hz), 1.77 (m, 1H), 1.45 (qd, 2H, J=12.5, 4 Hz), 1.19 (qd, 2H, J=12.5, 3.5 Hz), 1.01 (d, 3H, J=7 Hz). MS (M+1): 602.2

Example 258 methyl 3-((1-(5-(2-(4-phenylpiperidin-1-yl)-4-(trifluoromethyl)oxazole-5-carboxamido)pyridin-2-yl)piperidin-4-yl)methoxy)benzoate (258)

Compound 258 was prepared by the general procedure for compound 257. $^1$H NMR (500 MHz, CDCl$_3$) δ 8.20 (d, 1H, J=2.5 Hz), 8.04 (broad s, 1H), 7.68 (broad s, 1H), 7.65 (d, 1H, J=7.5 Hz), 7.57 (m, 1H), 7.36 (t, 3H, J=8 Hz), 7.26 (t, 2H, J=8 Hz), 7.12 (dd, 1H, J=8, 3 Hz), 6.73 (d, 1H, J=9 Hz), 4.39 (d, 2H, J=13 Hz), 4.34 (d, 2H, J=13 Hz), 3.94 (s, 3H), 3.90 (d, 2H, J=6 Hz), 3.23 (td, 2H, J=13, 2.5 Hz), 2.93 (td, 2H, J=12.5, 2.5 Hz), 2.80 (tt, 1H, J=12, 3.5 Hz), 2.10 (m, 1H), 2.03 (d, 2H, J=12.5 Hz), 1.98 (d, 2H, J=12 Hz), 1.84 (qd, 2H, J=13, 4.5 Hz), 1.46 (qd, 2H, J=12.5, 3.5 Hz). MS (M+1): 664.3

Example 259 methyl 2-((1-(5-(2-(3-methylpiperidin-1-yl)-4-(trifluoromethyl)oxazole-5-carboxamido)pyridin-2-yl)piperidin-4-yl)methoxy)benzoate (259)

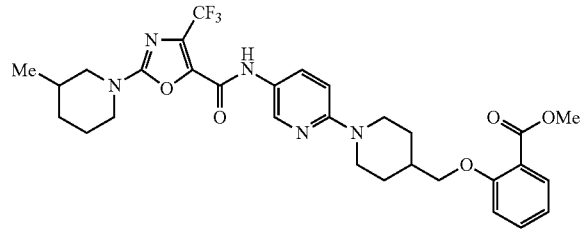

259

Compound 259 was prepared by the general procedure for compound 257. $^1$H NMR (500 MHz, CDCl$_3$) δ 8.18 (d, 1H, J=2.5 Hz), 7.99 (dd, 1H, J=9, 2.5 Hz), 7.82 (dd, 1H, J=8, 2 Hz), 7.54 (s, 1H), 7.47 (td, 1H, J=8, 1.5 Hz), 7.00 (d, 1H, J=7.5 Hz), 6.97 (d, 1H, J=8.5 Hz), 6.71 (d, 1H, J=9 Hz), 4.35 (d, 2H, J=13 Hz), 4.12 (t, 2H, J=15 Hz), 3.93 (d, 2H, J=7 Hz), 3.88 (s, 3H), 3.05 (td, 1H, J=13, 3 Hz), 2.92 (td, 2H, J=13, 2 Hz), 2.72 (t, 1H, J=11 Hz), 2.16 (m, 1H), 2.00 (d, 2H, J=12.5 Hz), 1.90 (d, 1H, J=12 Hz), 1.83 (dt, 1H, J=13.5, 3.5 Hz), 1.76 (m, 1H), 1.66 (m, 1H), 1.47 (qd, 2H, J=12.5, 3.5 Hz), 1.18 (qd, 1H, J=13, 4 Hz), 1.00 (d, 3H, J=6.5 Hz). MS (M+1): 602.3

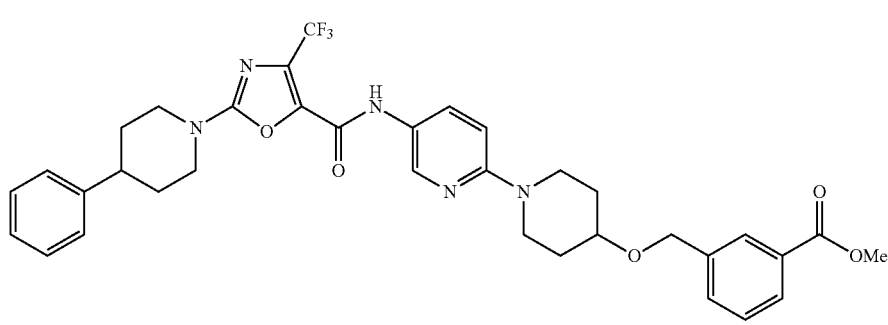

258

Example 260 methyl 2-((1-(5-(2-(4-phenylpiperidin-1-yl)-4-(trifluoromethyl)oxazole-5-carboxamido)pyridin-2-yl)piperidin-4-yl)methoxy)benzoate (260)

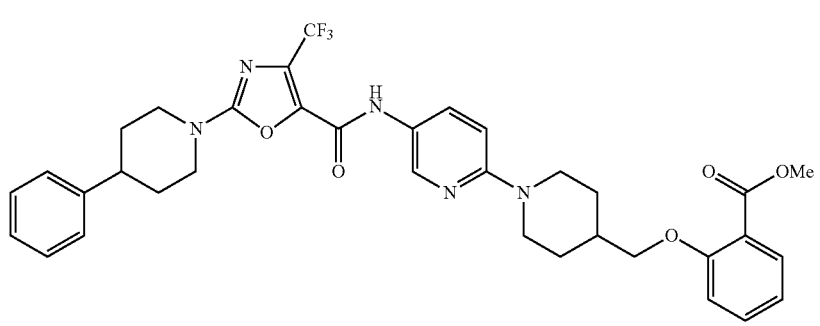

Compound 260 was prepared by the general procedure for compound 257. $^1$H NMR (500 MHz, CDCl$_3$) δ 8.18 (d, 1H, J=3 Hz), 7.99 (dd, 1H, J=9.5, 3 Hz), 7.82 (dd, 1H, J=8, 2 Hz), 7.61 (s, 1H), 7.46 (td, 1H, J=8.5, 1.5 Hz), 7.36 (t, 2H, J=7.5 Hz), 7.26 (t, 3H, J=7 Hz), 7.00 (d, 1H, J=7.5 Hz), 6.97 (d, 1H, J=9 Hz), 6.71 (d, 1H, J=9.5 Hz), 4.37 (m, 4H), 3.92 (d, 2H, J=6.5 Hz), 3.88 (s, 3H), 3.23 (t, 2H, J=13 Hz), 2.92 (t, 2H, J=12.5 Hz), 2.80 (t, 1H, J=12.5 Hz), 2.15 (m, 1H), 2.02 (m, 4H), 1.84 (qd, 2H, J=13, 4 Hz), 1.47 (qd, 2H, J=12.5, 3.5 Hz). MS (M+1): 664.3

Example 261 methyl 4-fluoro-3-((1-(5-(2-(3-methylpiperidin-1-yl)-4-(trifluoromethyl)oxazole-5-carboxamido)pyridin-2-yl)piperidin-4-yl)methoxy)benzoate (261)

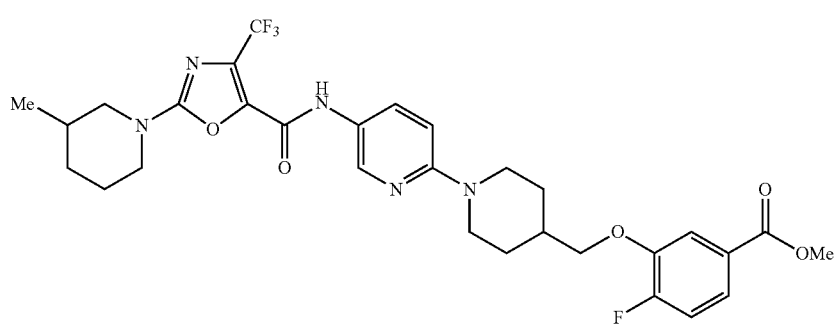

Compound 261 was prepared by the general procedure for compound 257. $^1$H NMR (500 MHz, CDCl$_3$) δ 8.18 (d, 1H, J=3 Hz), 7.99 (dd, 1H, J=9.5, 2.5 Hz), 7.66 (m, 2H), 7.55 (s, 1H), 7.14 (t, 1H, J=9 Hz), 6.71 (d, 1H, J=9 Hz), 4.34 (d, 2H, J=13 Hz), 4.12 (t, 2H, J=13.5 Hz), 3.97 (d, 2H, J=6.5 Hz), 3.93 (s, 3H), 3.05 (td, 1H, J=12.5, 3.5 Hz), 2.91 (t, 2H, J=13 Hz), 2.73 (t, 1H, J=11 Hz), 2.15 (m, 1H), 2.00 (d, 2H, J=12.5 Hz), 1.90 (d, 1H, J=14 Hz), 1.83 (dt, 1H, J=13.5, 3.5 Hz), 1.76 (m, 1H), 1.63 (m, 1H), 1.45 (qd, 2H, J=12.5, 4 Hz), 1.18 (q, 1H, J=12.5 Hz), 1.00 (d, 3H, J=6.5 Hz). MS (M+1): 620.3

Example 262 methyl 4-fluoro-3-((1-(5-(2-(4-phenylpiperidin-1-yl)-4-(trifluoromethyl)oxazole-5-carboxamido)pyridin-2-yl)piperidin-4-yl)methoxy)benzoate (262)

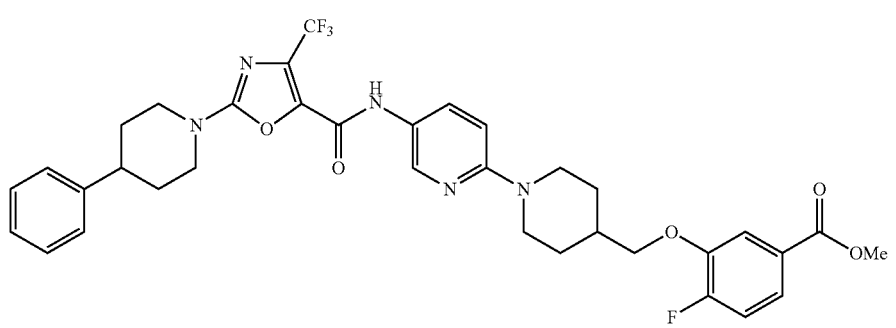

Compound 262 was prepared by the general procedure for compound 257. $^1$H NMR (500 MHz, CDCl$_3$) δ 8.19 (d, 1H, J=2.5 Hz), 8.03 (d, 1H, J=8.5 Hz), 7.66 (m, 3H), 7.36 (t, 2H, J=7.5 Hz), 7.25 (t, 3H, J=8.5 Hz), 7.14 (t, 1H, J=9.5 Hz), 6.72 (d, 1H, J=9.5 Hz), 4.39 (d, 2H, J=11 Hz), 4.34 (d, 2H, J=13.5 Hz), 3.97 (d, 2H, J=6.5 Hz), 3.93 (s, 3H), 3.23 (t, 2H, J=12.5 Hz), 2.93 (t, 2H, J=11 Hz), 2.80 (t, 1H, J=12.5 Hz), 2.16 (m, 1H), 2.02 (m, 3H), 1.83 (m, 3H), 1.46 (qd, 2H, J=13, 4 Hz). MS (M+1): 682.3

Example 263

3-((1-(5-(2-(3-methylpiperidin-1-yl)-4-(trifluoromethyl)oxazole-5-carboxamido)pyridin-2-yl)piperidin-4-yl)methoxy)benzoic acid (263)

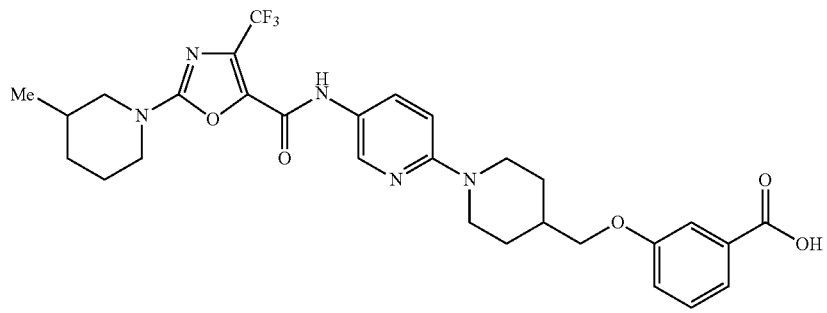

Compound 263 was prepared by hydrolysis of compound 257. $^1$H NMR (500 MHz, DMSO-d6) δ 10.03 (s, 1H), 8.33 (s, 1H), 7.81 (d, 1H, J=9 Hz), 7.53 (d, 1H, J=7.5 Hz), 7.45 (s, 1H), 7.41 (t, 1H, J=8 Hz), 7.20 (d, 1H, J=8.5 Hz), 6.94 (d, 1H, J=8.5 Hz), 4.30 (d, 2H, J=13.5 Hz), 4.12 (d, 1H, J=13 Hz), 4.07 (d, 1H, J=13.5 Hz), 3.92 (d, 2H, J=6 Hz), 3.05 (t, 1H, J=11.5 Hz), 2.87 (t, 2H, J=11 Hz), 2.75 (t, 1H, J=12.5 Hz), 2.05 (m, 2H), 1.87 (d, 2H, J=13.5 Hz), 1.77 (m, 2H), 1.66 (m, 1H), 1.53 (q, 1H, J=12.5 Hz), 1.33 (qd, 2H, J=12, 3 Hz), 1.16 (m, 1H), 0.93 (d, 3H, J=6.5 Hz). MS (M+1): 588.2

Example 264

3-((1-(5-(2-(4-phenylpiperidin-1-yl)-4-(trifluoromethyl)oxazole-5-carboxamido)pyridin-2-yl)piperidin-4-yl)methoxy)benzoic acid (264)

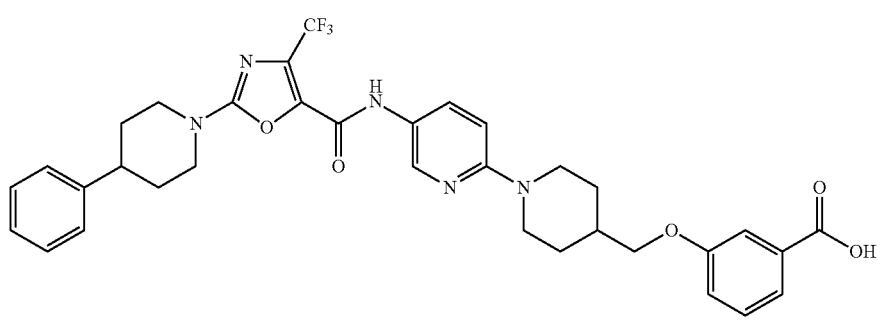

264

Compound 264 was prepared by hydrolysis of compound 258. ¹H NMR (500 MHz, DMSO-d6) δ 10.22 (s, 1H), 8.38 (d, 1H, J=2 Hz), 7.98 (d, 1H, J=9.5 Hz), 7.53 (d, 1H, J=8 Hz), 7.45 (s, 1H), 7.41 (t, 1H, J=7.5 Hz), 7.31 (m, 4H), 7.22 (m, 3H), 4.35 (d, 2H, J=13 Hz), 4.26 (d, 2H, J=13 Hz), 3.94 (d, 2H, J=6.5 Hz), 3.23 (t, 2H, J=11 Hz), 3.04 (t, 2H, J=12.5 Hz), 2.82 (t, 1H, J=12 Hz), 2.10 (broad s, 1H), 1.91 (m, 4H), 1.74 (qd, 2H, J=12.5, 3.5 Hz), 1.38 (q, 2H, J=11.5 Hz). MS (M+1): 650.3

Example 265

2-((1-(5-(2-(3-methylpiperidin-1-yl)-4-(trifluoromethyl)oxazole-5-carboxamido)pyridin-2-yl)piperidin-4-yl)methoxy)benzoic acid (265)

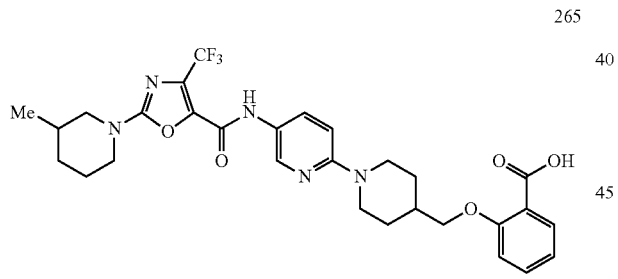

265

Compound 265 was prepared by hydrolysis of compound 259. ¹H NMR (500 MHz, DMSO-d6) δ 10.17 (broad s, 1H), 8.36 (d, 1H, J=2.5 Hz), 7.95 (d, 1H, J=7 Hz), 7.63 (dd, 1H, J=8, 2 Hz), 7.48 (td, 1H, J=8.5, 2 Hz), 7.17 (broad s, 1H), 7.12 (d, 1H, J=8.5 Hz), 6.99 (t, 1H, J=7.5 Hz), 4.26 (d, 1H, J=13 Hz), 4.12 (d, 1H, J=12.5 Hz), 4.07 (d, 1H, J=14 Hz), 3.94 (d, 2H, J=6.5 Hz), 3.05 (q, 2H, J=10 Hz), 3.01 (d, 1H, J=13 Hz), 2.76 (t, 1H, J=11 Hz), 2.09 (m, 1H), 1.92 (d, 2H, J=12.5 Hz), 1.77 (m, 2H), 1.66 (m, 1H), 1.53 (q, 1H, J=13 Hz), 1.39 (q, 2H, J=9 Hz), 1.16 (t, 1H, J=13.5 Hz), 0.94 (d, 3H, J=6.5 Hz). MS (M+1): 588.2

Example 266

2-((1-(5-(2-(4-phenylpiperidin-1-yl)-4-(trifluoromethyl)oxazole-5-carboxamido)pyridin-2-yl)piperidin-4-yl)methoxy)benzoic acid (266)

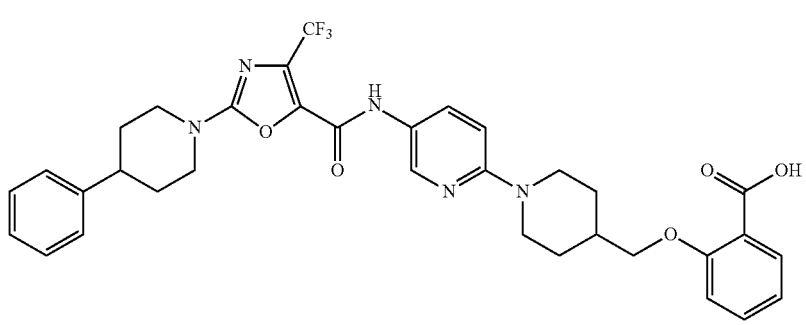

266

Compound 266 was prepared by hydrolysis of compound 260. $^1$H NMR (500 MHz, DMSO-d6) δ 10.19 (broad s, 1H), 8.37 (d, 1H, J=2 Hz), 7.95 (d, 1H, J=8 Hz), 7.62 (d, 1H, J=8 Hz), 7.48 (t, 1H, J=8.5 Hz), 7.31 (m, 4H), 7.22 (t, 1H, J=6.5 Hz), 7.16 (broad s, 1H), 7.12 (d, 1H, J=8.5 Hz), 6.99 (t, 1H, J=7.5 Hz), 4.35 (d, 2H, J=12 Hz), 4.27 (d, 2H, J=13.5 Hz), 3.94 (d, 2H, J=6.5 Hz), 3.23 (t, 2H, J=12 Hz), 3.00 (t, 2H, J=10 Hz), 2.82 (t, 1H, J=12.5 Hz), 2.09 (broad s, 1H), 1.91 (t, 4H, J=12 Hz), 1.74 (qd, 2H, J=13, 3.5 Hz), 1.39 (q, 2H, J=10.5 Hz). MS (M+1): 650.3

Example 267

4-fluoro-3-((1-(5-(2-(3-methylpiperidin-1-yl-4-(trifluoromethyl)oxazole-5-carboxamido)pyridin-2-yl)piperidin-4-yl)methoxy)benzoic acid (267)

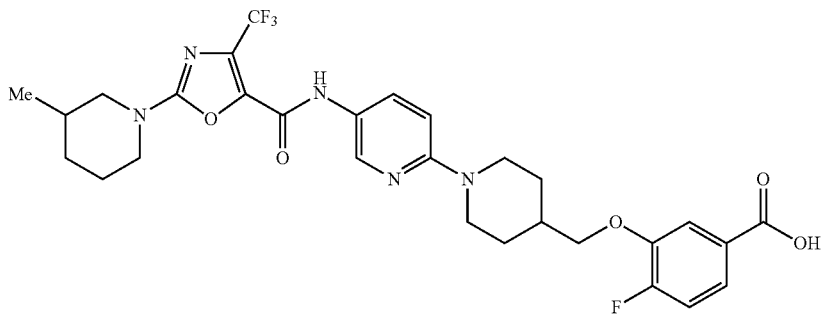

267

Compound 267 was prepared by hydrolysis of compound 261. $^1$H NMR (500 MHz, DMSO-d6) δ 10.14 (s, 1H), 8.36 (s, 1H), 7.93 (d, 1H, J=8.5 Hz), 7.65 (d, 1H, J=7.5 Hz), 7.57 (m, 1H), 7.34 (t, 1H, J=8.5 Hz), 7.14 (broad s, 1H), 4.27 (d, 2H, J=12.5 Hz), 4.12 (d, 1H, J=12.5 Hz), 4.07 (d, 2H, J=13.5 Hz), 4.03 (d, 2H, J=6.5 Hz), 3.03 (m, 3H), 2.76 (t, 1H, J=12 Hz), 2.12 (m, 1H), 1.90 (d, 2H, J=11 Hz), 1.77 (t, 2H, J=13.5 Hz), 1.67 (m, 1H), 1.53 (q, 1H, J=12 Hz), 1.38 (q, 2H, J=11.5 Hz), 1.15 (q, 1H, J=11 Hz), 0.94 (d, 3H, J=6.5 Hz). MS (M+1): 606.2

Example 268

4-fluoro-3-((1-(5-(2-(4-phenylpiperidin-1-yl)-4-(trifluoromethyl)oxazole-5-carboxamido)pyridin-2-yl)piperidin-4-yl)methoxy)benzoic acid (268)

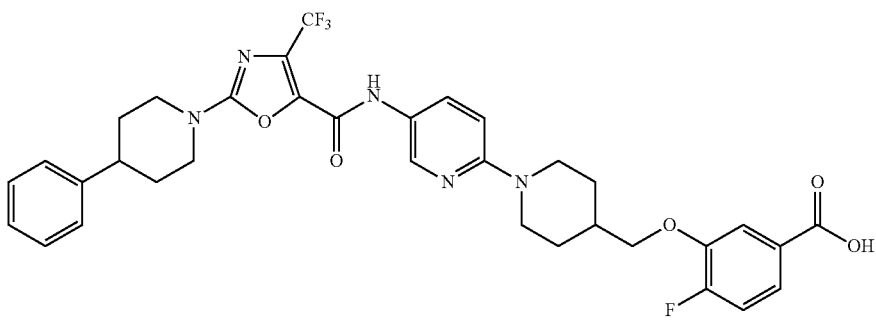

268

Compound 268 was prepared by hydrolysis of compound 262. ¹H NMR (500 MHz, DMSO-d6) δ 10.18 (s, 1H), 8.37 (s, 1H), 7.94 (d, 1H, J=8.5 Hz), 7.66 (d, 1H, J=8 Hz), 7.57 (m, 1H), 7.31 (m, 5H), 7.22 (t, 1H, J=7 Hz), 7.14 (m, 1H), 4.35 (d, 2H, J=13 Hz), 4.27 (d, 2H, J=13 Hz), 4.03 (d, 2H, J=6.5 Hz), 3.23 (t, 2H, J=13 Hz), 3.01 (t, 2H, J=11 Hz), 2.82 (t, 1H, J=11.5 Hz), 2.12 (m, 1H), 1.90 (d, 3H, J=12.5 Hz), 1.76 (m, 2H), 1.73 (t, 1H, J=12 Hz), 1.39 (q, 2H, J=11 Hz). MS (M+1): 668.2

Example 269

N-(6-(4-(2-chlorophenylcarbamoyl)piperazin-1-yl)pyridin-3-yl)-2-(piperidin-1-yl)-4-(trifluoromethyl)oxazole-5-carboxamide (269)

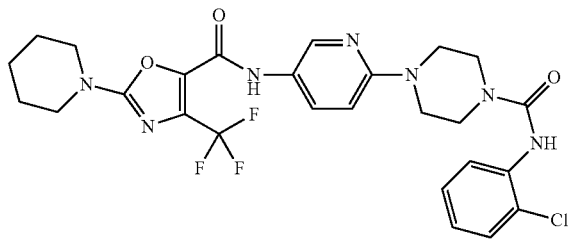

269

Compound 269 was prepared by the general procedure for compound 106. ¹H NMR (400 MHz, CDCl₃) δ 8.22 (d, 1H, J=1.5 Hz), 8.20 (m, 1H), 8.03 (dd, 1H, J=9.2, 2.9 Hz), 7.53 (s, 1H), 7.35 (dd, 1H, J=8.1, 1.5 Hz), 7.29-7.23 (m, 1H), 7.05 (s, 1H), 7.00-6.97 (m, 1H), 6.67 (d, 1H, J=9.2 Hz), 3.72-3.65 (m, 8H), 3.63 (bs, 4H), 1.70 (bs, 6H); LCMS (ESI) Rt=3.29 min, calcd for [M+1]⁺ 578.2. found 578.3.

Example 270 tert-butyl 4-(5-(2-(piperidin-1-yl)-4-(trifluoromethyl)oxazole-5-carboxamido)pyridin-2-yl)piperazine-1-carboxylate (270)

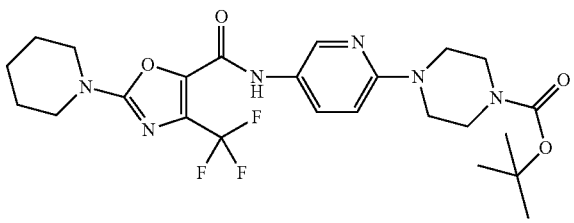

270

Compound 270 was prepared by the general procedure for compound 1. ¹H NMR (400 MHz, CDCl₃) δ 8.17 (d, 1H, J=2.6 Hz), 8.01 (dd, 1H, J=9.2, 2.9 Hz), 7.53 (s, 1H), 6.65 (d, 1H, J=9.2 Hz), 3.66-3.60 (m, 4H), 3.57-3.48 (m, 8H), 1.73-1.70 (m, 6H), 1.49 (s, 9H); LCMS (ESI) Rt=3.43 min, calcd for [M+1]⁺ 525.3. found 525.3.

Example 271

N-(6-(4-(2-chlorophenylcarbamoyl)-1,4-diazepan-1-yl)pyridin-3-yl)-2-(piperidin-1-yl)-4-(trifluoromethyl)oxazole-5-carboxamide (271)

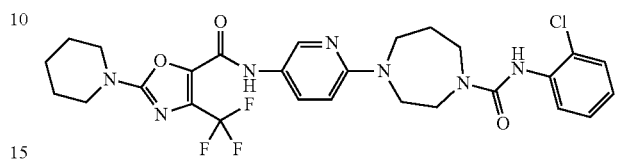

271

Compound 271 was prepared by the general procedure for compound 106. ¹H NMR (400 MHz, CDCl₃) δ 8.20 (dd, 1H, J=8.1, 1.5 Hz), 8.12 (d, 1H, J=2.9 Hz), 7.91 (dd, 1H, J=9.2, 2.9 Hz), 7.46 (s, 1H), 7.33 (dd, 1H, J=8.1, 1.5 Hz), 7.25-7.21 (m, 1H), 7.04 (s, 1H), 6.95 (dt, 1H, J=8.1, 1.5 Hz), 6.55 (d, 1H, J=9.2 Hz), 3.89 (t, 2H, J=4.4 Hz), 3.77-3.69 (m, 4H), 3.62 (bs, 4H), 3.47 (t, 2H, J=6.2 Hz), 2.18-2.08 (m, 2H), 1.70 (bs, 6H); LCMS (ESI) Rt=3.22 min, calcd for [M+1]⁺ 592.2. found 592.3.

Example 272

N-(6-(4-(2,6-difluorophenylcarbamoyl)-1,4-diazepan-1-yl)pyridin-3-yl)-2-(piperidin-1-yl)-4-(trifluoromethyl)oxazole-5-carboxamide (272)

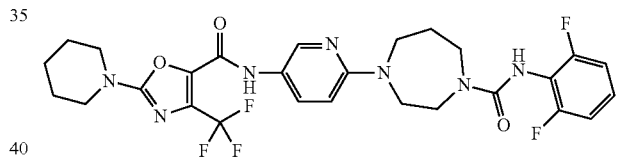

272

Compound 272 was prepared by the general procedure for compound 106. ¹H NMR (400 MHz, CDCl₃) δ 8.15 (d, 1H, J=2.9 Hz), 7.90 (dd, 1H, J=9.2, 2.6 Hz), 7.49 (s, 1H), 7.16-7.07 (m, 1H), 6.92 (t, 2H, J=7.7 Hz), 6.56 (d, 1H, J=9.2 Hz), 5.89 (s, 1H), 3.89 (t, 2H, J=4.8 Hz), 3.77-3.70 (m, 4H), 3.62 (bs, 4H), 3.45 (t, 2H, J=6.2 Hz), 2.15-2.05 (m, 2H), 1.70 (bs, 6H); LCMS (ESI) Rt=3.05 min, calcd for [M+1]⁺ 594.2. found 594.3.

Example 273

2-(piperidin-1-yl)-4-(trifluoromethyl)-N-(6-(4-(2-(trifluoromethyl)phenylcarbamoyl)-1,4-diazepan-1-yl)pyridin-3-yl)oxazole-5-carboxamide (273)

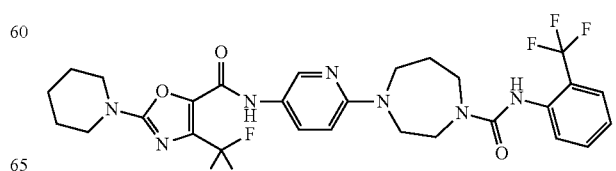

273

Compound 273 was prepared by the general procedure for compound 106. ¹H NMR (400 MHz, CDCl₃) δ 8.11 (d, 1H, J=2.6 Hz), 8.09 (s, 1H), 7.91 (d, 1H, J=8.8 Hz), 7.56 (d, 1H, J=8.1 Hz), 7.51 (t, 2H, J=7.7 Hz), 7.13 (t, 1H, J=7.7 Hz), 6.82 (s, 1H), 6.54 (d, 1H, J=9.2 Hz), 3.87 (t, 2H, J=4.8 Hz), 3.71 (t, 4H, J=5.5 Hz), 3.61 (s, 4H), 3.42 (t, 2H, J=6.2 Hz), 2.15-2.05 (m, 2H), 1.69 (bs, 6H); LCMS (ESI) Rt=3.17 min, calcd for [M+1]⁺ 626.2. found 626.3.

Example 274

N-(6-(4-(2-chlorophenylcarbamoyl)-1,4-diazepan-1-yl)pyridin-3-yl)-2-(3-methylpiperidin-1-yl)-4-(trifluoromethyl)oxazole-5-carboxamide (274)

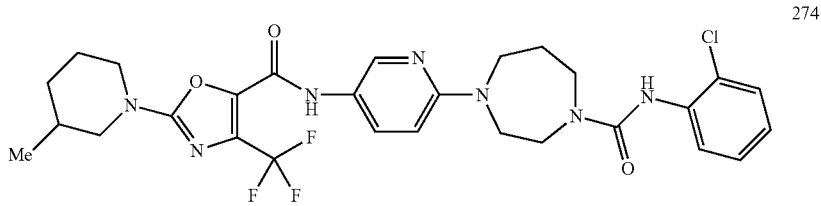 [SMILES: CC1CCCN(c2nc(C(F)(F)F)c(C(=O)Nc3ccc(N4CCCN(C(=O)Nc5ccccc5Cl)CC4)nc3)o2)C1]

Compound 274 was prepared by the general procedure for compound 106. ¹H NMR (400 MHz, CDCl₃) δ 8.18 (dd, 1H, J=8.1, 1.5 Hz), 8.11 (d, 1H, J=2.6 Hz), 7.88 (dd, 1H, J=8.8, 2.6 Hz), 7.45 (s, 1H), 7.31 (dd, 1H, J=8.1, 1.5 Hz), 7.23-7.21 (m, 1H), 7.02 (s, 1H), 6.96-6.91 (m, 1H), 6.55 (d, 1H, J=9.2 Hz), 4.08 (t, 2H, J=12.8 Hz), 3.87 (t, 2H J=9.2 Hz), 3.76-3.67 (m, 4H), 3.45 (t, 2H, J=6.2 Hz), 3.01 (dt, 1H, J=12.5, 2.9 Hz), 2.73-2.64 (m, 1H), 2.17-2.07 (m, 2H), 1.91-1.55 (m, 4H), 1.21-1.07 (m, 1H), 0.96 (d, 3H, 6.6 Hz); LCMS (ESI) Rt=3.36 min, calcd for [M+1]⁺ 606.2. found 606.3.

Example 275

N-(6-(4-(2,6-difluorophenylcarbamoyl)-1,4-diazepan-1-yl)pyridin-3-yl)-2-(3-methylpiperidin-1-yl)-4-(trifluoromethyl)oxazole-5-carboxamide (275)

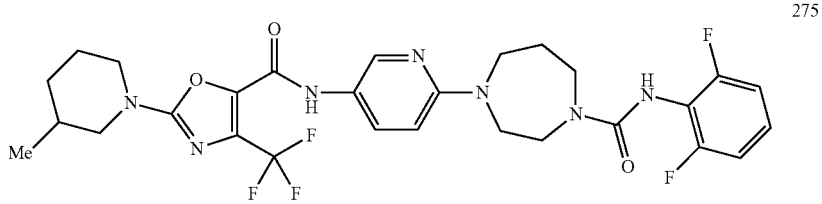 [SMILES: CC1CCCN(c2nc(C(F)(F)F)c(C(=O)Nc3ccc(N4CCCN(C(=O)Nc5c(F)cccc5F)CC4)nc3)o2)C1]

Compound 275 was prepared by the general procedure for compound 106. ¹H NMR (400 MHz, CDCl₃) δ 8.15 (d, 1H, J=2.6 Hz), 7.88 (dd, 1H, J=9.2, 2.6 Hz), 7.55 (s, 1H), 7.16-7.06 (m, 1H), 6.91 (t, 2H, J=7.7 Hz), 6.55 (d, 1H, J=8.8 Hz), 5.91 (s, 1H), 4.10 (t, 2H, J=12.5 Hz), 3.86 (t, 2H, 4.8 Hz), 3.77-3.69 (m, 4H), 3.45 (t, 2H, J=6.2 Hz), 3.07-2.98 (m, 1H), 2.74-2.65 (m, 1H), 2.15-2.05 (m, 2H), 1.93-1.55 (m, 4H), 1.22-1.10 (m, 1H), 0.98 (d, 3H, 6.6 Hz); LCMS (ESI) Rt=3.24 min, calcd for [M+1]⁺ 608.2. found 608.3.

Example 276

2-(3-methylpiperidin-1-yl)-4-(trifluoromethyl)-N-(6-(4-(2-(trifluoromethyl)phenylcarbamoyl)-1,4-diazepan-1-yl)pyridin-3-yl)oxazole-5-carboxamide (276)

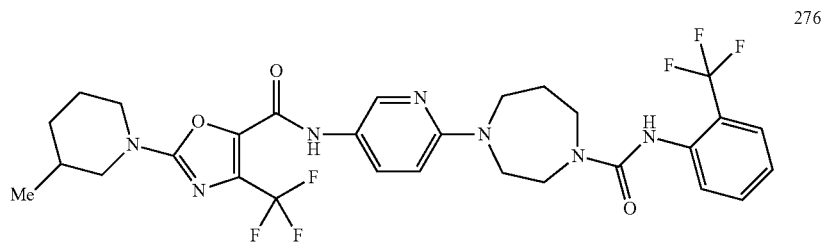 [SMILES: CC1CCCN(c2nc(C(F)(F)F)c(C(=O)Nc3ccc(N4CCCN(C(=O)Nc5ccccc5C(F)(F)F)CC4)nc3)o2)C1]

Compound 276 was prepared by the general procedure for compound 106.

$^1$H NMR (400 MHz, CDCl$_3$) δ 8.12 (d, 1H, J=2.6 Hz), 8.10 (s, 1H), 7.91 (dd, 1H, J=9.2, 2.9 Hz), 7.56 (d, 1H, J=8.1 Hz), 7.54-7.48 (m, 2H), 7.13 (t, 1H, J=7.3 Hz), 6.82 (s, 1H), 6.57 (d, 1H, J=9.2 Hz), 4.10 (t, 2H, J=12.8 Hz), 3.87 (t, 2H, J=4.8 Hz), 3.71 (t, 4H, J=5.9 Hz), 3.42 (t, 2H, J=6.2 Hz), 3.08-2.98 (m, 1H), 2.74-2.66 (m, 1H), 2.15-2.05 (m, 2H), 1.93-1.56 (m, 4H), 1.23-1.10 (m, 1H), 0.98 (d, 3H, 6.6 Hz); LCMS (ESI) Rt=3.34 min, calcd for [M+1]$^+$ 640.3. found 640.4.

Example 277

N-(6-(4-(2-chlorophenylcarbamoyl)-1,4-diazepan-1-yl)pyridin-3-yl)-2-(4-phenylpiperidin-1-yl)-4-(trifluoromethyl)oxazole-5-carboxamide (277)

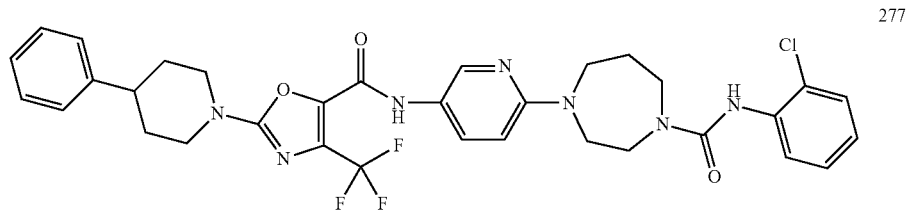 [SMILES: O=C(Nc1ccc(N2CCCN(C(=O)Nc3ccccc3Cl)CC2)nc1)c1oc(N2CCC(c3ccccc3)CC2)nc1C(F)(F)F]

Compound 277 was prepared by the general procedure for compound 106. $^1$H NMR (400 MHz, CDCl$_3$) δ 8.19 (dd, 1H, J=8.1, 1.5 Hz), 8.31 (d, 1H, J=2.6 Hz), 7.90 (dd, 1H, J=9.2, 2.9 Hz), 7.54 (s, 1H), 7.38-7.31 (m, 3H), 7.28-7.20 (m, 4H), 7.03 (s, 1H), 6.95 (dt, 1H, 7.7, 1.5 Hz), 6.55 (d, 1H, J=9.2 Hz), 4.36 (d, 2H, J=12.8 Hz), 3.88 (t, 2H J=4.8 Hz), 3.73 (q, 4H, J=11.0, 5.1 Hz), 3.47 (t, 2H, J=6.2 Hz), 3.20 (dt, 2H, J=12.8, 2.6 Hz), 2.77 (tt, 1H, J=12.5, 3.3 Hz), 2.17-2.09 (m, 2H), 2.00 (d, 2H, J=12.1 Hz), 1.82 (dq, 2H, J=12.8, 4.0 Hz), 1.61 (s, 2H); LCMS (ESI) Rt=3.68 min, calcd for [M+1]$^+$ 6686.2. found 668.4.

Example 278

N-(6-(4-(2,6-difluorophenylcarbamoyl)-1,4-diaz-
epan-1-yl)pyridin-3-yl)-2-(4-phenylpiperidin-1-yl)-
4-(trifluoromethyl)oxazole-5-carboxamide (278)

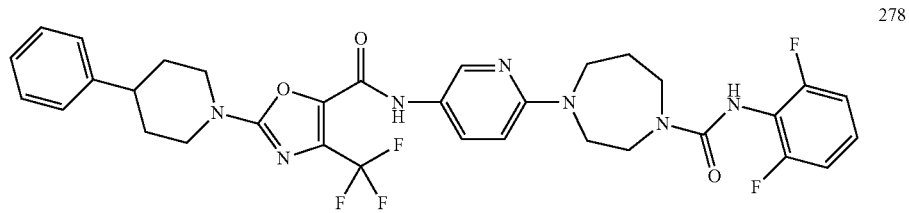 [SMILES: O=C(Nc1ccc(N2CCCN(C(=O)Nc3c(F)cccc3F)CC2)nc1)c1oc(N2CCC(c3ccccc3)CC2)nc1C(F)(F)F]

Compound 278 was prepared by the general procedure for compound 106. $^1$H NMR (400 MHz, CDCl$_3$) δ 8.52 (bs, 1H), 8.15 (d, 1H, J=2.6 Hz), 7.38-7.22 (m, 5H), 7.13-7.08 (m, 1H), 6.98-6.91 (m, 1H), 6.91-6.89 (m, 2H), 4.47 (d, 2H J=13.2 Hz), 4.05-3.96 (m, 2H), 3.85 (t, 4H, J=5.5 Hz), 3.57 (t, 2H, J=5.5 Hz), 3.21 (dt, 2H, J=12.8, 2.2 Hz), 2.79 (tt, 1H, J=12.5, 3.3 Hz), 2.15-2.06 (m, 2H), 2.00 (d, 2H, J=13.6 Hz), 1.82 (dq, 2H, J=12.8, 4.0 H); LCMS (ESI) Rt=3.53 min, calcd for [M+1]$^+$ 670.3. found 670.4.

Example 279

2-(4-phenylpiperidin-1-yl)-4-(trifluoromethyl)-N-(6-
(4-(2-(trifluoromethyl)phenylcarbamoyl)-1,4-diaz-
epan-1-yl)pyridin-3-yl)oxazole-5-carboxamide (279)

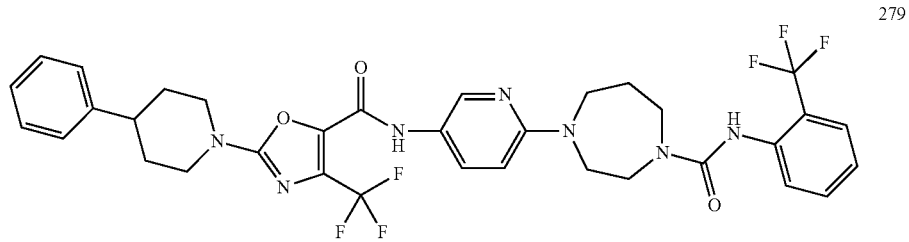 [SMILES: O=C(Nc1ccc(N2CCCN(C(=O)Nc3ccccc3C(F)(F)F)CC2)nc1)c1oc(N2CCC(c3ccccc3)CC2)nc1C(F)(F)F]

Compound 279 was prepared by the general procedure for compound 106. $^1$H NMR (400 MHz, CDCl$_3$) δ 8.13 (d, 1H, J=2.6 Hz), 8.10 (s, 1H), 7.91 (dd, 1H, J=9.2, 2.9 Hz), 7.56 (d, 1H, J=7.7 Hz), 7.51 (t, 2H, J=8.4 Hz), 7.37-7.31 (m, 2H), 7.28-7.21 (m, 3H), 7.13 (t, 1H, J=7.7 Hz), 6.82 (s, 1H), 6.55 (d, 1H, J=9.2 Hz), 4.36 (d, 2H, J=13.2 Hz), 3.87 (t, 2H, J=4.8 Hz), 3.71 (t, 4H, J=5.9 Hz), 3.42 (t, 2H, J=6.2 Hz), 3.21 (dt, 2H, J=13.2, 2.6 Hz), 2.78 (tt, 1H, J=11.8, 3.3 Hz), 2.14-2.05 (m, 2H), 2.00 (d, 2H, J=11.4 Hz), 1.82 (dq, 2H, J=12.8, 4.4 H); LCMS (ESI) Rt=3.68 min, calcd for [M+1]$^+$ 702.3. found 702.4.

Example 280

N-[6-(4-phenyl-1-piperidinyl)-3-pyridinyl]-2-(cyclohexyl(methyl)amino)-4-(trifluoromethyl)-5-oxazolecarboxamide (280)

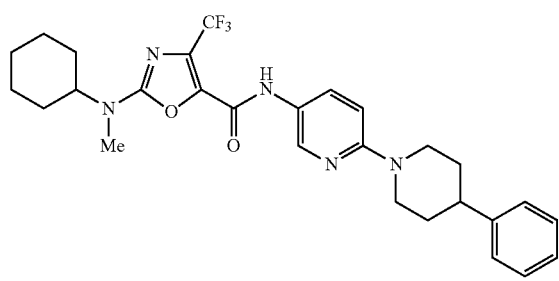

280

To intermediate A-34 (115 mg, 0.394 mmol) and intermediate B-6 (130 mg, 0.512 mmol) dissolved in DMF (6 mL) was added N,N-diisopropylamine (0.21 mL. 1.18 mmol) and N,N,N',N'-tetramethyl-O-(7-azabenzotriazol-1-yl)uronium hexafluorophosphate (HATU, 299 mg, 0.787 mmol). The reaction mixture was stirred at RT for 16 h then concentrated. Water (15 mL) was added, and the aqueous solution was extracted with $CH_2Cl_2$. The combined organic extract was dried ($MgSO_4$), filtered, and concentrated. Purification by silica gel chromatography (eluant: 10% EtOAc—$CH_2Cl$) gave a beige solid which was triturated with ether to give a white solid. Washed white solid with water then ethanol then ether and dried to give N-[6-(4-phenyl-1-piperidinyl)-3-pyridinyl]-2-(cyclohexyl(methyl)amino)-4-(trifluoromethyl)-5-oxazolecarboxamide (280) as a white solid (110 mg, 53% yield). $^1$H NMR (500 MHz, DMSO-D6) δ 10.00 (s, 1H), 8.35 (s, 1H), 7.75 (d, 1H, J=7 Hz), 7.30 (m, 2H), 7.25 (m, 2H), 7.20 (t, 1H, J=6.5 Hz), 6.95 (d, 1H, J=9.5 Hz), 4.40 (d, 2H, J=13 Hz), 4.00 (m, 1H), 3.05 (s, 3H), 2.85 (t, 2H, J=12.5 Hz), 2.75 (t, 1H, J=12 Hz), 1.85 (m, 4H), 1.50-1.75 (m, 7H), 1.40 (q, 2H, J=13 Hz), 1.15 (q, 1H, J=12.5 Hz). MS (M+1): 528.

Example 281

N-[6-(4-phenyl-1-piperidinyl)-3-pyridinyl]-2-(cyclopentyl(methyl)amino)-4-(trifluoromethyl)-5-oxazolecarboxamide (281)

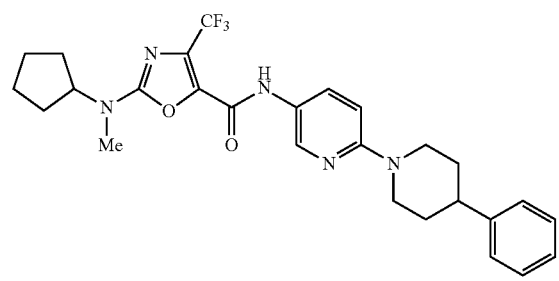

281

Compound 281 was prepared by the general procedure for compound 280, by using intermediates A-35 and B-6 as starting materials. $^1$H NMR (500 MHz, DMSO-d6) δ 10.00 (s, 1H), 8.35 (s, 1H), 7.75 (d, 1H, J=9 Hz), 7.30 (m, 2H), 7.25 (m, 2H), 7.20 (t, 1H, J=6.5 Hz), 6.90 (d, 1H, J=9 Hz), 4.65 (t, 1H, J=8 Hz), 4.40 (d, 2H, J=13 Hz), 3.05 (s, 3H), 2.85 (t, 2H, J=12.5 Hz), 2.75 (t, 1H, J=12 Hz), 1.85 (m, 4H), 1.65 (m, 8H). MS (M+1): 514.

Example 282

N-[6-(4-phenyl-1-piperidinyl)-3-pyridinyl]-2-(cyclohexylthio)-4-(trifluoromethyl)-5-oxazolecarboxamide (282)

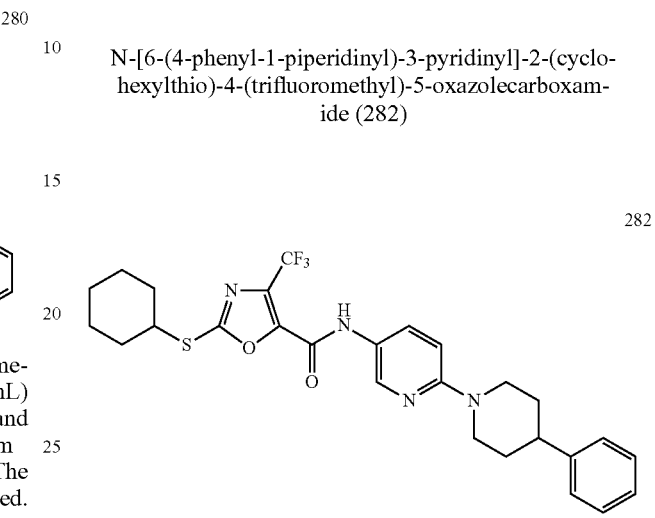

282

Compound 282 was prepared by the general procedure for compound 280, by using intermediates A-37 and B-6 as starting materials. $^1$H NMR (500 MHz, $CDCl_3$) δ 8.20 (d, 1H, J=2.5 Hz), 8.05 (dd, 1H, J=2.5, 9 Hz), 7.80 (s, 1H), 7.35 (t, 2H, J=8 Hz), 7.25 (m, 3H), 6.75 (d, 1H, J=9 Hz), 4.45 (d, 2H, J=12.5 Hz), 3.90 (m, 1H), 3.00 (td, 2H, J=13, 2.5 Hz), 2.80 (t, 1H, J=12.5 Hz), 2.20 (m, 2H), 1.95 (d, 2H, J=12 Hz), 1.80 (m, 4H), 1.65 (m, 4H), 1.50 (m, 1H), 1.40 (m, 1H). MS (M+1): 531.

Example 283 cyclopentyl 4-[5-(2-(cyclohexylthio)-4-(trifluoromethyl)oxazole-5-carboxamido)pyridin-2-yl]piperazine-1-carboxylate (283)

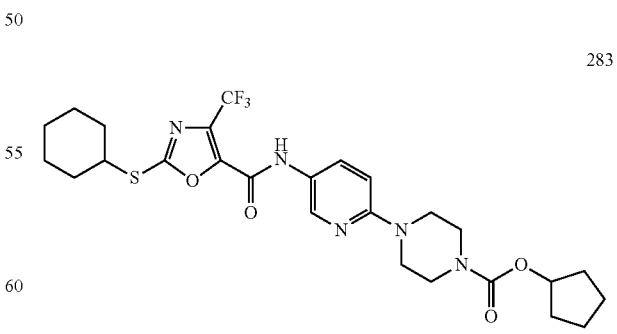

283

Compound 283 was prepared by the general procedure for compound 280, by using A-37 and B-10 as starting materials. $^1$H NMR (500 MHz, $CDCl_3$) δ 8.25 (d, 1H, J=2.5 Hz), 8.05 (dd, 1H, J=3, 9 Hz), 7.80 (s, 1H), 6.70 (d, 1H, J=9 Hz), 5.15

(m, 1H), 3.90 (m, 1H), 3.55 (m, 8H), 2.20 (m, 2H), 1.55-1.95 (m, 13H), 1.50 (m, 2H), 1.40 (m, 1H). MS (M+1): 568.

Example 284

2-(cyclohexyloxy)-N-(6-(4-phenylpiperidin-1-yl)pyridin-3-yl)-4-(trifluoromethyl)-oxazole-5-carboxamide (284)

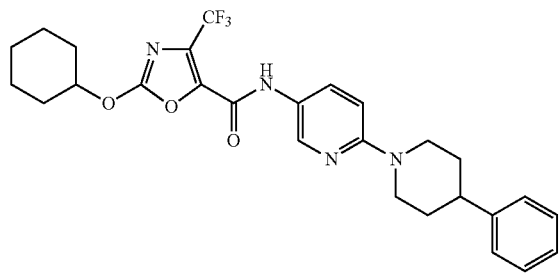

284

Sodium hydride (60 wt % in oil, 0.029 g, 0.72 mmol) was added to a solution of cyclohexanol (0.140 g, 1.44 mmol) in THF (5.0 mL) at RT followed by stirring for 10 min. The reaction mixture was then cooled down to −78° C., and intermediate A-40 dissolved in THF (2 mL) was added. The reaction mixture was stirred for 5 h while the temperature was slowly warmed to RT. The solvent was concentrated, and purification by chromatography on a silica-gel column (eluant: 0-30% EtOAc in $CH_2Cl_2$ gradient) gave 2-(cyclohexyloxy)-N-(6-(4-phenylpiperidin-1-yl)pyridin-3-yl)-4-(trifluoromethyl)oxazole-5-carboxamide (284) as a yellow solid (0.043 g, 23% yield). $^1$H NMR (500 MHz, $CDCl_3$) δ 8.19 (d, 1H, J=2.8 Hz), 8.05 (dd, 1H, J=9.2, 2.8 Hz), 7.73 (br s, 1H), 7.38-7.32 (m, 2H), 7.28-7.22 (m, 3H), 6.74 (d, 1H, J=9.1 Hz), 5.06 (m, 1H), 4.44 (m, 2H), 2.96 (m, 2H), 2.78 (m, 1H), 2.16-2.06 (m, 2H), 2.02-1.94 (m, 2H), 1.88-1.58 (m, 8H), 1.56-1.44 (m, 2H); LCMS (ESI) Rt=3.99 min, calcd for [M+1]$^+$ 515.2. found 515.3.

Example 285 cyclopentyl 4-(5-(2-(cyclohexyloxy)-4-(trifluoromethyl)oxazole-5-carboxamido)pyridin-2-yl)piperazine-1-carboxylate (285)

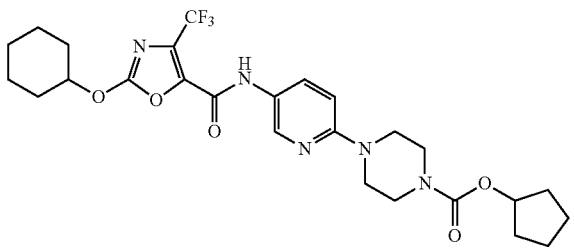

285

Compound 285 was prepared by the general procedure for compound 284, by using intermediates A-41 and cyclohexanol as starting materials. $^1$H NMR (500 MHz, $CDCl_3$) δ 8.20 (d, 1H, J=2.8 Hz), 8.06 (dd, 1H, J=9.1, 2.6 Hz), 7.74 (br s, 1H), 6.68 (d, 1H, J=9.1 Hz), 5.16 (m, 1H), 5.04 (m, 1H), 3.64-3.48 (m, 8H), 2.14-2.06 (m, 2H), 1.89-1.56 (m, 14H), 1.50-1.42 (m, 2H); LCMS (ESI) Rt=3.98 min, calcd for [M+1]$^+$ 552.2. found 552.3.

Example 286 cyclopentyl 4-(5-(2-(2,3-dihydro-1H-inden-2-yloxy)-4-(trifluoromethyl)oxazole-5-carboxamido)pyridin-2-yl)piperazine-1-carboxylate (286)

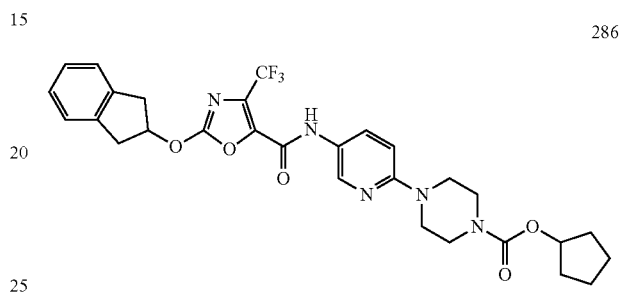

286

Compound 286 was prepared by the general procedure for compound 284, by using intermediates A-41 and 2-indanol as starting materials. $^1$H NMR (500 MHz, $CDCl_3$) δ 8.16 (d, 1H, J=2.6 Hz), 8.04 (dd, 1H, J=9.1, 2.7 Hz), 7.69 (br s, 1H), 7.34-7.24 (m, 4H), 6.66 (d, 1H, J=9.1 Hz), 5.83 (m, 1H), 5.16 (m, 1H), 3.62-3.46 (m, 10H), 3.31 (m, 2H), 1.92-1.82 (m, 2H), 1.78-1.68 (m, 4H), 1.66-1.56 (m, 2H); LCMS (ESI) Rt=4.09 min, calcd for [M+1]$^+$ 586.2. found 586.3.

Example 287 cyclopentyl 4-(5-(2-(cyclopentylmethoxy)-4-(trifluoromethyl)oxazole-5-carboxamido)pyridin-2-yl)piperazine-1-carboxylate (287)

287

Compound 287 was prepared by the general procedure for compound 284, by using intermediates A-41 and cyclopentanemethanol as starting materials. $^1$H NMR (500 MHz, $CDCl_3$) δ 8.20 (d, 1H, J=2.4 Hz), 8.07 (dd, 1H, J=9.2, 2.5 Hz), 7.23 (br s, 1H), 6.68 (d, 1H, J=9.1 Hz), 5.17 (m, 1H), 4.45 (d, 2H, J=9.1 Hz), 3.64-3.52 (m, 8H), 2.45 (m, 1H), 1.92-1.84 (m, 4H), 1.80-1.56 (m, 10H), 1.42-1.32 (m, 2H); LCMS (ESI) Rt=4.13 min, calcd for [M+1]$^+$ 552.2. found 552.3.

ASSAY

A useful assay to determine the DGAT inhibitory activity of the inventive compounds is described below:

The in vitro assay to identify DGAT1 inhibitors uses human DGAT1 enzyme expressed in Sf9 insect cells prepared as microsomes. The reaction is initiated by the addition of the combined substrates 1,2-dioleoyl-sn-glycerol and [$^{14}$C]-palmitoyl-Co A and incubated with test compounds and microsomal membranes for 2 hours at room temperature. The assay is stopped by adding 0.5 mg wheat germ agglutinin beads in assay buffer with 1% Brij-35 and 1% 3-cholamidopropyldimethyl-ammonio-1-propane sulfonate. Plates are sealed with TopSeal and incubated for 18 hours to allow the radioactive triglyceride product to come into proximity with the bead. Plates are read on a TopCount instrument.

Percent inhibition was calculated as the percent of (test compound inhibition minus non-specific binding) relative to (total binding minus non-specific binding). IC$_{50}$ values were determined by curve fitting the data to a Sigmoidal dose-response in GraphPad Prism utilizing the following equation:

$$Y=A+(B-A)/(1+10^{\wedge}((\text{Log IC}_{50}-X))),$$

where A and B are the bottom and top of the curve (highest and lowest inhibition), respectively, and X is the logarithm of concentration. The IC50 values for several illustrative compounds of the invention are shown in the Table below, where A represents IC50=1 to 10 nM, B represents IC50=11 to 100 nM, and C represents IC50=101 to 500 nM.

TABLE

| Compound | Structure | hDGAT IC50 (nM) |
|---|---|---|
| 221 | 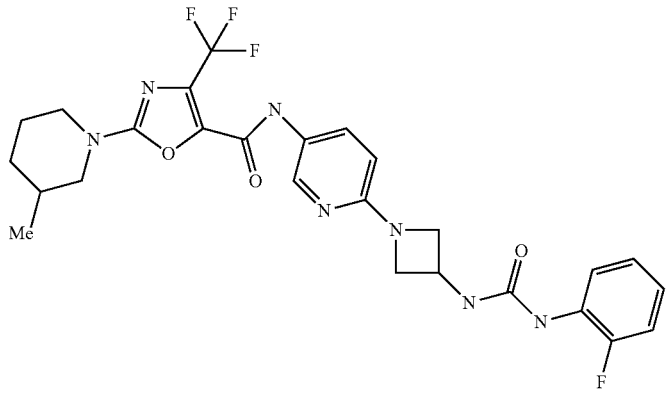 [SMILES: CC1CCCN(c2nc(C(F)(F)F)c(C(=O)Nc3ccc(N4CC(NC(=O)Nc5ccccc5F)C4)nc3)o2)C1] | C |
| 223 | 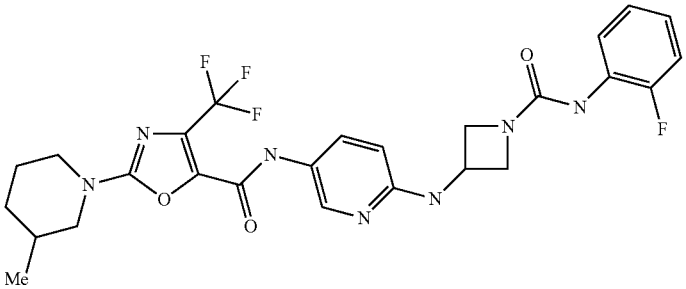 [SMILES: CC1CCCN(c2nc(C(F)(F)F)c(C(=O)Nc3ccc(NC4CN(C(=O)Nc5ccccc5F)C4)nc3)o2)C1] | C |
| 235 | 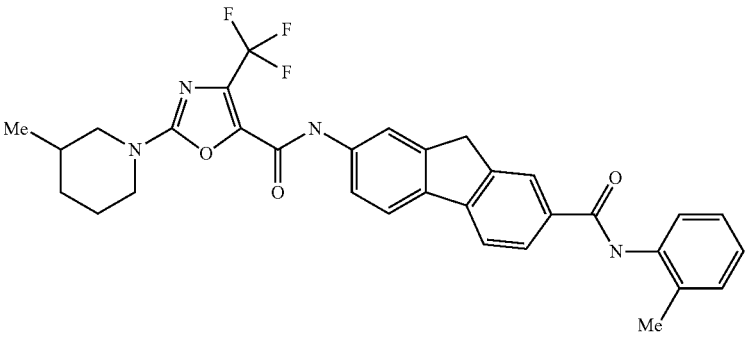 [SMILES: Cc1ccccc1NC(=O)c1ccc2c(c1)Cc1cc(NC(=O)c3oc(N4CCCC(C)C4)nc3C(F)(F)F)ccc1-2] | C |

TABLE-continued
| Compound | Structure | hDGAT IC50 (nM) |
|---|---|---|
| 185 | 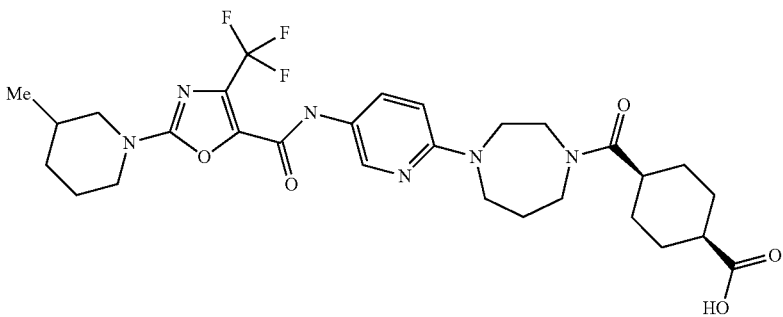 [SMILES: CC1CCCN(c2nc(C(F)(F)F)c(C(=O)Nc3ccc(N4CCCN(C(=O)[C@H]5CC[C@@H](C(=O)O)CC5)CC4)nc3)o2)C1] | C |
| 215 | 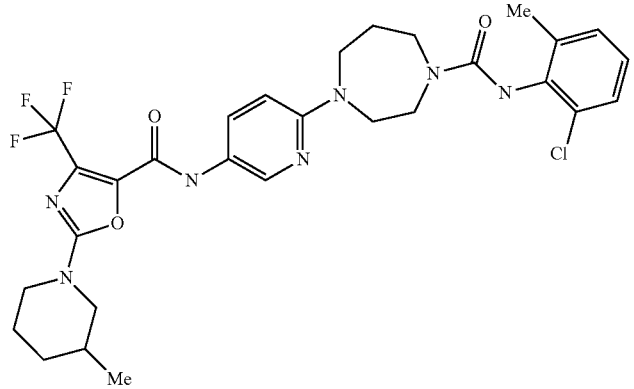 [SMILES: Cc1cccc(Cl)c1NC(=O)N1CCCN(c2ccc(NC(=O)c3oc(N4CCCC(C)C4)nc3C(F)(F)F)cn2)CC1] | B |
| 190 | 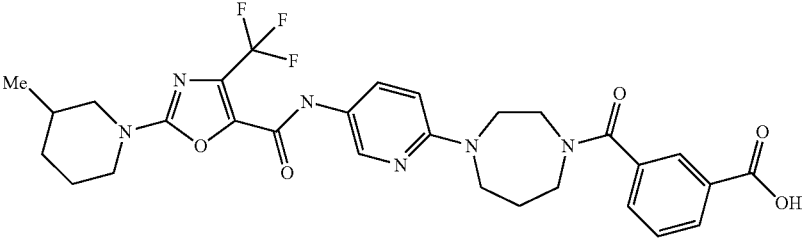 [SMILES: CC1CCCN(c2nc(C(F)(F)F)c(C(=O)Nc3ccc(N4CCCN(C(=O)c5cccc(C(=O)O)c5)CC4)nc3)o2)C1] | C |
| 236 | 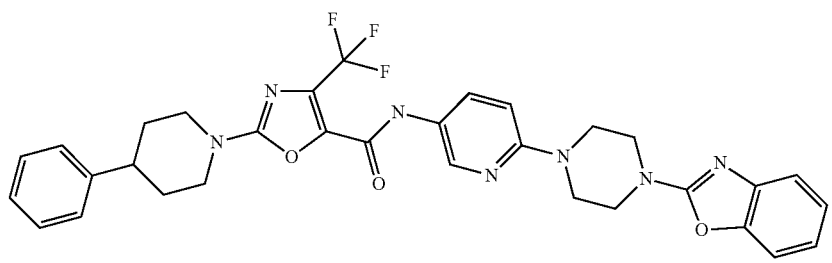 | C |

TABLE-continued

| Compound | Structure | hDGAT IC50 (nM) |
|---|---|---|
| 181 | 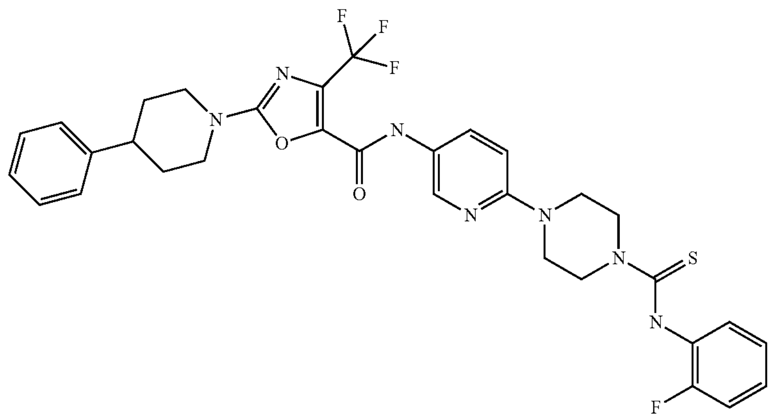 [SMILES: O=C(Nc1ccc(N2CCN(C(=S)Nc3ccccc3F)CC2)nc1)c1oc(N2CCC(c3ccccc3)CC2)nc1C(F)(F)F] | B |
| 216 | 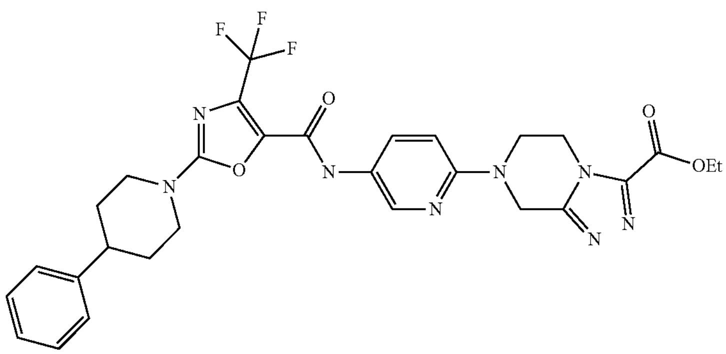 [SMILES: CCOC(=O)C(=N)N1CCN(c2ccc(NC(=O)c3oc(N4CCC(c5ccccc5)CC4)nc3C(F)(F)F)cn2)CC1=N] | C |
| 182 | 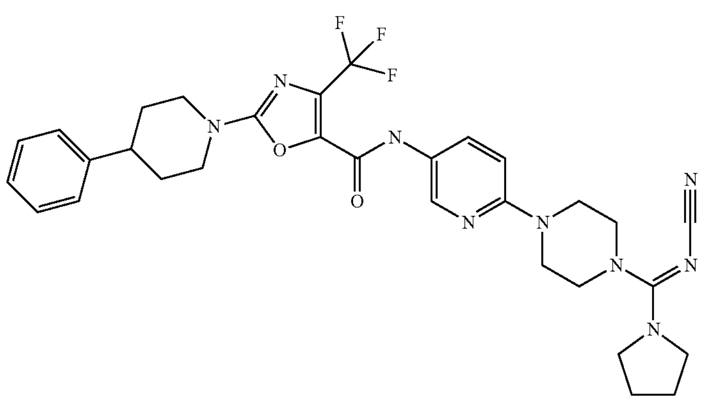 [SMILES: N#C/N=C(/N1CCCC1)N1CCN(c2ccc(NC(=O)c3oc(N4CCC(c5ccccc5)CC4)nc3C(F)(F)F)cn2)CC1] | C |
| 237 | 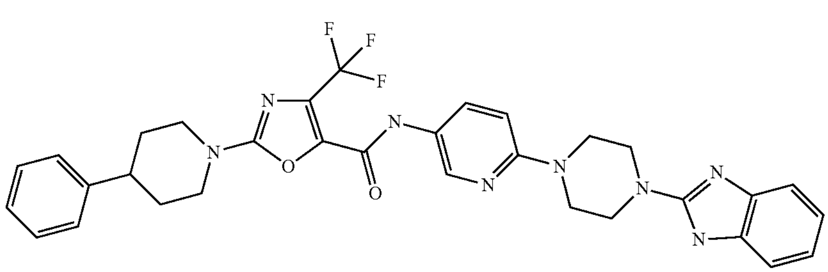 [SMILES: O=C(Nc1ccc(N2CCN(c3nc4ccccc4[nH]3)CC2)nc1)c1oc(N2CCC(c3ccccc3)CC2)nc1C(F)(F)F] | C |

| Compound | Structure | hDGAT IC50 (nM) |
|---|---|---|
| 164 | 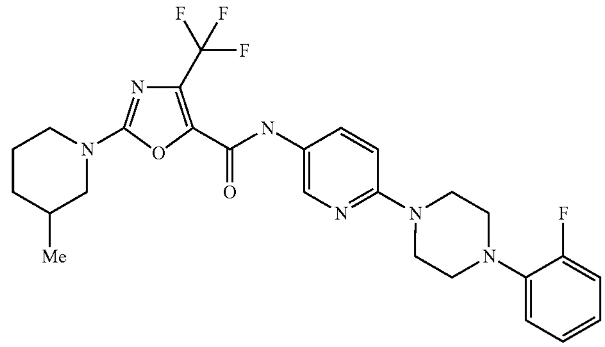 [SMILES: CC1CCCN(c2nc(C(F)(F)F)c(C(=O)Nc3ccc(N4CCN(c5ccccc5F)CC4)nc3)o2)C1] | B |
| 191 | 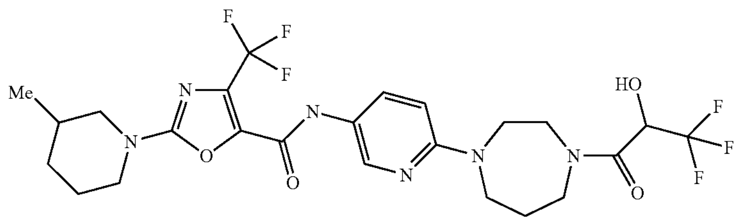 [SMILES: CC1CCCN(c2nc(C(F)(F)F)c(C(=O)Nc3ccc(N4CCCN(C(=O)C(O)C(F)(F)F)CC4)nc3)o2)C1] | C |
| 194 | 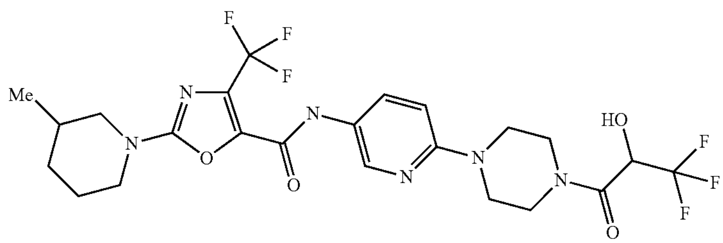 [SMILES: CC1CCCN(c2nc(C(F)(F)F)c(C(=O)Nc3ccc(N4CCN(C(=O)C(O)C(F)(F)F)CC4)nc3)o2)C1] | B |
| 196 | 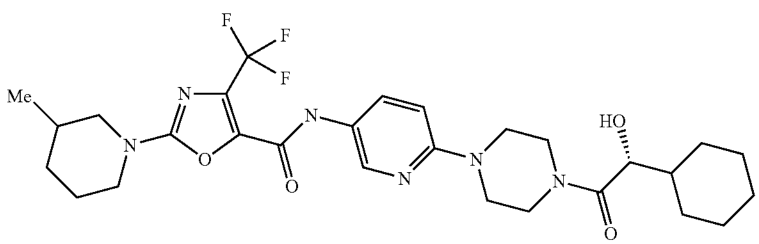 [SMILES: CC1CCCN(c2nc(C(F)(F)F)c(C(=O)Nc3ccc(N4CCN(C(=O)[C@H](O)C5CCCCC5)CC4)nc3)o2)C1] | B |
| 240 | 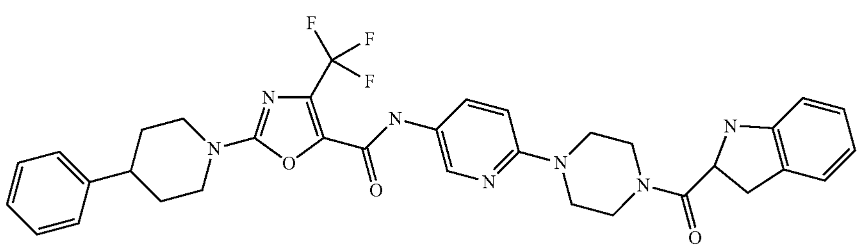 [SMILES: O=C(Nc1ccc(N2CCN(C(=O)C3Cc4ccccc4N3)CC2)nc1)c1oc(N2CCC(c3ccccc3)CC2)nc1C(F)(F)F] | C |
| 198 | 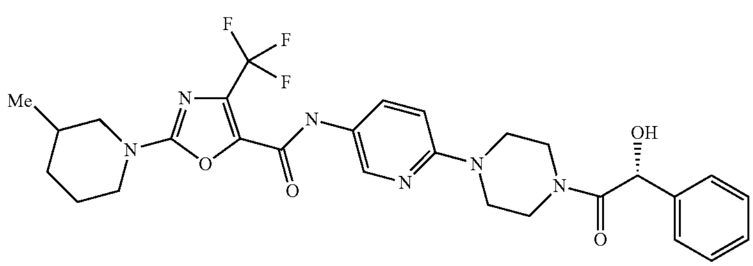 [SMILES: CC1CCCN(c2nc(C(F)(F)F)c(C(=O)Nc3ccc(N4CCN(C(=O)[C@H](O)c5ccccc5)CC4)nc3)o2)C1] | B |

TABLE-continued
| Compound | Structure | hDGAT IC50 (nM) |
|---|---|---|
| 200 | 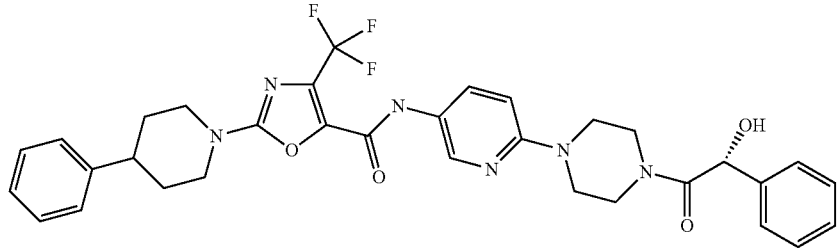 [SMILES: O=C(Nc1ccc(N2CCN(C(=O)[C@H](O)c3ccccc3)CC2)nc1)c1oc(N2CCC(c3ccccc3)CC2)nc1C(F)(F)F] | B |
| 225 | 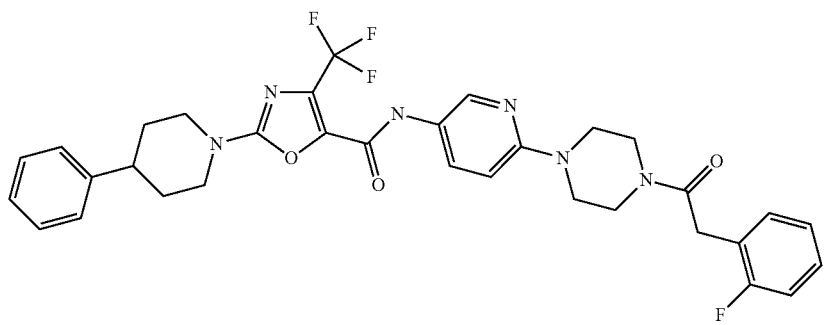 [SMILES: O=C(Nc1ccc(N2CCN(C(=O)Cc3ccccc3F)CC2)nc1)c1oc(N2CCC(c3ccccc3)CC2)nc1C(F)(F)F] | B |
| 202 | 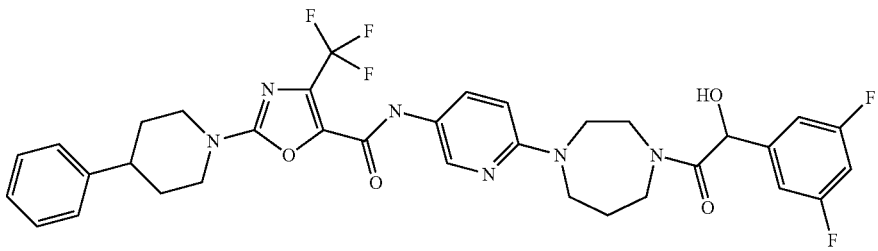 [SMILES: O=C(Nc1ccc(N2CCCN(C(=O)C(O)c3cc(F)cc(F)c3)CC2)nc1)c1oc(N2CCC(c3ccccc3)CC2)nc1C(F)(F)F] | B |
| 241 | 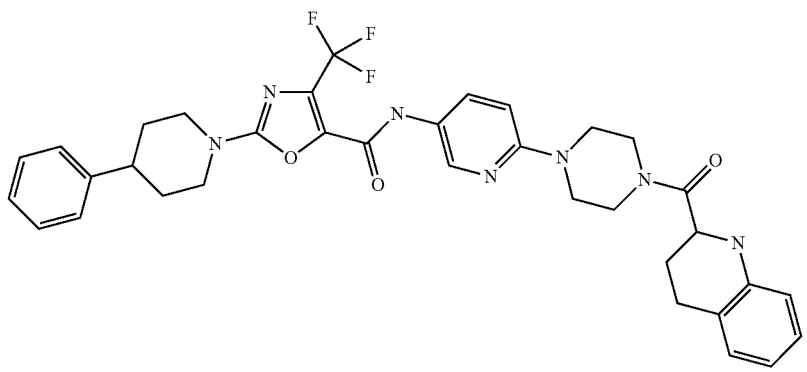 [SMILES: O=C(Nc1ccc(N2CCN(C(=O)C3CCc4ccccc4N3)CC2)nc1)c1oc(N2CCC(c3ccccc3)CC2)nc1C(F)(F)F] | C |
| 226 | 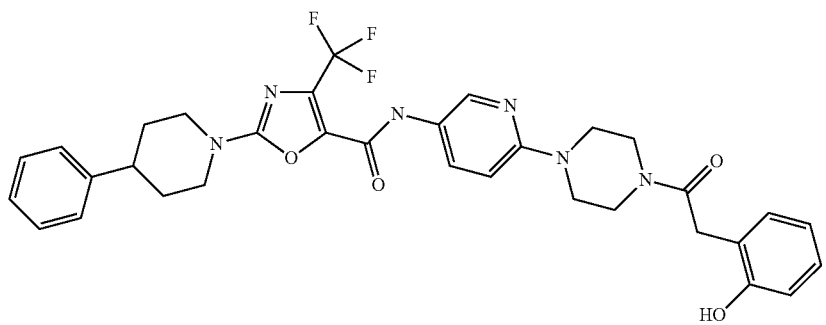 [SMILES: O=C(Nc1ccc(N2CCN(C(=O)Cc3ccccc3O)CC2)nc1)c1oc(N2CCC(c3ccccc3)CC2)nc1C(F)(F)F] | C |

TABLE-continued

| Compound | Structure | hDGAT IC50 (nM) |
|---|---|---|
| 242 | 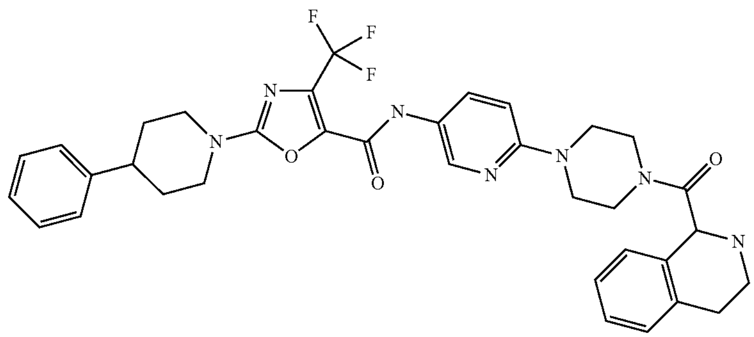 [SMILES: O=C(Nc1ccc(N2CCN(C(=O)C3NCCc4ccccc43)CC2)nc1)c1oc(N2CCC(c3ccccc3)CC2)nc1C(F)(F)F] | C |
| 168 | 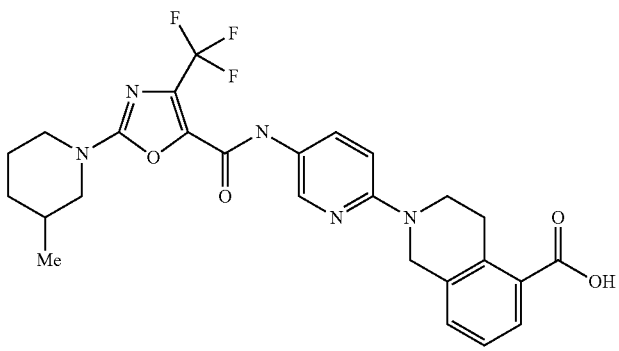 [SMILES: CC1CCCN(c2nc(C(F)(F)F)c(C(=O)Nc3ccc(N4CCc5c(cccc5C(=O)O)C4)nc3)o2)C1] | C |
| 169 | 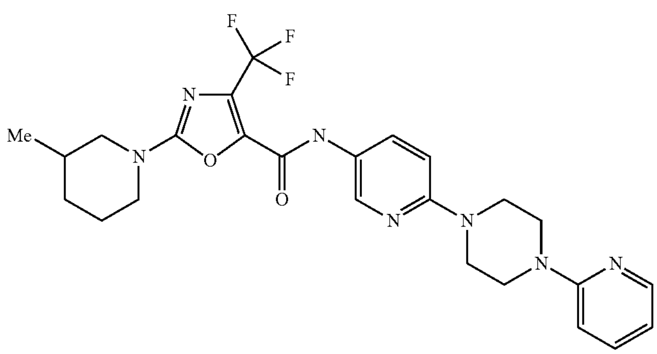 [SMILES: CC1CCCN(c2nc(C(F)(F)F)c(C(=O)Nc3ccc(N4CCN(c5ccccn5)CC4)nc3)o2)C1] | B |
| 207 | 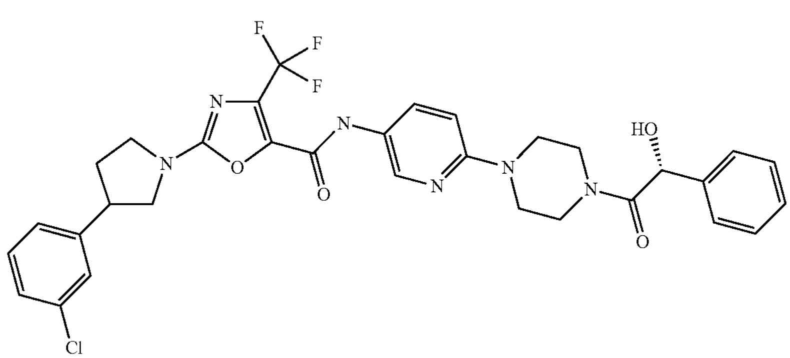 [SMILES: O=C(Nc1ccc(N2CCN(C(=O)[C@H](O)c3ccccc3)CC2)nc1)c1oc(N2CCC(c3cccc(Cl)c3)C2)nc1C(F)(F)F] | B |

TABLE-continued

| Compound | Structure | hDGAT IC50 (nM) |
|---|---|---|
| 212 | 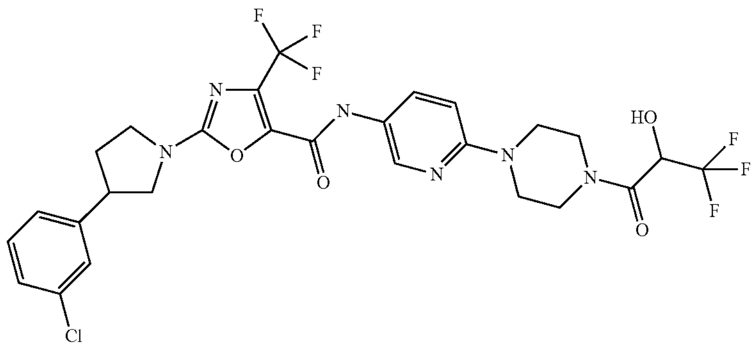 [SMILES: O=C(Nc1ccc(N2CCN(C(=O)C(O)C(F)(F)F)CC2)nc1)c1oc(N2CCC(c3cccc(Cl)c3)C2)nc1C(F)(F)F] | B |
| 213 | 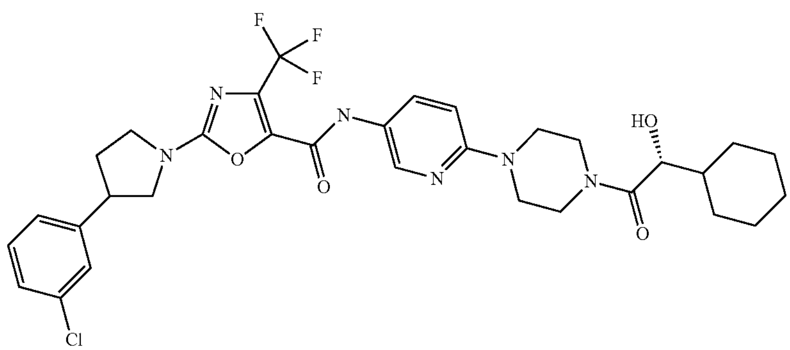 [SMILES: O=C(Nc1ccc(N2CCN(C(=O)[C@H](O)C3CCCCC3)CC2)nc1)c1oc(N2CCC(c3cccc(Cl)c3)C2)nc1C(F)(F)F] | B |
| 229 | 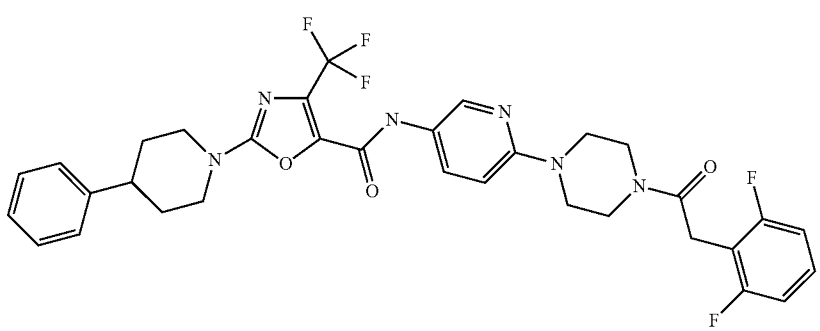 [SMILES: O=C(Nc1ccc(N2CCN(C(=O)Cc3c(F)cccc3F)CC2)nc1)c1oc(N2CCC(c3ccccc3)CC2)nc1C(F)(F)F] | B |
| 244 | 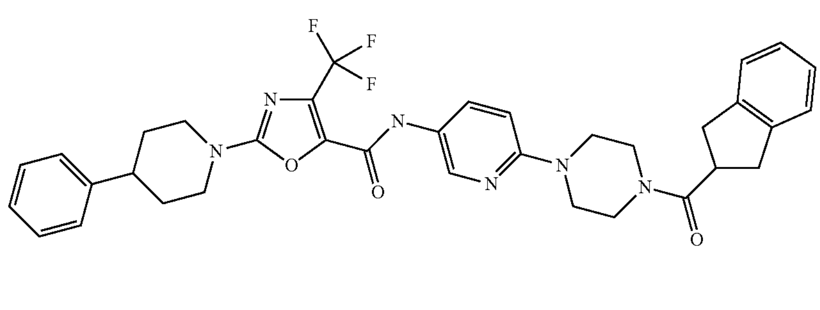 [SMILES: O=C(Nc1ccc(N2CCN(C(=O)C3Cc4ccccc4C3)CC2)nc1)c1oc(N2CCC(c3ccccc3)CC2)nc1C(F)(F)F] | C |

| Compound | Structure | hDGAT IC50 (nM) |
|---|---|---|
| 171 | 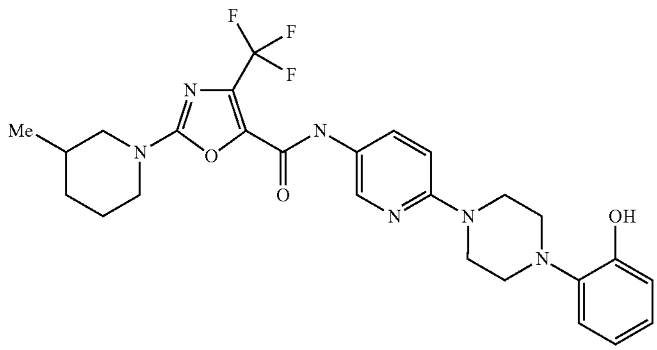 [SMILES: CC1CCCN(c2nc(C(F)(F)F)c(C(=O)Nc3ccc(N4CCN(c5ccccc5O)CC4)nc3)o2)C1] | B |
| 248 | 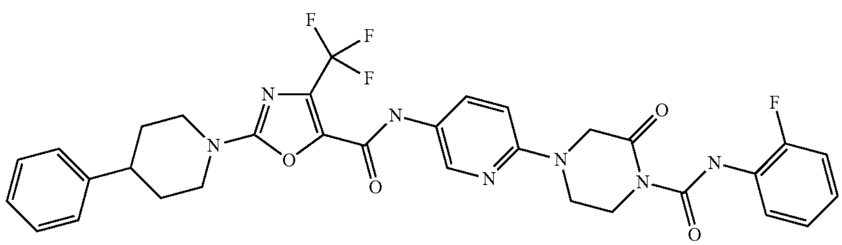 [SMILES: O=C(Nc1ccc(N2CCN(C(=O)Nc3ccccc3F)C(=O)C2)nc1)c1oc(N2CCC(c3ccccc3)CC2)nc1C(F)(F)F] | C |
| 174 | 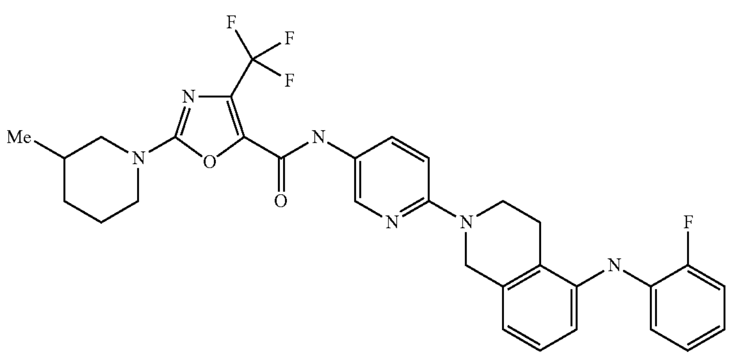 [SMILES: CC1CCCN(c2nc(C(F)(F)F)c(C(=O)Nc3ccc(N4CCc5c(cccc5Nc5ccccc5F)C4)nc3)o2)C1] | C |
| 254 | 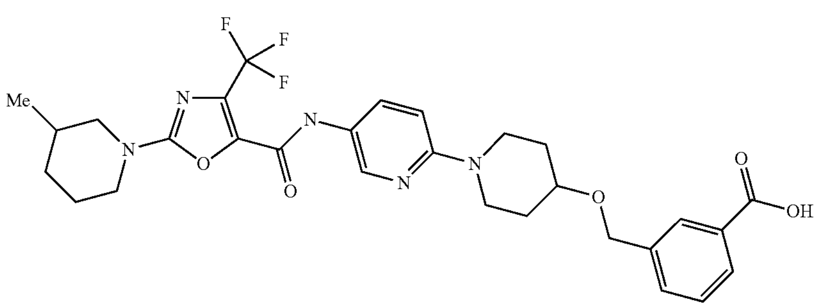 [SMILES: CC1CCCN(c2nc(C(F)(F)F)c(C(=O)Nc3ccc(N4CCC(OCc5cccc(C(=O)O)c5)CC4)nc3)o2)C1] | B |

TABLE-continued

| Compound | Structure | hDGAT IC50 (nM) |
|---|---|---|
| 255 | 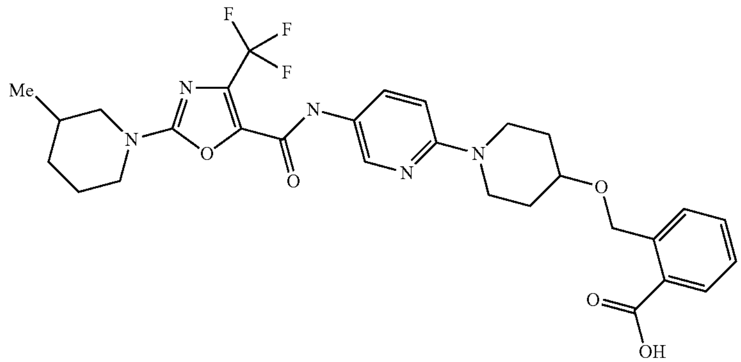 [SMILES: CC1CCCN(c2nc(C(F)(F)F)c(C(=O)Nc3ccc(N4CCC(OCc5ccccc5C(=O)O)CC4)nc3)o2)C1] | B |
| 256 | 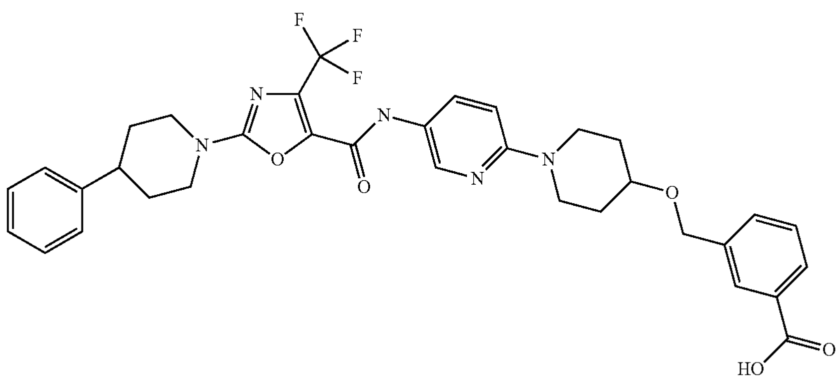 [SMILES: O=C(O)c1cccc(COC2CCN(c3ccc(NC(=O)c4oc(N5CCC(c6ccccc6)CC5)nc4C(F)(F)F)cn3)CC2)c1] | B |
| 263 | 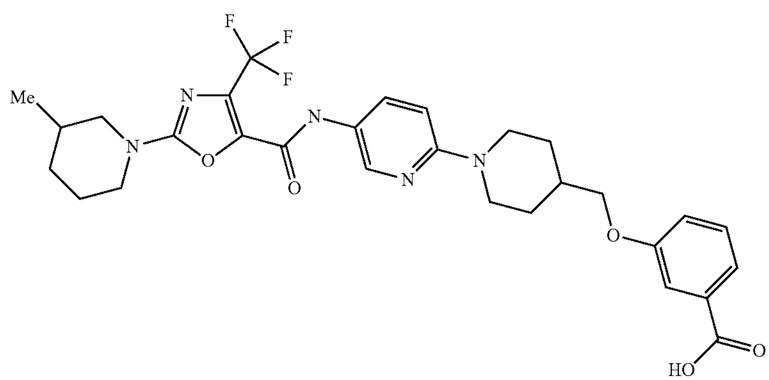 [SMILES: CC1CCCN(c2nc(C(F)(F)F)c(C(=O)Nc3ccc(N4CCC(COc5cccc(C(=O)O)c5)CC4)nc3)o2)C1] | B |
| 264 | 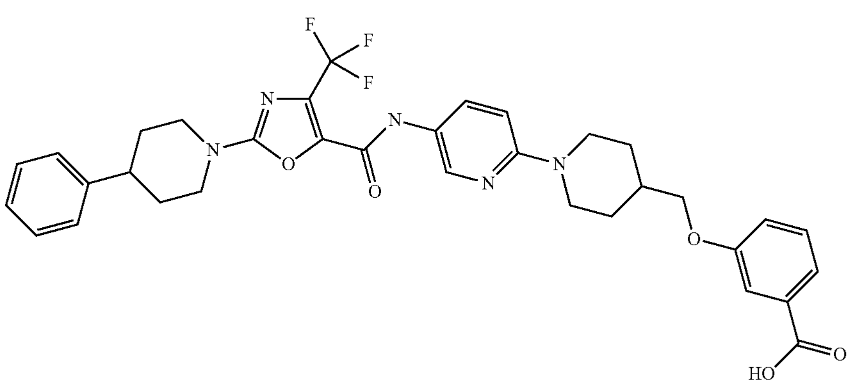 [SMILES: O=C(O)c1cccc(OCC2CCN(c3ccc(NC(=O)c4oc(N5CCC(c6ccccc6)CC5)nc4C(F)(F)F)cn3)CC2)c1] | B |

TABLE-continued

| Compound | Structure | hDGAT IC50 (nM) |
|---|---|---|
| 266 | 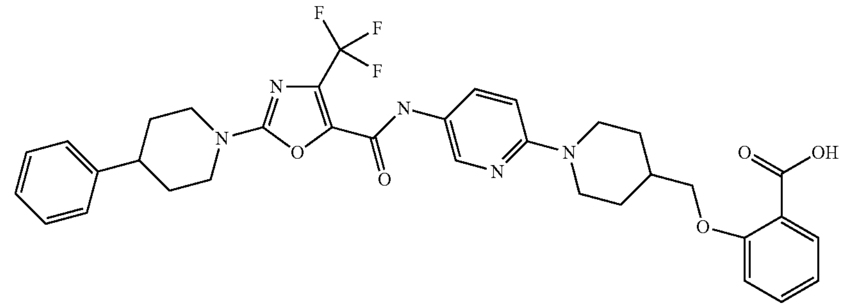 [SMILES: O=C(O)c1ccccc1OCC1CCN(c2ccc(NC(=O)c3oc(N4CCC(c5ccccc5)CC4)nc3C(F)(F)F)cn2)CC1] | C |
| 268 | 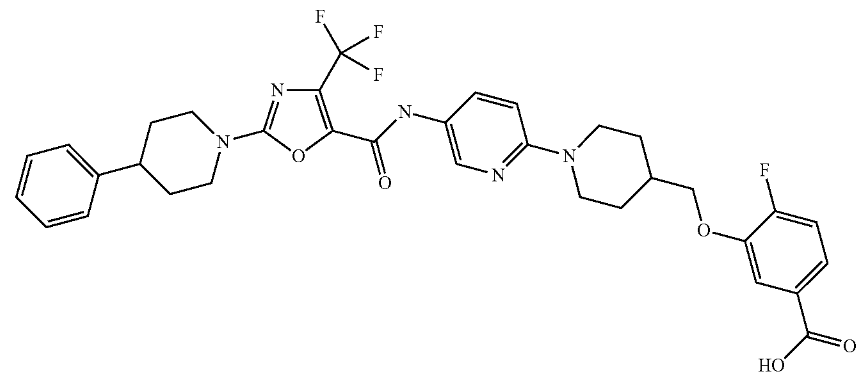 [SMILES: O=C(O)c1ccc(F)c(OCC2CCN(c3ccc(NC(=O)c4oc(N5CCC(c6ccccc6)CC5)nc4C(F)(F)F)cn3)CC2)c1] | B |

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound, or pharmaceutically acceptable salt thereof, the compound being represented by the formula I:

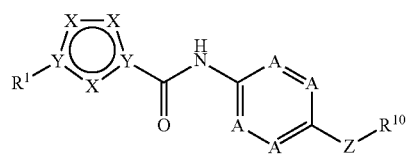

wherein:
the moiety:

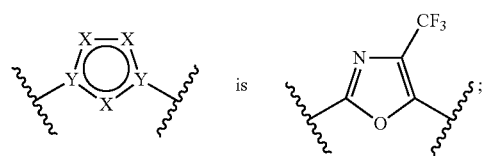

the moiety:

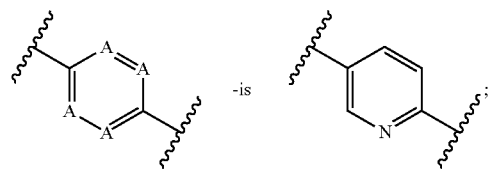

Z is a bond;

$R^1$ is selected from heterocycloalkyl containing 1 N atom, wherein said heterocycloalkyl is unsubstituted or optionally independently substituted with one or more moieties which are the same or different, each substituent being independently selected from the group consisting of alkyl, alkoxy, alkoxyalkyl, haloalkoxy, alkenyl, alkynyl, cycloalkyl, cycloalkylalkyl, cycloalkenyl, cycloalkenylalkyl, aryl, arylalkyl, heteroaryl, heteroarylalkyl, halo, —CN;

or alternatively, said heterocycloalkyl can be fused with aryl;

$R^5$ is selected from the group of lower alkyl, cycloalkyl, heterocyclyl, haloalkyl, aryl, and heteroaryl; and $R^{10}$ is either (i) a 4-8 membered heterocyclyl ring having from 1 to 2 ring N atoms, or (ii) a bicyclic heterocyclyl ring having from 1 to 3 ring N atoms, or (iv) a heteroaryl group, and further wherein said heterocyclyl ring for $R^{10}$ is unsubstituted or optionally substituted, off of either (i) a ring N atom or (ii) a ring carbon atom on said heterocyclyl ring, with one or more G moieties wherein said G moieties can be the same or different, each G moiety being independently selected from the group consisting of:

(a) ~~-(CHR$^{20}$)$_n$—C(O)—NR$^a$R$^b$, with the proviso that R$^{10}$ is not a 5- or 6-membered heterocyclyl ring when R$^{20}$ is hydrogen and R$^{10}$ can be a 5- or 6-membered heterocyclyl ring when G is present as an oxo group;

(b) ~~-(CHR$^{20}$)$_n$—C(O)—O—R$^5$, with the proviso that R$^{10}$ is not a 5- or 6-membered heterocyclyl ring when R$^{20}$ is hydrogen;

(c) ~~-(CHR$^{20}$)$_n$—C(O)—OH, with the proviso that R$^{10}$ is not a 5- or 6-membered heterocyclyl ring when R$^{20}$ is hydrogen;

(d) ~~-(CHR$^{20}$)$_n$—C(O)—R$^a$;

(e) ~~(CHR$^{20}$)$_n$—S(O$_2$)—NR$^a$R$^b$;

(f) ~~-(CHR$^{20}$)$_n$—R$^a$;

(g) ~~-(CHR$^{20}$)$_n$—O—R$^a$;

(h) ~~-NH—C(O)—R$^a$ off of only C and not off of N;

(i) ~~-NH—C(O)—NR$^a$R$^b$ off of only C and not off of N;

(j) ~~-O—CH(R$^a$)$_2$ off of only C and not off of N;

(k) an oxo group off of only C and not off of N;

(l) ~~-C(O)—(CHR$^{20}$)$_n$—R$^a$;

(m) ~~-C(O)-(cycloalkyl)--C(O)—N(R$^b$)—R$^a$, with the proviso that R$^{10}$ is not a 5- or 6-membered heterocyclyl ring;

(n) ~~-C(O)-(cycloalkyl)--C(O)—OR$^5$, with the proviso that R$^{10}$ is not a 5- or 6-membered heterocyclyl ring;

(o) ~~-C(O)-(cycloalkyl)-C(O)OH, with the proviso that R$^{10}$ is not a 5- or 6-membered heterocyclyl ring;

(p) ~~-C(O)-(cycloalkyl)-C(O)OH bioisostere, with the proviso that R$^{10}$ is not a 5- or 6-membered heterocyclyl ring; and (q) ~~-C(O)-(aryl)-C(O)OH, wherein R$^a$ is selected from the group consisting of hydrogen, hydroxy, CN, halo, alkyl, alkenyl, alkynyl, aryl, (aryl)alkyl-, heteroaryl, (heteroaryl)alkyl-, heterocyclyl, (heterocyclyl)alkyl-, cycloalkyl, (cycloalkyl)alkyl-, spirocyclyl or a bicyclic heterocyclyl, wherein each of said alkyl, alkenyl, alkynyl, aryl, heteroaryl, heterocyclyl and cycloalkyl is unsubstituted or optionally independently substituted with one or more moieties which are the same or different, each moiety being selected independently from the group consisting of O-haloalkyl, S-haloalkyl, CN, NO$_2$, CF$_3$, cycloalkyl, heterocyclyl, haloalkyl, aryl, heteroaryl, N-alkyl, N-haloalkyl, N-cycloalkyl; alkyl, alkenyl, alkynyl, cycloalkylalkyl, cycloalkenyl, heterocyclylalkyl, aryl, arylalkyl, heteroaryl, heteroarylalkyl, halo, —OR$^c$, —C(O)R$^c$, —C(O)OR$^c$, —C(O)N(R$^c$)(R$^d$), —SF$_5$, —OSF$_5$, —Si(R$^c$)$_3$, —SR$^C$, —S(O)N(R$^c$)(R$^d$), —CH(R$^c$)(R$^d$), —S(O)$_2$N(R$^c$)(R$^d$), —C(=NOR$^c$)R$^d$, —P(O)(OR$^c$)(OR$^d$), —N(R$^c$)(R$^d$), -alkyl-N(R$^c$)(R$^d$), —N(R$^c$)C(O)R$^d$, —CH$_2$—N(R$^c$)C(O)R$^d$, —CH$_2$—N(R$^c$)C(O)N(R$^d$)(R$^b$), —CH$_2$—R$^c$; —CH$_2$N(R$^c$)(R$^d$), —N(R$^c$)S(O)R$^d$, —N(R$^c$)S(O)$_2$R$^d$, —CH$_2$—N(R$^c$)S(O)$_2$R$^d$, —N(R$^c$)S(O)$_2$N(R$^d$)(R$^b$), —N(R$^c$)S(O)N(R$^d$)(R$^b$), —N(R$^c$)C(O)N(R$^d$)(R$^b$), —CH$_2$—N(R$^c$)C(O)N(R$^d$)(R$^b$), —N(R$^c$)C(O)OR$^d$, —CH$_2$—N(R$^c$)C(O)OR$^d$, —S(O)R$^c$, =NOR$^c$, —N$_3$, and —S(O)$_2$R$^c$;

wherein each R$^b$, R$^c$ and R$^d$ is independently selected;

R$^b$ is H, lower alkyl, cycloalkyl, aryl, heteroaryl or heterocycloalkyl;

R$^c$ is H, lower alkyl, cycloalkyl, aryl, heteroaryl or heterocycloalkyl;

R$^d$ is H, lower alkyl, cycloalkyl, aryl, heteroaryl or heterocycloalkyl;

wherein each of said alkyl, cycloalkyl, aryl, heteroaryl or heterocycloalkyl in R$^b$, R$^c$, and R$^d$ can be unsubstituted or optionally independently substituted with 1-2 substituents independently selected from halo, OH, NH$_2$, CF$_3$, CN, Oalkyl, NHalkyl, N(alkyl)$_2$ and Si(alkyl)$_3$;

R$^{20}$ is H, —OH, halo, or —CF$_3$;

and m is 1-3, n is 0-3.

2. A compound of claim 1, or a pharmaceutically acceptable salt thereof, wherein the compound is selected from the group consisting of the following:

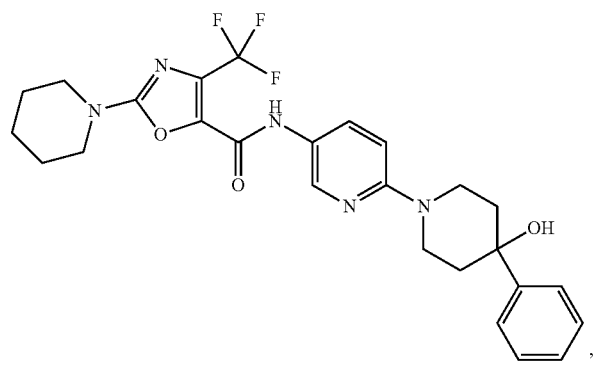

-continued
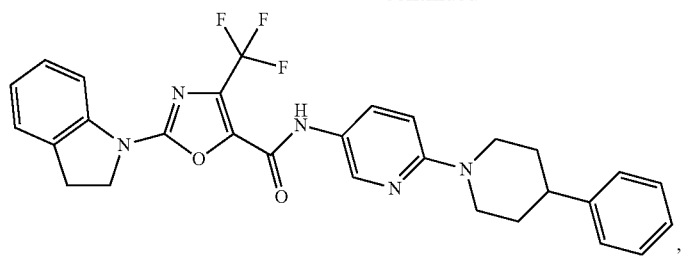
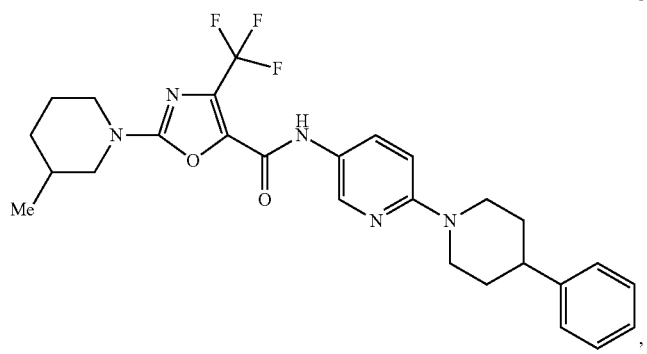
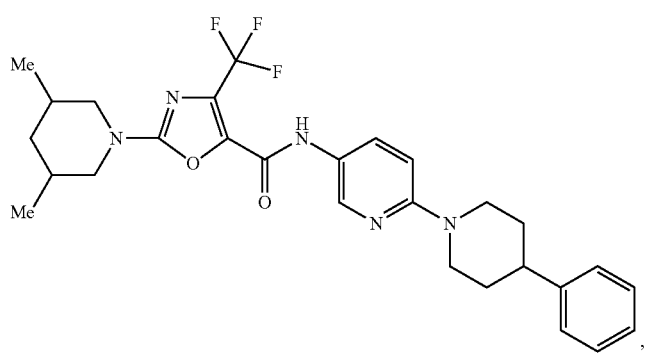
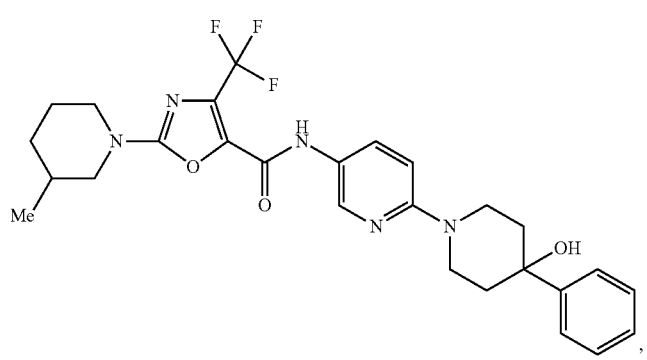
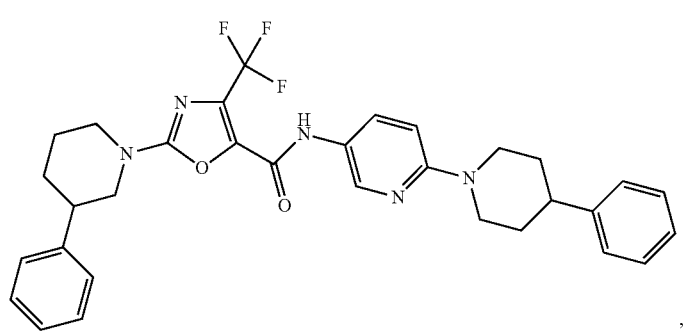

-continued
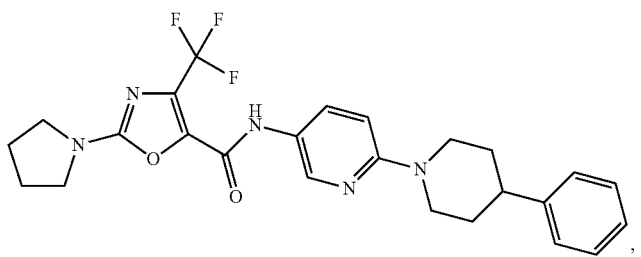
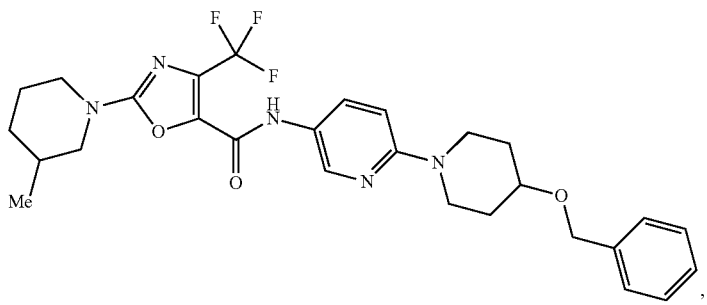
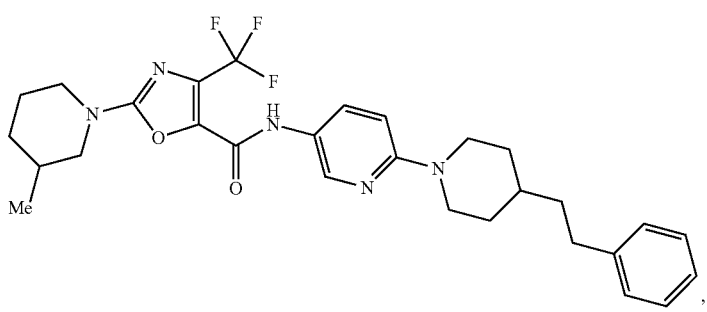
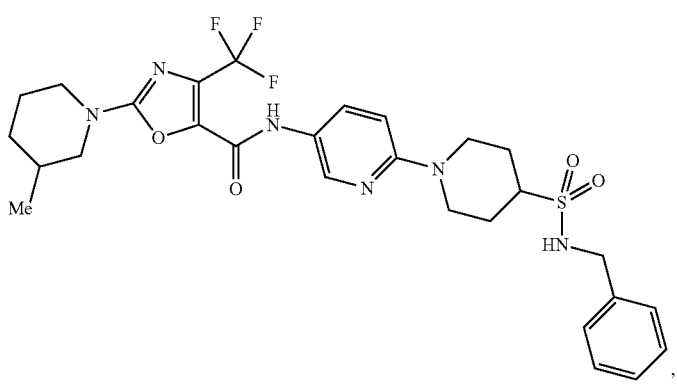
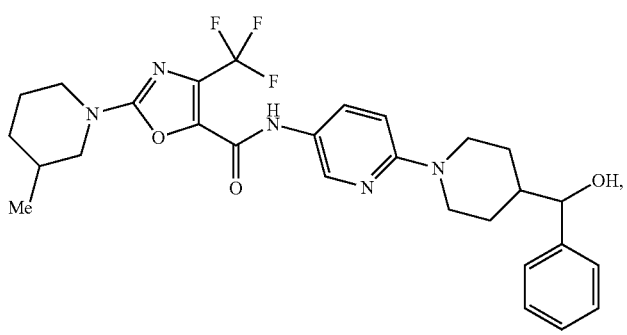

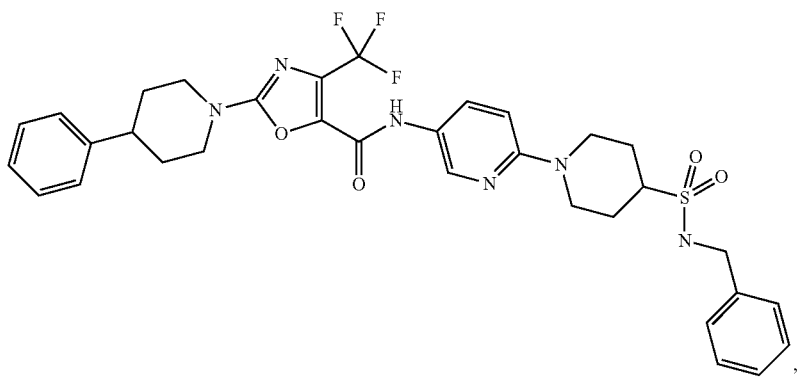
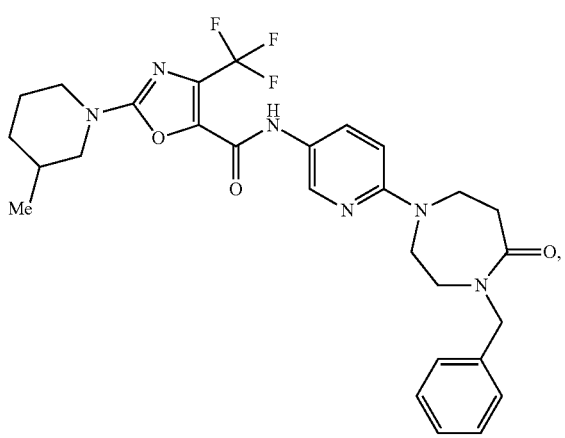
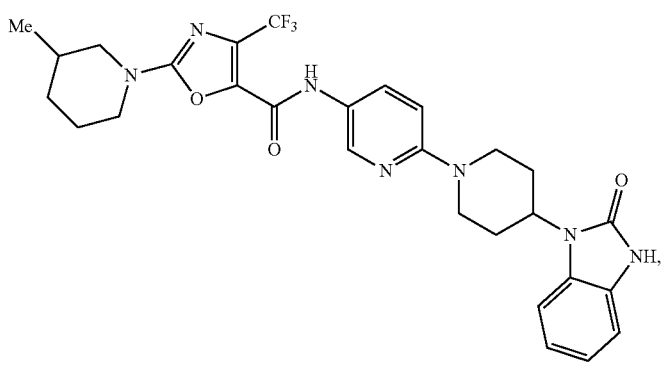
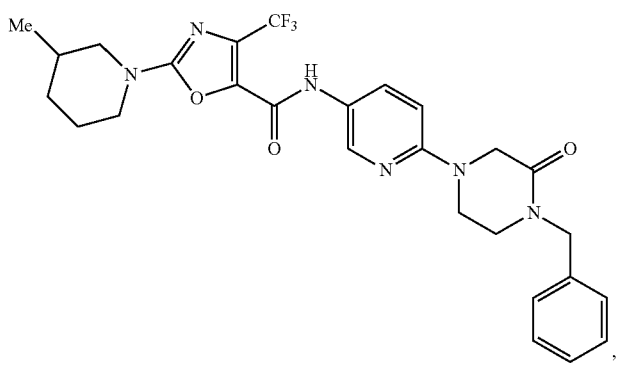

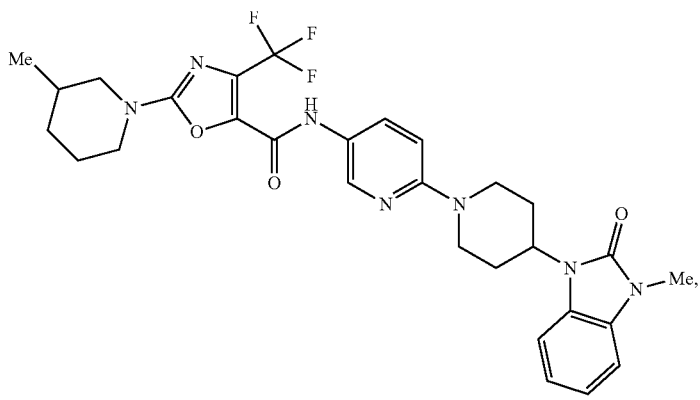
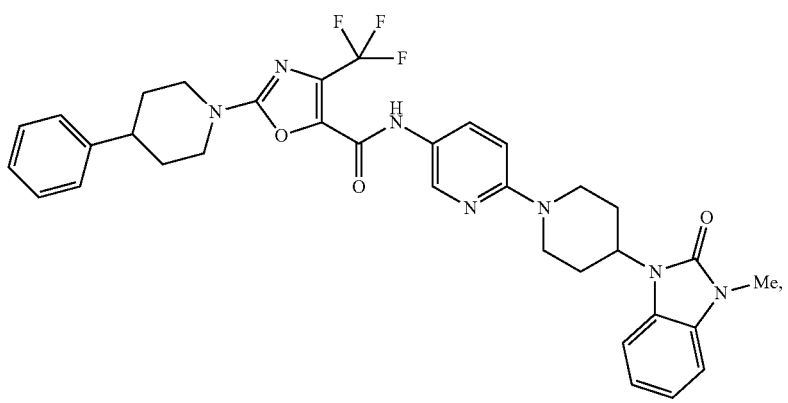
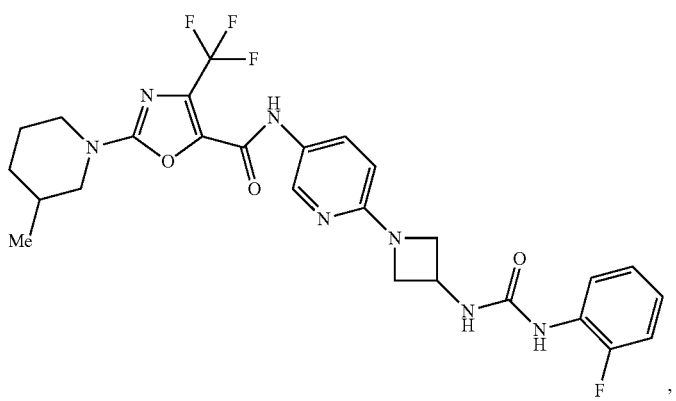
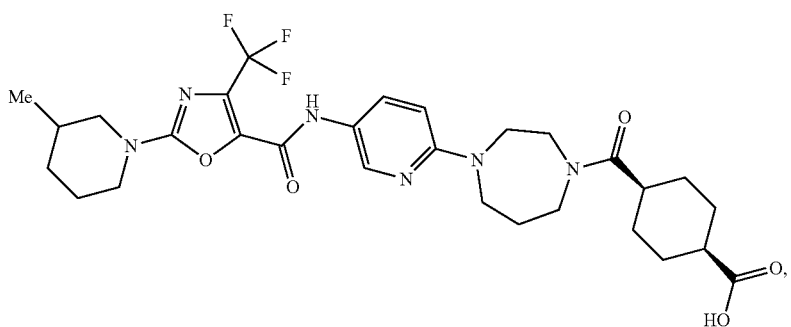

-continued
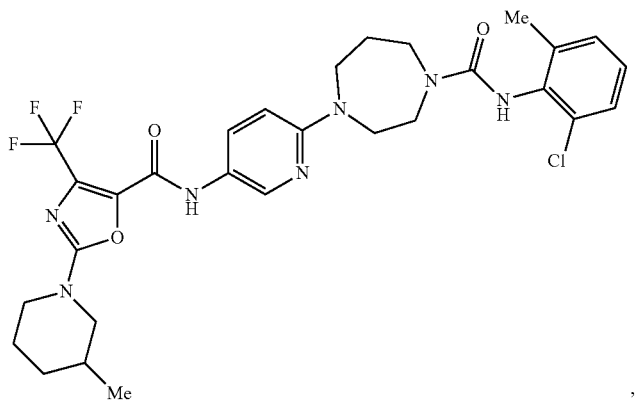
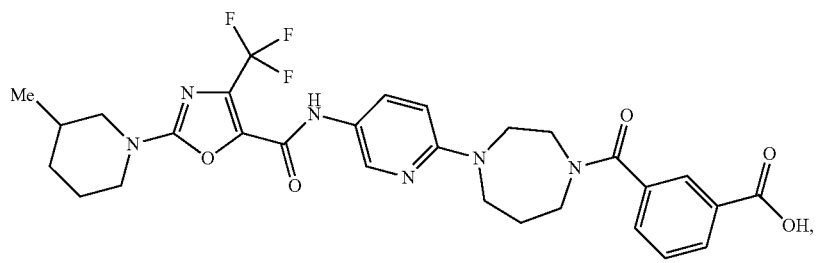
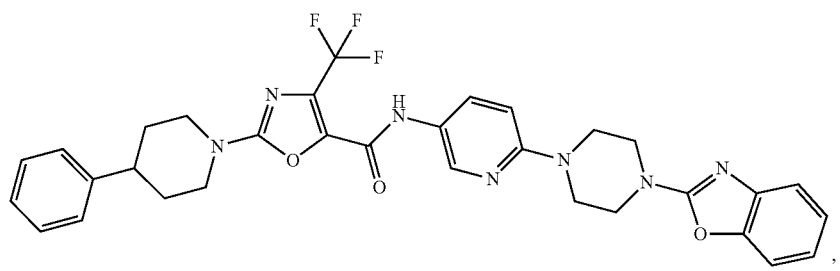
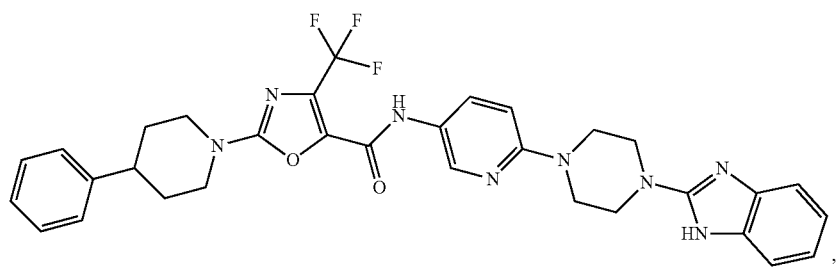
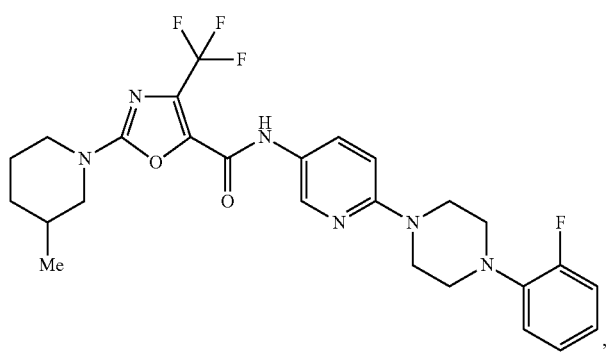

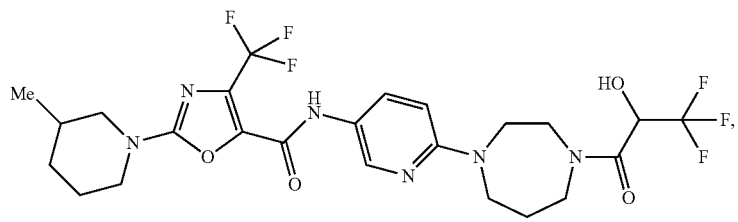
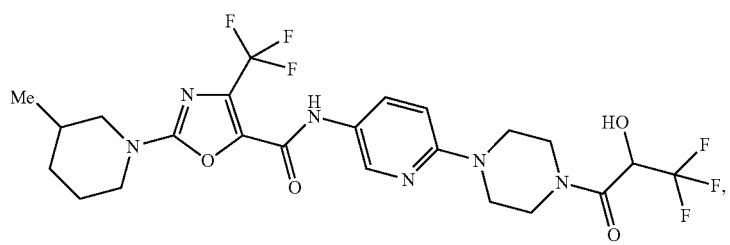
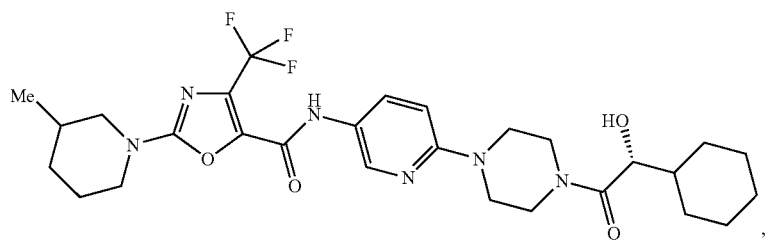
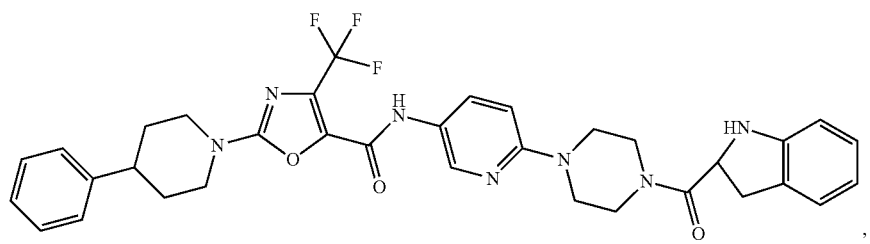
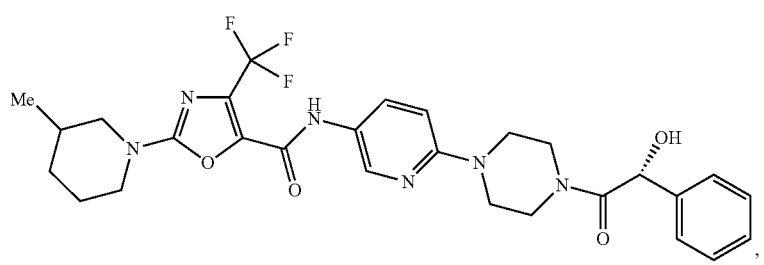
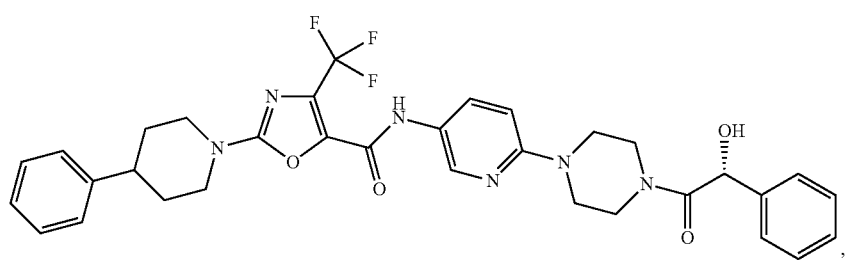

-continued
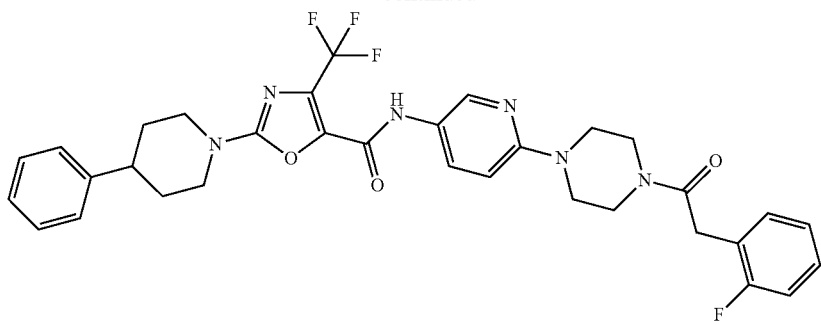
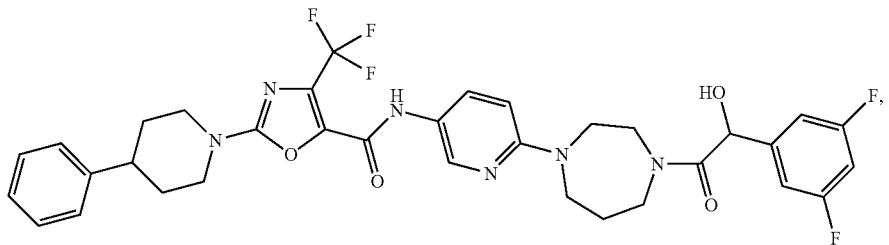
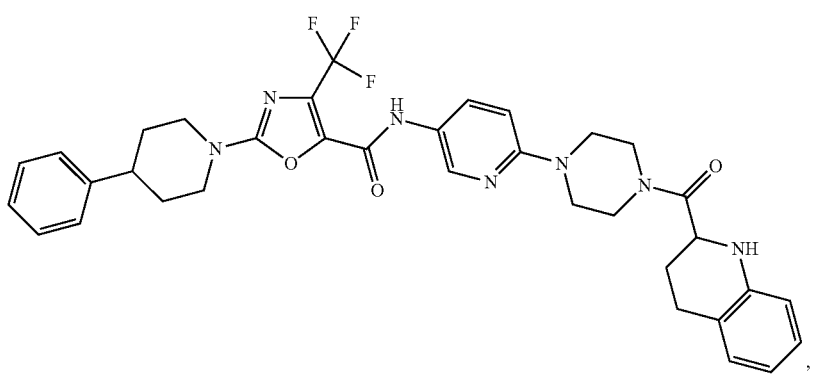
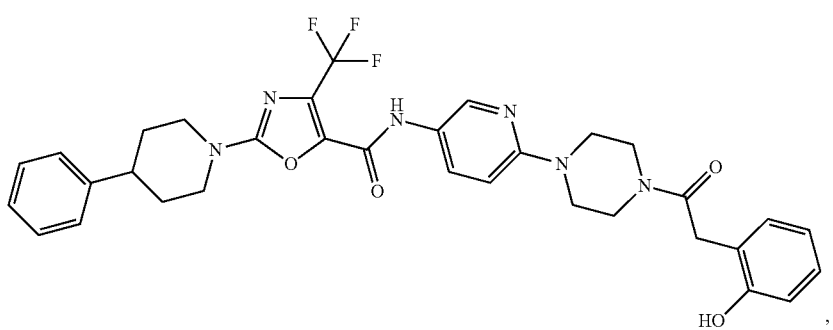
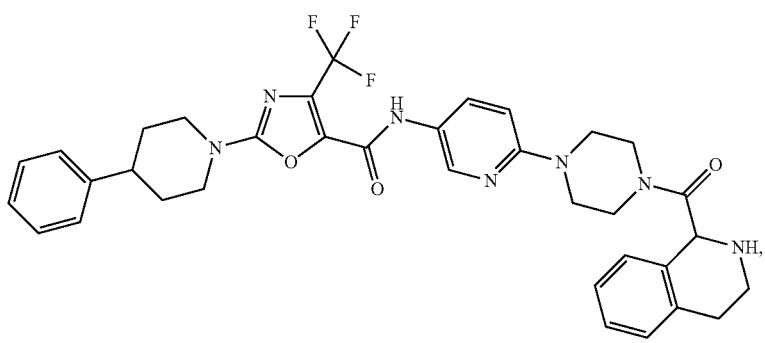

-continued
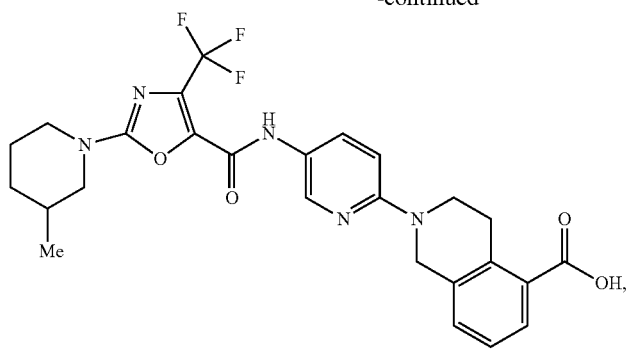
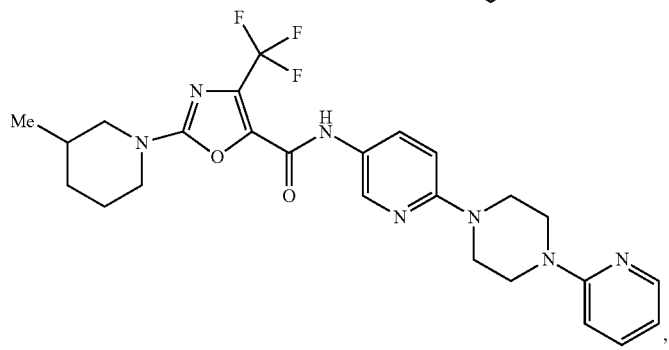
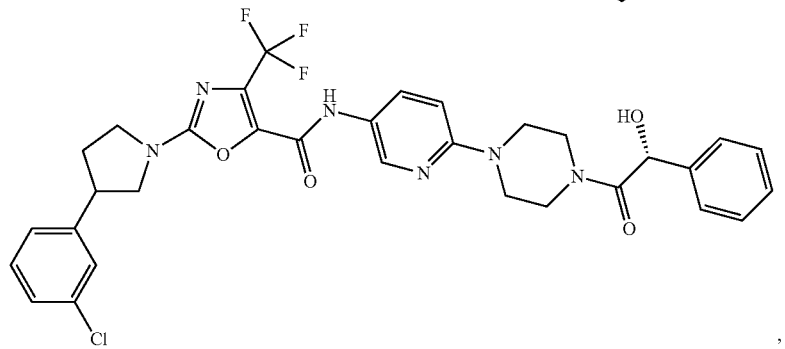
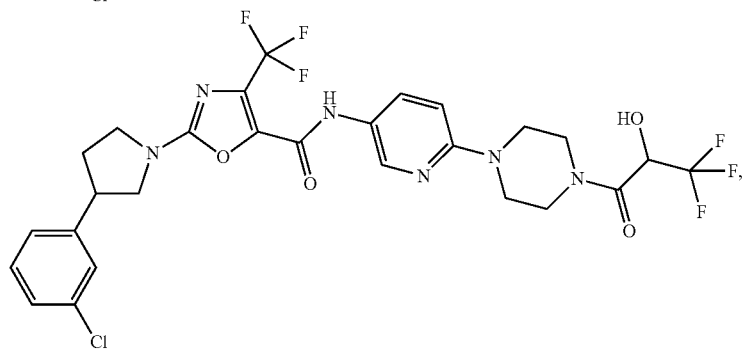
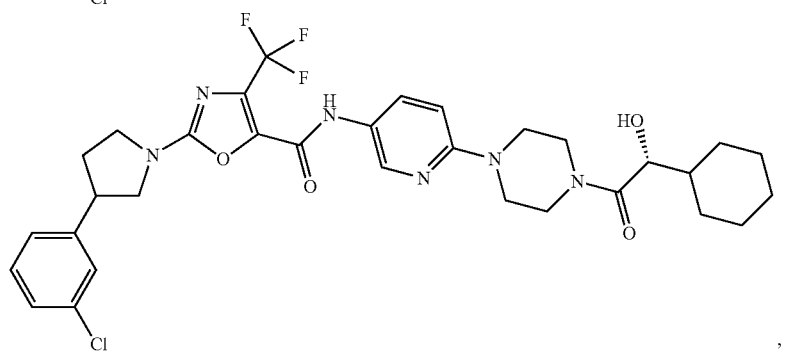

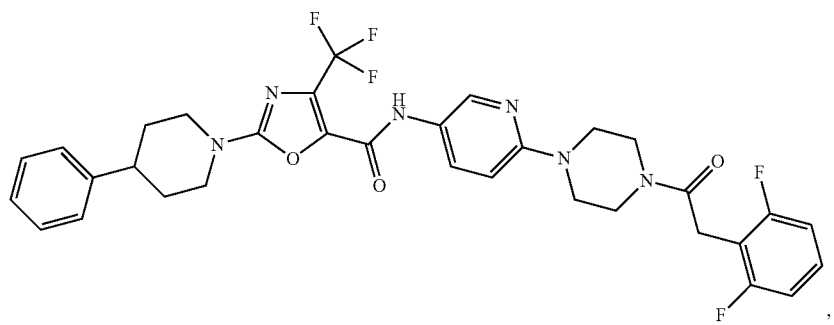
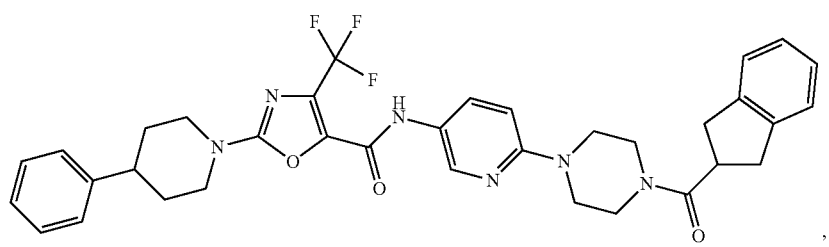
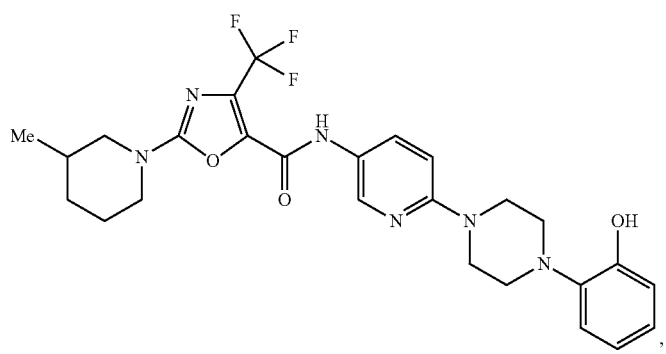
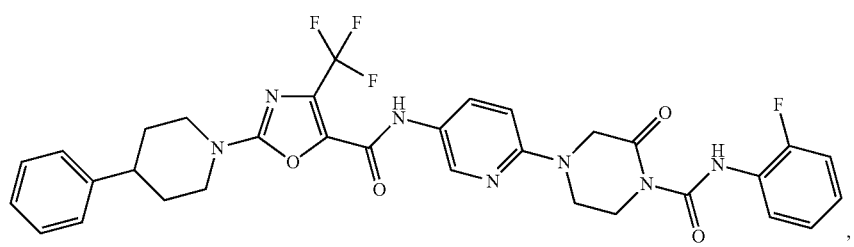
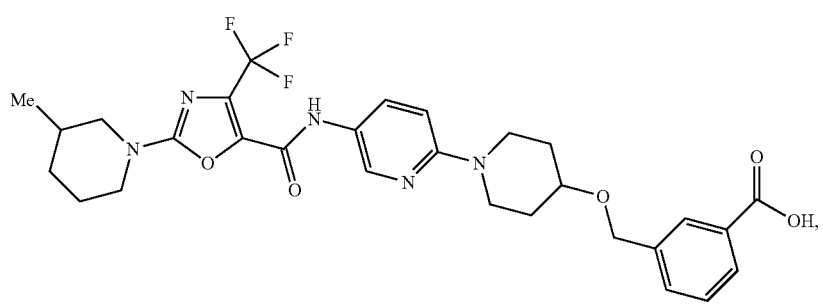

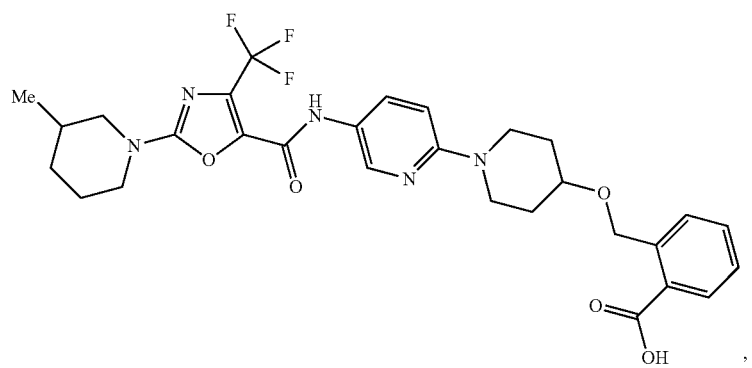
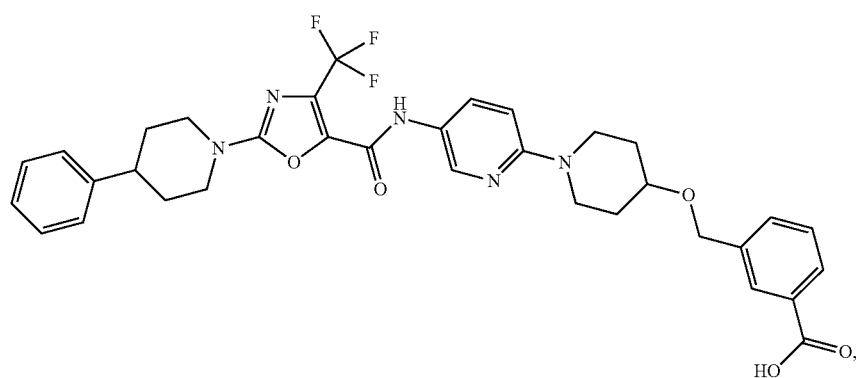
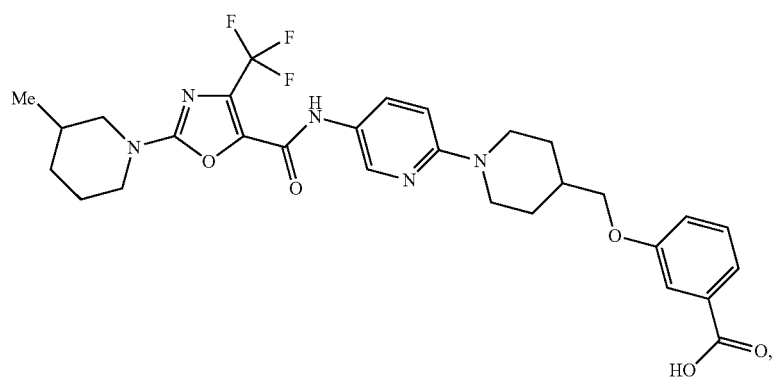
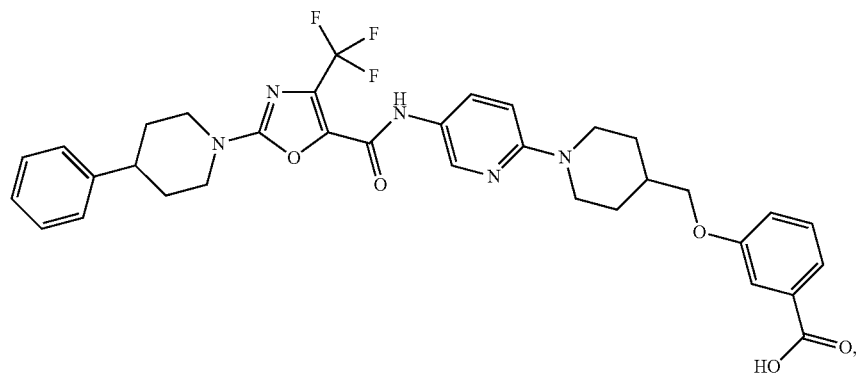 [SMILES: O=C(O)c1ccc(F)c(OCC2CCN(c3ccc(NC(=O)c4oc(N5CCC(c6ccccc6)CC5)nc4C(F)(F)F)cn3)CC2)c1]

-continued

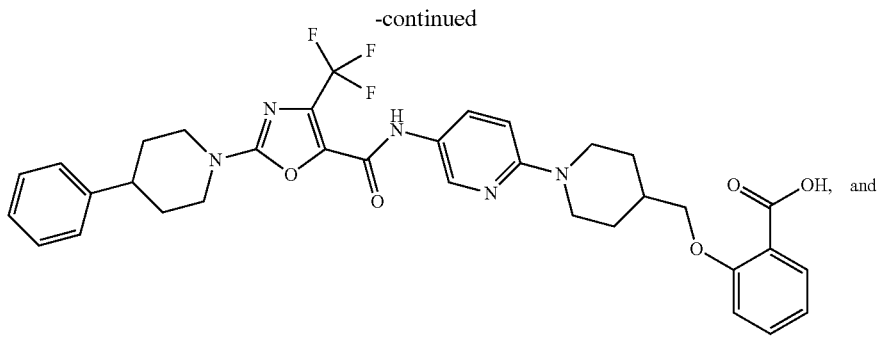

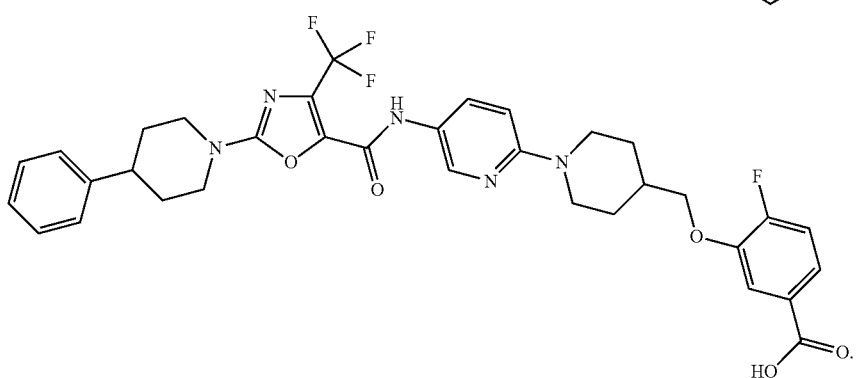

3. A pharmaceutical composition comprising an effective amount of at least one compound of claim 1 or 2, or a pharmaceutically acceptable salt thereof, and a pharmaceutically acceptable carrier.

4. A method of treating obesity, an obesity-related disorder, dyslipidemia, diabetes, a diabetic complication, impaired glucose tolerance or impaired fasting glucose in a patient, comprising administering to the patient an effective amount of at least one compound of claim 1 or 2, or a pharmaceutically acceptable salt thereof.

5. The method of claim 4, wherein the disease treated is diabetes.

6. The method of claim 4, wherein the disease treated is obesity.

* * * * *